United States Patent
Yanagisawa et al.

(10) Patent No.: US 10,538,516 B2
(45) Date of Patent: Jan. 21, 2020

(54) OXADIAZOLE DERIVATIVE AND PHARMACEUTICAL CONTAINING SAME

(71) Applicant: National Center for Geriatrics and Gerontology, Obu-shi, Aichi (JP)

(72) Inventors: Katsuhiko Yanagisawa, Obu (JP); Akiyoshi Kawai, Obu (JP)

(73) Assignee: National Center for Geriatrics and Gerontology, Obu-Shi, Aichi (JP)

( * ) Notice: Subject to any disclaimer, the term of this patent is extended or adjusted under 35 U.S.C. 154(b) by 0 days.

(21) Appl. No.: 15/560,345

(22) PCT Filed: Mar. 25, 2016

(86) PCT No.: PCT/JP2016/059576
§ 371 (c)(1),
(2) Date: Sep. 21, 2017

(87) PCT Pub. No.: WO2016/153023
PCT Pub. Date: Sep. 29, 2016

(65) Prior Publication Data
US 2018/0072708 A1 Mar. 15, 2018

(30) Foreign Application Priority Data
Mar. 25, 2015 (JP) ................. 2015-062815

(51) Int. Cl.
| | | |
|---|---|---|
| *C07D 413/04* | (2006.01) | |
| *C07D 413/14* | (2006.01) | |
| *C07D 413/12* | (2006.01) | |
| *C07D 413/06* | (2006.01) | |
| *C07D 285/08* | (2006.01) | |
| *C07D 285/12* | (2006.01) | |
| *C07D 271/06* | (2006.01) | |
| *C07D 271/10* | (2006.01) | |
| *A61K 31/4196* | (2006.01) | |
| *A61K 31/4709* | (2006.01) | |

(Continued)

(52) U.S. Cl.
CPC ............ *C07D 413/04* (2013.01); *A61K 31/41* (2013.01); *A61K 31/4178* (2013.01); *A61K 31/4196* (2013.01); *A61K 31/4245* (2013.01); *A61K 31/4709* (2013.01); *A61K 31/5377* (2013.01); *C07D 271/06* (2013.01); *C07D 271/10* (2013.01); *C07D 285/08* (2013.01); *C07D 285/12* (2013.01); *C07D 413/06* (2013.01); *C07D 413/12* (2013.01); *C07D 413/14* (2013.01)

(58) Field of Classification Search
CPC .. C07D 413/04; C07D 271/06; C07D 271/10; C07D 285/08; C07D 285/12; C07D 413/06; C07D 413/12; C07D 413/14; A61K 31/41; A61K 31/4178; A61K 31/4196; A61K 31/4245; A61K 31/4709; A61K 31/5377

USPC ......................................................... 514/364
See application file for complete search history.

(56) References Cited

U.S. PATENT DOCUMENTS

| | | |
|---|---|---|
| 7,687,512 B2 | 3/2010 | Bilbe |
| 2005/0054732 A1 | 3/2005 | Meguro et al. |

(Continued)

FOREIGN PATENT DOCUMENTS

| | | |
|---|---|---|
| JP | 4102850 | 6/2008 |
| WO | 2005/103020 | 11/2005 |

(Continued)

OTHER PUBLICATIONS

Registry [online], STN International, 2001, Retrieved from Chemical Library, RN316182-52-2; XP002402789.

(Continued)

*Primary Examiner* — Kristin A Vajda
(74) *Attorney, Agent, or Firm* — Myers Bigel, P.A.

(57) ABSTRACT

An amyloid fibril formation inhibitor comprising a compound represented by the following general formulae (I) to (III):

[Formula 1]

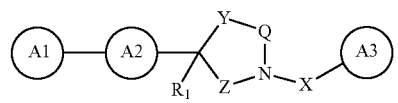

(I)

[Formula 2]

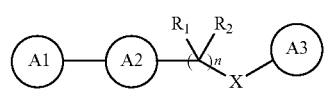

(II)

[Formula 3]

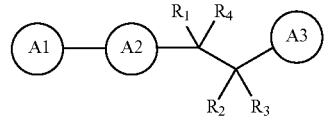

(III)

wherein
Q is —C(=O)—;
X is —C(=O)—, —NH—C(=O)—;
Y is —(CH$_2$)$_m$—;
Z is —(CH$_2$)$_n$—;
R$_1$, R$_2$, and R$_3$ are each independently a hydrogen atom, an alkyl group, a hydroxyalkyl group, an alkylaminoalkyl group; and
R$_4$ is an amino group, an alkylamino group or the like; or a pharmaceutically acceptable salt thereof or a solvate thereof.

16 Claims, No Drawings

(51) Int. Cl.
  *A61K 31/5377* (2006.01)
  *A61K 31/41* (2006.01)
  *A61K 31/4245* (2006.01)
  *A61K 31/4178* (2006.01)

(56) References Cited

U.S. PATENT DOCUMENTS

| | | | |
|---|---|---|---|
| 2006/0223812 | A1 | 10/2006 | Mandelkow et al. |
| 2007/0244119 | A1 | 10/2007 | Barrow et al. |
| 2008/0139538 | A1 | 6/2008 | McGaughey et al. |
| 2009/0170830 | A1 | 7/2009 | Nantermet |
| 2009/0197897 | A1 | 8/2009 | Bugada et al. |
| 2009/0215822 | A1 | 8/2009 | Farina et al. |
| 2010/0041680 | A1 | 2/2010 | Rivkin |
| 2010/0063077 | A1 | 3/2010 | Horwell et al. |
| 2010/0233156 | A1 | 9/2010 | Burns et al. |
| 2012/0053165 | A1 | 3/2012 | Allen et al. |

FOREIGN PATENT DOCUMENTS

| | | |
|---|---|---|
| WO | 2006/078577 | 7/2006 |
| WO | 2006/123249 | 11/2006 |
| WO | 2006/123255 | 11/2006 |
| WO | 2008/107677 | 9/2008 |
| WO | 2009/103652 | 8/2009 |
| WO | 2010/100606 | 9/2010 |
| WO | 2011/001931 | 1/2011 |

OTHER PUBLICATIONS

Registry [online], STN International, 2001, Retrieved from Chemical Library, RN316182-40-8 XP002402788.
Registry [online], STN International, 2001, Retrieved from Chemical Library, RN316182-51-1 XP002402787.
Registry [online], Interchim Intermediates, 2005, Retrieved from Chemical Library, Accession No. 2005:4859342, XP002401649.
Registry [online], ComGenex Product List, 2005, Retrieved from Chemical Library, Accession No. 2005:3064898, XP002401648.
Registry [online], ZRegistry, Retrieved from Chemical Library, RN316182-88-4, XP002401647, 2001.
Extended European Search Report corresponding to European Serial No. EP16768926 dated Jun. 27, 2018, 10 pages.
Yanagisawa K et al. GM1 ganglioside-bound amyloid (beta)-protein (A(beta)): a possible form of preamyloid in Alzheimer's disease. Nature Medicine. Oct. 1995; 1(10): 1062-1066.
Yanagisawa K and Ihara Y. GM1 ganglioside-bound amyloid (beta)-protein in Alzheimer's disease brain. Neurobiology of Aging. 1998; 19(1S) S65-S67.
Kakio A et al. Cholersterol-dependent formation of GM1 ganglioside-bound amyloid (beta)-protein, and endogenous seed for Alzheimer amyloid. Journal of Biological Chemistry. Jul. 6, 2001; 276(27): 24985-24990.
Yanagisawa K et al. Amyloid (beta)-protein (A(beta)) associated with lipid molecules: immunoreactivity distinct from that of soluble A(beta). FEB Letters. 1997; 420: 43-46.
McLaurin J and Chakrabartty A. Membrane disruption by Alzheimer (beta)-amyloid peptides mediated through specific binding to either phospholipids or gangliosides. Journal of Biological Chemistry. Oct. 25, 1996; 271-(43): 26482-26489.
Choo-Smith L-P et al. The interaction between Alzheimer amyloid (beta)(1-40) peptide and ganglioside GM1-containing membranes. FEBS Letters. 1997; 402: 95-98.
Choo-Smith L-P et al. Acceleration of amyloid fibril formation by specific binding of A(beta)-(1-40) peptide to ganglioside-containing membrane vesicles. Journal of Biological Chemistry. Sep. 12, 1997; 272(37): 22987-22990.
Matasuzaki K and Horikiri C. Interactions of amyloid (beta)-peptide (1-40) with ganglioside-containing membranes. Biochemistry. 1999; 38: 4137-4142.
Koppaka V and Axelsen PH. Accelerated accumulation of amyloid (beta) proteins on oxidatively damaged lipid membranes. Biochemistry. 2000; 39: 10011-10016.
Shuto D et al. KMI-008, a novel (beta)-secretase inhibitor containing a hydroxymethylcarbonyl isostere as a transition-state mimic: design and synthesis of substrate-based octapeptides. Bioorganic & Medicinal Chemistry Letters. 2003; 13: 4273-4276.
International Search Report and Written Opinion, PCT/JP2016/059576, dated Jun. 21, 2016.
Cabrol C et al. Small molecule activators of insulin-degrading enzyme discovered through high-throughput compound screening. PLOS One. Apr. 2009; 4(4): e5274.
Pettersson M et al. Design and synthesis of dihydrobenzofuran amides as orally bioavailable, centrally active (gamma)-secretase modulators. Bioorganic & Medicinal Chemistry Letters. 2012; 22(8): 2906-2911.
Dominguez JL et al. Effect of the protonation state of the titratable residues on the inhibitor affinity to BACE-1. Biochemistry. 2010; 49(34): 7255-7263.
Registry [online], STN International, 2007, [retrieved on Apr. 14, 2016], Retrieved from Chemical Library, RN941997-57-5, RN941960-60-7.
Registry [online], STN International, 2009, [retrieved on Apr. 14, 2016], Retrieved from Chemical Library, RN1172305-23-5, RN1170828-86-0, RN1169990-38-8, RN1171989-38-0, RN1170117-23-3, RN1173028-57-3, RN1171561-71-9, RN1171150-08-5, RN1171495-97-8, RN1172828-31-7.
Registry [online], STN International, 2010, [retrieved on Apr. 14, 2016], Retrieved from Chemical Library, RN1212695-47-0.
Registry [online], STN International, 2006, [retrieved on Jun. 2, 2016], Retrieved from Chemical Library, RN901267-80-9, RN901267-74-1.
Registry [online], STN International, 2004, [retrieved on Jun. 2, 2016], Retrieved from Chemical Library, RN688759-03-7.

OXADIAZOLE DERIVATIVE AND PHARMACEUTICAL CONTAINING SAME

This application is a 35 U.S.C. § 371 national phase entry of PCT Application PCT/JP2016/059576, filed Mar. 25, 2016, and published in Japanese on Sep. 29, 2016, as International Publication No. WO 2016/153023, and which claims the benefit of Japanese Application No. 2015-062815, filed Mar. 25, 2015, the disclosure of each of which is incorporated herein by reference in its entirety.

TECHNICAL FIELD

The present invention relates to an amyloid fibril formation inhibitor. In particular, the present invention relates to a therapeutic agent or a preventive agent of a neurodegenerative disease by inhibition of amyloid fibril formation.

BACKGROUND ART

The population of Japan is currently aging at a progressively faster rate, and the number of patients with dementia such as Alzheimer's disease is correspondingly increasing. The number of dementia patients at present is estimated to be approximately 4,500,000 people and it is predicted that the number of patients will continue to increase with aging in future. The care of such dementia patients involves large economic burden as well. The establishment of an effective therapy as soon as possible is urgently sought.

The three pathological features: (1) loss of nerve cells, (2) formation of plaque amyloid deposits (senile plaque), and (3) accumulation of fiber aggregates in nerve cells (neurofibrillary tangle) are commonly observed in patients with Alzheimer's disease, and these are causes of cognitive impairment (Alzheimer-type dementia), which is a clinical manifestation of Alzheimer's disease. Treatments of Alzheimer-type dementia currently conducted are symptomatic treatments which temporarily ameliorate symptoms of the dementia using a choline esterase inhibitor, an NMDA inhibitor, and the like. However, their effects are very limited and the establishment of a causal therapy that suppresses development and progression of Alzheimer's disease is strongly sought.

The establishment of a causal therapy of Alzheimer's disease requires elucidation of the pathogenic mechanism of Alzheimer's disease. Known Alzheimer's disease includes familial (hereditary) Alzheimer's disease, which is caused by genetic factors, and sporadic Alzheimer's disease, which has no genetic history. Currently, causative genes and risk factors of familial Alzheimer's disease are being revealed. Since pathological findings and clinical manifestations are common between familial Alzheimer's disease and sporadic Alzheimer's disease, it is predicted that a common mechanism exists in the process of disease onset. It is hoped that the study of the pathogenic mechanism of familial Alzheimer's disease leads to elucidation of the onset mechanism of sporadic Alzheimer's disease.

One of the causative genes of familial Alzheimer's disease is a gene encoding amyloid precursor protein (hereinafter, referred to as APP). APP is cleaved by β-secretase and γ-secretase to produce amyloid β (hereinafter, referred to as Aβ). There are two different Aβs that differ in the cleavage point in APP: Aβ40 consisting of 40 amino acids, and Aβ42 in which 2 amino acids are added to the C-terminus of Aβ40. Whereas Aβ40 is dominant in physiological amount of production, more Aβ42 is contained in senile plaques. Furthermore, it has been revealed that mutated APPs increase the expression ratio of Aβ42 and that Aβ42 is easier to agglutinate in comparison with Aβ40. From these facts, the following theory is proposed: Aβ42 first aggregates and, having them as nuclei, Aβ40 aggregates and accumulates, the formation of amyloid fibrils thereby progress, and Alzheimer's disease develops.

It has been found that the aggregation of Aβ in the brain starts with binding of Aβ to GM1 ganglioside (hereinafter, referred to as GM1), constituting the nerve cell membrane, to form a complex (GM1-bound Aβ: hereinafter referred to as GAβ) (Non-Patent Documents 1 and 2). Moreover, it has been confirmed by the analysis using vesicles of artificial lipid membrane that GM1 assembles in the nerve cell membrane in a cholesterol concentration-dependent manner to form clusters and Aβ forms GAβ by specifically binding to these GM1 clusters (Non-Patent Document 3). Furthermore, it has been confirmed by the analysis using antibodies that specifically recognize GAβ that GAβ has a structure different from that of soluble Aβ (Non-Patent Document 4). From these findings, a hypothesis was proposed that when Aβ binds to GM1 clusters, it changes into GAβ having a different structure and this GAβ serves as "seeds" and promotes the aggregation of Aβ and a large number of research results that support this hypothesis have been obtained subsequently (Non-Patent Documents 5 to 9).

Various compounds have been developed and tested in clinical trials so far for developing a method for radical treatment/prevention of Alzheimer's disease. Examples of such conventionally well-known compounds include inhibitors of β-secretase, which cleaves at the N-terminal side of Aβ when Aβ is generated, and inhibitors of γ-secretase, which cleaves at the C-terminal side of Aβ (Patent Document 1, Non-Patent Document 10). These inhibitors have been expected to be capable of suppressing formation of amyloid fibrils by inhibiting the production of Aβ. However, APP is not the only specific substrate of 1-secretase or γ-secretase. As a result, the γ-secretase inhibitors, in particular, have the problem of serious side effects due to the inhibition of Notch signals deeply involved in development and differentiation and also due to the inhibition of the physiological metabolism of APP itself. Also, a large number of low molecular weight compounds that inhibit polymerization of Aβ have been developed (Patent Documents 2 to 6). These compounds prevent the elongation of amyloid fibrils or divide the fibrils by inhibiting the polymerization of Aβ. However, it is suggested that polymerization of Aβ is restarted if the administration of the compound is stopped and there may be the possibility that the division of fibrils itself generates new seeds of polymerization and a sufficient suppressant effect has not been obtained on the formation of amyloid fibrils.

Meanwhile, a method for suppressing amyloid fibril formation using an antibody (4396C antibody) that specifically binds to GAβ has been reported (Patent Document 7). The 4396C antibody radically suppresses the formation of amyloid fibrils by specifically recognizing and binding to GAβ and inhibiting the Aβ polymerization with GAβ. However, there are problems in that production of an antibody is time consuming and costly. Moreover, agents containing an antibody have the problem that the mode of their administration is limited and clinical use thereof is difficult because there is a problem in delivery to the brain.

CITATION LIST

Patent Document

[Patent Document 1] US patent application publication No. 20100233156

[Patent Document 2] WO 2009/103652
[Patent Document 3] WO 2003/045923
[Patent Document 4] U.S. Pat. No. 7,687,512
[Patent Document 5] US patent application publication No. 20100063077
[Patent Document 6] US patent application publication No. 20060223812
[Patent Document 7] Japanese patent publication No. 4102850

Non-Patent Document

[Non-Patent Document 1] Yanagisawa, K. et al., Nat. Med., Vol. 1, pp. 1062-1066 (1995)
[Non-Patent Document 2] Yanagisawa, K. et al., Neurobiol. Aging, Vol. 19, pp. S65-67 (1998)
[Non-Patent Document 3] Kakio, A. et al., J. Biol. Chem., Vol. 276, pp. 24985-24990 (2001)
[Non-Patent Document 4] Yanagisawa, K. et al., FEBS Lett., Vol. 420, pp. 43-46 (1997)
[Non-Patent Document 5] McLaurin, J., and Chakrabartty, A., J. Biol. Chem., Vol. 271, pp. 26482-26489 (1996)
[Non-Patent Document 6] Choo-Smith, L. P., and Surewicz, W. K., FEBS Lett., Vol. 402, pp. 95-98 (1997)
[Non-Patent Document 7] Choo-Smith, L. P. et al., J. Biol. Chem., Vol. 272, pp. 22987-22990 (1997)
[Non-Patent Document 8] Matsuzaki, K. et al., Biochemistry, Vol. 38, pp. 4137-4142 (1999)
[Non-Patent Document 9] Koppaka, V. and Axelsen, P. H., Biochemistry, Vol. 39, pp. 10011-10016 (2000)
[Non-Patent Document 10] Shuto, D. et al., Bioorg. Med. Chem. Lett., Vol. 13, pp. 4273-4276 (2003)

SUMMARY OF THE INVENTION

Technical Problem

An object of the present invention is to provide a method for radical prevention/treatment of a neurodegenerative disease such as Alzheimer's disease, which method overcomes the problems of the prior art, and to provide an inhibitor of amyloid fibril formation, which inhibitor can specifically inhibit the polymerization of Aβ and is excellent in clinical application.

Solution to the Problem

As a result of diligent studies, the present inventors have succeeded in obtaining low molecular weight compounds that inhibit the polymerization of Aβ by specifically binding to GAβ.

Accordingly, according to one embodiment, the present invention provides an amyloid fibril formation inhibitor comprising a compound represented by a general formula (I):

[Formula 1]

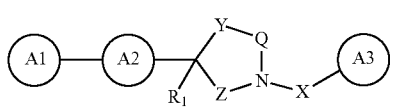

(I)

wherein
Ring A1 and Ring A3 are each independently a substituted or unsubstituted $C_{5-14}$ aryl group or a substituted or unsubstituted $C_{1-14}$ heteroaryl group;

Ring A2 is 1,2,4-oxadiazolyl, 1,3,4-oxadiazolyl, 1,2,4-thiadiazolyl, 1,3,4-thiadiazolyl, 1,2,4-triazolyl, imidazolyl, pyrazolyl, or tetrazolyl;

Q is —C(=O)—, —CH$_2$—, —CH(OH)—, —C(=O)—CH$_2$—, or —CH(OH)—CH$_2$—;

X is a bond, —C(=O)—, —C(=O)—(CR$_{xa}$R$_{xb}$)$_l$—, —C(=O)NR$_{xc}$—, —SO$_2$—, —SO$_2$NR$_{xc}$—, or —(CR$_{xa}$R$_{xb}$)$_l$—, where l is an integer of 1 to 3; R$_{xa}$, R$_{xb}$, and R$_{xc}$ are independently a hydrogen atom, a $C_{1-20}$ alkyl group, a $C_{1-20}$ alkoxy group, a $C_{1-20}$ hydroxyalkyl group, a $C_{1-20}$ alkoxyalkyl group, a $C_{1-20}$ alkylaminoalkyl group, a $C_{1-20}$ dialkylaminoalkyl group, or a $C_{1-20}$ aminoalkyl group; and R$_{xa}$ and R$_{xb}$ may together form a ring;

Y is —(CH$_2$)$_m$—, —O—, —NH—, —(CH$_2$)$_m$—O—, or —(CH$_2$)$_m$—NH—;

Z is —(CH$_2$)—, —O—, —NH—, —(CH$_2$)—O—, or —(CH$_2$)$_n$—NH—;

m and n are each independently an integer of 0 to 2, provided that m and n are not 0 at the same time; and R$_1$ is a hydrogen atom, a $C_{1-20}$ alkyl group, a hydroxyl group, a $C_{1-20}$ alkoxy group, a $C_{1-20}$ hydroxyalkyl group, a $C_{1-20}$ alkoxyalkyl group, a carboxyl group, an aminocarbonyl group, a $C_{1-20}$ alkylaminocarbonyl group, a $C_{1-20}$ dialkylaminocarbonyl group, a $C_{1-20}$ alkylaminoalkyl group, a $C_{1-20}$ dialkylaminoalkyl group, or a $C_{1-20}$ aminoalkyl group;
or a pharmaceutically acceptable salt thereof or a solvate thereof.

Moreover, according to one embodiment, the present invention provides an amyloid fibril formation inhibitor comprising a compound represented by a general formula (II):

[Formula 2]

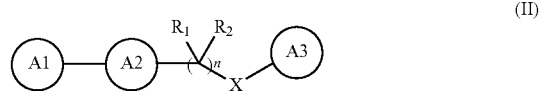

(II)

wherein
Ring A1 and Ring A3 are each independently a substituted or unsubstituted $C_{5-14}$ aryl group or a substituted or unsubstituted $C_{1-14}$ heteroaryl group;

Ring A2 is 1,2,4-oxadiazolyl, 1,3,4-oxadiazolyl, 1,2,4-thiadiazolyl, 1,3,4-thiadiazolyl, 1,2,4-triazolyl, imidazolyl, pyrazolyl, or tetrazolyl;

n is an integer of 0 to 3;

R$_1$ and R$_2$ are each independently a hydrogen atom, a $C_{1-20}$ alkyl group, a $C_{1-20}$ alkoxy group, a $C_{1-20}$ hydroxyalkyl group, a $C_{1-20}$ alkoxyalkyl group, a carboxyl group, an aminocarbonyl group, a $C_{1-20}$ alkylaminocarbonyl group, a $C_{1-20}$ dialkylaminocarbonyl group, a $C_{1-20}$ alkylaminoalkyl group, a $C_{1-20}$ dialkylaminoalkyl group, or a $C_{1-20}$ aminoalkyl group;

X is —NR$_x$—Y— or —Y—NR$_x$—(CH$_2$)$_l$—;

where l is an integer of 0 to 3;

R$_x$ is a hydrogen atom, a $C_{1-20}$ alkyl group, a $C_{1-20}$ alkoxy group, a $C_{1-20}$ hydroxyalkyl group, a $C_{1-20}$ alkoxyalkyl group, a carboxyl group, an aminocarbonyl group, a $C_{1-20}$ alkylaminocarbonyl group, a $C_{1-20}$ dialkylaminocarbonyl group, a $C_{1-20}$ alkylaminoalkyl group, a $C_{1-20}$ dialkylaminoalkyl group, or a $C_{1-20}$ aminoalkyl group;

Y is —C(=O)—, —C(=O)—(CR$_{ya}$R$_{yb}$)$_l$—, —C(=O)NR$_{yc}$—, —SO$_2$—, —SO$_2$NR$_{yc}$—, or —(CR$_{ya}$R$_{yb}$)$_l$—;

$R_{ya}$, $R_{yb}$, and $R_{yc}$ are independently a hydrogen atom, a $C_{1-20}$ alkyl group, a $C_{1-20}$ alkoxy group, a $C_{1-20}$ hydroxyalkyl group, a $C_{1-20}$ alkoxyalkyl group, a $C_{1-20}$ alkylaminoalkyl group, a $C_{1-20}$ dialkylaminoalkyl group, or a $C_{1-20}$ aminoalkyl group, and $R_{ya}$ and $R_{yb}$ may together form a ring; and $R_1$ and $R_2$, $R_1$ and $R_x$, or $R_2$ and $R_x$ may together form a 3 to 7-membered ring;

or a pharmaceutically acceptable salt thereof or a solvate thereof.

Moreover, according to one embodiment, the present invention provides an amyloid fibril formation inhibitor comprising a compound represented by a general formula (III):

[Formula 3]

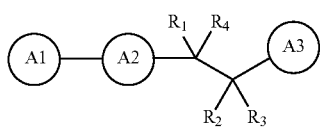

(III)

wherein

Ring A1 and Ring A3 are each independently a substituted or unsubstituted $C_{5-14}$ aryl group or a substituted or unsubstituted $C_{1-14}$ heteroaryl group;

Ring A2 is 1,2,4-oxadiazolyl, 1,3,4-oxadiazolyl, 1,2,4-thiadiazolyl, 1,3,4-thiadiazolyl, 1,2,4-triazolyl, imidazolyl, pyrazolyl, or tetrazolyl;

$R_1$, $R_2$, and $R_3$ are each independently a hydrogen atom, a $C_{1-20}$ alkyl group, a $C_{1-20}$ alkoxy group, a $C_{1-20}$ hydroxyalkyl group, a $C_{1-20}$ alkoxyalkyl group, a carboxyl group, an aminocarbonyl group, a $C_{1-20}$ alkylaminocarbonyl group, a $C_{1-20}$ dialkylaminocarbonyl group, a $C_{1-20}$ alkylaminoalkyl group, a $C_{1-20}$ dialkylaminoalkyl group, or a $C_{1-20}$ aminoalkyl group; and $R_4$ is a hydroxyl group, an amino group, a $C_{1-20}$ alkoxy group, a $C_{1-20}$ aminoalkyl group, a $C_{1-20}$ alkylamino group, or a $C_{1-20}$ dialkylamino group;

or a pharmaceutically acceptable salt thereof or a solvate thereof.

The general formula (I) is preferably as follows:

Ring A1 and Ring A3 are each independently a substituted or unsubstituted $C_{6-12}$ aryl group or a substituted or unsubstituted $C_{1-12}$ heteroaryl group;

Ring A2 is 1,2,4-oxadiazolyl, 1,3,4-oxadiazolyl, 1,2,4-thiadiazolyl, or 1,3,4-thiadiazolyl;

Q is —C(=O)—;

X is —C(=O)—;

Y is —(CH$_2$)$_m$—, where m is 1 or 2;

Z is —(CH$_2$)$_n$—, where n is 1 or 2; and $R_1$ is a hydrogen atom, a $C_{1-10}$ alkyl group, a $C_{1-10}$ alkoxy group, a $C_{1-10}$ hydroxyalkyl group, or a $C_{1-10}$ alkoxyalkyl group.

The general formula (II) is preferably as follows:

Ring A1 and Ring A3 are each independently a substituted or unsubstituted $C_{6-12}$ aryl group or a substituted or unsubstituted $C_{1-12}$ heteroaryl group;

Ring A2 is 1,2,4-oxadiazolyl, 1,3,4-oxadiazolyl, 1,2,4-thiadiazolyl, or 1,3,4-thiadiazolyl;

n is 1 or 2;

$R_1$ and $R_2$ are each independently a hydrogen atom, a $C_{1-10}$ alkyl group, a $C_{1-10}$ alkoxy group, a $C_{1-10}$ hydroxyalkyl group, a $C_{1-10}$ alkoxyalkyl group, a carboxyl group, an aminocarbonyl group, a $C_{1-10}$ alkylaminocarbonyl group, a $C_{1-10}$ dialkylaminocarbonyl group, a $C_{1-10}$ alkylaminoalkyl group, a $C_{1-10}$ dialkylaminoalkyl group, or a $C_{1-10}$ aminoalkyl group;

X is —NR$_x$—C(=O)—(CH$_2$)$_l$—, —NR$_x$—SO$_2$—, —C(=O)—NR$_x$—(CH$_2$)$_l$—, or —NR$_x$—(CH$_2$)$_l$—;

l is 1 or 2; and $R_x$ is a hydrogen atom, a $C_{1-10}$ alkyl group, a $C_{1-10}$ alkoxy group, a $C_{1-10}$ hydroxyalkyl group, a $C_{1-10}$ alkoxyalkyl group, a carboxyl group, an aminocarbonyl group, a $C_{1-10}$ alkylaminocarbonyl group, a $C_{1-10}$ dialkylaminocarbonyl group, a $C_{1-10}$ alkylaminoalkyl group, a $C_{1-10}$ dialkylaminoalkyl group, or a $C_{1-10}$ aminoalkyl group.

The general formula (III) is preferably as follows:

Ring A1 and Ring A3 are each independently a substituted or unsubstituted $C_{5-12}$ aryl group or a substituted or unsubstituted indol-3-yl group;

Ring A2 is 1,2,4-oxadiazolyl, 1,3,4-oxadiazolyl, 1,2,4-thiadiazolyl, or 1,3,4-thiadiazolyl;

$R_1$ is a hydrogen atom, a $C_{1-10}$ alkyl group, a $C_{1-10}$ hydroxyalkyl group, a $C_{1-10}$ alkoxyalkyl group, a $C_{1-10}$ alkylaminoalkyl group, a $C_{1-10}$ dialkylaminoalkyl group, or a $C_{1-10}$ aminoalkyl group;

$R_2$ and $R_3$ are each independently a hydrogen atom, a $C_{1-10}$ alkyl group, a $C_{1-10}$ hydroxyalkyl group, a $C_{1-10}$ alkylaminoalkyl group or a $C_{1-10}$ dialkylaminoalkyl group; and $R_4$ is an amino group, a $C_{1-10}$ alkylamino group, or a $C_{1-10}$ dialkylamino group.

Moreover, according to one embodiment, the present invention provides an amyloid fibril formation inhibitor comprising a compound selected from the group consisting of compounds of compound numbers 1 to 133 and 142 to 265 set forth in Table 1A to Table 1Q; or a pharmaceutically acceptable salt thereof or a solvate thereof.

The compound is preferably selected from the group consisting of compounds of compound numbers 2, 5 to 7, 9, 11 to 13, 17 to 20, 23 to 28, 32 to 34, 38 to 43, 45, 46, 48 to 50, 52 to 55, 58, 61 to 69, 71 to 78, 80, 81, 83 to 85, 87, 89 to 94, 96, 97, 99 to 104, 106, 107, 110, 112, 114, 116 to 119, 121, 125 to 133, 142 to 148, 150 to 153, 156 to 158, 161 to 170, 172, 175 to 179, 181 to 212, 214, 215, 217, 218, 220 to 227, 229 to 239, 242, and 245 to 267.

Alternatively, the compound is preferably selected from the group consisting of compounds of compound numbers 18, 25, 32, 39, 40, 63, 69, 72, 73, 78, 80, 83, 92 to 94, 101, 114, 116, 125, 129, 130, 132, 133, 143, 144, 146, 150, 157, 164, 165, 167, 168, 172, 175 to 177, 183, 188, 192, 195, 196, 198, 199, 201, 203, 207, 209 to 211, 220 to 222, 224, 232, 236, 237, 266, and 267.

Moreover, according to one embodiment, the present invention provides a therapeutic or preventive agent for a neurodegenerative disease, containing the aforementioned amyloid fibril formation inhibitor.

The neurodegenerative disease is preferably Alzheimer's disease.

Moreover, according to one embodiment, the present invention provides a compound selected from the group consisting of compound numbers 1 to 133 and 142 to 267 or a pharmaceutically acceptable salt thereof or a solvate thereof.

The compound is preferably selected from the group consisting of compound numbers 1, 3 to 6, 9, 11 to 22, 25, 29 to 41, 45 to 49, 51 to 58, 60, 62, 63, 65 to 76, 78 to 133 and 142 to 267.

Advantageous Effects of Invention

The amyloid fibril inhibitors according to the present invention can surely inhibit the formation of amyloid fibrils by specifically binding to GAβ and blocking the initiation of the polymerization of amyloid fibrils as the existing anti-GAβ antibody (4396C antibody) does. Moreover, the active ingredients of the amyloid fibril inhibitors according to the present invention are low molecular weight compounds, and they are therefore superior to antibodies in that: (1) they are easy to synthesize and can be prepared in large quantities at low cost, (2) they do not show antigenicity and they are therefore safe, and (3) their molecules are highly stable and maintain the stable GAβ binding capacity in various dosage forms.

Use of the amyloid fibril inhibitors according to the present invention also allows the provision of methods of radical prevention and treatment of neurodegenerative diseases including Alzheimer's disease.

DESCRIPTION OF EMBODIMENTS

The present invention will be described in detail below; however, the present invention is not limited to the embodiments described herein.

According to a first embodiment, the present invention is an amyloid fibril formation inhibitor comprising: a compound (hereinafter, referred to as "Compound (I)"), represented by a general formula (I):

[Formula 4]

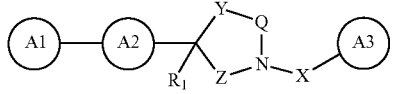

(I)

wherein

Ring A1 and Ring A3 are each independently a substituted or unsubstituted $C_{5-14}$ aryl group or a substituted or unsubstituted $C_{1-14}$ heteroaryl group;

Ring A2 is 1,2,4-oxadiazolyl, 1,3,4-oxadiazolyl, 1,2,4-thiadiazolyl, 1,3,4-thiadiazolyl, 1,2,4-triazolyl, imidazolyl, pyrazolyl, or tetrazolyl;

Q is —C(=O)—, —CH$_2$—, —CH(OH)—, —C(=O)—CH$_2$—, or —CH(OH)—CH$_2$—;

X is a bond, —C(=O)—, —C(=O)—(CR$_{xa}$R$_{xb}$)$_l$—, —C(=O)NR$_{xc}$—, —SO$_2$—, —SO$_2$NR$_{xc}$—, or —(CR$_{xa}$R$_{xb}$)$_l$—, where l is an integer of 1 to 3; R$_{xa}$, R$_{xb}$, and R$_{xc}$ are independently a hydrogen atom, a $C_{1-20}$ alkyl group, a $C_{1-20}$ alkoxy group, a $C_{1-20}$ hydroxyalkyl group, a $C_{1-20}$ alkoxyalkyl group, a $C_{1-20}$ alkylaminoalkyl group, a $C_{1-20}$ dialkylaminoalkyl group, or a $C_{1-20}$ aminoalkyl group; and R$_{xa}$ and R$_{xb}$ may together form a ring;

Y is —(CH$_2$)$_m$—, —O—, —NH—, —(CH$_2$)$_m$—O—, or —(CH$_2$)$_m$—NH—;

Z is —(CH$_2$)$_n$—, —O—, —NH—, —(CH$_2$)$_n$—O—, or —(CH$_2$)$_n$—NH—;

where m and n are each independently an integer of 0 to 2, provided that m and n are not 0 at the same time;

R$_1$ is a hydrogen atom, a $C_{1-20}$ alkyl group, a hydroxyl group, a $C_{1-20}$ alkoxy group, a $C_{1-20}$ hydroxyalkyl group, a $C_{1-20}$ alkoxyalkyl group, a carboxyl group, an aminocarbonyl group, a $C_{1-20}$ alkylaminocarbonyl group, a $C_{1-20}$ dialkylaminocarbonyl group, a $C_{1-20}$ alkylaminoalkyl group, a $C_{1-20}$ dialkylaminoalkyl group, or a $C_{1-20}$ aminoalkyl group; or a compound (hereinafter, referred to as "Compound (II)"), represented by a general formula (II):

[Formula 5]

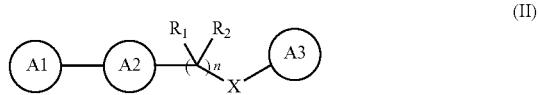

(II)

wherein

Ring A1 and Ring A3 are each independently a substituted or unsubstituted $C_{5-14}$ aryl group or a substituted or unsubstituted $C_{1-14}$ heteroaryl group;

Ring A2 is 1,2,4-oxadiazolyl, 1,3,4-oxadiazolyl, 1,2,4-thiadiazolyl, 1,3,4-thiadiazolyl, 1,2,4-triazolyl, imidazolyl, pyrazolyl, or tetrazolyl;

n is an integer of 0 to 3;

R$_1$ and R$_2$ are each independently a hydrogen atom, a $C_{1-20}$ alkyl group, a $C_{1-20}$ alkoxy group, a $C_{1-20}$ hydroxyalkyl group, a $C_{1-20}$ alkoxyalkyl group, a carboxyl group, an aminocarbonyl group, a $C_{1-20}$ alkylaminocarbonyl group, a $C_{1-20}$ dialkylaminocarbonyl group, a $C_{1-20}$ alkylaminoalkyl group, a $C_{1-20}$ dialkylaminoalkyl group, or a $C_{1-20}$ aminoalkyl group;

X is —NR$_x$—Y— or —Y—NR$_x$—(CH$_2$)$_l$—;

where l is an integer of 0 to 3;

R$_x$ is a hydrogen atom, a $C_{1-20}$ alkyl group, a $C_{1-20}$ alkoxy group, a $C_{1-20}$ hydroxyalkyl group, a $C_{1-20}$ alkoxyalkyl group, a carboxyl group, an aminocarbonyl group, a $C_{1-20}$ alkylaminocarbonyl group, a $C_{1-20}$ dialkylaminocarbonyl group, a $C_{1-20}$ alkylaminoalkyl group, a $C_{1-20}$ dialkylaminoalkyl group, or a $C_{1-20}$ aminoalkyl group;

Y is —C(=O)—, —C(=O)—(CR$_{ya}$R$_{yb}$)$_l$—, —C(=O)NR$_{yc}$—, —SO$_2$—, —SO$_2$NR$_{yc}$—, or —(CR$_{ya}$R$_{yb}$)$_l$—;

R$_{ya}$, R$_{yb}$, and R$_{yc}$ are independently a hydrogen atom, a $C_{1-20}$ alkyl group, a $C_{1-20}$ alkoxy group, a $C_{1-20}$ hydroxyalkyl group, a $C_{1-20}$ alkoxyalkyl group, a $C_{1-20}$ alkylaminoalkyl group, a $C_{1-20}$ dialkylaminoalkyl group, or a $C_{1-20}$ aminoalkyl group and R$_{ya}$ and R$_{yb}$ may together form a ring;

R$_1$ and R$_2$, R$_1$ and R$_x$, or R$_2$ and R$_x$ may together form a 3 to 7-membered ring; or a compound (hereinafter, referred to as "Compound (III)"), represented by a general formula (III):

[Formula 6]

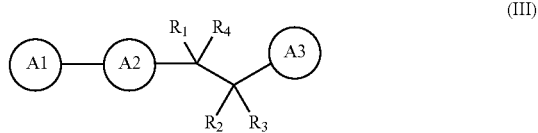

(III)

wherein

Ring A1 and Ring A3 are each independently a substituted or unsubstituted $C_{5-14}$ aryl group or a substituted or unsubstituted $C_{1-14}$ heteroaryl group;

Ring A2 is 1,2,4-oxadiazolyl, 1,3,4-oxadiazolyl, 1,2,4-thiadiazolyl, 1,3,4-thiadiazolyl, 1,2,4-triazolyl, imidazolyl, pyrazolyl, or tetrazolyl;

R$_1$, R$_2$, and R$_3$ are each independently a hydrogen atom, a $C_{1-20}$ alkyl group, a $C_{1-20}$ alkoxy group, a $C_{1-20}$ hydroxyalkyl group, a $C_{1-20}$ alkoxyalkyl group, a carboxyl group, an aminocarbonyl group, a $C_{1-20}$ alkylaminocarbonyl group, a $C_{1-20}$ dialkylaminocarbonyl group, a $C_{1-20}$ alkylaminoalkyl group, a $C_{1-20}$ dialkylaminoalkyl group, or a $C_{1-20}$ aminoalkyl group; and $R_4$ is a hydroxyl group, an amino group, a $C_{1-20}$ alkoxy group, a $C_{1-20}$ aminoalkyl group, a $C_{1-20}$ alkylamino group, or a $C_{1-20}$ dialkylamino group;

or a pharmaceutically acceptable salt thereof or a solvate thereof.

"Amyloid fibril" is an insoluble material formed by fibrillar aggregation of Aβ. The amyloid fibril is formed by first binding of Aβ to GM1 constituting the nerve cell membrane to form a complex GAβ that serves "seeds" and aggregation of Aβ on the seeds. The amyloid fibril formation inhibitor according to this embodiment can suppress the formation of the amyloid fibril by inhibiting aggregation of Aβ on GAβ.

"Aβ" is a peptide produced by cleaving of APP with β-secretase and γ-secretase and includes Aβ40 and Aβ42 that differ in the number of amino acids due to the difference of the cleavage point in APP.

The "APP" may encompass human APPs consisting of amino acid sequences registered with RefSeq accession numbers NP_001129601.1, NP_001129602.1, NP_001191232.2, NP_958817.1, NP_001191231.1, NP_958816.1, NP_001191230.1, NP_000475.1, NP_001129488.1, and NP_001129603.1 in the RefSeq database at NCBI (http://www.ncbi.nlm.nih.gov/RefSeq/) as well as proteins consisting of an amino acid sequence having 80% or more, preferably 90% or more, more preferably 95% or more, identity with an amino acid sequence listed above with the proviso that the protein produces Aβ by cleavage with β-secretase and γ-secretase. The identity of amino acid sequences can be determined by using a sequence analysis software or a conventional program in the field (FASTA, BLAST, etc.).

Moreover, "APP" may encompass proteins consisting of an amino acid sequence having substitution, deletion, insertion, and/or addition of one to several amino acids in an amino acid sequence listed above with proviso that the protein produces Aβ by cleavage with β-secretase and γ-secretase. The "one to several" above is, for example, "1 to 30", preferably "1 to 10", particularly preferably "1 to 5".

The amyloid fibril formation inhibitor according to this embodiment comprises Compound (I), Compound (II), or Compound (III) or a pharmaceutically acceptable salt thereof or a solvate thereof.

In Compound (I), Ring A1 and Ring A3 are each independently a substituted or unsubstituted $C_{5-14}$ aryl group or a substituted or unsubstituted $C_{1-14}$ heteroaryl group and, preferably, each independently a substituted or unsubstituted $C_{6-12}$ aryl group or a substituted or unsubstituted $C_{1-12}$ heteroaryl group.

In Compound (I) and Compounds (II) and (III) described below, "aryl group" means an aromatic hydrocarbon ring group. The aryl group in this embodiment may be a fusion of 2 or more aromatic hydrocarbon rings. Examples of the aryl group include a phenyl group, an indenyl group, a naphthyl group, a phenanthryl group, and an anthryl group and preferably, a phenyl group or a naphthyl group.

In Compound (I) and Compounds (II) and (III) described below, "heteroaryl group" means a group in which one or more carbon atoms in the ring(s) of an aryl group are replaced with a heteroatom(s). A preferred heteroatom may be selected from the group consisting of an oxygen atom, a nitrogen atom, and a sulfur atom. Examples of the heteroaryl group include a pyridyl group, a pyrazinyl group, a pyrimidinyl group, a pyridazinyl group, a pyrrolyl group, an imidazolyl group, a pyrazolyl group, a triazolyl group, a triazinyl group, a tetrazolyl group, an oxazolyl group, an indolizinyl group, an indolyl group, an isoindolyl group, an azaindolyl group, an indazolyl group, a purinyl group, a quinolizinyl group, an isoquinolyl group, a quinolyl group, a phthalazinyl group, a naphthyridinyl group, a quinoxalinyl group, an oxadiazolyl group, a thiazolyl group, a thiadiazolyl group, a benzothiazolyl group, a benzimidazolyl group, a benzotriazolyl group, a thieno group, a furyl group, and a thienyl group, and the heteroaryl group is preferably a pyridyl group, a pyridyl group, a quinolyl group, an indolyl group, an azaindolyl group, a thieno group, a furyl group, or an oxazolyl group.

In Compound (I) and Compounds (II) and (III) described below, the aryl group and the heteroaryl group may be unsubstituted or may be substituted with one or more substituents (for one or more hydrogen atoms). The substituent above may be selected from the group consisting of a $C_{1-20}$ alkyl group, a $C_{1-20}$ haloalkyl group, a $C_{1-20}$ alkoxy group, a $C_{1-20}$ haloalkoxy group, a $C_{1-20}$ hydroxyalkoxy group, a $C_{1-20}$ alkoxyalkyl group, a $C_{1-20}$ haloalkoxyalkyl group, a $C_{1-20}$ alkoxyalkoxy group, a $C_{1-20}$ haloalkoxyalkoxy group, a $C_{1-20}$ hydroxyalkyl group, a $C_{1-20}$ aminoalkyl group, a $C_{1-20}$ alkylaminoalkyl group, a $C_{1-20}$ dialkylaminoalkyl group, a $C_{1-20}$ alkylamino group, a $C_{1-20}$ alkylaminocarbonyl group, a $C_{1-20}$ dialkylaminocarbonyl group, a $C_{1-20}$ alkoxycarbonyl group, a $C_{1-20}$ alkoxycarbonylalkyl group, a $C_{1-20}$ acyl group, a $C_{1-20}$ acylalkyl group, a $C_{1-20}$ alkylthio group, a $C_{1-20}$ alkylenedioxy group, a $C_{1-20}$ haloalkylenedioxy group, a halogen atom, an amino group, a nitro group, an aminosulfonyl group, a $C_{1-20}$ alkylaminosulfonyl group, a $C_{1-20}$ alkylsulfonylamino group, an aryl group, a heteroaryl group, a cyano group, a thiol group, and a hydroxyl group and preferably a $C_{1-20}$ alkyl group, a $C_{1-20}$ haloalkyl group, a $C_{1-20}$ alkoxy group, a $C_{1-20}$ haloalkoxy group, a $C_{1-20}$ hydroxyalkoxy group, a $C_{1-20}$ alkoxyalkyl group, a $C_{1-20}$ alkoxyalkoxy group, a $C_{1-20}$ hydroxyalkyl group, a $C_{1-20}$ aminoalkyl group, a $C_{1-20}$ alkylaminoalkyl group, a $C_{1-20}$ dialkylaminoalkyl group, a $C_{1-20}$ alkylaminocarbonyl group, a $C_{1-20}$ dialkylaminocarbonyl group, a $C_{1-20}$ alkoxycarbonyl group, a $C_{1-20}$ alkoxycarbonylalkyl group, a $C_{1-20}$ acyl group, a $C_{1-20}$ acylalkyl group, a $C_{1-20}$ alkylthio group, a $C_{1-20}$ alkylenedioxy group, a $C_{1-20}$ haloalkylenedioxy group, a halogen atom, an amino group, a nitro group, an aminosulfonyl group, a $C_{1-20}$ alkylaminosulfonyl group, $C_{1-20}$ alkylsulfonylamino group, an aryl group, a heteroaryl group, a cyano group, a thiol group, and a hydroxyl group. When a substituent is a heteroaryl group, the heteroaryl group is preferably not tetrazole, triazole, or imidazole. The number and the substituted position of the substituents are not particularly limited, but the number of the substituents is preferably 0 to 3.

In Compound (I), Ring A2 is 1,2,4-oxadiazolyl, 1,3,4-oxadiazolyl, 1,2,4-thiadiazolyl, 1,3,4-thiadiazolyl, 1,2,4-triazolyl, imidazolyl, tetrazolyl or pyrazolyl and preferably 1,2,4-oxadiazolyl, 1,3,4-oxadiazolyl, 1,2,4-thiadiazolyl, or 1,3,4-thiadiazolyl. Here, the Ring A2 has two bonds and either bond may be a bond with Ring A1.

In Compound (I), Q is —C(=O)—, —CH$_2$—, —CH(OH)—, —C(=O)—CH$_2$—, or —CH(OH)—CH$_2$— and preferably —C(=O)—.

In Compound (I), X is a bond, —C(=O)—, —C(=O)—(CR$_{xa}$R$_{xb}$)$_f$—, —C(=O)NR$_{xc}$—, —SO$_2$—, —SO$_2$NR$_{xc}$—, or —(CR$_{xa}$R$_{xb}$)$_f$— and preferably —C(=O)—. Here, the notation of these groups for the X does not limit the direction of each bond of the groups in the compound, and either of the left and the right bonds of the groups for the X may be the bond with Ring A3.

In the above formulae, l is an integer of 1 to 3 and preferably 1 or 2. $R_{xa}$, $R_{xb}$, and $R_{xc}$ are independently a hydrogen atom, a $C_{1-20}$ alkyl group, a $C_{1-20}$ alkoxy group, a $C_{1-20}$ hydroxyalkyl group, a $C_{1-20}$ alkoxyalkyl group, a $C_{1-20}$ alkylaminoalkyl group, a $C_{1-20}$ dialkylaminoalkyl group, or a $C_{1-20}$ aminoalkyl group. Here, $R_{xa}$ and $R_{xb}$ may be the same or different from one another and $R_{xa}$ and $R_{xb}$ may together form a ring; the $C_{1-20}$ alkyl group, $C_{1-20}$ alkoxy group, $C_{1-20}$ hydroxyalkyl group, $C_{1-20}$ alkoxyalkyl group, $C_{1-20}$ alkylaminoalkyl group, $C_{1-20}$ dialkylaminoalkyl group, or $C_{1-20}$ aminoalkyl group is preferably $C_{1-10}$ and particularly preferably $C_{1-6}$. The alkyl group and the hydroxyalkyl group include those in linear and branched forms.

In Compound (I), Y is —$(CH_2)_m$—, —O—, —NH—, —$(CH_2)_m$—O—, or —$(CH_2)_m$—NH— and preferably —$(CH_2)_m$—. In Compound (I), Z is —$(CH_2)_n$—, —O—, —NH—, —$(CH_2)_n$—O—, or —$(CH_2)_n$—NH— and preferably —$(CH_2)_n$—. Here, m and n in the formulae are each independently an integer of 0 to 2 but m and n are not 0 at the same time and preferably each 1 or 2.

In Compound (I), $R_1$ is a hydrogen atom, a $C_{1-20}$ alkyl group, a hydroxyl group, a $C_{1-20}$ alkoxy group, a $C_{1-20}$ hydroxyalkyl group, a $C_{1-20}$ alkoxyalkyl group, a carboxyl group, an aminocarbonyl group, a $C_{1-20}$ alkylaminocarbonyl group, a $C_{1-20}$ dialkylaminocarbonyl group, a $C_{1-20}$ alkylaminoalkyl group, a $C_{1-20}$ dialkylaminoalkyl group, or a $C_{1-20}$ aminoalkyl group, and preferably a hydrogen atom, a $C_{1-10}$ alkyl group, a $C_{1-10}$ alkoxy group, a $C_{1-10}$ hydroxyalkyl group, or a $C_{1-10}$ alkoxyalkyl group.

In Compound (II), Ring A1 and Ring A3 are each independently a substituted or unsubstituted $C_{5-14}$ aryl group or a substituted or unsubstituted $C_{1-14}$ heteroaryl group, and preferably each independently a substituted or unsubstituted $C_{6-12}$ aryl group or a substituted or unsubstituted $C_{1-12}$ heteroaryl group. "Aryl group" and "heteroaryl group" are as defined above.

In Compound (II), Ring A2 is 1,2,4-oxadiazolyl, 1,3,4-oxadiazolyl, 1,2,4-thiadiazolyl, 1,3,4-thiadiazolyl, 1,2,4-triazolyl, imidazolyl, pyrazolyl, or tetrazolyl, and preferably 1,2,4-oxadiazolyl, 1,3,4-oxadiazolyl, 1,2,4-thiadiazolyl, or 1,3,4-thiadiazolyl. Here, the ring A2 has two bonds and either bond may be a bond with Ring A1.

In Compound (II), n is an integer of 0 to 3 and preferably 1 or 2.

In Compound (II), $R_1$ and $R_2$ are each independently a hydrogen atom, a $C_{1-20}$ alkyl group, a $C_{1-20}$ alkoxy group, a $C_{1-20}$ hydroxyalkyl group, a $C_{1-20}$ alkoxyalkyl group, a carboxyl group, an aminocarbonyl group, a $C_{1-20}$ alkylaminocarbonyl group, a $C_{1-20}$ dialkylaminocarbonyl group, a $C_{1-20}$ alkylaminoalkyl group, a $C_{1-20}$ dialkylaminoalkyl group, or a $C_{1-20}$ aminoalkyl group, and preferably each independently a hydrogen atom, a $C_{1-10}$ alkyl group, a $C_{1-10}$ alkoxy group, a $C_{1-10}$ hydroxyalkyl group, a $C_{1-10}$ alkoxyalkyl group, a carboxyl group, an aminocarbonyl group, a $C_{1-10}$ alkylaminocarbonyl group, a $C_{1-10}$ dialkylaminocarbonyl group, a $C_{1-10}$ alkylaminoalkyl group, a $C_{1-10}$ dialkylaminoalkyl group, or a $C_{1-10}$ aminoalkyl group.

In Compound (II), X is —$NR_x$—Y— or —Y—$NR_x$—$(CH_2)_l$—, wherein Y is —C(=O)—, —C(=O)—$(CR_{ya}R_{yb})_l$—, —C(=O)$NR_{yc}$—, —$SO_2$—, —$SO_2NR_{yc}$—, or —$(CR_{ya}R_{yb})_l$—; and preferably X is —$NR_x$—C(=O)—$(CH_2)_l$—, —$NR_x$—$SO_2$—, —C(=O)—$NR_x$—$(CH_2)_l$—, or —NR—$(CH_2)_l$—. Here, the notation of these groups for the X and Y above does not limit the direction of each bond of the groups in the compound, and either of the left and the right bonds of the groups for the X may be a bond with Ring A3 and either of the left and the right bonds in the groups for the Y may be the bond with $R_x$.

In the formulae above, n is an integer of 0 to 3, and is preferably an integer of 0 to 2. $R_{ya}$, $R_{yb}$, and $R_{yc}$ are independently a hydrogen atom, a $C_{1-20}$ alkyl group, a $C_{1-20}$ alkoxy group, a $C_{1-20}$ hydroxyalkyl group, a $C_{1-20}$ alkoxyalkyl group, a $C_{1-20}$ alkylaminoalkyl group, a $C_{1-20}$ dialkylaminoalkyl group, or a $C_{1-20}$ aminoalkyl group. Here, $R_{ya}$ and $R_{yb}$ may be the same or different from one another and $R_{ya}$ and $R_{yb}$ may together form a ring. The above $C_{1-20}$ alkyl group, $C_{1-20}$ alkoxy group, $C_{1-20}$ hydroxyalkyl group, $C_{1-20}$ alkoxyalkyl group, $C_{1-20}$ alkylaminoalkyl group, $C_{1-20}$ dialkylaminoalkyl group, or $C_{1-20}$ aminoalkyl group is preferably $C_{1-10}$ and particularly preferably $C_{1-6}$. The alkyl group and the hydroxyalkyl group may include those in linear and branched forms.

In Compound (II), $R_1$, $R_2$, and $R_x$ may be the same or different from one another and $R_1$ and $R_2$, $R_1$ and $R_x$, or $R_2$ and $R_x$ may together form a 3, 4, 5, 6, or 7-membered ring.

In Compound (III), Ring A1 and Ring A3 are each independently a substituted or unsubstituted $C_{5-14}$ aryl group or a substituted or unsubstituted $C_{1-14}$ heteroaryl group and preferably each independently a substituted or unsubstituted $C_{5-12}$ aryl group or a substituted or unsubstituted indol-3-yl group. "Aryl group" and "heteroaryl group" are as defined above.

In Compound (III), Ring A2 is 1,2,4-oxadiazolyl, 1,3,4-oxadiazolyl, 1,2,4-thiadiazolyl, 1,3,4-thiadiazolyl, 1,2,4-triazolyl, imidazolyl, pyrazolyl, or tetrazolyl, and preferably 1,2,4-oxadiazolyl, 1,3,4-oxadiazolyl, 1,2,4-thiadiazolyl, or 1,3,4-thiadiazolyl. Here, the ring A2 has two bonds and either bond may be a bond with Ring A1.

In Compound (III), $R_1$, $R_2$, and $R_3$ are each independently a hydrogen atom, a $C_{1-20}$ alkyl group, a $C_{1-20}$ alkoxy group, a $C_{1-20}$ hydroxyalkyl group, a $C_{1-20}$ alkoxyalkyl group, a carboxyl group, an aminocarbonyl group, a $C_{1-20}$ alkylaminocarbonyl group, a $C_{1-20}$ dialkylaminocarbonyl group, a $C_{1-20}$ alkylaminoalkyl group, a $C_{1-20}$ dialkylaminoalkyl group, or a $C_{1-20}$ aminoalkyl group, and preferably $R_1$ is a hydrogen atom, a $C_{1-10}$ alkyl group, a $C_{1-10}$ hydroxyalkyl group, a $C_{1-10}$ alkoxyalkyl group, a $C_{1-10}$ alkylaminoalkyl group, a $C_{1-10}$ dialkylaminoalkyl group, or a $C_{1-10}$ aminoalkyl group and $R_2$ and $R_3$ are each independently a hydrogen atom, a $C_{1-10}$ alkyl group, a $C_{1-10}$ hydroxyalkyl group, a $C_{1-10}$ alkylaminoalkyl group or a $C_{1-10}$ dialkylaminoalkyl group.

In Compound (III), $R_4$ is a hydroxyl group, an amino group, a $C_{1-20}$ alkoxy group, a $C_{1-20}$ aminoalkyl group, a $C_{1-20}$ alkylamino group, or a $C_{1-20}$ dialkylamino group, and preferably an amino group, a $C_{1-10}$ alkylamino group, or a $C_{1-10}$ dialkylamino group.

Unless otherwise specified, compounds (I) to (III) used in this embodiment may include their stereoisomers such as tautomers, geometric isomers (e.g., E bodies, Z bodies), and enantiomers.

Compounds (I) to (III) used in this embodiment can be synthesized by methods of chemical synthesis described in Examples below and other methods of chemical synthesis corresponding thereto in combination with various methods conventionally known as appropriate.

Alternatively, when Compounds (I) to (III) used in this embodiment are selected from commercially available compounds, commercially available compounds may be purchased. Such commercially available compounds may be purchased, for example, from Ambinter, Enamine Ltd., Aurora Fine Chemicals LLC, UORSY Ltd., Vitas-M Laboratory Ltd., Interbioscreen Ltd., Interchim Inc., Ryan Scientific Inc., ChemDiv Inc., through Namiki Shoji Co., Ltd. or Kishida Chemical Co., Ltd., when purchased in Japan.

The amyloid fibril formation inhibitors of this embodiment may encompass those comprising Compounds (I) to (III) described above as well as those comprising pharmaceutically acceptable salts of Compounds (I) to (III) described above or solvates thereof.

In this embodiment, "pharmaceutically acceptable" means not being harmful in use of the agent. Examples of the pharmaceutically acceptable salt in this embodiment may include, for example, when there is an acid group in Compounds (I) to (III), alkali metal salts or alkaline earth metal salts, such as lithium salts, sodium salts, potassium salts, magnesium salts, and calcium salts; amine-addition salts such as ammonia, methylamine, dimethylamine, trimethylamine, dicyclohexylamine, tris(hydroxymethyl) aminomethane, N,N-bis(hydroxyethyl)piperazine, 2-amino-2-methyl-1-propanol, ethanolamine, N-methyl glucamine, and L-glucamine; or basic amino acid addition salts such as lysine, 6-hydroxylysine, and arginine. Examples of the pharmaceutically acceptable salt in this embodiment include, for example, when there is a basic group in Compounds (I) to (III), inorganic acid salts such as hydrochlorides, hydrobromides, nitrates, sulfates, and phosphates; organic acid salts such as methanesulfonic acid, benzenesulphonic acid, para-toluenesulfonic acid, acetic acid, propionate, tartaric acid, fumaric acid, maleic acid, malic acid, oxalic acid, succinic acid, citric acid, benzoic acid, mandelic acid, cinnamic acid, lactic acid, glycolic acid, glucuronic acid, ascorbic acid, nicotinic acid, and salicylic acid; and acidic amino acid addition salts such as aspartic acid and glutamic acid.

Examples of the pharmaceutically acceptable "solvates" in this embodiment may include hydrates and alcoholates as well as solvates with pharmaceutically acceptable solvents selected from the group consisting of; dimethylformamide, dimethylacetamide, N-methyl-2-pyrrolidone, chloroform, dichloroethane, dichloromethane, diethyl ether, methyl t-butyl ether, ethylene glycol monomethyl ether, ethylene glycol dimethyl ether, ethylene glycol monoethyl ether, ethylene glycol diethyl ether, diisopropyl ether, tetrahydrofuran, dioxane, acetone, methyl ethyl ketone, isobutyl methyl ketone, toluene, benzene, o-xylene, m-xylene, p-xylene, ethyl acetate, propyl acetate, butyl acetate, propylene carbonate, diethyl carbonate, dimethyl carbonate, hexane, pentane, heptane, octane, and cyclohexane and the pharmaceutically acceptable "solvates" in this embodiment are preferably hydrates.

A compound or a mixture of two or more selected from the compounds represented by Compounds (I) to (III) or pharmaceutically acceptable salts thereof or solvates thereof may be used as an active ingredient of an amyloid fibril formation inhibitor. The amyloid fibril formation inhibitor of this embodiment may be composed of only the active ingredient, but may usually further include a pharmaceutically acceptable known diluent, carrier, or excipient as an optional component.

The amyloid fibril formation inhibitor of this embodiment may be produced by formulating one of the compounds represented by Compounds (I) to (III) or pharmaceutically acceptable salts thereof or solvates thereof, in combination with one of the known carriers described above as needed, according to a conventional method. In the amyloid fibril formation inhibitor, the one of the compounds represented by Compounds (I) to (III) or pharmaceutically acceptable salts thereof or solvates thereof may be contained as an active ingredient in such a range that is suitable for its form and results in an appropriate amount of intake. In the amyloid fibril formation inhibitor, the content of the one of the compounds represented by Compounds (I) to (III) or pharmaceutically acceptable salts thereof or solvates thereof in the agent is usually preferably determined so that the dose thereof will be 0.001 mg/kg (body weight) or more, preferably 0.01 mg/kg (body weight) or more, for an adult, per day, but it is not limited to such a range and may be adjusted as appropriate depending on symptoms, age, and sex of the patient and the like. The upper limit of the dose is preferably 100 mg/kg (body weight) or less and more preferably 10 mg/kg (body weight) or less per day.

The amyloid fibril formation inhibitor of this embodiment may be formulated into various dosage forms and examples of such dosage forms include tablets, capsules, granules, powders, syrups, suspensions, suppositories, ointments, creams, gels, patches, inhalants, and injections. Accordingly, the amyloid fibril formation inhibitor of this embodiment may be administered by various modes such as oral administration, intraperitoneal administration, intradermal administration, intravenous administration, intramuscular administration, and intracerebral administration.

When the amyloid fibril formation inhibitor is administered as an oral preparation, it may be formulated into, for example, solid preparations such as tablets, capsules, powders, and granules. In this case, an appropriate additive, for example, an excipient such as starch, lactose, sucrose, mannitol, carboxymethylcellulose, cornstarch, or an inorganic salt and, as desired, a binder, a disintegrator, a lubricant, a colorant, or a flavor may be blended. When the solid preparation is a tablet or a pill, the preparation may be coated with a sugarcoating such as sucrose, gelatin, hydroxypropyl cellulose or a film of a gastrosoluble or enterosoluble substance, as desired. Alternatively, the oral preparation of the amyloid fibril formation inhibitor may be, for example, a solution such as syrup. In this case, sterile water, saline, ethanol, or the like may be used as a carrier. Furthermore, an adjuvant such as a suspending agent, an edulcorant, a flavorant, a preservative, or the like may be added, as desired.

When the amyloid fibril formation inhibitor is formulated into a parenteral preparation, the preparation may be, for example, a solution such as an injection or a preparation for rectal administration. In this case, the preparation may be prepared by dissolving or suspending an active ingredient by a conventional method in a diluent such as distilled water for injection, physiological saline, an aqueous glucose solution, a vegetable oil for injection, sesame oil, peanut oil, soybean oil, corn oil, propylene glycol, polyethyleneglycol; and adding a biocide, a stabilizer, an isotonizing agent, a soothing agent, or the like as needed. It is also possible to produce a solid composition and dissolve the composition in sterile water or a sterile vehicle for injection before use.

The parenteral preparation of the amyloid fibril formation inhibitor may be formulated, for example, as a sustained release preparation such as a microcapsule and may also be administered to the brain directly. The sustained release preparation may be prepared with a carrier that can be prevented from being removed immediately from the body. Examples of preferable carriers that may be used include biodegradable/biocompatible polymers such as ethylene-vinyl acetate, polyanhydride, polyglycolic acid, collagen, polyorthoester, and polylactic acid. Liposomes may be used as a carrier. The liposomes are not particularly limited, but preferable liposomes may be those purified by reverse phase evaporation using a lipid composition containing phosphatidylcholine, cholesterol, and PEG-derivatized phosphatidyl ethanolamine (PEG-PE).

Furthermore, the amyloid fibril formation inhibitor of this embodiment may contain a pharmaceutically acceptable additive such as a colorant, a preservative, a flavor, a flavoring agent, and an edulcorant and another therapeutic agent, as desired.

A stabilizer is preferably blended in the formulation of the amyloid fibril formation inhibitor. Examples of the stabilizer may include albumin, globulin, gelatin, mannitol, glucose, dextran, and ethylene glycol.

The amount of the active ingredient contained in the formulation may vary depending on various conditions, for example, the type of the extraction solvent, the amount of the solvent used, and the like. Therefore, an amount of the active ingredient less than the aforementioned preferred amount of intake may be sufficient or an amount exceeding the range may be necessary.

The amyloid fibril formation inhibitor of this embodiment can suppress the formation of the amyloid fibril radically and surely. Therefore it is useful for applications such as treatment or prevention of diseases related to the formation of amyloid fibrils.

According to the second embodiment, the present invention is an amyloid fibril formation inhibitor comprising a compound selected from the group consisting of compounds of compound numbers 1 to 133 and 142 to 267 or a pharmaceutically acceptable salt thereof or a solvate thereof. The compounds of compound numbers 1 to 133 and 142 to 267 indicated below can inhibit the polymerization of Aβ onto GAβ and suppress the formation of amyloid fibrils.

TABLE 1A

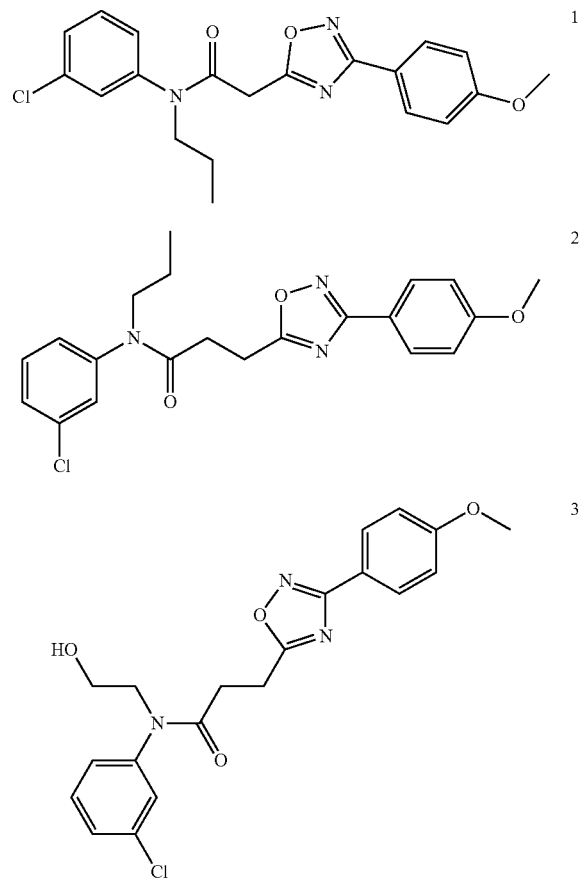

TABLE 1A-continued

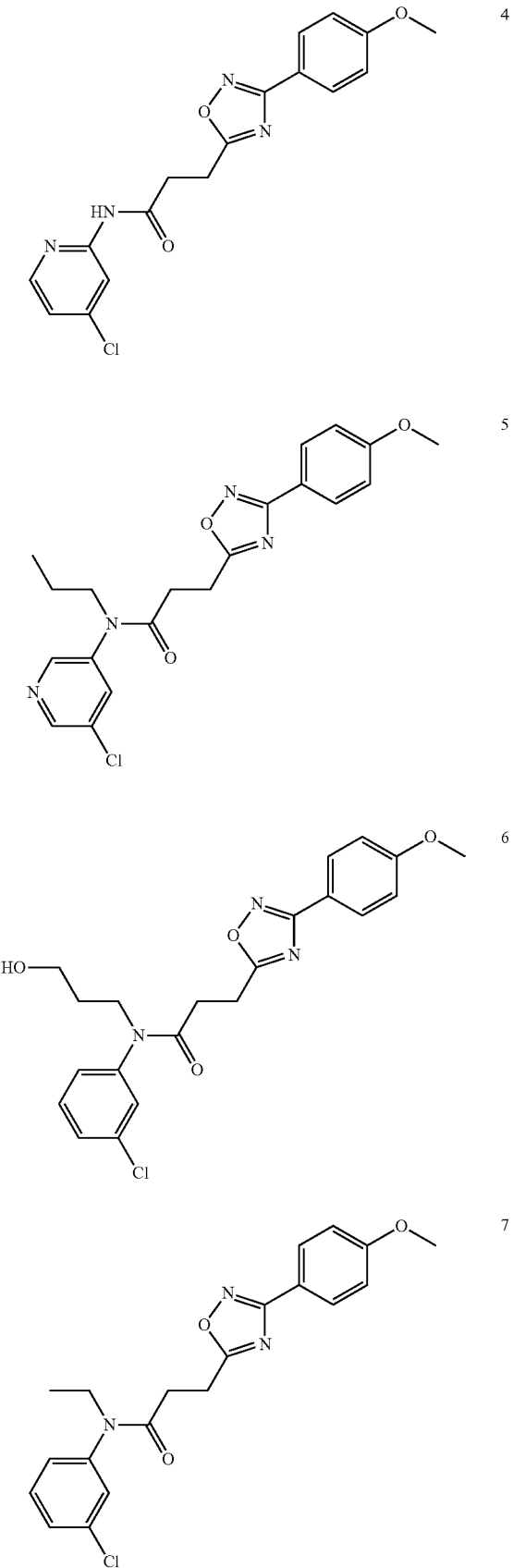

TABLE 1A-continued
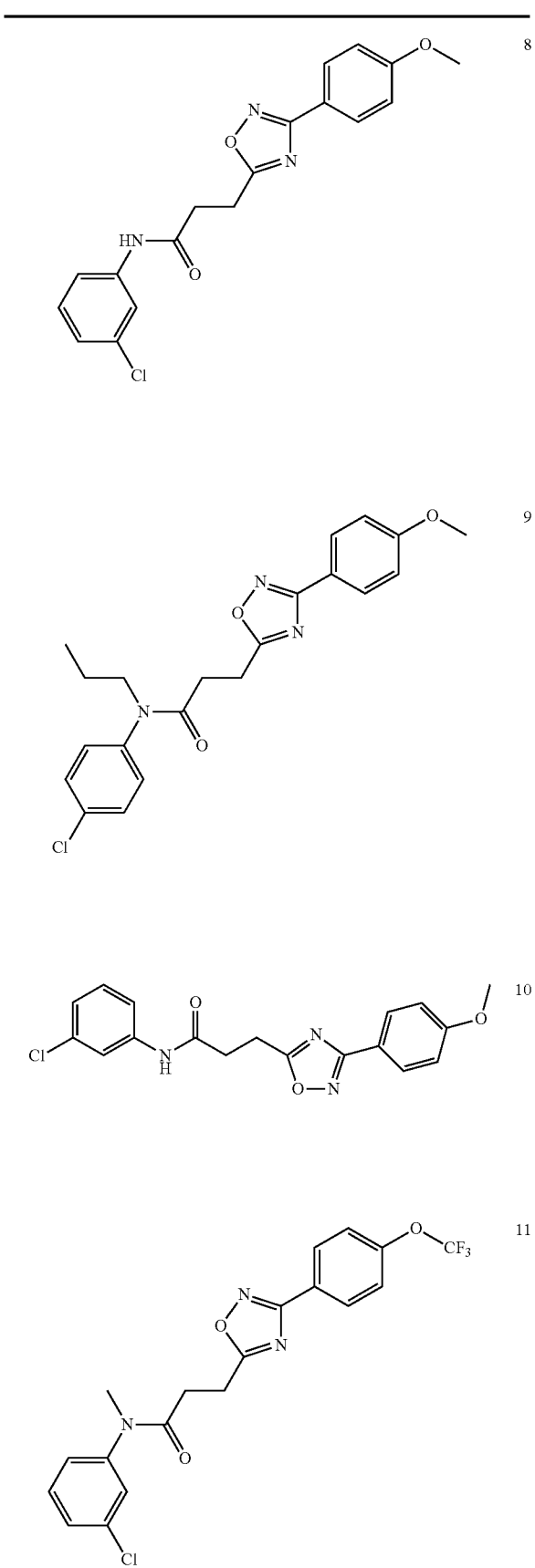
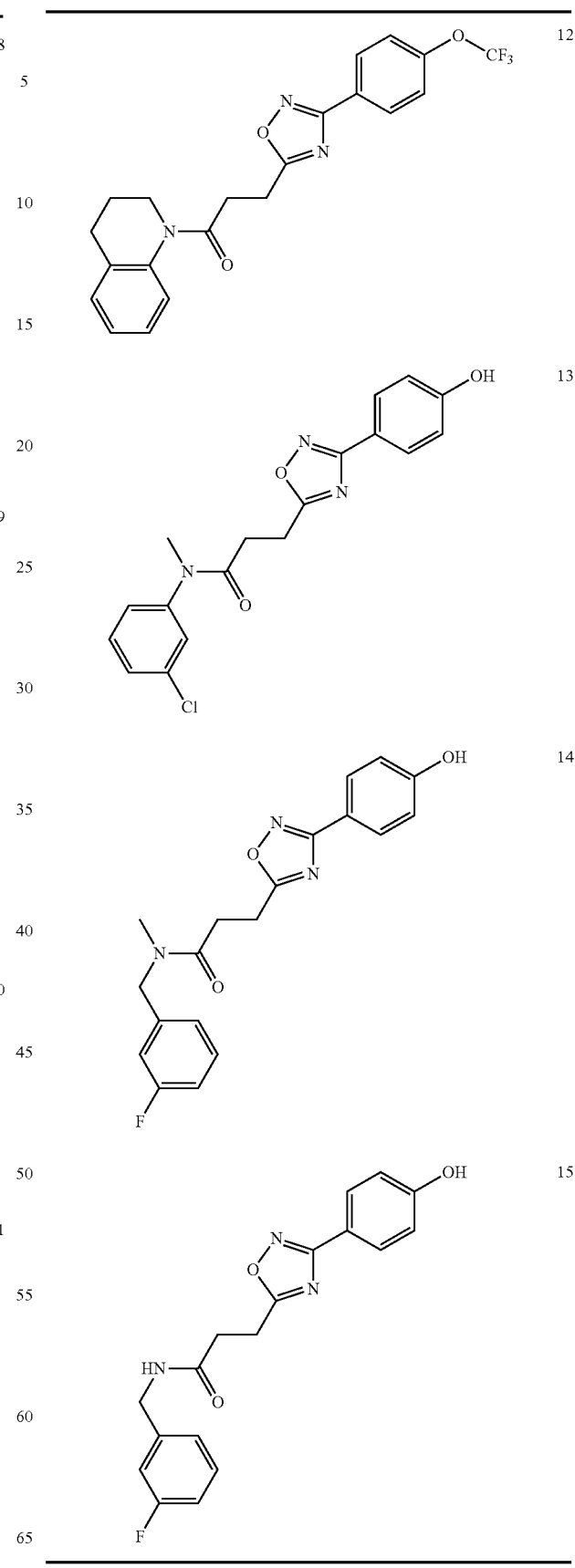

TABLE 1B
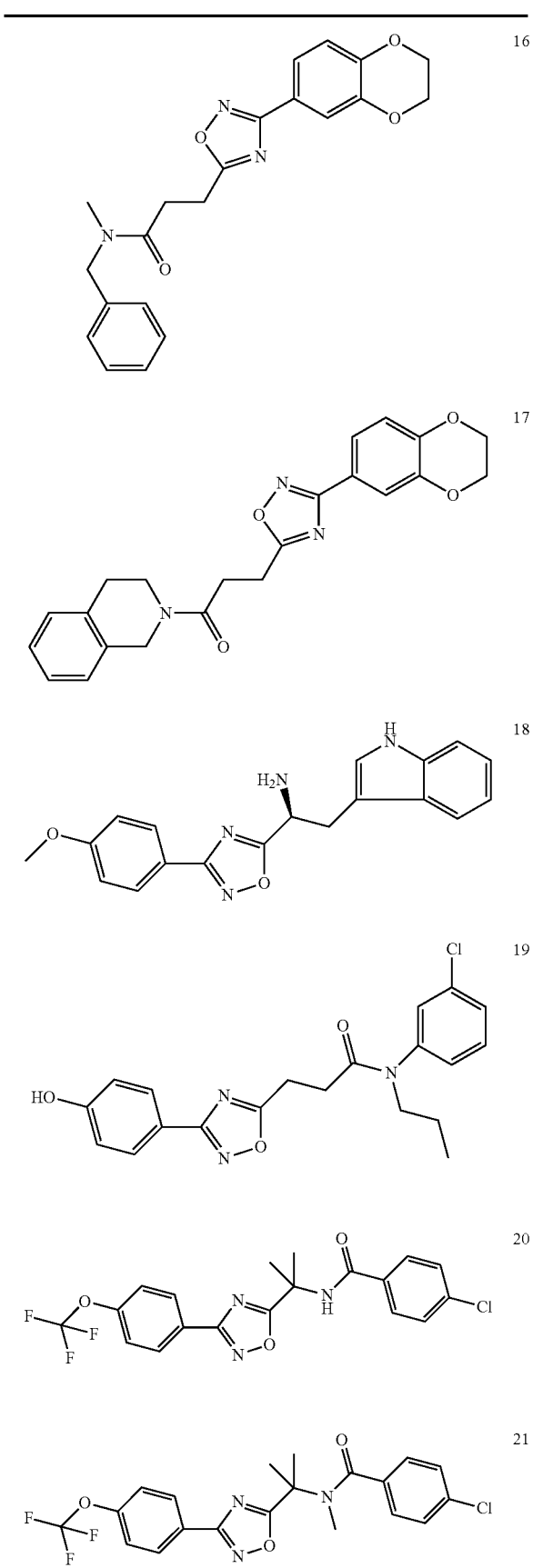

TABLE 1B-continued
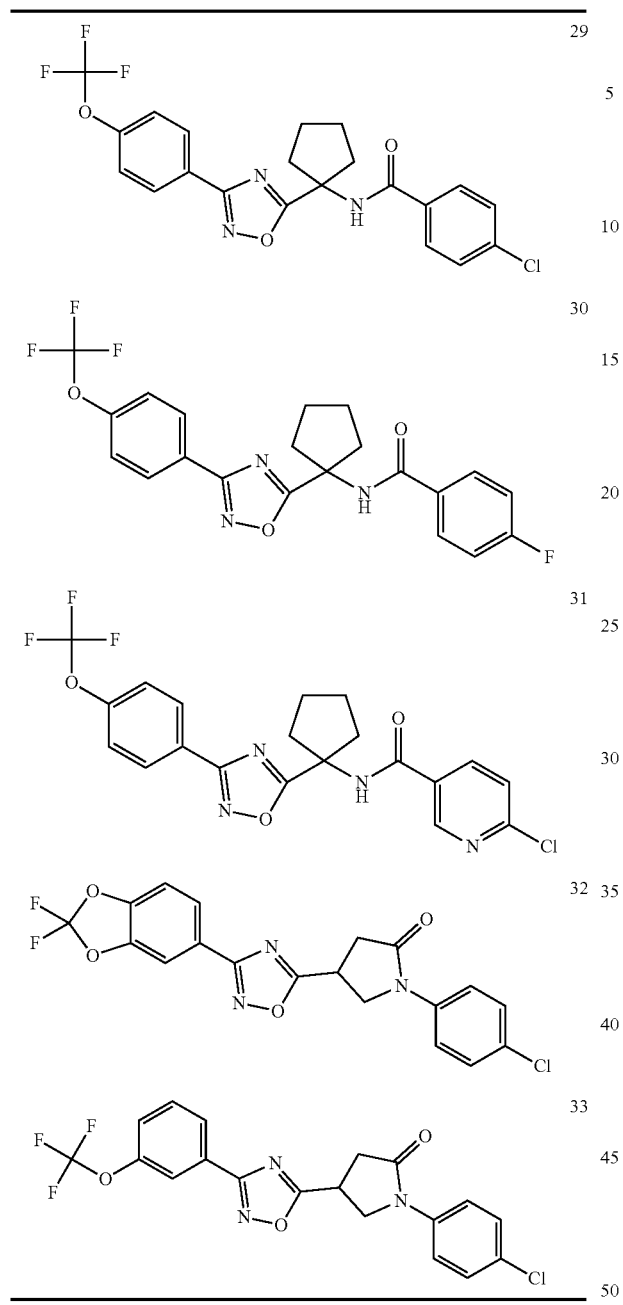
TABLE 1C
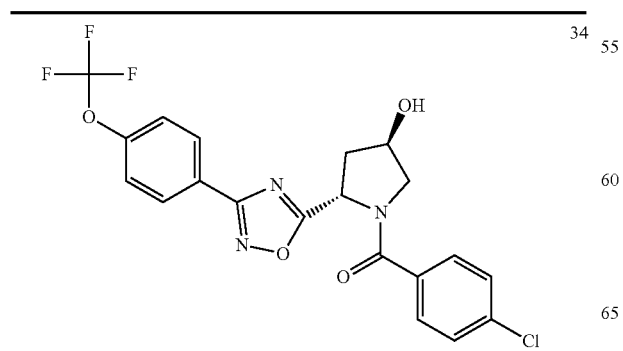
TABLE 1C-continued
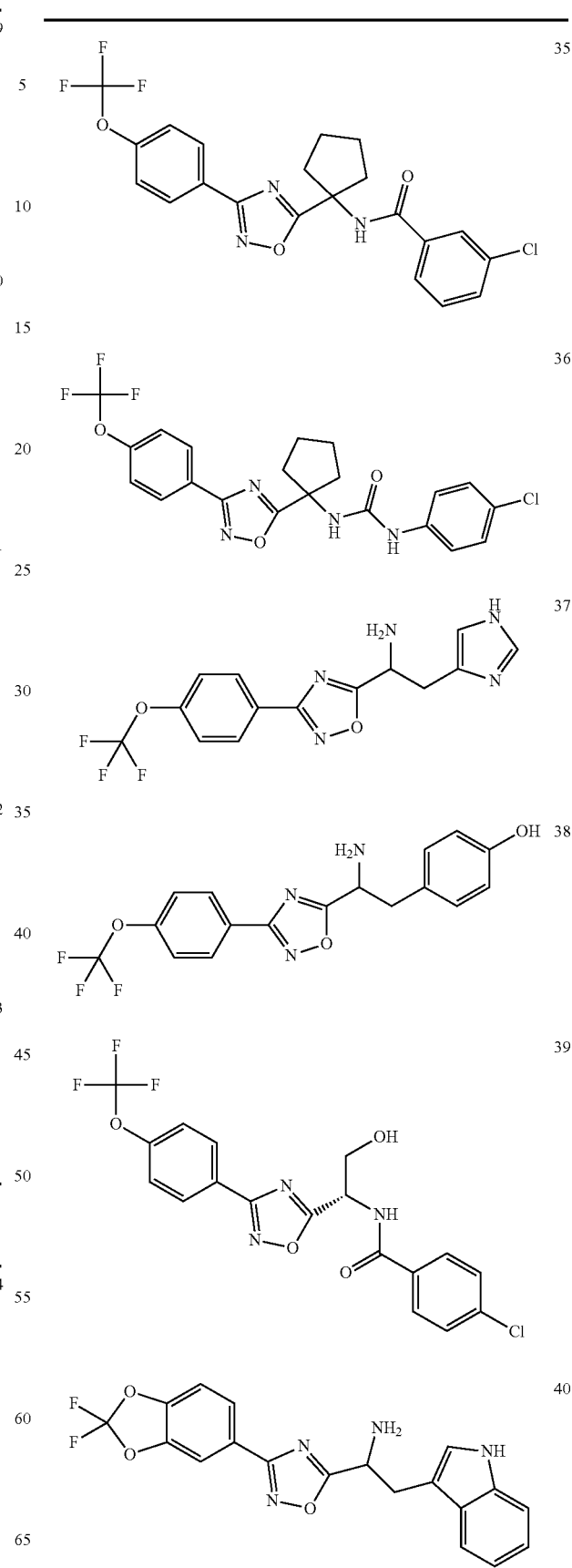

TABLE 1C-continued
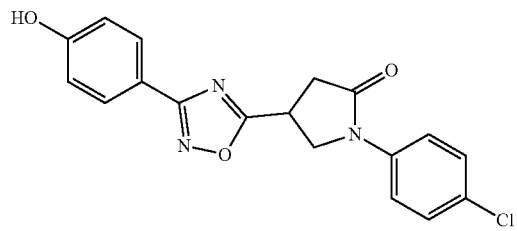 [SMILES: O=C1CC(c2nc(-c3ccc(O)cc3)no2)CN1c1ccc(Cl)cc1]
41
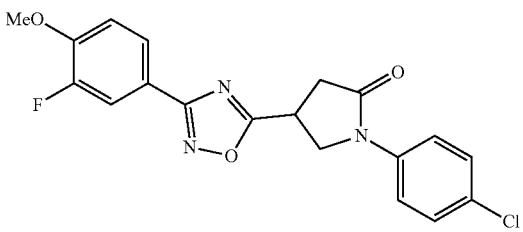 [SMILES: COc1ccc(-c2noc(C3CC(=O)N(c4ccc(Cl)cc4)C3)n2)cc1F]
42
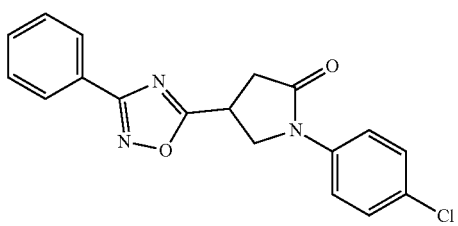 [SMILES: O=C1CC(c2nc(-c3ccccc3)no2)CN1c1ccc(Cl)cc1]
43
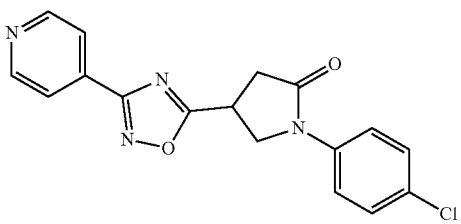 [SMILES: O=C1CC(c2nc(-c3ccncc3)no2)CN1c1ccc(Cl)cc1]
44
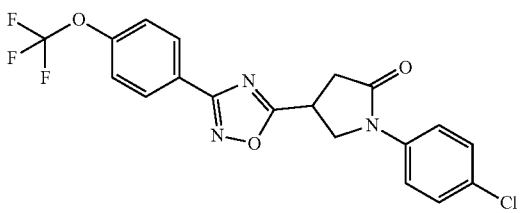 [SMILES: O=C1CC(c2nc(-c3ccc(OC(F)(F)F)cc3)no2)CN1c1ccc(Cl)cc1]
45
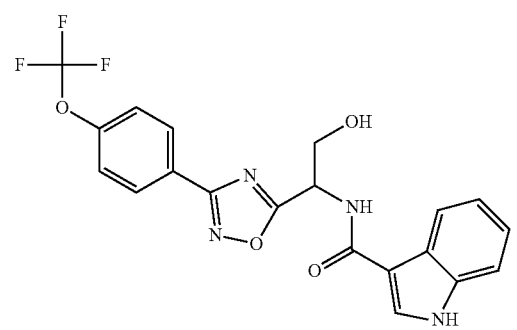 [SMILES: O=C(NC(CO)c1nc(-c2ccc(OC(F)(F)F)cc2)no1)c1c[nH]c2ccccc12]
46
TABLE 1C-continued
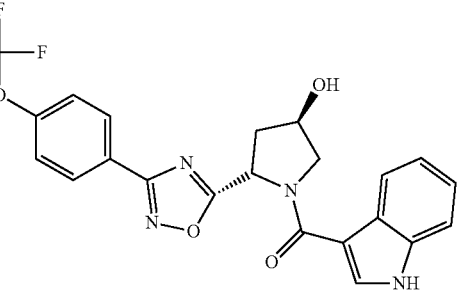
47
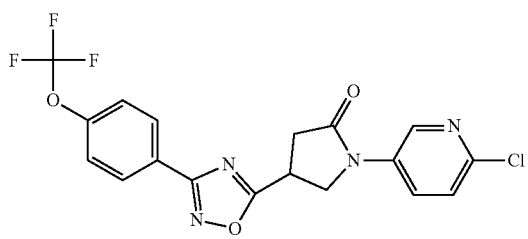 [SMILES: O=C1CC(c2nc(-c3ccc(OC(F)(F)F)cc3)no2)CN1c1ccc(Cl)nc1]
48
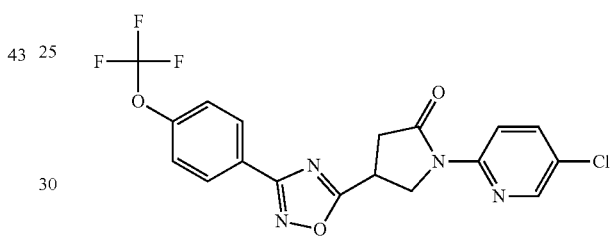
49
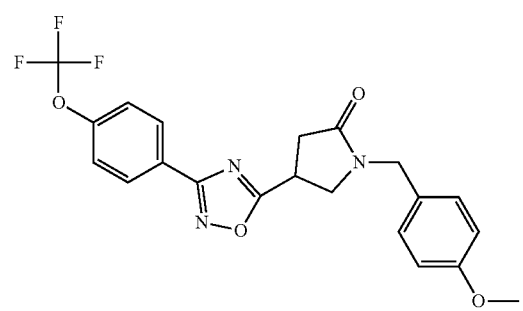 [SMILES: COc1ccc(CN2CC(c3nc(-c4ccc(OC(F)(F)F)cc4)no3)CC2=O)cc1]
50
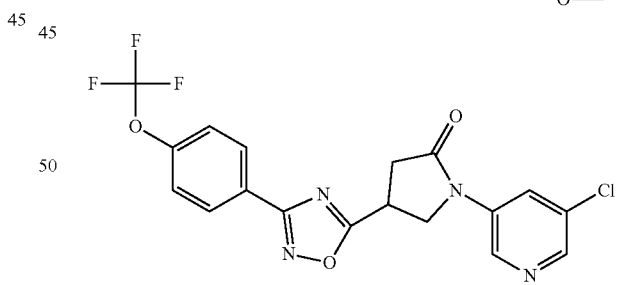
51
TABLE 1D
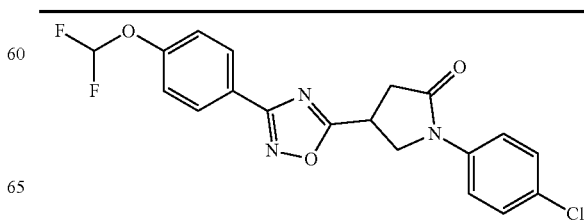
52

TABLE 1D-continued
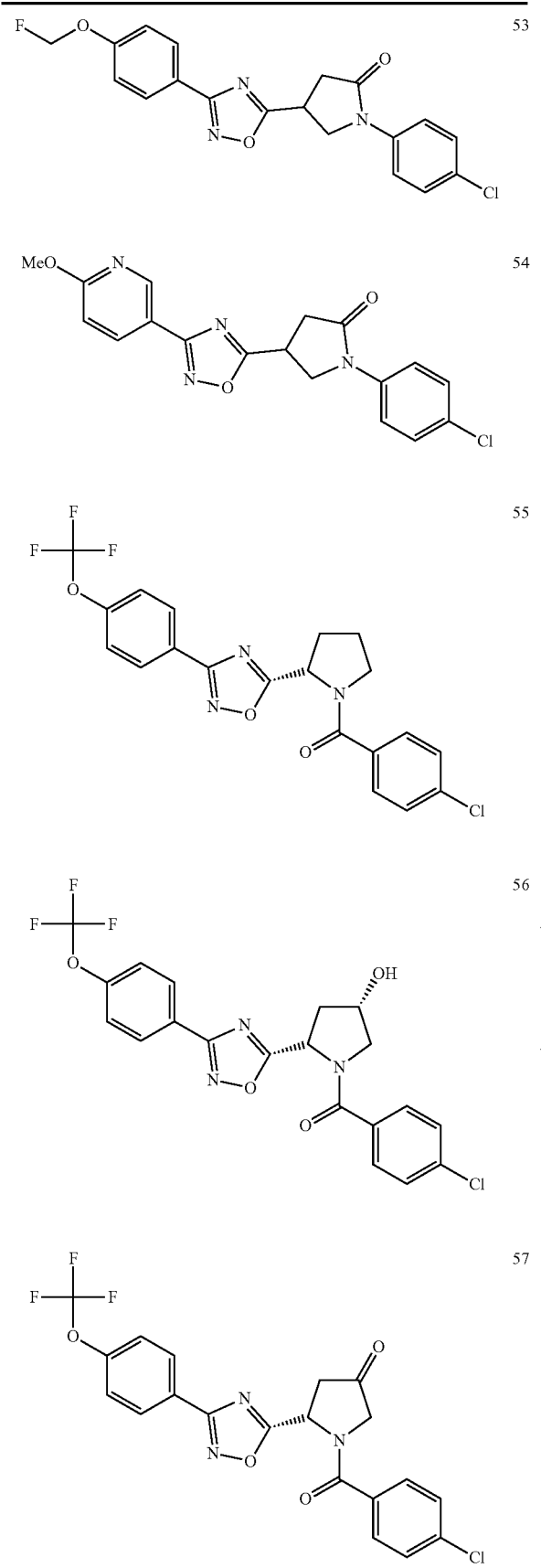
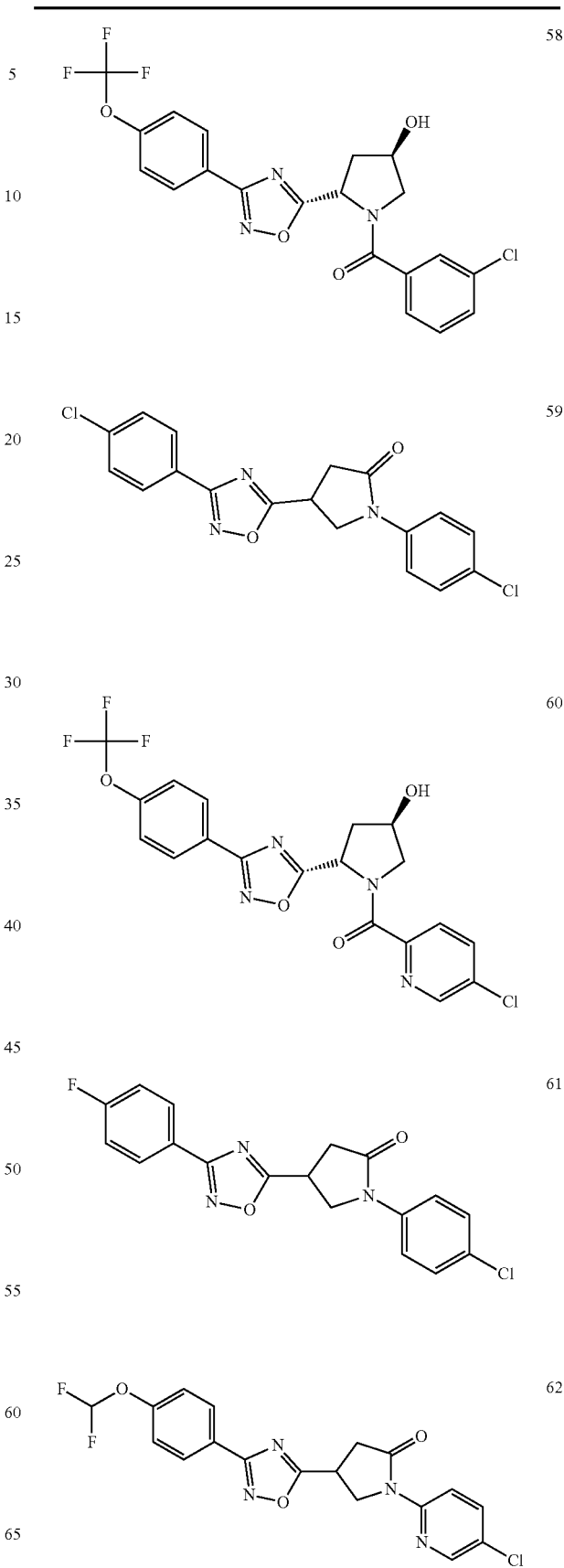

TABLE 1D-continued
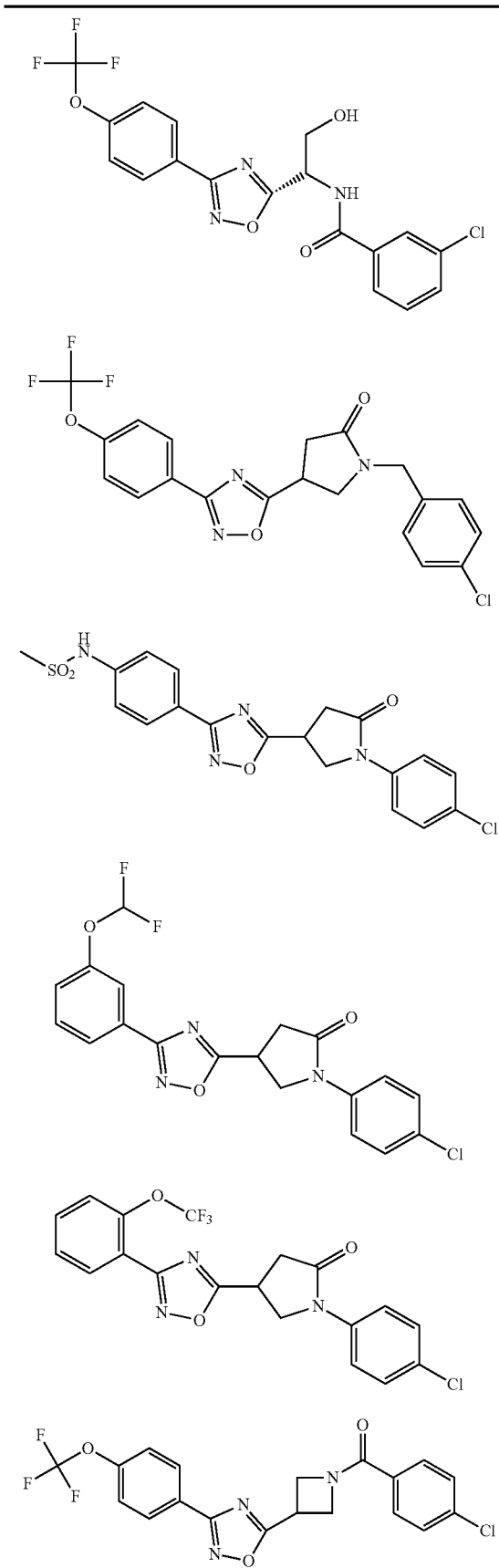
TABLE 1E

TABLE 1E-continued
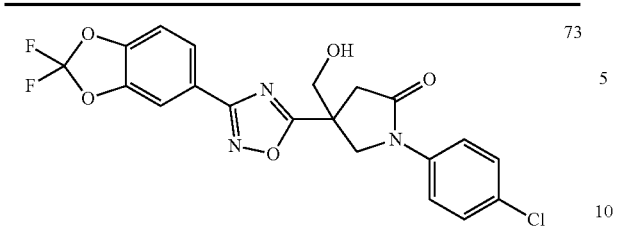 73
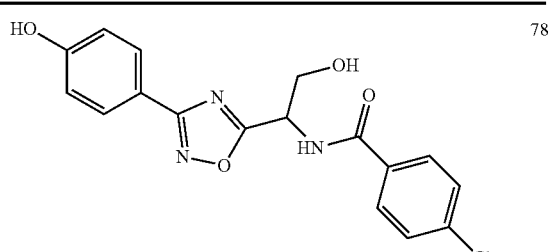 78
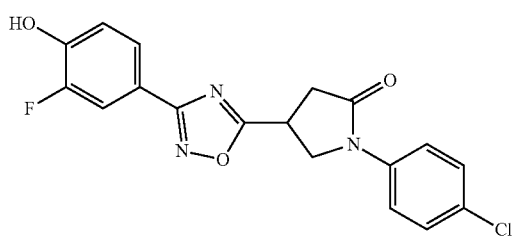 [SMILES: O=C1CC(c2nc(-c3ccc(O)c(F)c3)no2)CN1c1ccc(Cl)cc1] 74
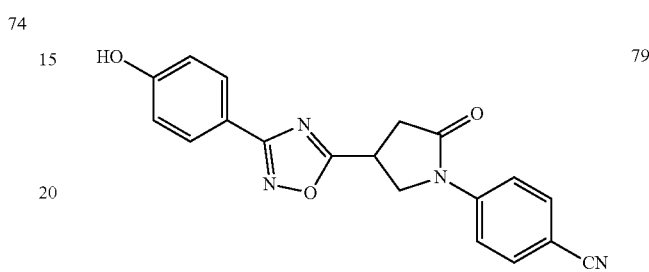 79
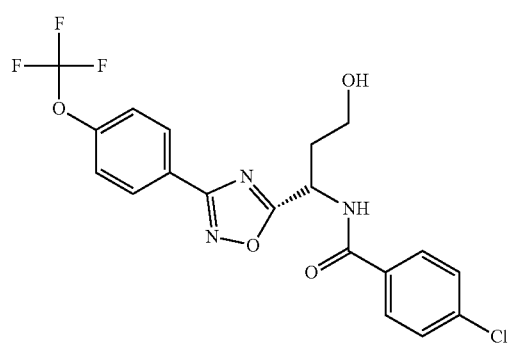 75
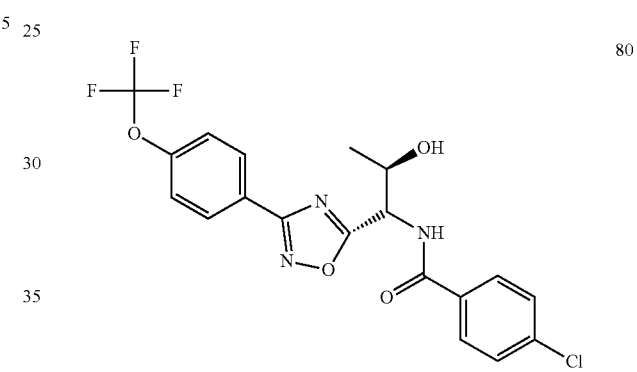 80
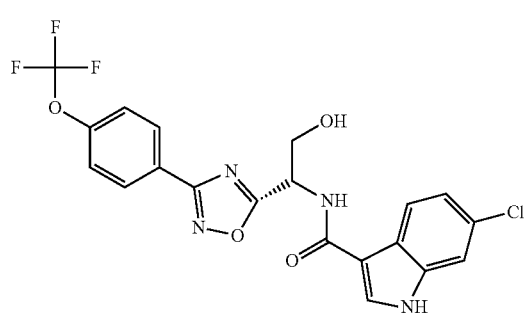 76
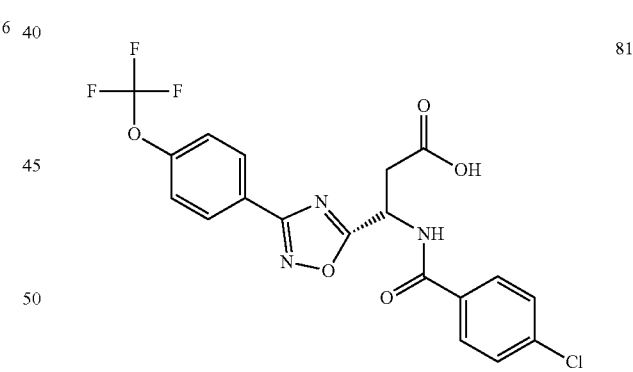 81
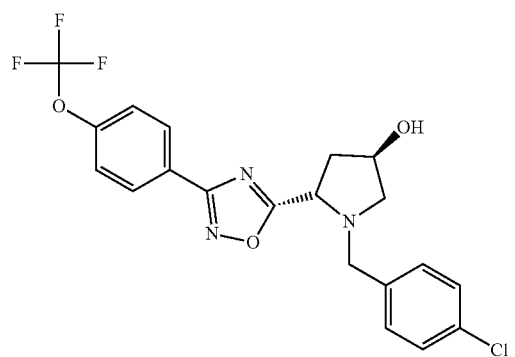 77
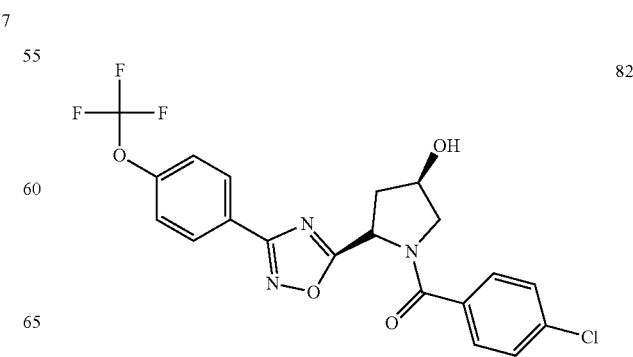 82

TABLE 1E-continued
83
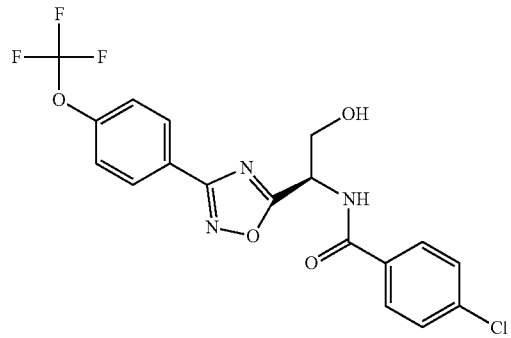 [SMILES: O=C(N[C@H](CO)c1nc(-c2ccc(OC(F)(F)F)cc2)no1)c1ccc(Cl)cc1]
84
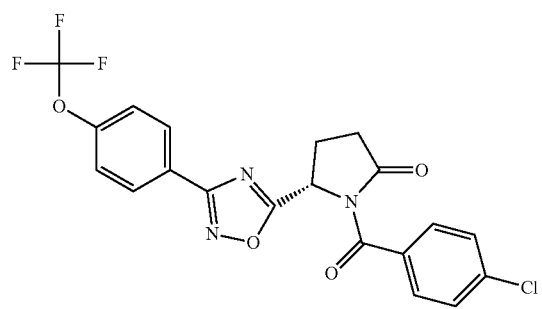 [SMILES: O=C1CC[C@@H](c2nc(-c3ccc(OC(F)(F)F)cc3)no2)N1C(=O)c1ccc(Cl)cc1]
TABLE 1F
85
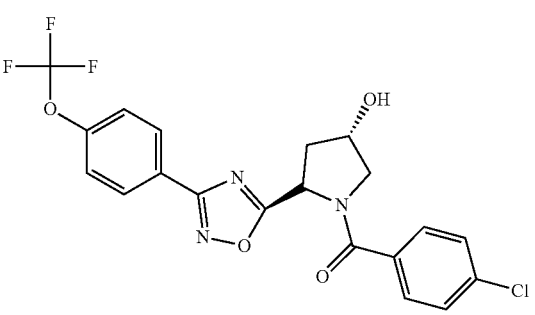
86
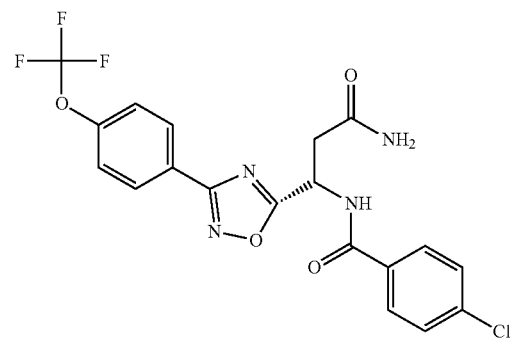
TABLE 1F-continued
87
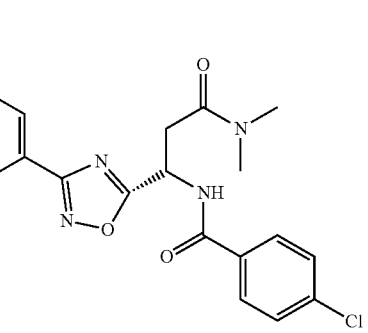
88
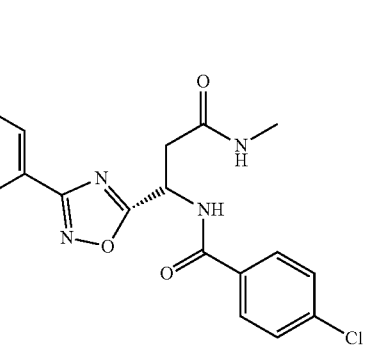
89
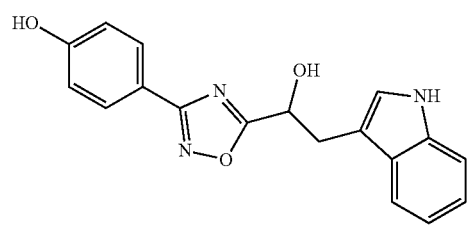 [SMILES: Oc1ccc(-c2noc(C(O)Cc3c[nH]c4ccccc34)n2)cc1]
90
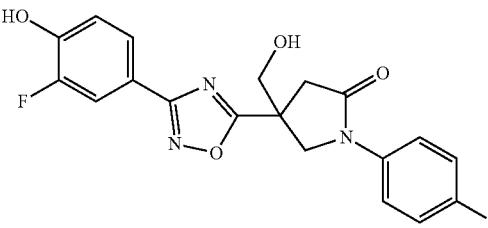
91
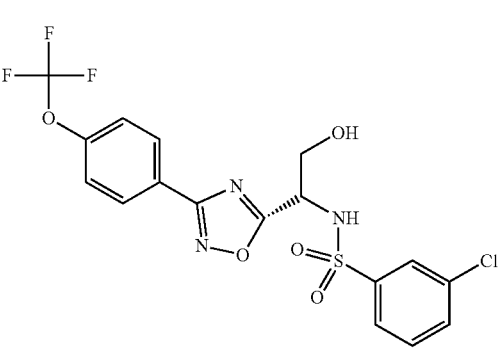

TABLE 1F-continued
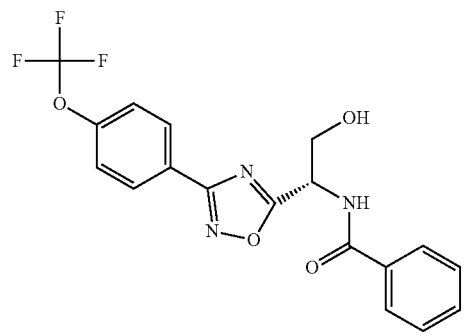 [SMILES: O=C(N[C@@H](CO)c1nc(-c2ccc(OC(F)(F)F)cc2)no1)c1ccccc1]
92
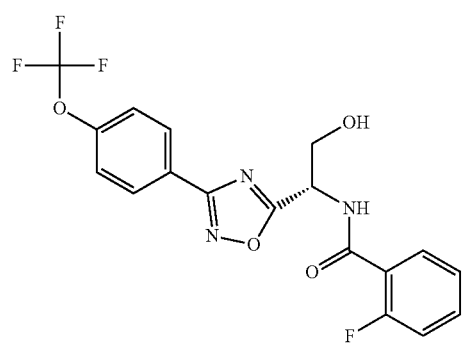 [SMILES: O=C(N[C@@H](CO)c1nc(-c2ccc(OC(F)(F)F)cc2)no1)c1ccccc1F]
93
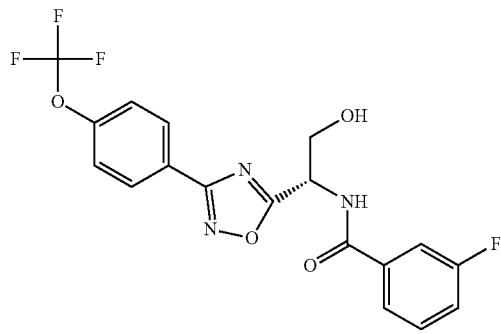 [SMILES: O=C(N[C@@H](CO)c1nc(-c2ccc(OC(F)(F)F)cc2)no1)c1cccc(F)c1]
94
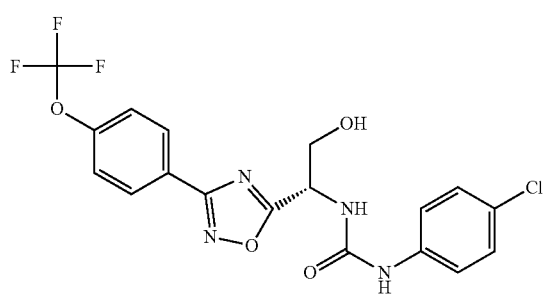 [SMILES: O=C(Nc1ccc(Cl)cc1)N[C@@H](CO)c1nc(-c2ccc(OC(F)(F)F)cc2)no1]
95
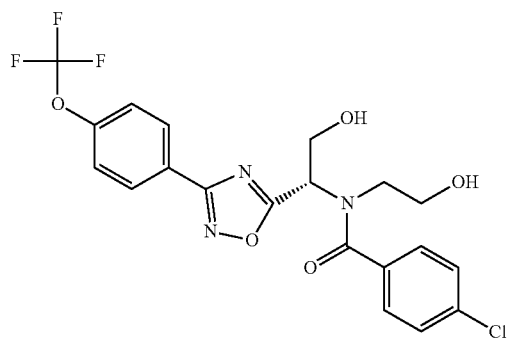 [SMILES: O=C(c1ccc(Cl)cc1)N(CCO)[C@@H](CO)c1nc(-c2ccc(OC(F)(F)F)cc2)no1]
96
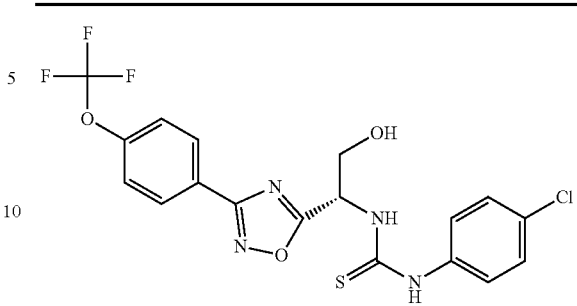
97
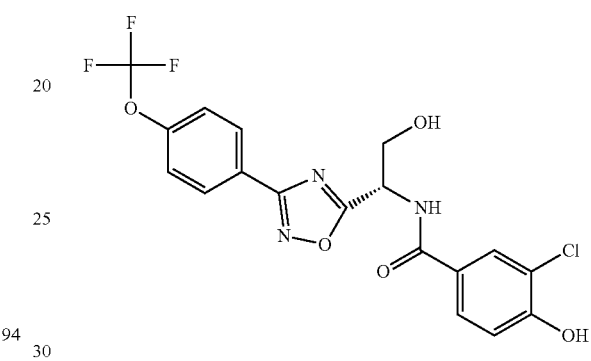
98
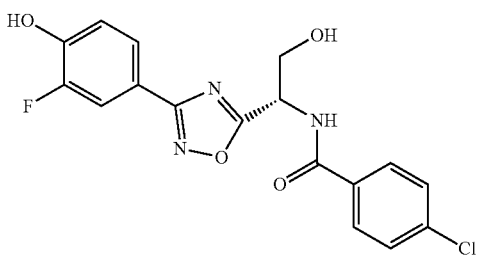 [SMILES: O=C(N[C@@H](CO)c1nc(-c2ccc(O)c(F)c2)no1)c1ccc(Cl)cc1]
99
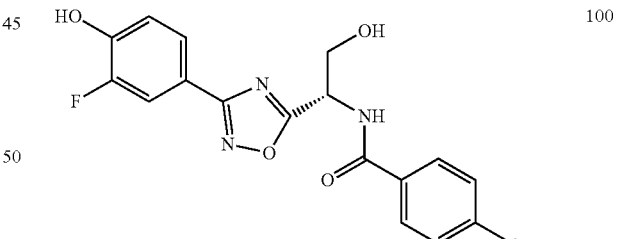
100
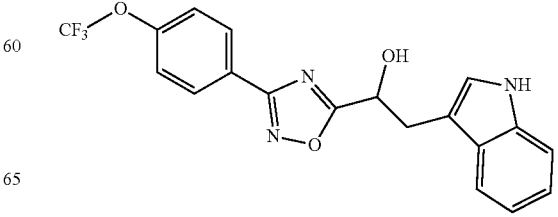
101

TABLE 1F-continued
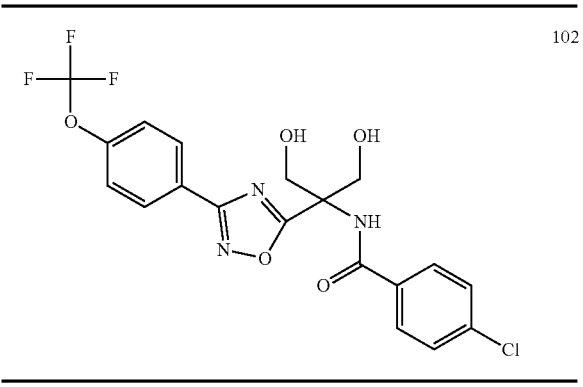
102
TABLE 1G
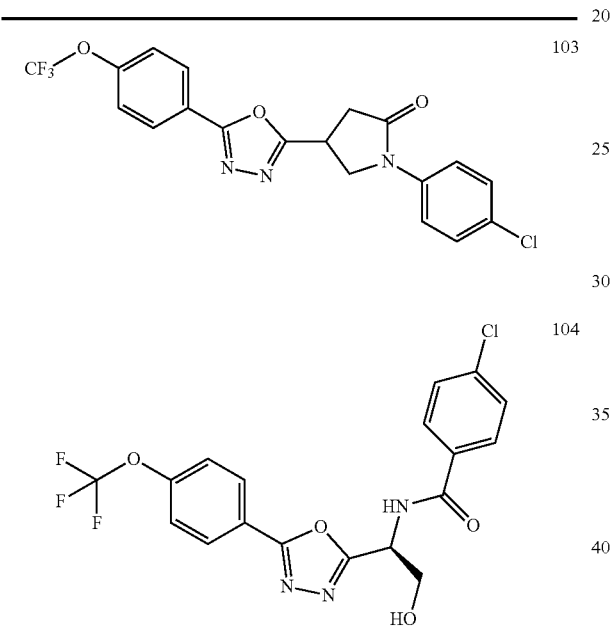
103
104
105
106
TABLE 1G-continued
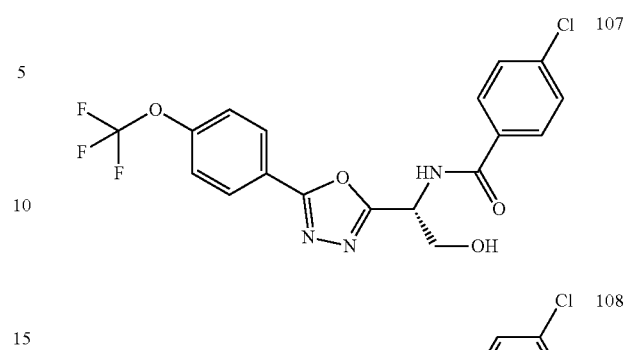
107
108
109
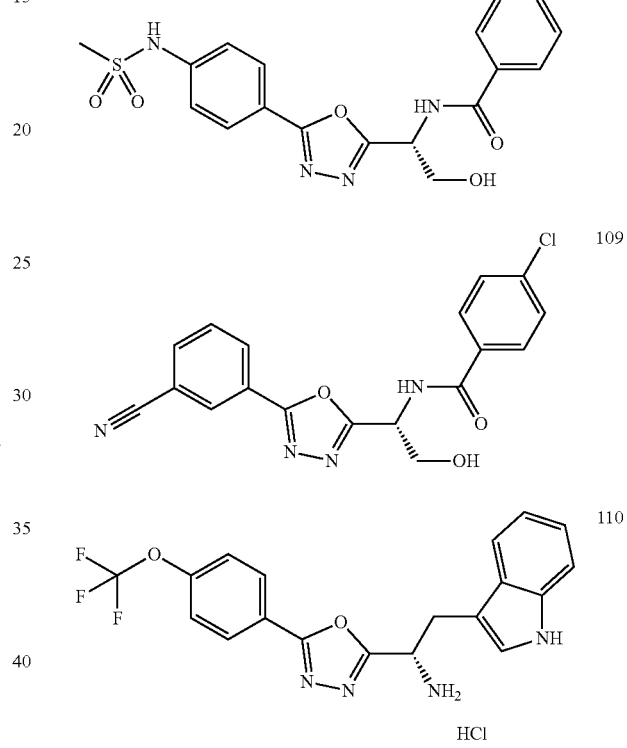
110
111
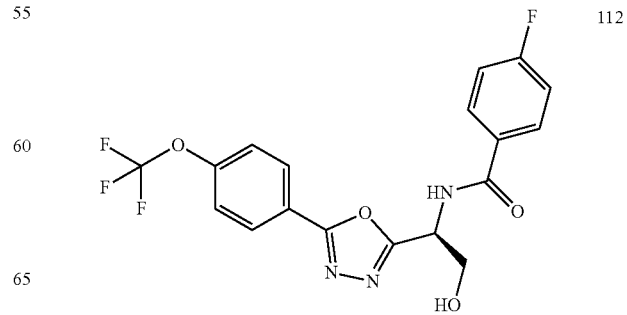
112

TABLE 1G-continued
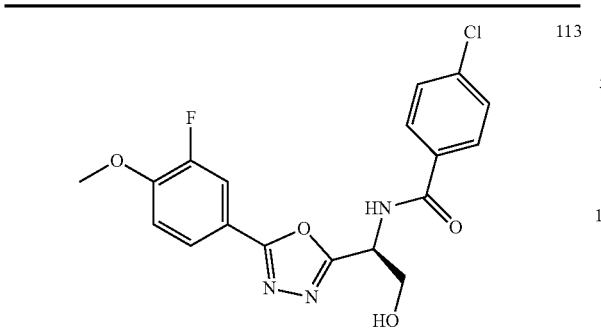
113
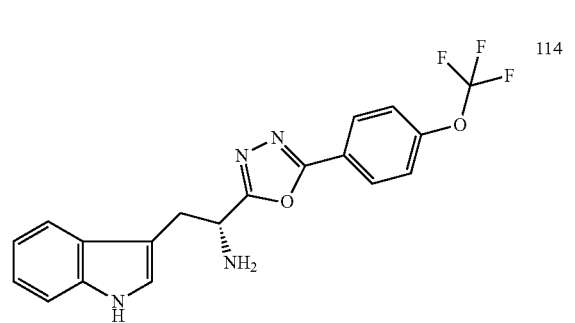
114
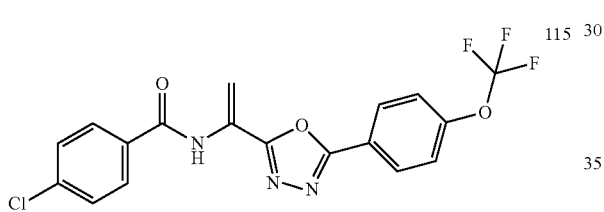
115
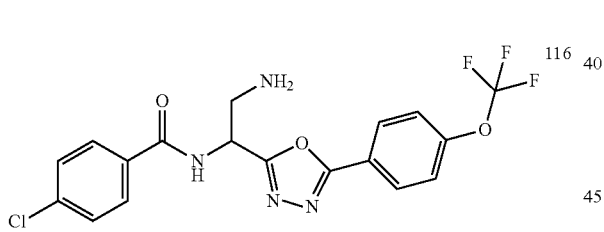
116
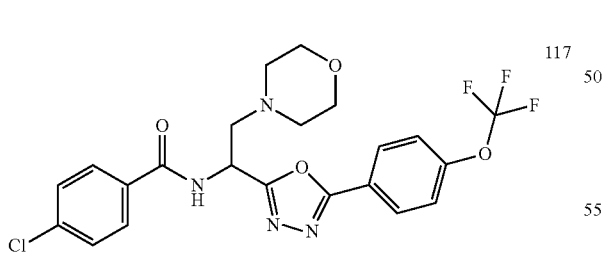
117
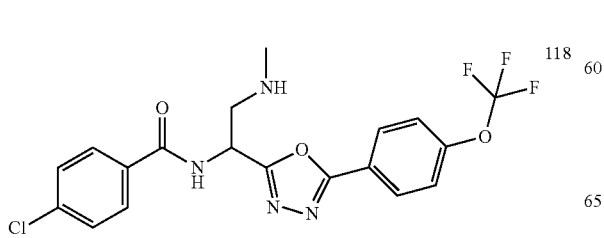
118
TABLE 1G-continued
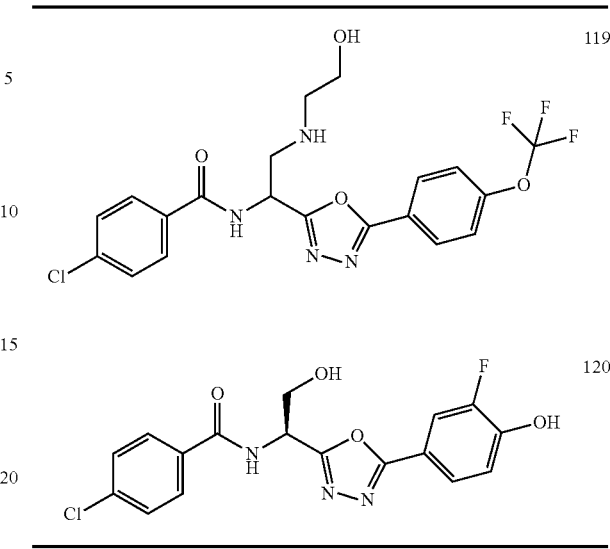
119
120
TABLE 1H
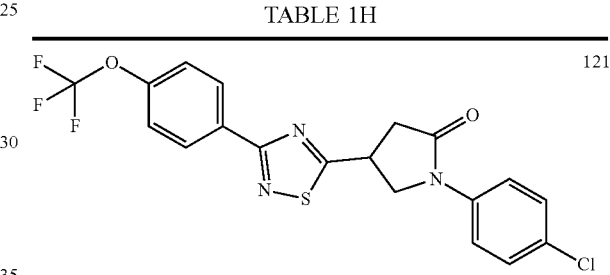
121
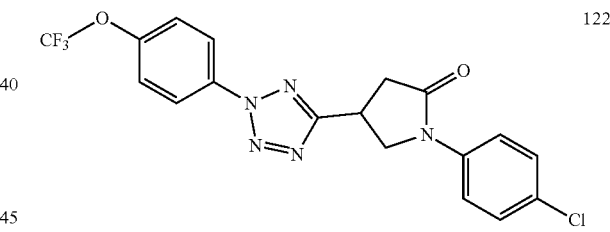
122
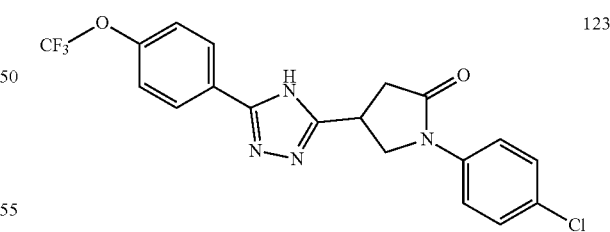
123
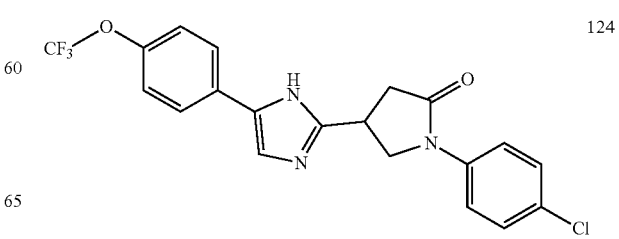
124

TABLE 1H-continued
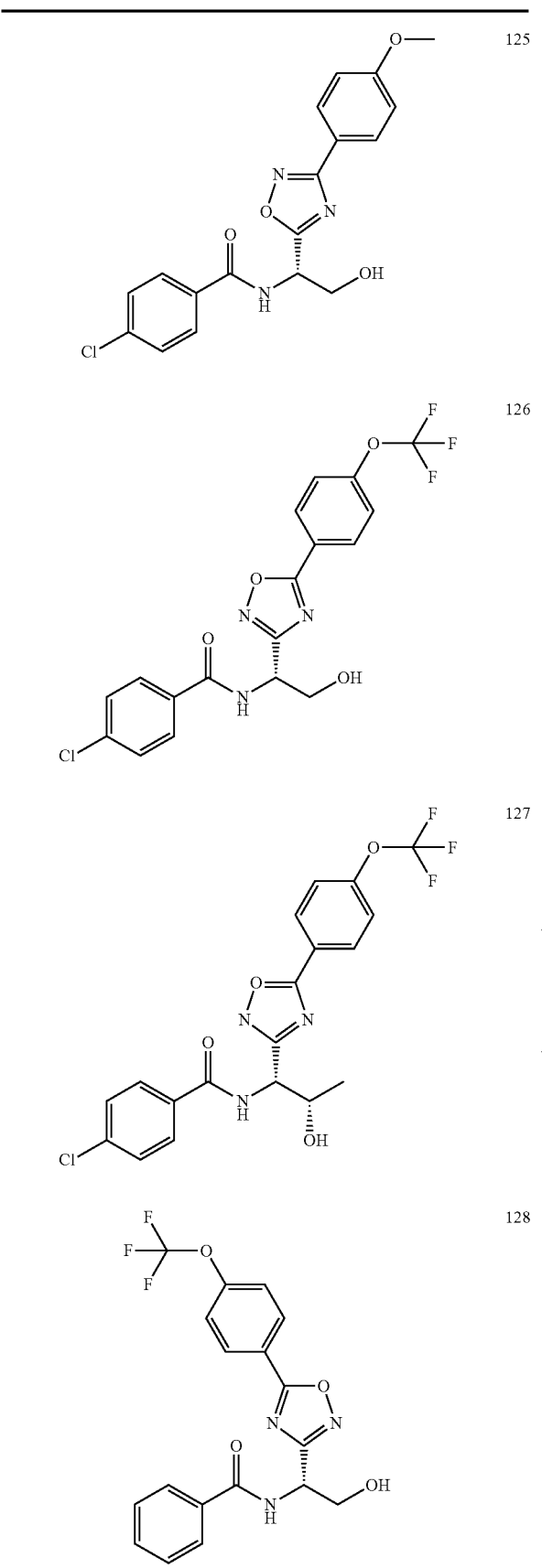
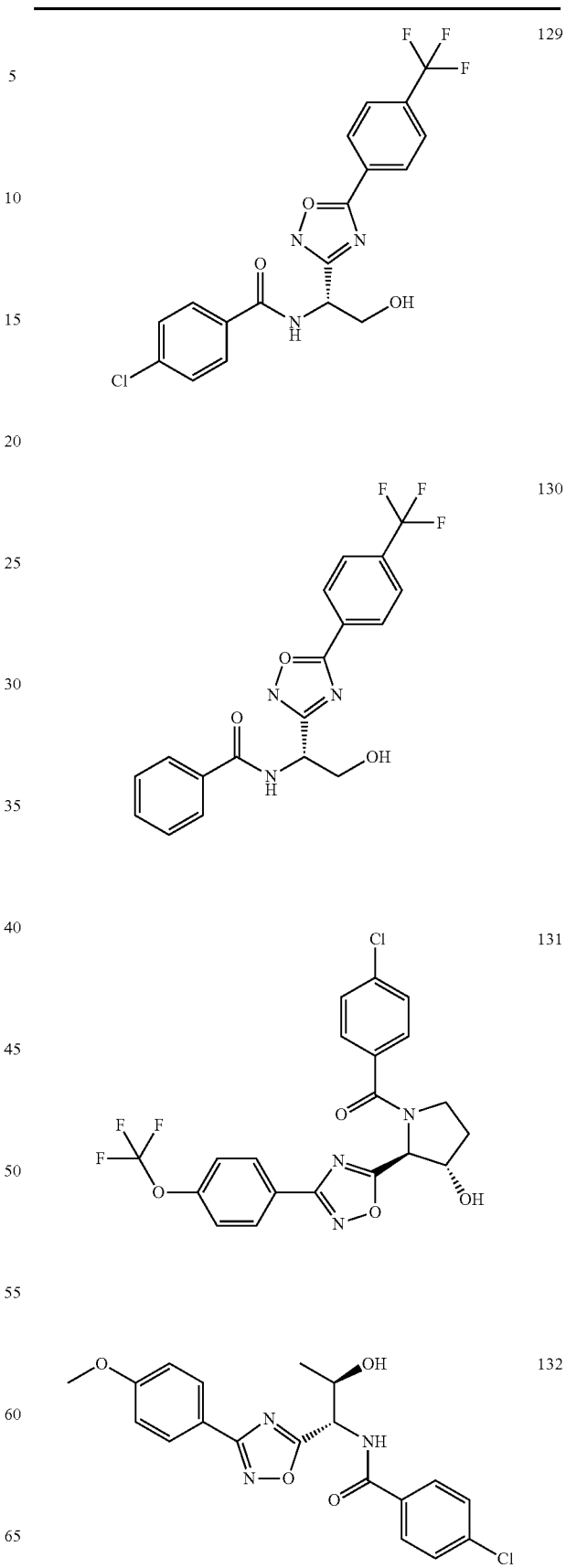

TABLE 1H-continued
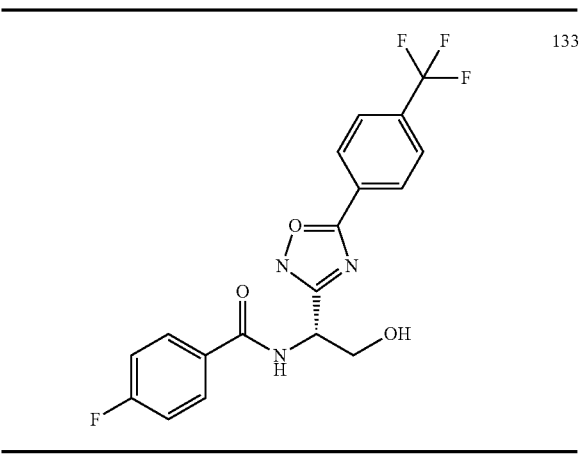
133
TABLE 1I
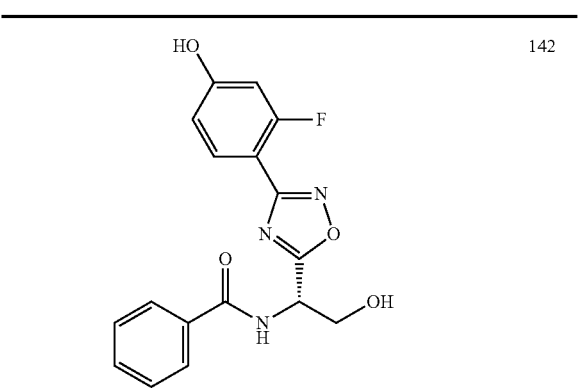
142
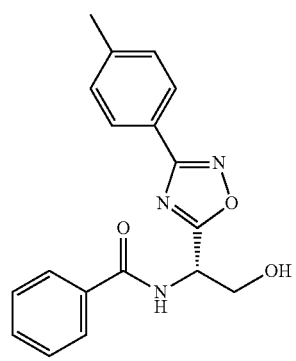 [SMILES: Cc1ccc(-c2noc([C@H](CO)NC(=O)c3ccccc3)n2)cc1]
143
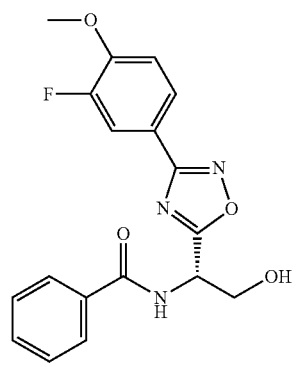 [SMILES: COc1ccc(-c2noc([C@H](CO)NC(=O)c3ccccc3)n2)cc1F]
144
TABLE 1I-continued
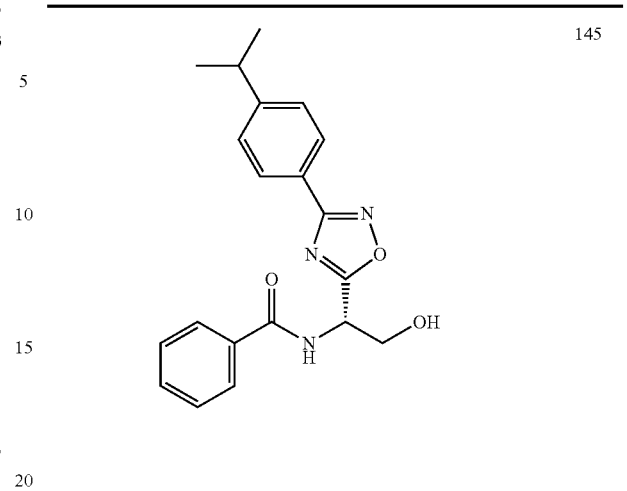
145
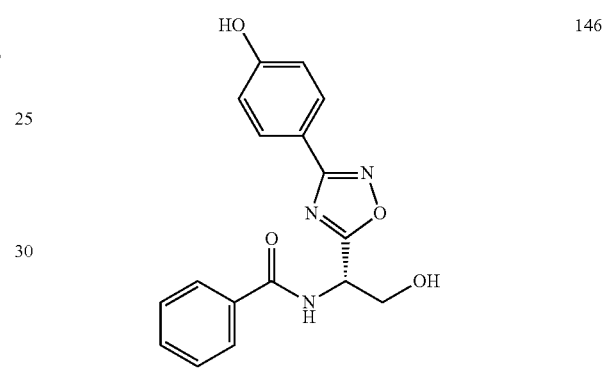
146
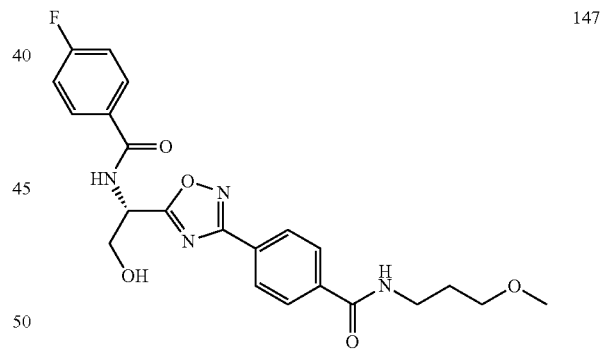
147
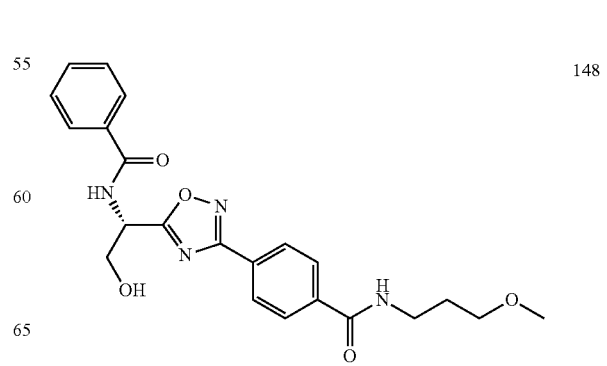
148

TABLE 1I-continued

149

150

TABLE 1J

151

152

TABLE 1J-continued

153

154

155

156

TABLE 1J-continued
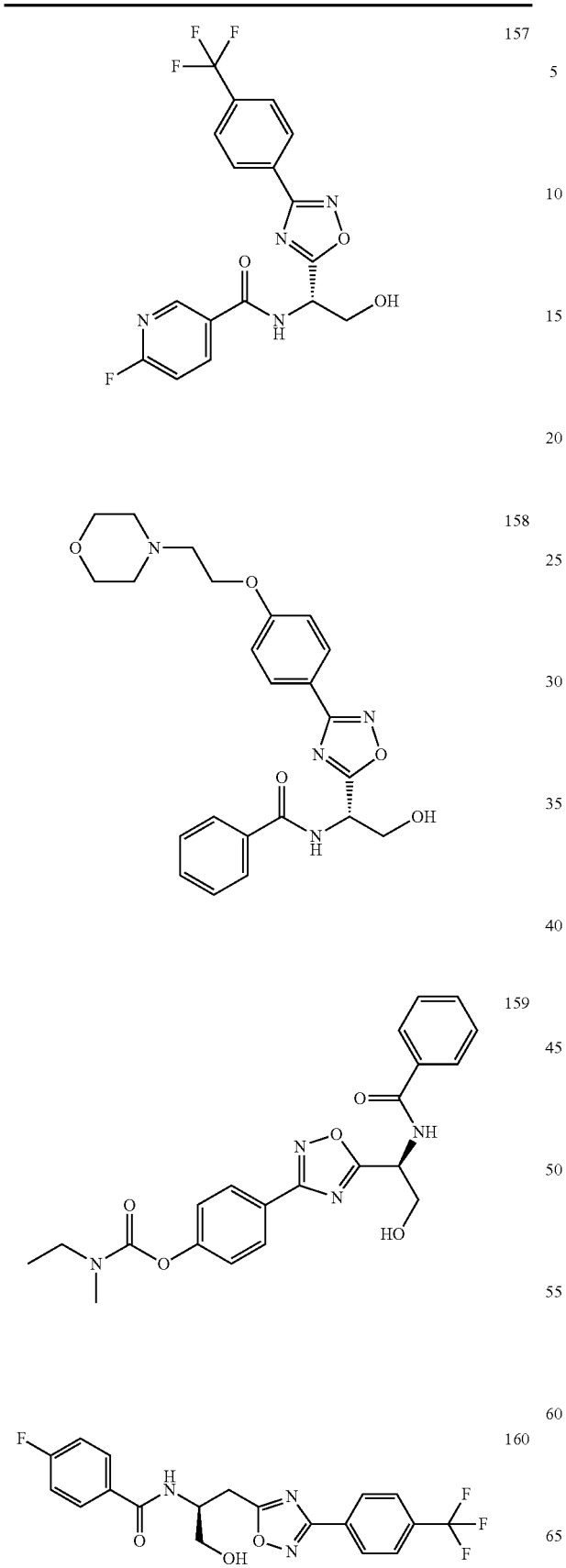
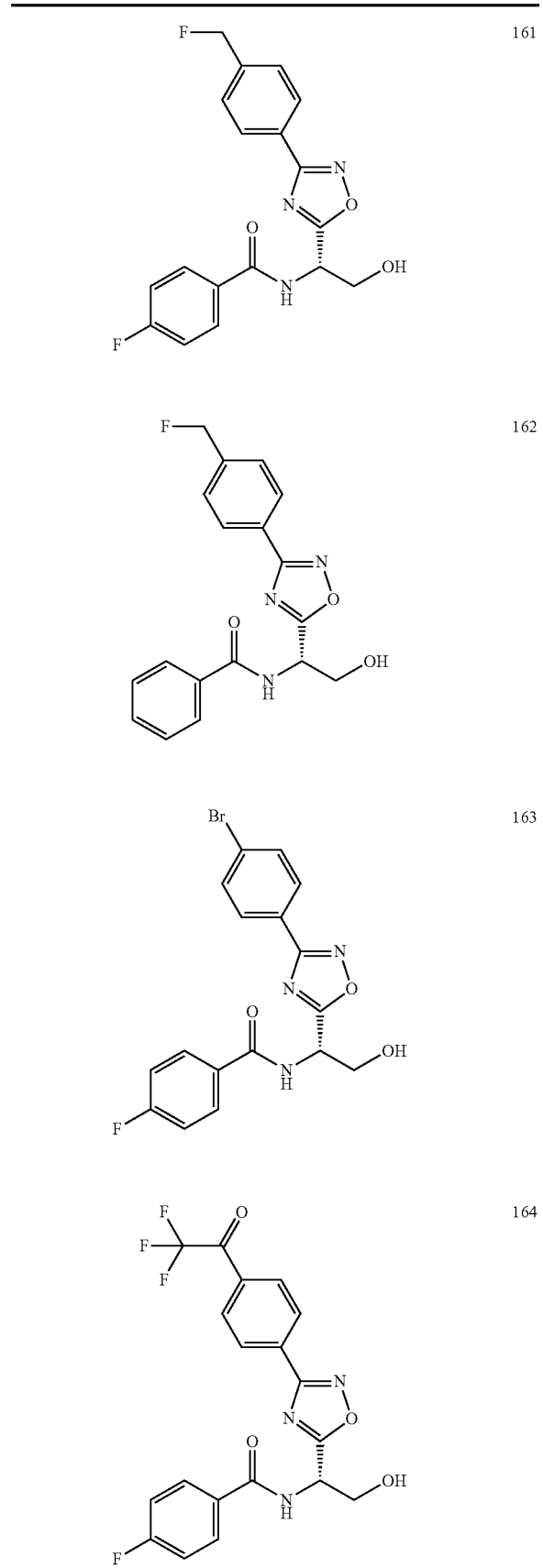

TABLE 1J-continued
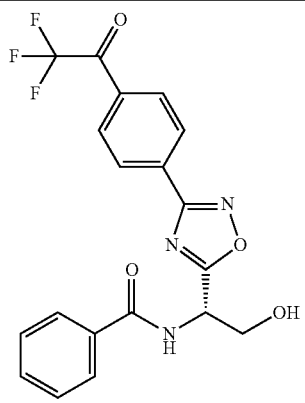
165
TABLE 1K
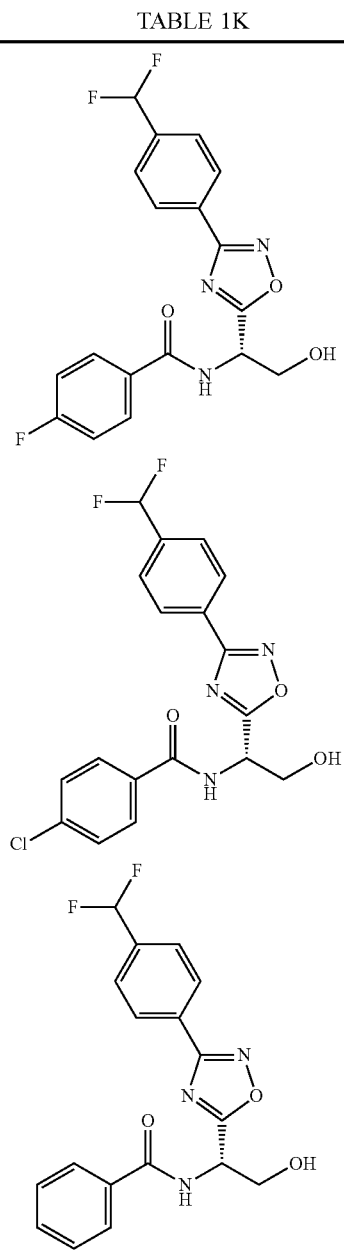
166
167
168
TABLE 1K-continued
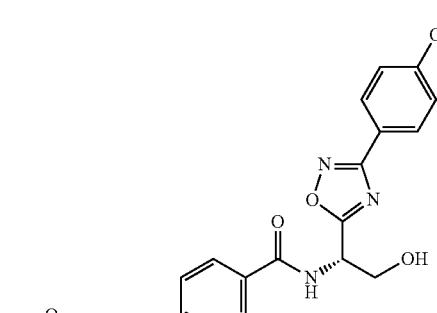
169
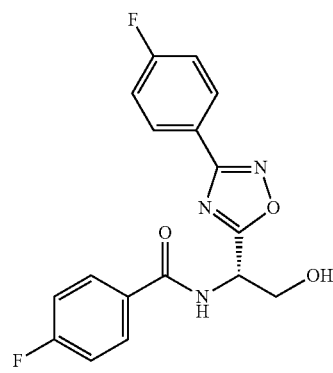 [SMILES: O=C(N[C@@H](CO)c1nc(-c2ccc(F)cc2)no1)c1ccc(F)cc1]
170
171
172

TABLE 1K-continued
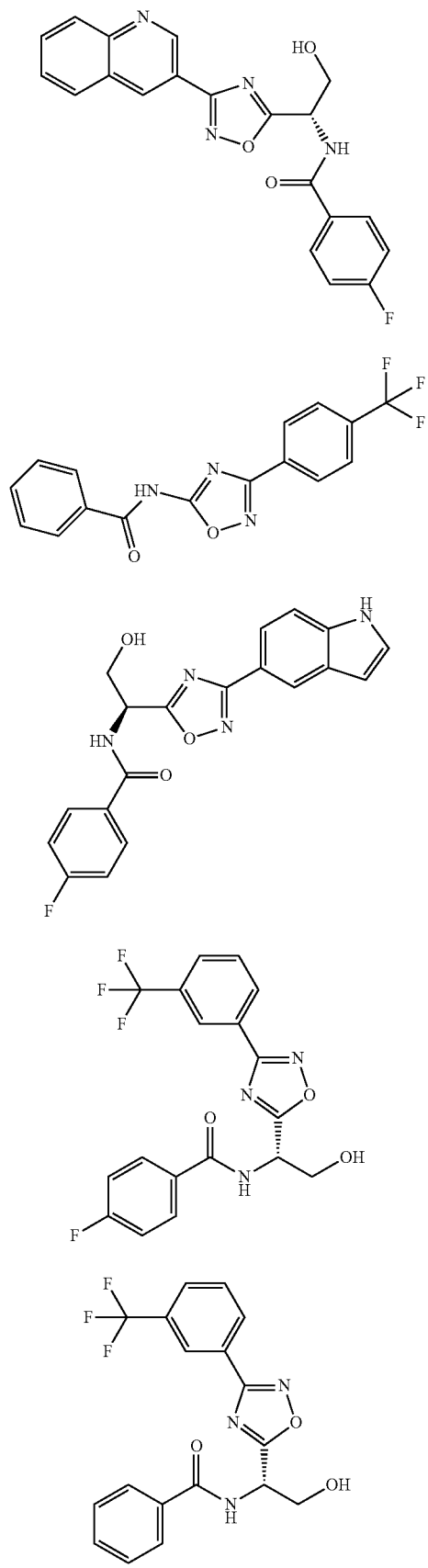
TABLE 1K-continued
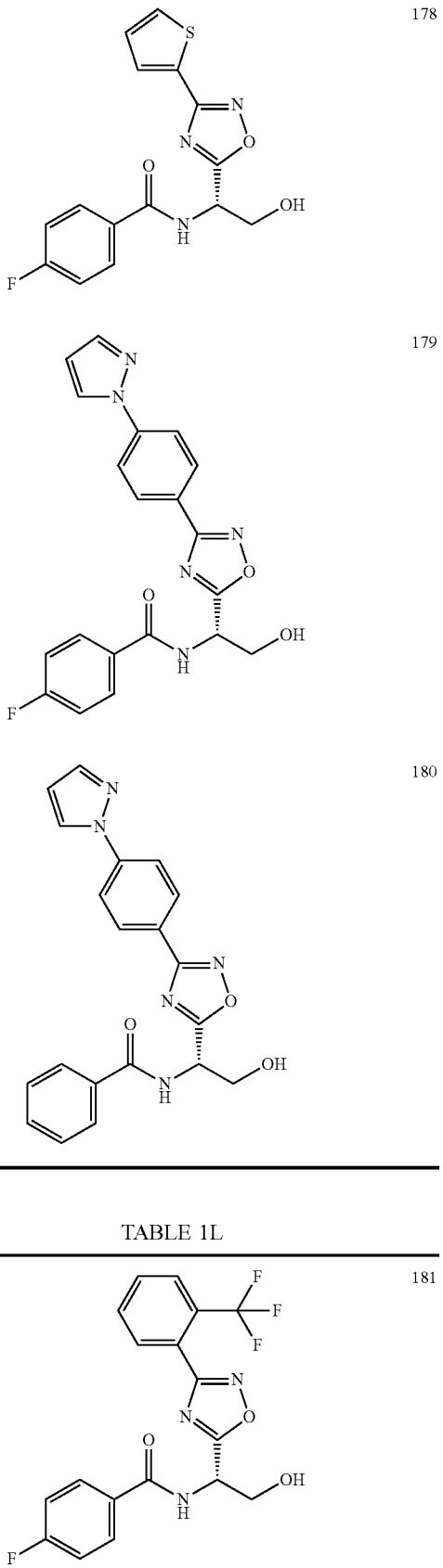
TABLE 1L
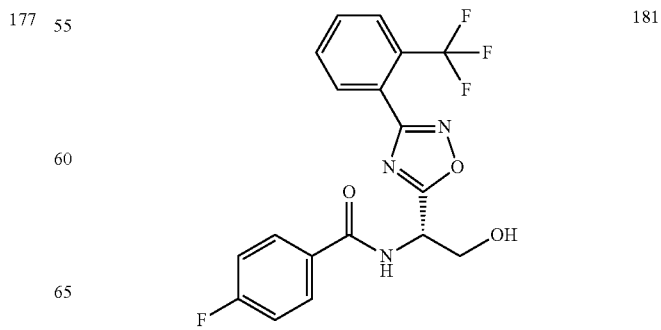

TABLE 1L-continued
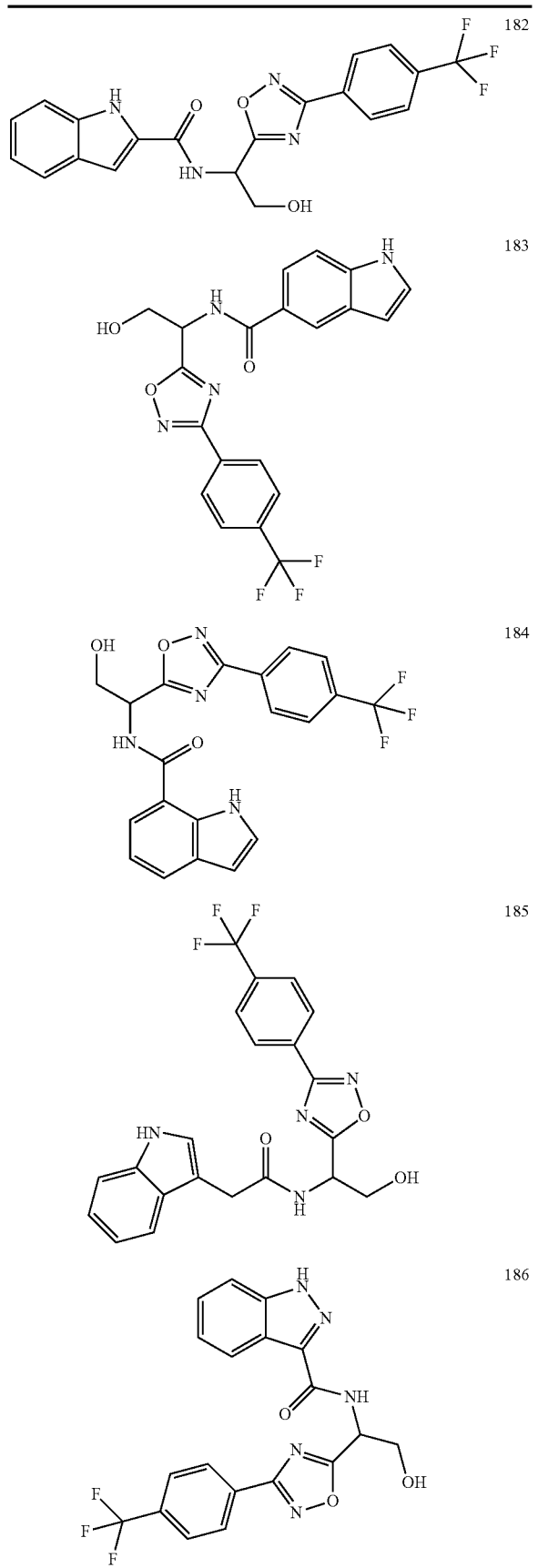
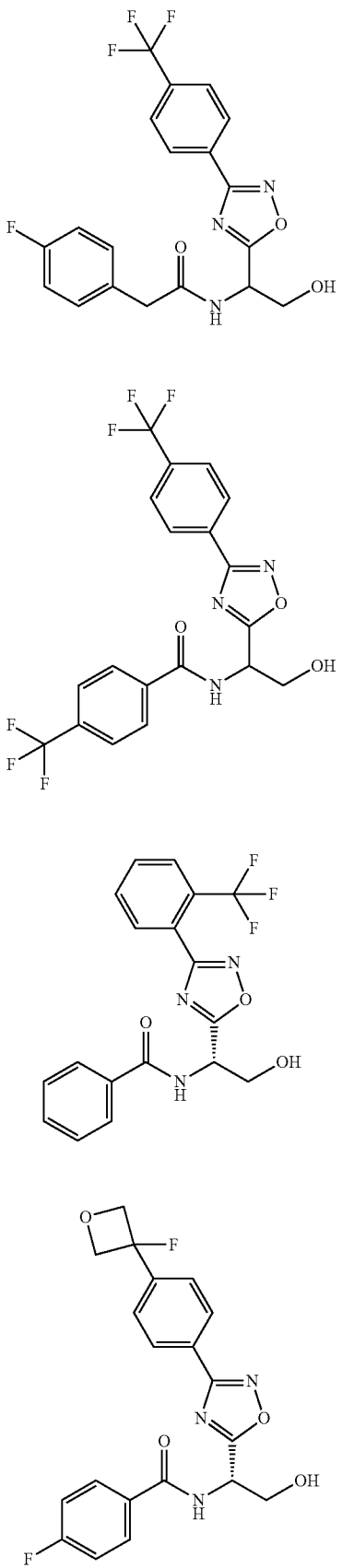

TABLE 1L-continued
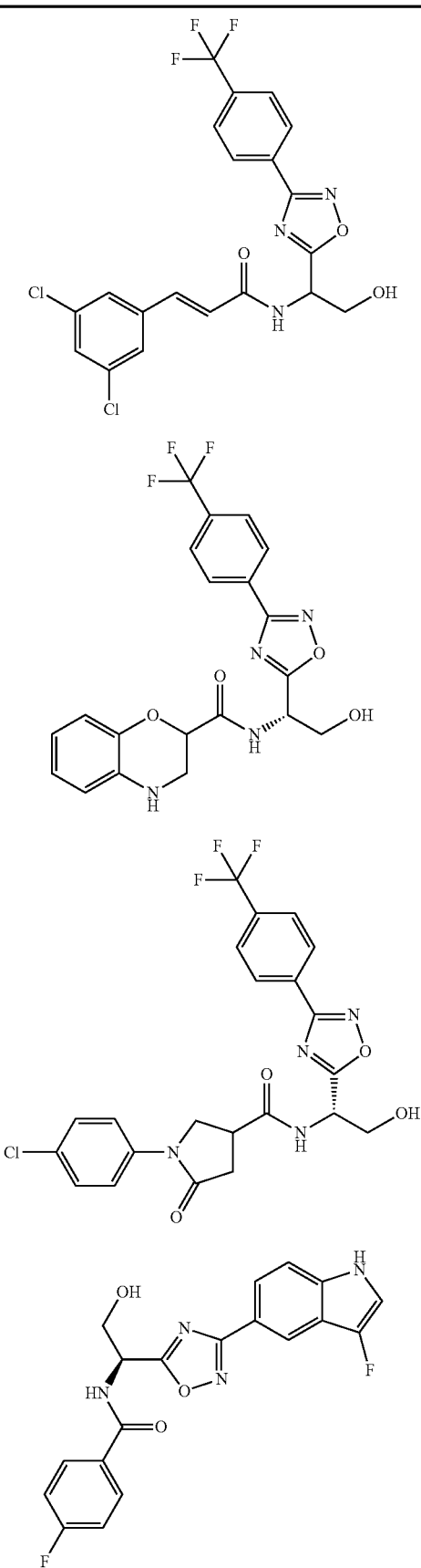
TABLE 1L-continued
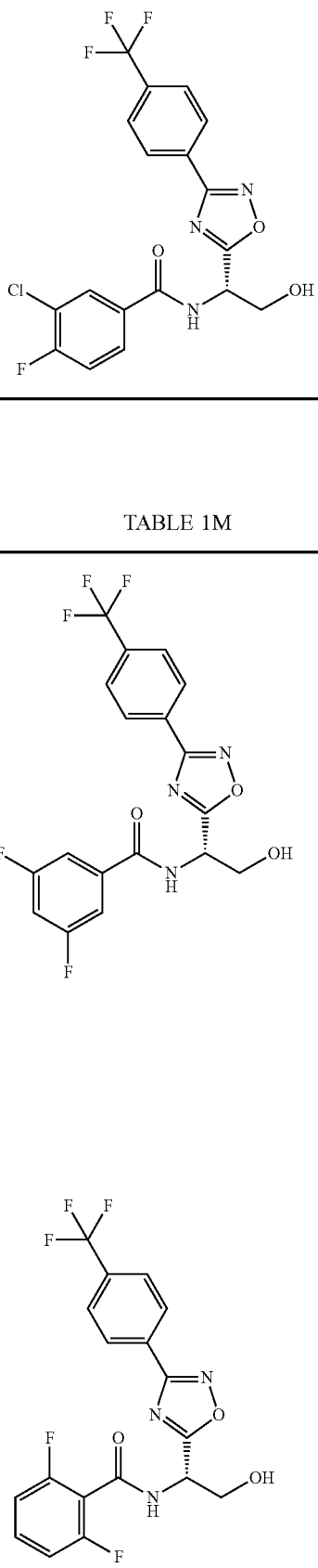
TABLE 1M

TABLE 1M-continued
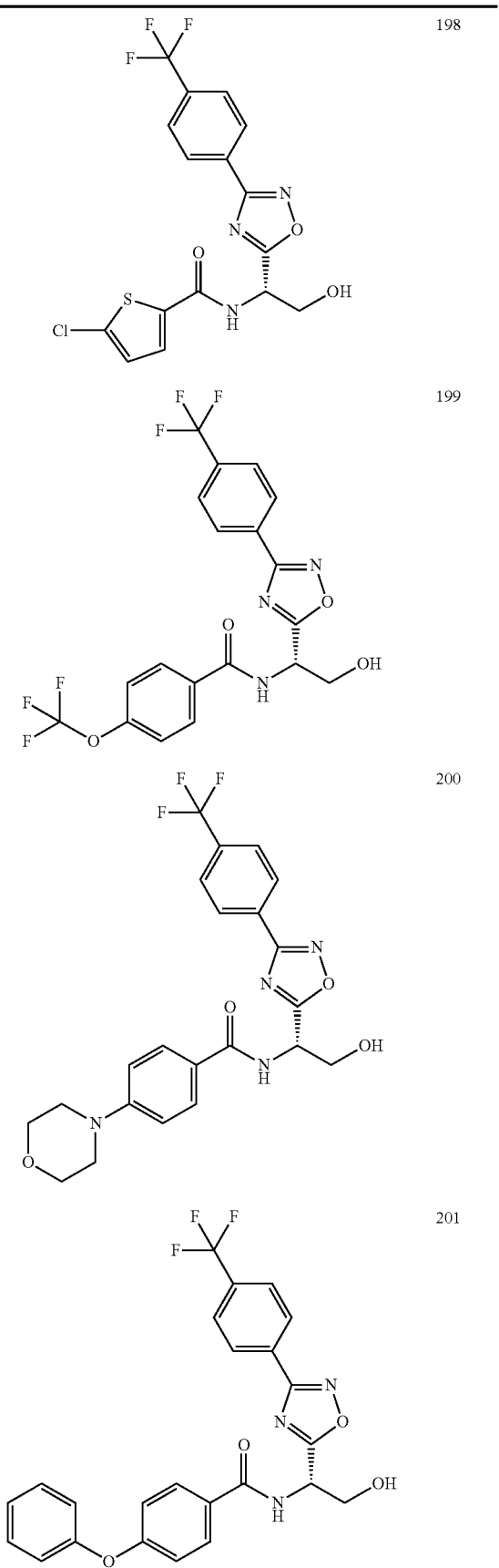
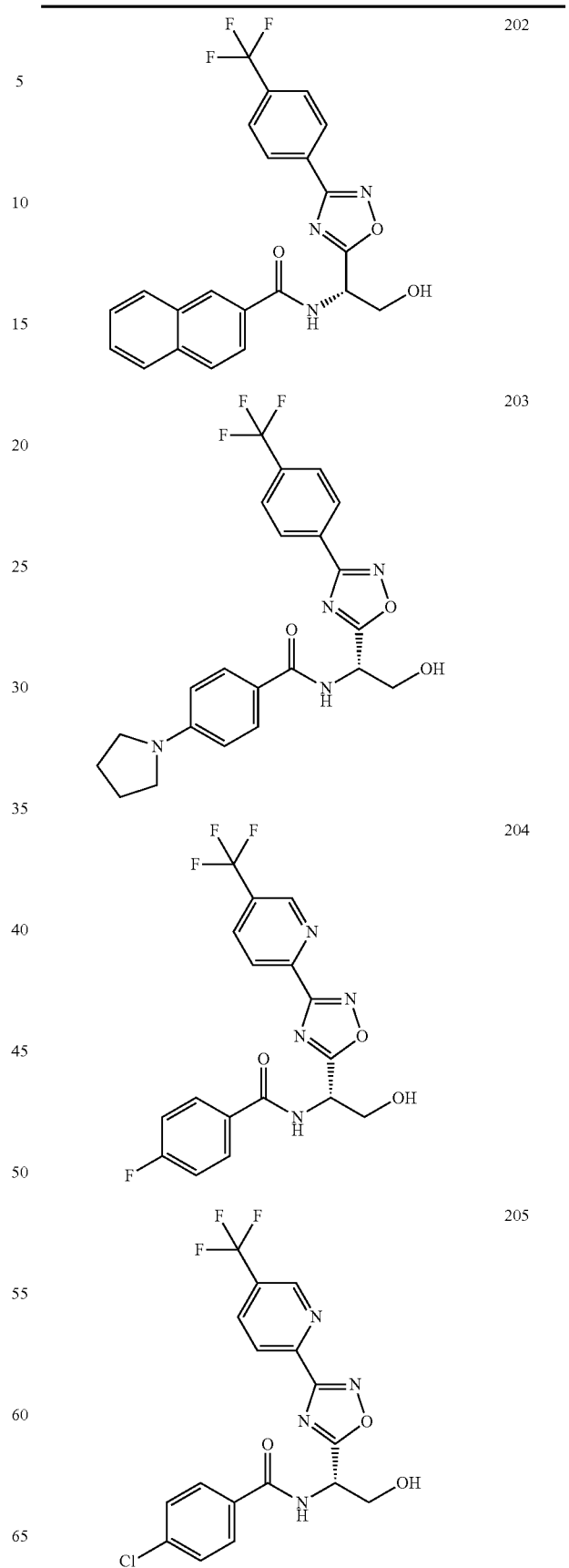

TABLE 1M-continued
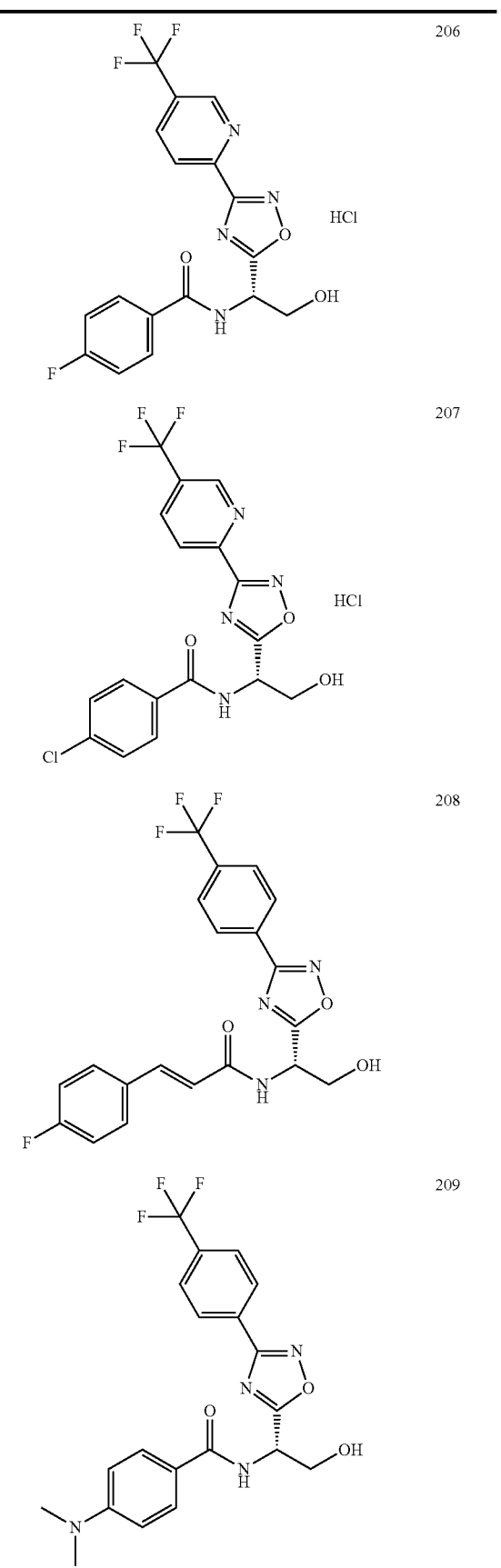
TABLE 1M-continued
TABLE 1N
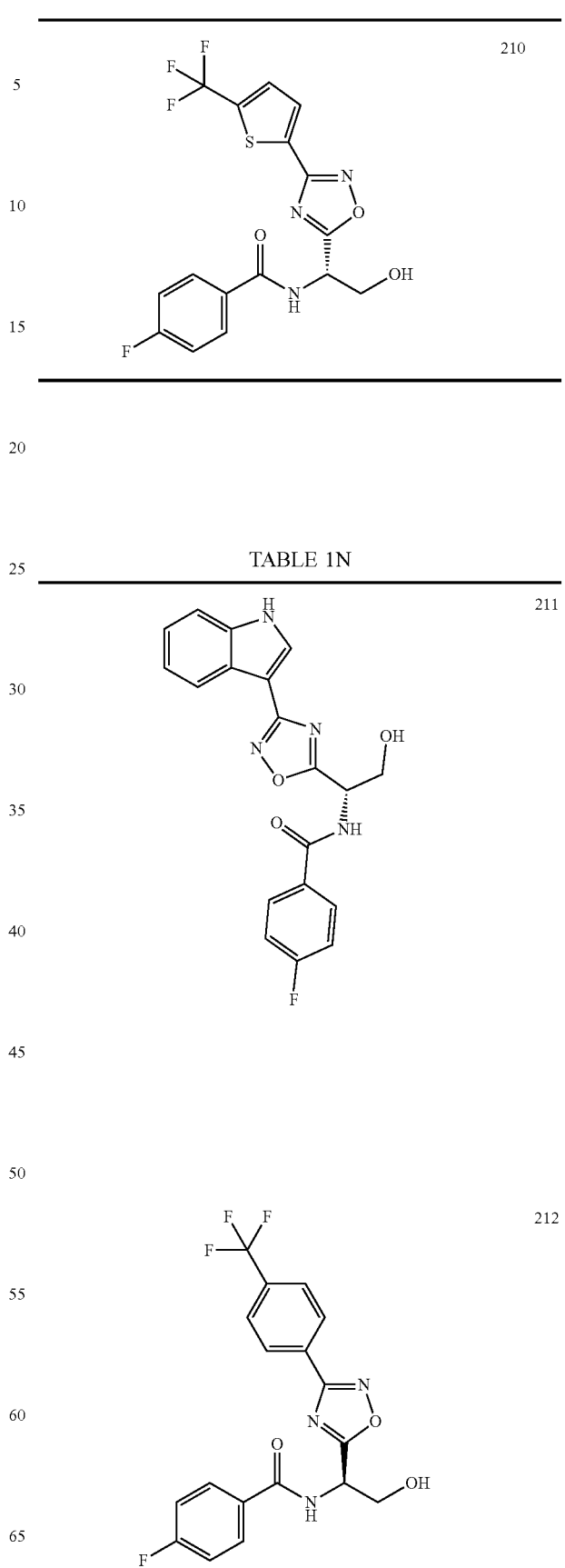

TABLE 1N-continued
| | |
|---|---|
| 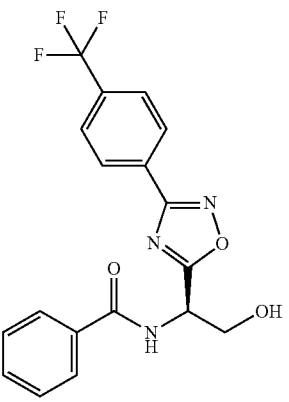 [SMILES: O=C(N[C@H](CO)c1nc(-c2ccc(C(F)(F)F)cc2)no1)c1ccccc1] 213 | 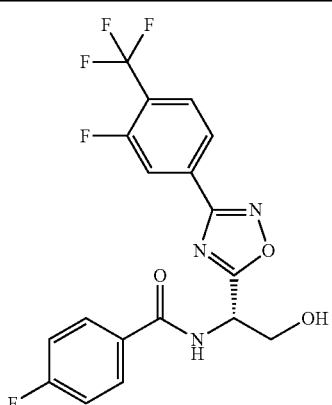 217 |
| 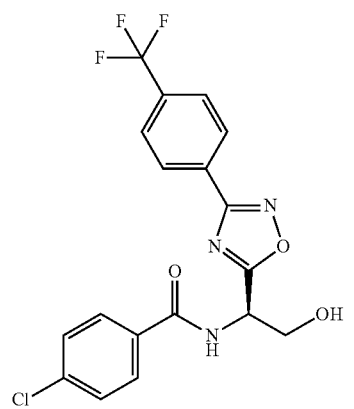 [SMILES: O=C(N[C@H](CO)c1nc(-c2ccc(C(F)(F)F)cc2)no1)c1ccc(Cl)cc1] 214 | 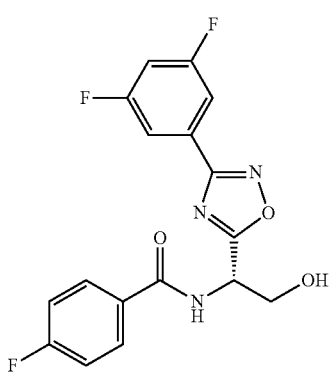 218 |
| 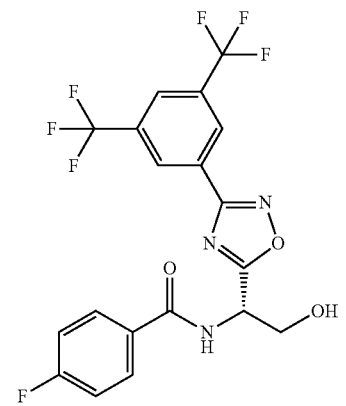 [SMILES: O=C(N[C@@H](CO)c1nc(-c2cc(C(F)(F)F)cc(C(F)(F)F)c2)no1)c1ccc(F)cc1] 215 | 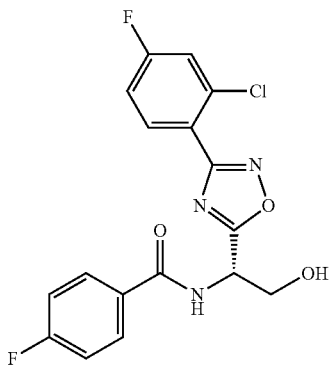 219 |
| 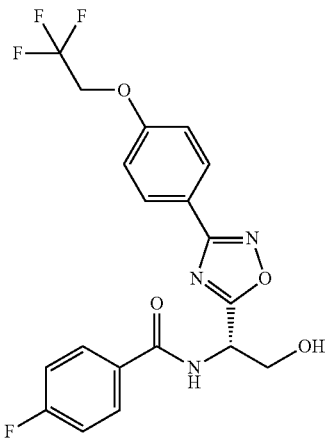 [SMILES: O=C(N[C@@H](CO)c1nc(-c2ccc(OCC(F)(F)F)cc2)no1)c1ccc(F)cc1] 216 | 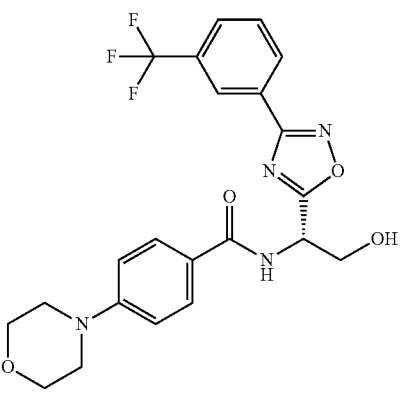 [SMILES: O=C(N[C@@H](CO)c1nc(-c2cccc(C(F)(F)F)c2)no1)c1ccc(N2CCOCC2)cc1] 220 |

TABLE 1N-continued
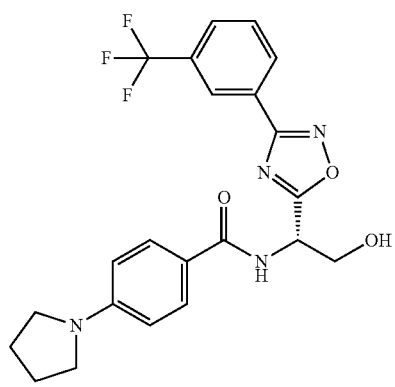 [SMILES: O=C(N[C@@H](CO)c1nc(-c2cccc(C(F)(F)F)c2)no1)c1ccc(N2CCCC2)cc1]
221
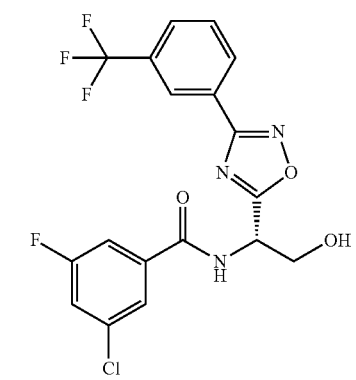 [SMILES: O=C(N[C@@H](CO)c1nc(-c2cccc(C(F)(F)F)c2)no1)c1cc(F)cc(Cl)c1]
222
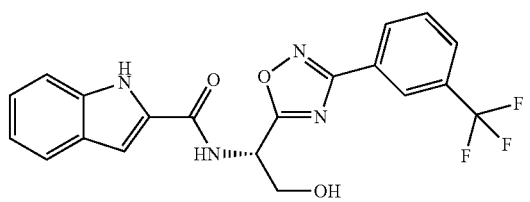 [SMILES: O=C(N[C@@H](CO)c1nc(-c2cccc(C(F)(F)F)c2)no1)c1cc2ccccc2[nH]1]
223
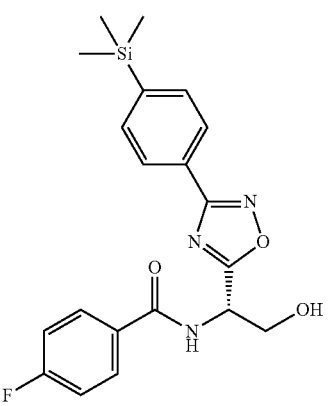 [SMILES: C[Si](C)(C)c1ccc(-c2noc([C@H](CO)NC(=O)c3ccc(F)cc3)n2)cc1]
224
TABLE 1N-continued
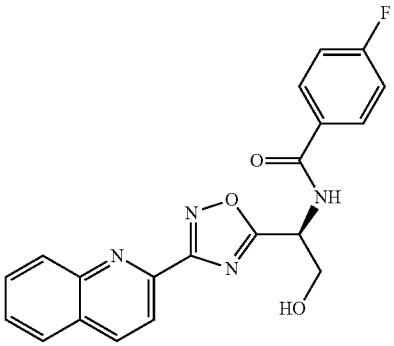 [SMILES: O=C(N[C@@H](CO)c1nc(-c2ccc3ccccc3n2)no1)c1ccc(F)cc1]
225
TABLE 1O
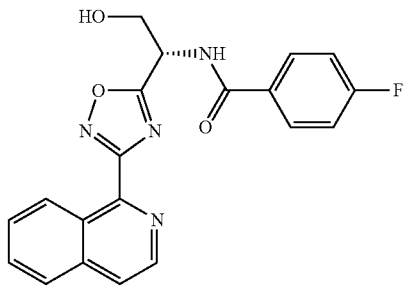 [SMILES: O=C(N[C@@H](CO)c1nc(-c2nccc3ccccc23)no1)c1ccc(F)cc1]
226
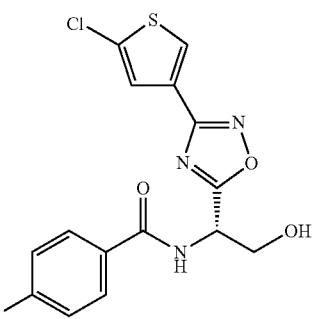
227
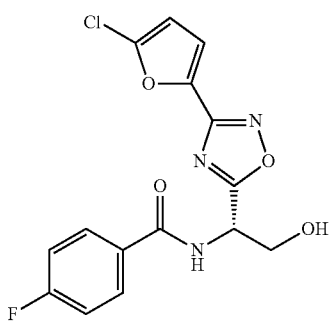 [SMILES: O=C(N[C@@H](CO)c1nc(-c2ccc(Cl)o2)no1)c1ccc(F)cc1]
228

TABLE 1O-continued
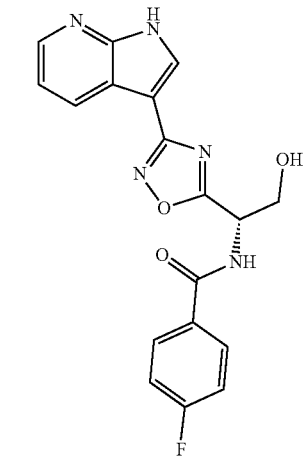 [SMILES: O=C(N[C@@H](CO)c1nc(-c2c[nH]c3ncccc23)no1)c1ccc(F)cc1]
229
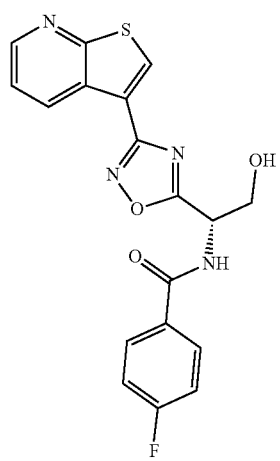 [SMILES: O=C(N[C@@H](CO)c1nc(-c2csc3ncccc23)no1)c1ccc(F)cc1]
230
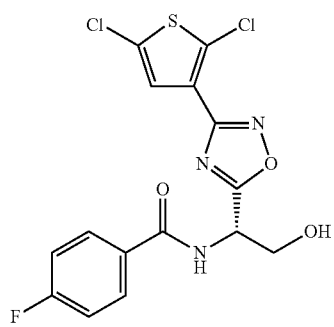 [SMILES: O=C(N[C@@H](CO)c1nc(-c2cc(Cl)sc2Cl)no1)c1ccc(F)cc1]
231
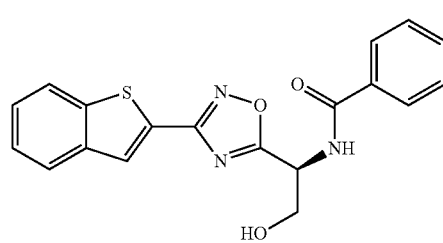
232
TABLE 1O-continued
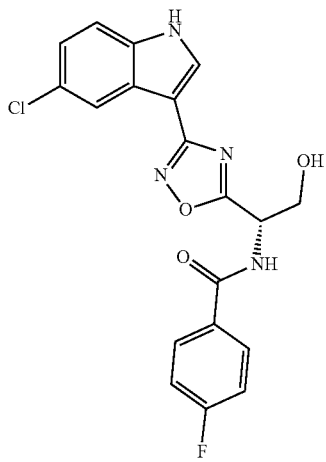 [SMILES: O=C(N[C@@H](CO)c1nc(-c2c[nH]c3ccc(Cl)cc23)no1)c1ccc(F)cc1]
233
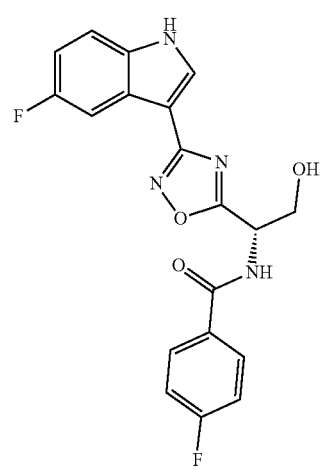 [SMILES: O=C(N[C@@H](CO)c1nc(-c2c[nH]c3ccc(F)cc23)no1)c1ccc(F)cc1]
234
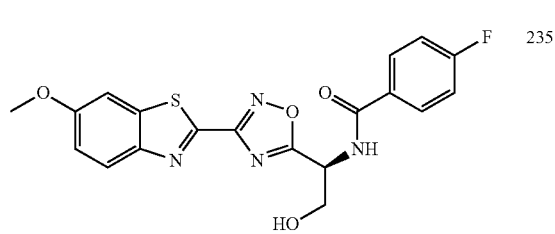
235
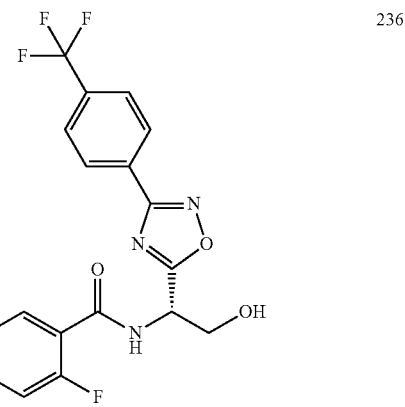
236

TABLE 1O-continued
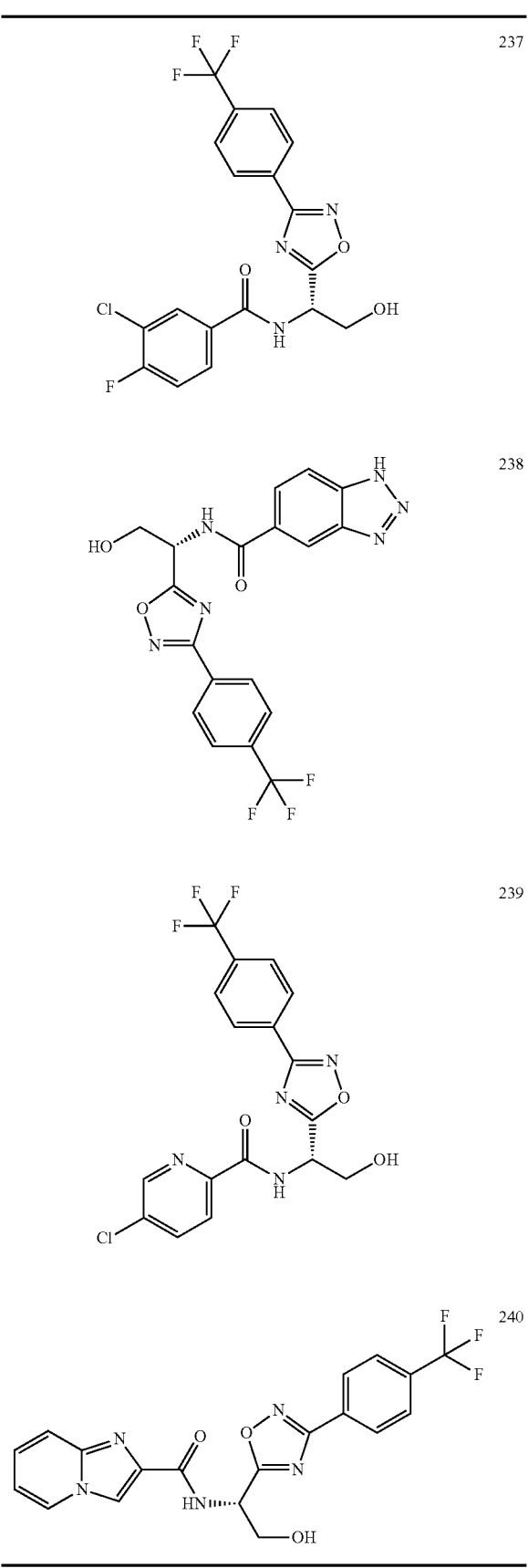
TABLE 1P
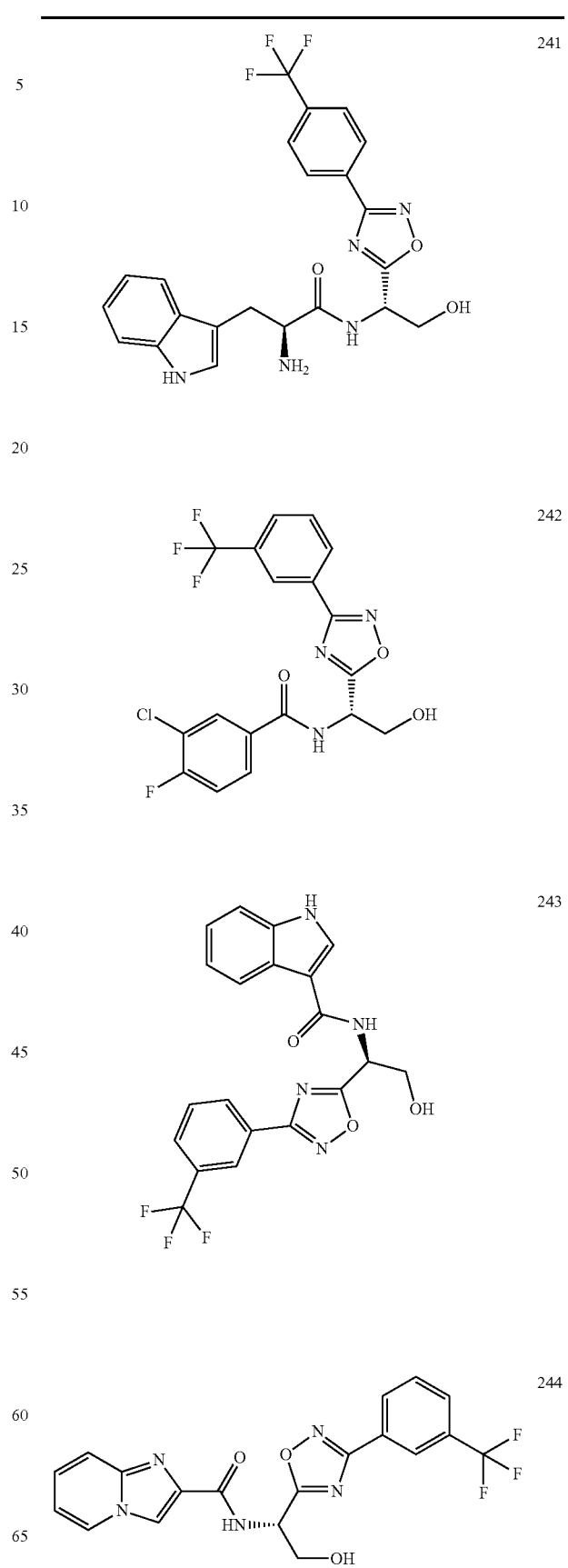

TABLE 1P-continued
| 245 | 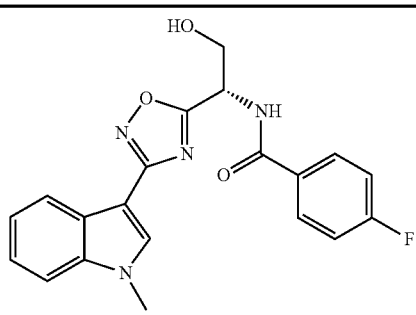 |
| 246 | 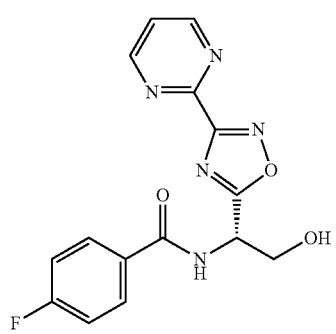 [SMILES: O=C(N[C@@H](CO)c1nc(-c2ncccn2)no1)c1ccc(F)cc1] |
| 247 | 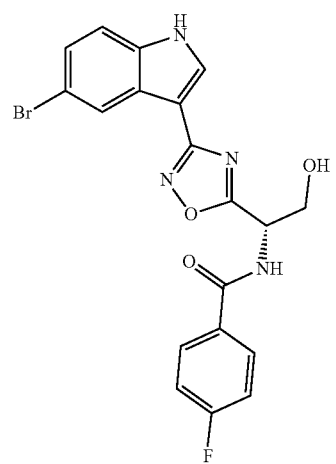 |
| 248 | 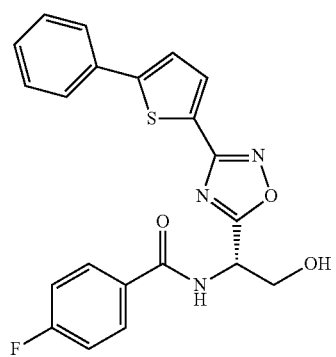 [SMILES: O=C(N[C@@H](CO)c1nc(-c2ccc(-c3ccccc3)s2)no1)c1ccc(F)cc1] |
TABLE 1P-continued
| 249 | 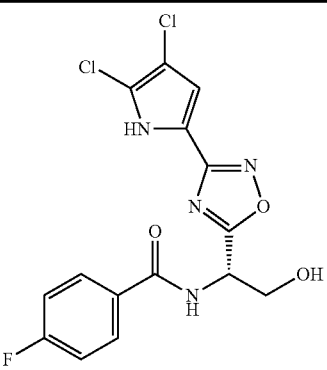 |
| 250 | 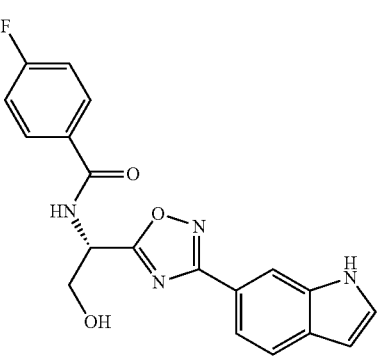 [SMILES: O=C(N[C@@H](CO)c1nc(-c2ccc3cc[nH]c3c2)no1)c1ccc(F)cc1] |
| 251 | 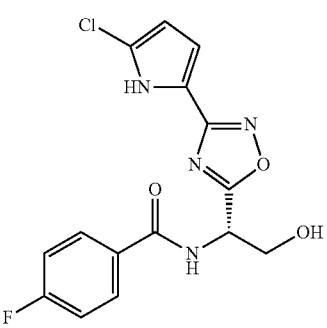 |
| 252 | 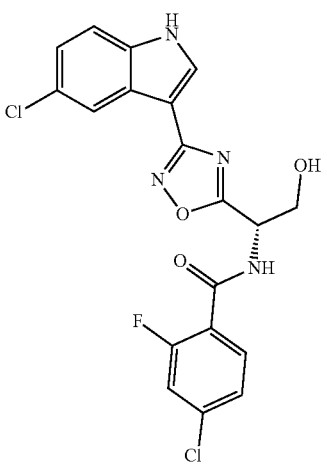 [SMILES: O=C(N[C@@H](CO)c1nc(-c2c[nH]c3ccc(Cl)cc23)no1)c1ccc(Cl)cc1F] |

TABLE 1P-continued
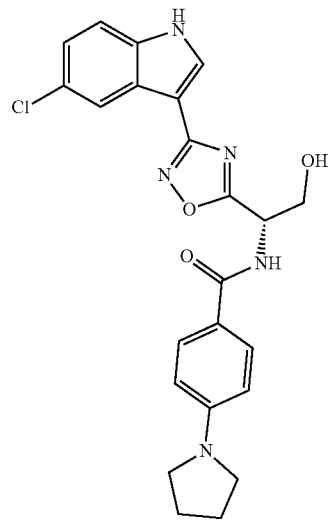 [SMILES: O=C(N[C@@H](CO)c1nc(-c2c[nH]c3ccc(Cl)cc23)no1)c1ccc(N2CCCC2)cc1]
253
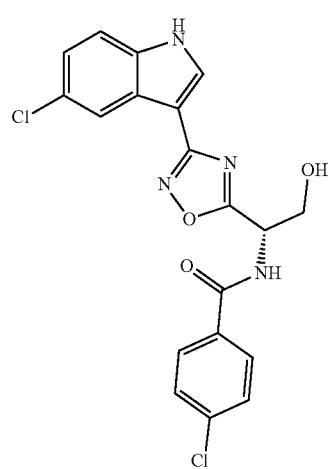 [SMILES: O=C(N[C@@H](CO)c1nc(-c2c[nH]c3ccc(Cl)cc23)no1)c1ccc(Cl)cc1]
254
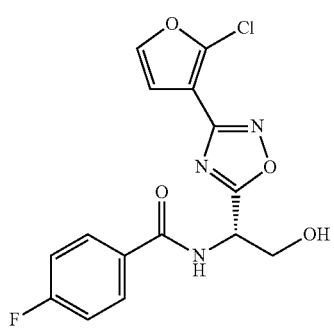 [SMILES: O=C(N[C@@H](CO)c1nc(-c2ccoc2Cl)no1)c1ccc(F)cc1]
255
TABLE 1Q
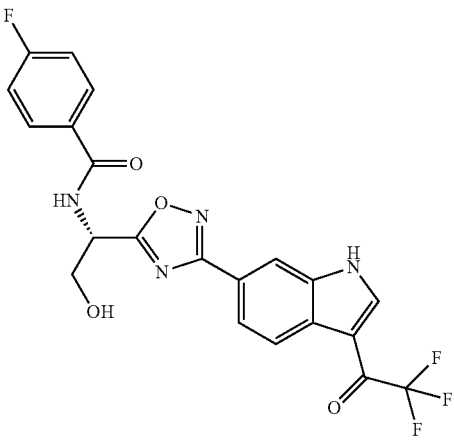 [SMILES: O=C(N[C@@H](CO)c1nc(-c2ccc3c(C(=O)C(F)(F)F)c[nH]c3c2)no1)c1ccc(F)cc1]
256
257
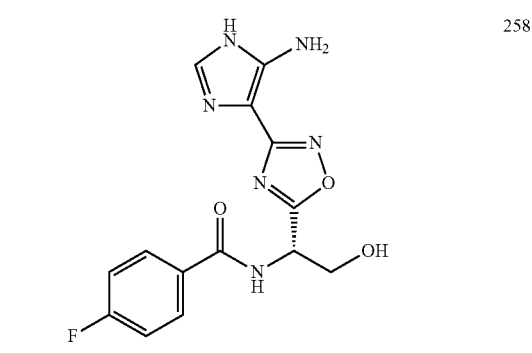
258
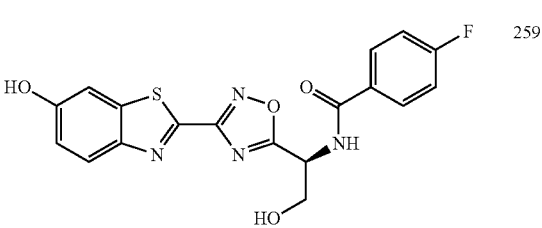
259

TABLE 1Q-continued
260 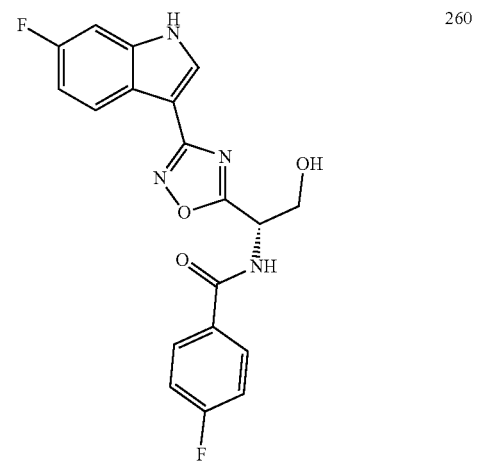
261 
262 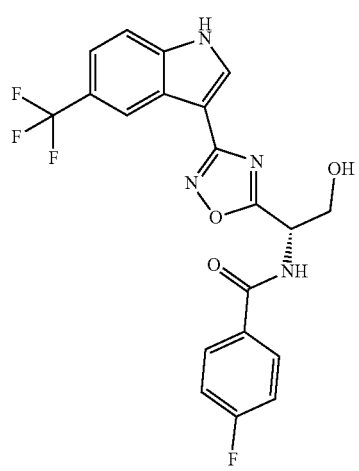 [SMILES: O=C(N[C@@H](CO)c1nc(-c2c[nH]c3ccc(C(F)(F)F)cc23)no1)c1ccc(F)cc1]
TABLE 1Q-continued
263 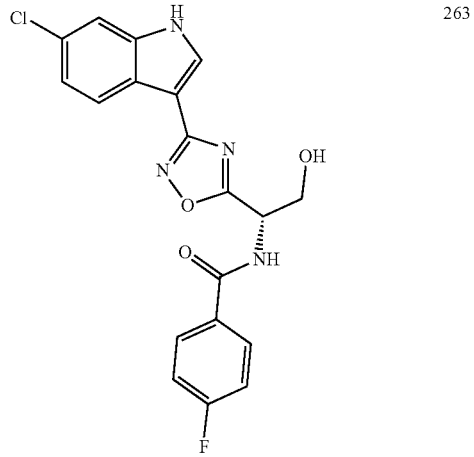
264 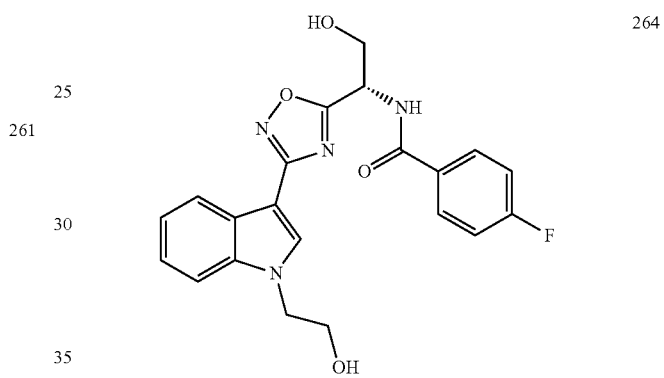
265 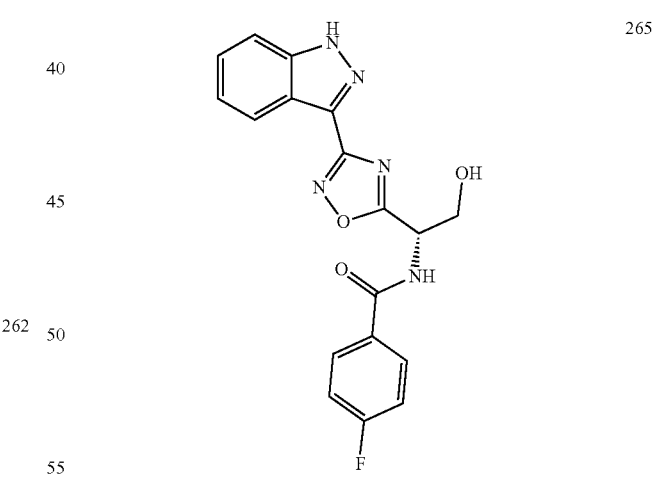
266 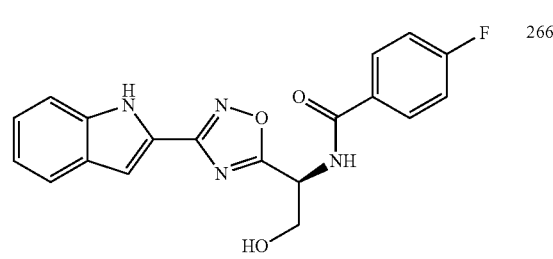

TABLE 1Q-continued

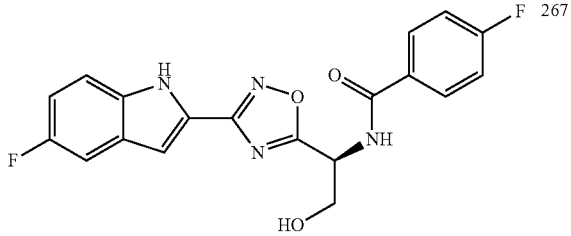
267

[1] N-(3-chlorophenyl)-2-{3-(4-methoxyphenyl)-1,2,4-oxadiazol-5-yl}-N-propylacetamide (Compound No. 1),
[2] N-(3-chlorophenyl)-3-{3-(4-methoxyphenyl)-1,2,4-oxadiazol-5-yl}-N-propylpropanamide (Compound No. 2),
[3] N-(3-chlorophenyl)-N-(2-hydroxyethyl)-3-{3-(4-methoxyphenyl)-1,2,4-oxadiazol-5-yl}propanamide (Compound No. 3),
[4] N-(4-chloropyridin-2-yl)-3-{3-(4-methoxyphenyl)-1,2,4-oxadiazol-5-yl}propanamide (Compound No. 4),
[5] N-(5-chloropyridin-3-yl)-3-{3-(4-methoxyphenyl)-1,2,4-oxadiazol-5-yl}-N-propylpropanamide (Compound No. 5),
[6] N-(3-chlorophenyl)-N-(3-hydroxypropyl)-3-{3-(4-methoxyphenyl)-1,2,4-oxadiazol-5-yl}propanamide (Compound No. 6),
[7] N-(3-chlorophenyl)-N-ethyl-3-{3-(4-methoxyphenyl)-1,2,4-oxadiazol-5-yl}propanamide (Compound No. 7),
[8] N-(3-chlorophenyl)-3-{3-(4-methoxyphenyl)-1,2,4-oxadiazol-5-yl} propanamide (Compound No. 8),
[9] N-(3-chlorobenzyl)-3-{3-(4-methoxyphenyl)-1,2,4-oxadiazol-5-yl}-N-propylpropanamide (Compound No. 9),
[10] N-(3-chlorophenyl)-3-{3-(4-methoxyphenyl)-1,2,4-oxadiazol-5-yl}propanamide (Compound No. 10),
[11] N-(3-chlorophenyl)-N-methyl-3-[3-{4-(trifluoromethoxy)phenyl}-1,2,4-oxadiazol-5-yl]propanamide (Compound No. 11),
[12] 1-{3,4-dihydroquinolin-1(2H)-yl}-3-[3-{4-(trifluoromethoxy)phenyl}-1,2,4-oxadiazol-5-yl]propan-1-one (Compound No. 12),
[13] N-(3-chlorophenyl)-3-{3-(4-hydroxyphenyl)-1,2,4-oxadiazol-5-yl}-N-methylpropanamide (Compound No. 13),
[14] N-(3-fluorobenzyl)-3-{3-(4-hydroxyphenyl)-1,2,4-oxadiazol-5-yl}-N-methylpropanamide (Compound No. 14),
[15] N-(3-fluorobenzyl)-3-{3-(4-hydroxyphenyl)-1,2,4-oxadiazol-5-yl} propanamide (Compound No. 15),
[16] N-benzyl-3-{3-(2,3-dihydrobenzo[b][1,4]dioxin-6-yl)-1,2,4-oxadiazol-5-yl}-N-methylpropanamide (Compound No. 16),
[17] 3-{3-(2,3-dihydrobenzo[b][1,4]dioxin-6-yl)-1,2,4-oxadiazol-5-yl}-1-{3,4-dihydroisoquinolin-2(1H)-yl} propan-1-one (Compound No. 17),
[18] (S)-2-(1H-indol-3-yl)-1-{3-(4-methoxyphenyl)-1,2,4-oxadiazol-5-yl}ethan-1-amine (Compound No. 18),
[19] N-(3-chlorophenyl)-3-{3-(4-hydroxyphenyl)-1,2,4-oxadiazol-5-yl}-N-propylpropanamide (Compound No. 19),
[20] 4-chloro-N-(2-[3-{4-(trifluoromethoxy)phenyl}-1,2,4-oxadiazol-5-yl]propan-2-yl)benzamide (Compound No. 20),
[21] 4-chloro-N-methyl-N-(2-[3-{4-(trifluoromethoxy)phenyl}-1,2,4-oxadiazol-5-yl]propan-2-yl)benzamide (Compound No. 21),
[22] 4-chloro-N-[2-{3-(4-methoxyphenyl)-1,2,4-oxadiazol-5-yl}propan-2-yl]-N-methylbenzamide (Compound No. 22),
[23] 1-(4-chlorophenyl)-4-[3-{4-(trifluoromethoxy)phenyl}-1,2,4-oxadiazol-5-yl]pyrrolidin-2-one (Compound No. 23),
[24] 1-(4-chlorophenyl)-4-{3-(4-methoxyphenyl)-1,2,4-oxadiazol-5-yl}pyrrolidin-2-one (Compound No. 24),
[25] (S)-2-(1H-indol-3-yl)-1-[3-{4-(trifluoromethoxy)phenyl}-1,2,4-oxadiazol-5-yl]ethan-1-amine (Compound No. 25),
[26] 1-(4-fluorophenyl)-4-[3-{4-(trifluoromethoxy)phenyl}-1,2,4-oxadiazol-5-yl]pyrrolidin-2-one (Compound No. 26),
[27] 1-(3-chlorophenyl)-4-[3-{4-(trifluoromethoxy)phenyl}-1,2,4-oxadiazol-5-yl]pyrrolidin-2-one (Compound No. 27),
[28] 1-(4-chloro-2-fluorophenyl)-4-[3-{4-(trifluoromethoxy)phenyl}-1,2,4-oxadiazol-5-yl]pyrrolidin-2-one (Compound No. 28),
[29] 4-chloro-N-(1-[3-{4-(trifluoromethoxy)phenyl}-1,2,4-oxadiazol-5-yl]cyclopentyl)benzamide (Compound No. 29),
[30] 4-fluoro-N-(1-[3-{4-(trifluoromethoxy)phenyl}-1,2,4-oxadiazol-5-yl]cyclopentyl)benzamide (Compound No. 30),
[31] 6-chloro-N-(1-[3-{4-(trifluoromethoxy)phenyl}-1,2,4-oxadiazol-5-yl]cyclopentyl)nicotinamide (Compound No. 31),
[32] 1-(4-chlorophenyl)-4-{3-(2,2-difluorobenzo[d][1,3]dioxol-5-yl)-1,2,4-oxadiazol-5-yl}pyrrolidin-2-one (Compound No. 32),
[33] 1-(4-chlorophenyl)-4-[3-{3-(trifluoromethoxy)phenyl}-1,2,4-oxadiazol-5-yl]pyrrolidin-2-one (Compound No. 33),
[34] (4-chlorophenyl)((2S,4R)-4-hydroxy-2-[3-{4-(trifluoromethoxy)phenyl}-1,2,4-oxadiazol-5-yl]pyrrolidin-1-yl)methanone (Compound No. 34),
[35] 3-chloro-N-(1-[3-{4-(trifluoromethoxy)phenyl}-1,2,4-oxadiazol-5-yl]cyclopentyl)benzamide (Compound No. 35),
[36] 1-(4-chlorophenyl)-3-(1-[3-{4-(trifluoromethoxy)phenyl}-1,2,4-oxadiazol-5-yl]cyclopentyl)urea (Compound No. 36),
[37] 2-(1H-imidazol-4-yl)-1-[3-{4-(trifluoromethoxy)phenyl}-1,2,4-oxadiazol-5-yl]ethan-1-amine (Compound No. 37),
[38] 4-(2-amino-2-[3-{4-(trifluoromethoxy)phenyl}-1,2,4-oxadiazol-5-yl]ethyl)phenol (Compound No. 38),
[39] (S)-4-chloro-N-(2-hydroxy-1-[3-{4-(trifluoromethoxy)phenyl}-1,2,4-oxadiazol-5-yl]ethyl)benzamide (Compound No. 39),
[40] 1-{3-(2,2-difluorobenzo[d][1,3]dioxol-5-yl)-1,2,4-oxadiazol-5-yl}-2-(1H-indol-3-yl)ethan-1-amine (Compound No. 40),
[41] 1-(4-chlorophenyl)-4-{3-(4-hydroxyphenyl)-1,2,4-oxadiazol-5-yl}pyrrolidin-2-one (Compound No. 41),
[42] 1-(4-chlorophenyl)-4-{3-(3-fluoro-4-methoxyphenyl)-1,2,4-oxadiazol-5-yl}pyrrolidin-2-one (Compound No. 42),
[43] 1-(4-chlorophenyl)-4-(3-phenyl-1,2,4-oxadiazol-5-yl) pyrrolidin-2-one (Compound No. 43),
[44] 1-(4-chlorophenyl)-4-{3-(pyridin-4-yl)-1,2,4-oxadiazol-5-yl} pyrrolidin-2-one (Compound No. 44),
[45] 1-(4-chlorophenyl)-4-[5-{4-(trifluoromethoxy)phenyl}-1,2,4-oxadiazol-3-yl]pyrrolidin-2-one (Compound No. 45),

[46] N-(2-hydroxy-1-[3-{4-(trifluoromethoxy)phenyl}-1,2,4-oxadiazol-5-yl]ethyl)-1H-indole-3-carboxamide (Compound No. 46),
[47] ((2S,4R)-4-hydroxy-2-[3-{4-(trifluoromethoxy)phenyl}-1,2,4-oxadiazol-5-yl]pyrrolidin-1-yl)(1H-indol-3-yl)methanone (Compound No. 47),
[48] 1-(6-chloropyridin-3-yl)-4-[3-{4-(trifluoromethoxy)phenyl}-1,2,4-oxadiazol-5-yl]pyrrolidin-2-one (Compound No. 48),
[49] 1-(5-chloropyridin-2-yl)-4-[3-{4-(trifluoromethoxy)phenyl}-1,2,4-oxadiazol-5-yl]pyrrolidin-2-one (Compound No. 49),
[50] 1-(4-methoxybenzyl)-4-[3-{4-(trifluoromethoxy)phenyl}-1,2,4-oxadiazol-5-yl]pyrrolidin-2-one (Compound No. 50),
[51] 1-(5-chloropyridin-3-yl)-4-[3-{4-(trifluoromethoxy)phenyl}-1,2,4-oxadiazol-5-yl]pyrrolidin-2-one (Compound No. 51),
[52] 1-(4-chlorophenyl)-4-[3-{4-(difluoromethoxy)phenyl}-1,2,4-oxadiazol-5-yl]pyrrolidin-2-one (Compound No. 52),
[53] 1-(4-chlorophenyl)-4-[3-{4-(fluoromethoxy)phenyl}-1,2,4-oxadiazol-5-yl]pyrrolidin-2-one (Compound No. 53),
[54] 1-(4-chlorophenyl)-4-{3-(6-methoxypyridin-3-yl)-1,2,4-oxadiazol-5-yl}pyrrolidin-2-one (Compound No. 54),
[55] (S)-(4-chlorophenyl)(2-[3-{4-(trifluoromethoxy)phenyl}-1,2,4-oxadiazol-5-yl]pyrrolidin-1-yl)methanone (Compound No. 55),
[56] (4-chlorophenyl)((2S,4S)-4-hydroxy-2-[3-{4-(trifluoromethoxy)phenyl}-1,2,4-oxadiazol-5-yl]pyrrolidin-1-yl)methanone (Compound No. 56),
[57] (S)-1-(4-chlorobenzoyl)-5-[3-{4-(trifluoromethoxy)phenyl}-1,2,4-oxadiazol-5-yl]pyrrolidin-3-one (Compound No. 57),
[58] (3-chlorophenyl)((2S,4R)-4-hydroxy-2-[3-{4-(trifluoromethoxy)phenyl}-1,2,4-oxadiazol-5-yl]pyrrolidin-1-yl)methanone (Compound No. 58),
[59] 1-(4-chlorophenyl)-4-{3-(4-chlorophenyl)-1,2,4-oxadiazol-5-yl} pyrrolidin-2-one (Compound No. 59),
[60] (5-chloropyridin-2-yl)((2S,4R)-4-hydroxy-2-[3-{4-(trifluoromethoxy)phenyl}-1,2,4-oxadiazol-5-yl]pyrrolidin-1-yl)methanone (Compound No. 60),
[61] 1-(4-chlorophenyl)-4-{3-(4-fluorophenyl)-1,2,4-oxadiazol-5-yl} pyrrolidin-2-one (Compound No. 61),
[62] 1-(5-chloropyridin-2-yl)-4-[3-{4-(difluoromethoxy)phenyl}-1,2,4-oxadiazol-5-yl]pyrrolidin-2-one (Compound No. 62),
[63] (S)-3-chloro-N-(2-hydroxy-1-[3-{4-(trifluoromethoxy)phenyl}-1,2,4-oxadiazol-5-yl]ethyl)benzamide (Compound No. 63),
[64] 1-(4-chlorobenzyl)-4-[3-{4-(trifluoromethoxy)phenyl}-1,2,4-oxadiazol-5-yl]pyrrolidin-2-one (Compound No. 64),
[65] N-(4-[5-{1-(4-chlorophenyl)-5-oxopyrrolidin-3-yl}-1,2,4-oxadiazol-3-yl]phenyl)methanesulfonamide (Compound No. 65),
[66] 1-(4-chlorophenyl)-4-[3-{3-(difluoromethoxy)phenyl}-1,2,4-oxadiazol-5-yl]pyrrolidin-2-one (Compound No. 66),
[67] 1-(4-chlorophenyl)-4-[3-{2-(trifluoromethoxy)phenyl}-1,2,4-oxadiazol-5-yl]pyrrolidin-2-one (Compound No. 67),
[68] (4-chlorophenyl)(3-[3-{4-(trifluoromethoxy)phenyl}-1,2,4-oxadiazol-5-yl]azetidin-1-yl)methanone (Compound No. 68),
[69] (S)-4-fluoro-N-(2-hydroxy-1-[3-{4-(trifluoromethoxy)phenyl}-1,2,4-oxadiazol-5-yl]ethyl)benzamide (Compound No. 69),
[70] N-[2-{3-(1H-indol-3-yl)-1,2,4-oxadiazol-5-yl} ethyl]-2-(7-methoxy-1H-indol-3-yl)acetamide (Compound No. 70),
[71] N-[2-{3-(1H-indol-3-yl)-1,2,4-oxadiazol-5-yl} ethyl]-4-chlorobenzamide (Compound No. 71),
[72] 1-(4-chlorophenyl)-4-(hydroxymethyl)-4-{3-(4-hydroxyphenyl)-1,2,4-oxadiazol-5-yl}pyrrolidin-2-one (Compound No. 72),
[73] 1-(4-chlorophenyl)-4-{3-(2,2-difluorobenzo[d][1,3]dioxol-5-yl)-1,2,4-oxadiazol-5-yl}-4-(hydroxymethyl)pyrrolidin-2-one (Compound No. 73),
[74] 1-(4-chlorophenyl)-4-{3-(3-fluoro-4-hydroxyphenyl)-1,2,4-oxadiazol-5-yl}pyrrolidin-2-one (Compound No. 74),
[75] (S)-4-chloro-N-(3-hydroxy-1-[3-{4-(trifluoromethoxy)phenyl}-1,2,4-oxadiazol-5-yl]propyl)benzamide (Compound No. 75),
[76] (S)-6-chloro-N-(2-hydroxy-1-[3-{4-(trifluoromethoxy)phenyl}-1,2,4-oxadiazol-5-yl]ethyl)-1H-indole-3-carboxamide (Compound No. 76),
[77] (3R,5 S)-1-(4-chlorobenzyl)-5-[3-{4-(trifluoromethoxy)phenyl}-1,2,4-oxadiazol-5-yl]pyrrolidin-3-ol (Compound No. 77),
[78] 4-chloro-N-[2-hydroxy-1-{3-(4-hydroxyphenyl)-1,2,4-oxadiazol-5-yl}ethyl]benzamide (Compound No. 78),
[79] 4-[4-{3-(4-hydroxyphenyl)-1,2,4-oxadiazol-5-yl}-2-oxopyrrolidin-1-yl]benzonitrile (Compound No. 79),
[80] 4-chloro-N-((1S,2R)-2-hydroxy-1-[3-{4-(trifluoromethoxy)phenyl}-1,2,4-oxadiazol-5-yl]propyl)benzamide (Compound No. 80),
[81] (S)-3-(4-chlorobenzamido)-3-[3-{4-(trifluoromethoxy)phenyl}-1,2,4-oxadiazol-5-yl]propanoic acid (Compound No. 81),
[82] (4-chlorophenyl)((2S,4R)-4-hydroxy-2-[3-{4-(trifluoromethoxy)phenyl}-1,2,4-oxadiazol-5-yl]pyrrolidin-1-yl)methanone (Compound No. 82),
[83] (R)-4-chloro-N-(2-hydroxy-1-[3-{4-(trifluoromethoxy)phenyl}-1,2,4-oxadiazol-5-yl]ethyl)benzamide (Compound No. 83),
[84] (S)-1-(4-chlorobenzoyl)-5-[3-{4-(trifluoromethoxy)phenyl}-1,2,4-oxadiazol-5-yl]pyrrolidin-2-one (Compound No. 84),
[85] (4-chlorophenyl)((2S,4S)-4-hydroxy-2-[3-{4-(trifluoromethoxy)phenyl}-1,2,4-oxadiazol-5-yl]pyrrolidin-1-yl)methanone (Compound No. 85),
[86] (S)-N-(3-amino-3-oxo-1-[3-{4-(trifluoromethoxy)phenyl}-1,2,4-oxadiazol-5-yl]propyl)-4-chlorobenzamide (Compound No. 86),
[87] (S)-4-chloro-N-(3-(dimethylamino)-3-oxo-1-[3-{4-(trifluoromethoxy)phenyl}-1,2,4-oxadiazol-5-yl]propyl) benzamide (Compound No. 87),
[88] (S)-4-chloro-N-(3-(methylamino)-3-oxo-1-[3-{4-(trifluoromethoxy)phenyl}-1,2,4-oxadiazol-5-yl]propyl)benzamide (Compound No. 88),
[89] 4-[5-{1-hydroxy-2-(1H-indol-3-yl)ethyl}-1,2,4-oxadiazol-3-yl]phenol (Compound No. 89),
[90] 1-(4-chlorophenyl)-4-{3-(3-fluoro-4-hydroxyphenyl)-1,2,4-oxadiazol-5-yl}-4-(hydroxymethyl)pyrrolidin-2-one (Compound No. 90),
[91] (S)-3-chloro-N-(2-hydroxy-1-[3-{4-(trifluoromethoxy)phenyl}-1,2,4-oxadiazol-5-yl]ethyl)benzenesulfonamide (Compound No. 91),

[92] (S)-N-(2-hydroxy-1-[3-{4-(trifluoromethoxy)phenyl}-1,2,4-oxadiazol-5-yl]ethyl)benzamide (Compound No. 92),

[93] (S)-2-fluoro-N-(2-hydroxy-1-[3-{4-(trifluoromethoxy)phenyl}-1,2,4-oxadiazol-5-yl]ethyl)benzamide (Compound No. 93),

[94] (S)-3-fluoro-N-(2-hydroxy-1-[3-{4-(trifluoromethoxy)phenyl}-1,2,4-oxadiazol-5-yl]ethyl)benzamide (Compound No. 94),

[95] (S)-1-(4-chlorophenyl)-3-(2-hydroxy-1-[3-{4-(trifluoromethoxy)phenyl}-1,2,4-oxadiazol-5-yl]ethyl)urea (Compound No. 95),

[96] (S)-4-chloro-N-(2-hydroxy-1-[3-{4-(trifluoromethoxy)phenyl}-1,2,4-oxadiazol-5-yl]ethyl)-N-(2-hydroxyethyl)benzamide (Compound No. 96),

[97] (S)-1-(4-chlorophenyl)-3-(2-hydroxy-1-[3-{4-(trifluoromethoxy)phenyl}-1,2,4-oxadiazol-5-yl]ethyl)thiourea (Compound No. 97),

[98] (S)-3-chloro-4-hydroxy-N-(2-hydroxy-1-[3-{4-(trifluoromethoxy)phenyl}-1,2,4-oxadiazol-5-yl]ethyl)benzamide (Compound No. 98),

[99] (S)-4-chloro-N-(1-(3-(3-fluoro-4-hydroxyphenyl)-1,2,4-oxadiazol-5-yl)-2-hydroxyethyl)benzamide (Compound No. 99),

[100] (S)-4-cyano-N-(1-(3-(3-fluoro-4-hydroxyphenyl)-1,2,4-oxadiazol-5-yl)-2-hydroxyethyl)benzamide (Compound No. 100),

[101] 2-(1H-indol-3-yl)-1-(3-(4-(trifluoromethoxy)phenyl)-1,2,4-oxadiazol-5-yl)ethan-1-ol (Compound No. 101),

[102] 4-chloro-N-(1,3-dihydroxy-2-(3-(4-(trifluoromethoxy)phenyl)-1,2,4-oxadiazol-5-yl)propan-2-yl)benzamide (Compound No. 102),

[103] 1-(4-chlorophenyl)-4-(5-(4-(trifluoromethoxy)phenyl)-1,3,4-oxadiazol-2-yl)pyrrolidin-2-one (Compound No. 103),

[104] (S)-4-chloro-N-(2-hydroxy-1-(5-(4-(trifluoromethoxy)phenyl)-1,3,4-oxadiazol-2-yl)ethyl)benzamide (Compound No. 104),

[105] (S)-4-chloro-N-(2-hydroxy-1-(5-(4-(methylsulfonamido)phenyl)-1,3,4-oxadiazol-2-yl)ethyl)benzamide (Compound No. 105),

[106] (S)-4-chloro-N-(1-(5-(3-cyanophenyl)-1,3,4-oxadiazol-2-yl)-2-hydroxyethyl)benzamide (Compound No. 106),

[107] (R)-4-chloro-N-(2-hydroxy-1-(5-(4-(trifluoromethoxy)phenyl)-1,3,4-oxadiazol-2-yl)ethyl)benzamide (Compound No. 107),

[108] (R)-4-chloro-N-(2-hydroxy-1-(5-(4-(methylsulfonamido)phenyl)-1,3,4-oxadiazol-2-yl)ethyl)benzamide (Compound No. 108),

[109] (R)-4-chloro-N-(1-(5-(3-cyanophenyl)-1,3,4-oxadiazol-2-yl)-2-hydroxyethyl)benzamide (Compound No. 109),

[110] (S)-2-(1H-indol-3-yl)-1-(5-(4-(trifluoromethoxy)phenyl)-1,3,4-oxadiazol-2-yl)ethan-1-amine hydrochloride (Compound No. 110),

[111] (S)-N-(4-(5-(1-amino-2-(1H-indol-3-yl)ethyl)-1,3,4-oxadiazol-2-yl)phenyl)methanesulfonamide hydrochloride (Compound No. 111),

[112] (S)-4-fluoro-N-(2-hydroxy-1-(5-(4-(trifluoromethoxy)phenyl)-1,3,4-oxadiazol-2-yl)ethyl)benzamide (Compound No. 112),

[113] (S)-4-chloro-N-(1-(5-(3-fluoro-4-methoxyphenyl)-1,3,4-oxadiazol-2-yl)-2-hydroxyethyl)benzamide (Compound No. 113),

[114] (R)-2-(1H-indol-3-yl)-1-(5-(4-(trifluoromethoxy)phenyl)-1,3,4-oxadiazol-2-yl)ethan-1-amine (Compound No. 114),

[115] 4-chloro-N-(1-(5-(4-(trifluoromethoxy)phenyl)-1,3,4-oxadiazol-2-yl)vinyl)benzamide (Compound No. 115),

[116] N-(2-amino-1-(5-(4-(trifluoromethoxy)phenyl)-1,3,4-oxadiazol-2-yl)ethyl)-4-chlorobenzamide (Compound No. 116),

[117] 4-chloro-N-(2-morpholino-1-(5-(4-(trifluoromethoxy)phenyl)-1,3,4-oxadiazol-2-yl)ethyl)benzamide (Compound No. 117),

[118] 4-chloro-N-(2-(methylamino)-1-(5-(4-(trifluoromethoxy)phenyl)-1,3,4-oxadiazol-2-yl)ethyl)benzamide (Compound No. 118),

[119] 4-chloro-N-(2-((2-hydroxyethyl)amino)-1-(5-(4-(trifluoromethoxy)phenyl)-1,3,4-oxadiazol-2-yl)ethyl)benzamide (Compound No. 119),

[120] (S)-4-chloro-N-(1-(5-(3-fluoro-4-hydroxyphenyl)-1,3,4-oxadiazol-2-yl)-2-hydroxyethyl)benzamide (Compound No. 120),

[121] 1-(4-chlorophenyl)-4-(3-(4-(trifluoromethoxy)phenyl)-1,2,4-thiadiazol-5-yl)pyrrolidin-2-one (Compound No. 121),

[122] 1-(4-chlorophenyl)-4-(2-(4-(trifluoromethoxy)phenyl)-2H-tetrazol-5-yl)pyrrolidin-2-one (Compound No. 122),

[123] 1-(4-chlorophenyl)-4-(5-(4-(trifluoromethoxy)phenyl)-4H-1,2,4-triazol-3-yl)pyrrolidin-2-one (Compound No. 123),

[124] 1-(4-chlorophenyl)-4-(5-(4-(trifluoromethoxy)phenyl)-1H-imidazol-2-yl)pyrrolidin-2-one (Compound No. 124),

[125] (S)-4-chloro-N-(2-hydroxy-1-(3-(4-methoxyphenyl)-1,2,4-oxadiazol-5-yl)ethyl)benzamide (Compound No. 125),

[126] (R)-4-chloro-N-(2-hydroxy-1-(5-(4-(trifluoromethoxy)phenyl)-1,2,4-oxadiazol-3-yl)ethyl)benzamide (Compound No. 126),

[127] 4-chloro-N-((1S,2S)-2-hydroxy-1-(3-(4-(trifluoromethoxy)phenyl)-1,2,4-oxadiazol-5-yl)propyl)benzamide (Compound No. 127),

[128] (R)-N-(2-hydroxy-1-(5-(4-(trifluoromethoxy)phenyl)-1,2,4-oxadiazol-3-yl)ethyl)benzamide (Compound No. 128),

[129] (S)-4-chloro-N-(2-hydroxy-1-(3-(4-(trifluoromethyl)phenyl)-1,2,4-oxadiazol-5-yl)ethyl)benzamide (Compound No. 129),

[130] (S)-N-(2-hydroxy-1-(3-(4-(trifluoromethyl)phenyl)-1,2,4-oxadiazol-5-yl)ethyl)benzamide (Compound No. 130),

[131] (4-chlorophenyl)((2S,3S)-3-hydroxy-2-(3-(4-(trifluoromethoxy)phenyl)-1,2,4-oxadiazol-5-yl)pyrrolidin-1-yl)methanone (Compound No. 131),

[132] 4-chloro-N-((1S,2R)-2-hydroxy-1-(3-(4-methoxyphenyl)-1,2,4-oxadiazol-5-yl)propyl)benzamide (Compound No. 132),

[133] (S)-4-fluoro-N-(2-hydroxy-1-(3-(4-(trifluoromethyl)phenyl)-1,2,4-oxadiazol-5-yl)ethyl)benzamide (Compound No. 133),

[142] N-[(1S)-1-[3-(2-fluoro-4-hydroxyphenyl)-1,2,4-oxadiazol-5-yl]-2-hydroxyethyl]benzamide (Compound No. 142),

[143] N-[(1S)-2-hydroxy-1-[3-(4-methylphenyl)-1,2,4-oxadiazol-5-yl]ethyl]benzamide (Compound No. 143),

[144] N-[(1S)-1-[3-(3-fluoro-4-methoxyphenyl)-1,2,4-oxadiazol-5-yl]-2-hydroxyethyl]benzamide (Compound No. 144),

[145] N-[(1S)-2-hydroxy-1-{3-[4-(propan-2-yl)phenyl]-1,2,4-oxadiazol-5-yl}ethyl]benzamide (Compound No. 145),

[146] N-[(1S)-2-hydroxy-1-[3-(4-hydroxyphenyl)-1,2,4-oxadiazol-5-yl]ethyl]benzamide (Compound No. 146),

[147] 4-{5-[(1S)-1-[(4-fluorophenyl)formamido]-2-hydroxyethyl]-1,2,4-oxadiazol-3-yl}-N-(3-methoxypropyl)benzamide (Compound No. 147),

[148] 4-{5-[(1S)-2-hydroxy-1-(phenylformamido)ethyl]-1,2,4-oxadiazol-3-yl}-N-(3-methoxypropyl)benzamide (Compound No. 148),

[149] N-[(1S)-2-amino-1-{3-[4-(trifluoromethoxy)phenyl]-1,2,4-oxadiazol-5-yl}ethyl]benzamide (Compound No. 149),

[150] N-[(1S)-1-{3-[4-(dimethylamino)phenyl]-1,2,4-oxadiazol-5-yl}-2-hydroxyethyl]benzamide (Compound No. 150),

[151] 4-fluoro-N-(3-hydroxy-2-{3-[4-(trifluoromethyl)phenyl]-1,2,4-oxadiazol-5-yl} propyl)benzamide (Compound No. 151),

[152] 4-fluoro-N-[(1R)-2-hydroxy-1-{3-[4-(trifluoromethyl)phenyl]-1,2,4-oxadiazol-5-yl}ethyl]benzamide (Compound No. 152),

[153] N-[(1S)-1-[3-(4-acetylphenyl)-1,2,4-oxadiazol-5-yl]-2-hydroxyethyl]benzamide (Compound No. 153),

[1544] N-[(1S)-2-hydroxy-1-{3-[4-(1-hydroxyethyl)phenyl]-1,2,4-oxadiazol-5-yl}ethyl]benzamide (Compound No. 154),

[155] N-[(1S)-2-hydroxy-1-{3-[4-(2-hydroxypropan-2-yl)phenyl]-1,2,4-oxadiazol-5-yl}ethyl]benzamide (Compound No. 155),

[156] N-[(1S)-2-hydroxy-1-{3-[4-(2-hydroxyethoxy)phenyl]-1,2,4-oxadiazol-5-yl}ethyl]benzamide (Compound No. 156),

[157] 6-fluoro-N-[(1S)-2-hydroxy-1-{3-[4-(trifluoromethyl)phenyl]-1,2,4-oxadiazol-5-yl}ethyl]pyridine-3-carboxamide (Compound No. 157),

[158] N-[(1S)-2-hydroxy-1-(3-{4-[2-(morpholin-4-yl)ethoxy]phenyl}-1,2,4-oxadiazol-5-yl)ethyl]benzamide (Compound No. 158),

[159] 4-{5-[(1S)-2-hydroxy-1-(phenylformamido)ethyl]-1,2,4-oxadiazol-3-yl}phenyl N-ethyl-N-methylcarbamate (Compound No. 159),

[160] 4-fluoro-N-[(2S)-1-hydroxy-3-{3-[4-(trifluoromethyl)phenyl]-1,2,4-oxadiazol-5-yl}propan-2-yl]benzamide (Compound No. 160),

[161] 4-fluoro-N-[(1S)-1-{3-[4-(fluoromethyl)phenyl]-1,2,4-oxadiazol-5-yl}-2-hydroxyethyl]benzamide (Compound No. 161),

[162] N-[(1S)-1-{3-[4-(fluoromethyl)phenyl]-1,2,4-oxadiazol-5-yl}-2-hydroxyethyl]benzamide (Compound No. 162),

[163] N-[(1S)-1-[3-(4-bromophenyl)-1,2,4-oxadiazol-5-yl]-2-hydroxyethyl]-4-fluorobenzamide (Compound No. 163),

[164] 4-fluoro-N-[(1S)-2-hydroxy-1-{3-[4-(2,2,2-trifluoroacetyl)phenyl]-1,2,4-oxadiazol-5-yl} ethyl]benzamide (Compound No. 164),

[165] N-[(1S)-2-hydroxy-1-{3-[4-(2,2,2-trifluoroacetyl)phenyl]-1,2,4-oxadiazol-5-yl}ethyl]benzamide (Compound No. 165),

[166] N-[(1S)-1-{3-[4-(difluoromethyl)phenyl]-1,2,4-oxadiazol-5-yl}-2-hydroxyethyl]-4-fluorobenzamide (Compound No. 166),

[167] 4-chloro-N-[(1S)-1-{3-[4-(difluoromethyl)phenyl]-1,2,4-oxadiazol-5-yl}-2-hydroxyethyl]benzamide (Compound No. 167),

[168] N-[(1S)-1-{3-[4-(difluoromethyl)phenyl]-1,2,4-oxadiazol-5-yl}-2-hydroxyethyl]benzamide (Compound No. 168),

[169] 4-(2-ethoxyethoxy)-N-[(1S)-2-hydroxy-1-{3-[4-(trifluoromethoxy)phenyl]-1,2,4-oxadiazol-5-yl}ethyl]benzamide (Compound No. 169),

[170] 4-(2-ethoxyethoxy)-N-[(1S)-2-hydroxy-1-{3-[4-(trifluoromethyl)phenyl]-1,2,4-oxadiazol-5-yl}ethyl]benzamide (Compound No. 170),

[171] 4-[2-(diethylamino)ethoxy]-N-[(1S)-2-hydroxy-1-{3-[4-(trifluoromethoxy)phenyl]-1,2,4-oxadiazol-5-yl} ethyl]benzamide (Compound No. 171),

[172] 4-fluoro-N-[(1S)-1-[3-(4-fluorophenyl)-1,2,4-oxadiazol-5-yl]-2-hydroxyethyl]benzamide (Compound No. 172),

[173] 4-fluoro-N-[(1S)-2-hydroxy-1-[3-(quinolin-3-yl)-1,2,4-oxadiazol-5-yl]ethyl]benzamide (Compound No. 173),

[174] N-{3-[4-(trifluoromethyl)phenyl]-1,2,4-oxadiazol-5-yl} benzamide (Compound No. 174),

[175] 4-fluoro-N-[(1S)-2-hydroxy-1-[3-(1H-indol-5-yl)-1,2,4-oxadiazol-5-yl]ethyl]benzamide (Compound No. 175),

[176] 4-fluoro-N-[(1S)-2-hydroxy-1-{3-[3-(trifluoromethyl)phenyl]-1,2,4-oxadiazol-5-yl}ethyl]benzamide (Compound No. 176),

[177] N-[(1S)-2-hydroxy-1-{3-[3-(trifluoromethyl)phenyl]-1,2,4-oxadiazol-5-yl}ethyl]benzamide (Compound No. 177),

[178] 4-fluoro-N-[(1 S)-2-hydroxy-1-[3-(thiophen-2-yl)-1,2,4-oxadiazol-5-yl]ethyl]benzamide (Compound No. 178),

[179] 4-fluoro-N-[(1S)-2-hydroxy-1-{3-[4-(1H-pyrazol-1-yl)phenyl]-1,2,4-oxadiazol-5-yl}ethyl]benzamide (Compound No. 179),

[180] N-[(1S)-2-hydroxy-1-{3-[4-(1H-pyrazol-1-yl)phenyl]-1,2,4-oxadiazol-5-yl}ethyl]benzamide (Compound No. 180),

[181] 4-fluoro-N-[(1S)-2-hydroxy-1-{3-[2-(trifluoromethyl)phenyl]-1,2,4-oxadiazol-5-yl}ethyl]benzamide (Compound No. 181),

[182] N-(2-hydroxy-1-{3-[4-(trifluoromethyl)phenyl]-1,2,4-oxadiazol-5-yl}ethyl)-1H-indole-2-carboxamide (Compound No. 182),

[183] N-(2-hydroxy-1-{3-[4-(trifluoromethyl)phenyl]-1,2,4-oxadiazol-5-yl} ethyl)-1H-indole-5-carboxamide (Compound No. 183),

[184] N-(2-hydroxy-1-{3-[4-(trifluoromethyl)phenyl]-1,2,4-oxadiazol-5-yl} ethyl)-1H-indole-7-carboxamide (Compound No. 184),

[185] N-(2-hydroxy-1-{3-[4-(trifluoromethyl)phenyl]-1,2,4-oxadiazol-5-yl}ethyl)-2-(1H-indol-3-yl)acetamide (Compound No. 185),

[186] N-(2-hydroxy-1-{3-[4-(trifluoromethyl)phenyl]-1,2,4-oxadiazol-5-yl}ethyl)-1H-indazole-3-carboxamide (Compound No. 186),

[187] 2-(4-fluorophenyl)-N-(2-hydroxy-1-{3-[4-(trifluoromethyl)phenyl]-1,2,4-oxadiazol-5-yl}ethyl)acetamide (Compound No. 187),

[188] N-(2-hydroxy-1-{3-[4-(trifluoromethyl)phenyl]-1,2,4-oxadiazol-5-yl} ethyl)-4-(trifluoromethyl)benzamide (Compound No. 188),

[189] N-[(1S)-2-hydroxy-1-{3-[2-(trifluoromethyl)phenyl]-1,2,4-oxadiazol-5-yl}ethyl]benzamide (Compound No. 189),

[190] 4-fluoro-N-[(1S)-1-{3-[4-(3-fluorooxetan-3-yl)phenyl]-1,2,4-oxadiazol-5-yl}-2-hydroxyethyl]benzamide (Compound No. 190),

[191] (2E)-3-(3,5-dichlorophenyl)-N-(2-hydroxy-1-{3-[4-(trifluoromethyl)phenyl]-1,2,4-oxadiazol-5-yl}ethyl)prop-2-enamide (Compound No. 191),

[192] N-[(1S)-2-hydroxy-1-{3-[4-(trifluoromethyl)phenyl]-1,2,4-oxadiazol-5-yl}ethyl]-3,4-dihydro-2H-1,4-benzoxazine-2-carboxamide (Compound No. 192),

[193] 1-(4-chlorophenyl)-N-[(1S)-2-hydroxy-1-{3-[4-(trifluoromethyl)phenyl]-1,2,4-oxadiazol-5-yl}ethyl]-5-oxopyrrolidine-3-carboxamide (Compound No. 193),

[194] 4-fluoro-N-[(1S)-1-[3-(3-fluoro-1H-indol-5-yl)-1,2,4-oxadiazol-5-yl]-2-hydroxyethyl]benzamide (Compound No. 194),

[195] 3-chloro-4-fluoro-N-[(1S)-2-hydroxy-1-{3-[4-(trifluoromethyl)phenyl]-1,2,4-oxadiazol-5-yl}ethyl]benzamide (Compound No. 195),

[196] 3,5-difluoro-N-[(1S)-2-hydroxy-1-{3-[4-(trifluoromethyl)phenyl]-1,2,4-oxadiazol-5-yl}ethyl]benzamide (Compound No. 196),

[197] 2,6-difluoro-N-[(1S)-2-hydroxy-1-{3-[4-(trifluoromethyl)phenyl]-1,2,4-oxadiazol-5-yl}ethyl]benzamide (Compound No. 197),

[198] 5-chloro-N-[(1S)-2-hydroxy-1-{3-[4-(trifluoromethyl)phenyl]-1,2,4-oxadiazol-5-yl}ethyl]thiophene-2-carboxamide (Compound No. 198),

[199] N-[(1S)-2-hydroxy-1-{3-[4-(trifluoromethyl)phenyl]-1,2,4-oxadiazol-5-yl}ethyl]-4-(trifluoromethoxy)benzamide (Compound No. 199),

[200] N-[(1S)-2-hydroxy-1-{3-[4-(trifluoromethyl)phenyl]-1,2,4-oxadiazol-5-yl}ethyl]-4-(morpholin-4-yl)benzamide (Compound No. 200),

[201] N-[(1S)-2-hydroxy-1-{3-[4-(trifluoromethyl)phenyl]-1,2,4-oxadiazol-5-yl}ethyl]-4-phenoxybenzamide (Compound No. 201),

[202] N-[(1S)-2-hydroxy-1-{3-[4-(trifluoromethyl)phenyl]-1,2,4-oxadiazol-5-yl}ethyl]naphthalene-2-carboxamide (Compound No. 202),

[203] N-[(1S)-2-hydroxy-1-{3-[4-(trifluoromethyl)phenyl]-1,2,4-oxadiazol-5-yl}ethyl]-4-(pyrrolidin-1-yl)benzamide (Compound No. 203),

[204] 4-fluoro-N-[(1S)-2-hydroxy-1-{3-[5-(trifluoromethyl)pyridin-2-yl]-1,2,4-oxadiazol-5-yl}ethyl]benzamide (Compound No. 204),

[205] 4-chloro-N-[(1S)-2-hydroxy-1-{3-[5-(trifluoromethyl)pyridin-2-yl]-1,2,4-oxadiazol-5-yl}ethyl]benzamide (Compound No. 205),

[206] 4-fluoro-N-[(1S)-2-hydroxy-1-{3-[5-(trifluoromethyl)pyridin-2-yl]-1,2,4-oxadiazol-5-yl}ethyl]benzamide hydrochloride (Compound No. 206),

[207] 4-chloro-N-[(1S)-2-hydroxy-1-{3-[5-(trifluoromethyl)pyridin-2-yl]-1,2,4-oxadiazol-5-yl}ethyl]benzamide hydrochloride (Compound No. 207),

[208] (2E)-3-(4-fluorophenyl)-N-[(1S)-2-hydroxy-1-{3-[4-(trifluoromethyl)phenyl]-1,2,4-oxadiazol-5-yl}ethyl]prop-2-enamide (Compound No. 208),

[209] 4-(dimethylamino)-N-[(1S)-2-hydroxy-1-{3-[4-(trifluoromethyl)phenyl]-1,2,4-oxadiazol-5-yl}ethyl]benzamide (Compound No. 209),

[210] 4-fluoro-N-[(1S)-2-hydroxy-1-{3-[5-(trifluoromethyl)thiophen-2-yl]-1,2,4-oxadiazol-5-yl}ethyl]benzamide (Compound No. 210),

[211] 4-fluoro-N-[(1S)-2-hydroxy-1-[3-(1H-indol-3-yl)-1,2,4-oxadiazol-5-yl]ethyl]benzamide (Compound No. 211),

[212] 4-fluoro-N-[(1R)-2-hydroxy-1-{3-[4-(trifluoromethyl)phenyl]-1,2,4-oxadiazol-5-yl}ethyl]benzamide (Compound No. 212),

[213] N-[(1R)-2-hydroxy-1-{3-[4-(trifluoromethyl)phenyl]-1,2,4-oxadiazol-5-yl}ethyl]benzamide (Compound No. 213),

[214] 4-chloro-N-[(1R)-2-hydroxy-1-{3-[4-(trifluoromethyl)phenyl]-1,2,4-oxadiazol-5-yl}ethyl]benzamide (Compound No. 214),

[215] N-[(1S)-1-{3-[3,5-bis(trifluoromethyl)phenyl]-1,2,4-oxadiazol-5-yl}-2-hydroxyethyl]-4-fluorobenzamide (Compound No. 215),

[216] 4-fluoro-N-[(1S)-2-hydroxy-1-{3-[4-(2,2,2-trifluoroethoxy)phenyl]-1,2,4-oxadiazol-5-yl}ethyl]benzamide (Compound No. 216),

[217] 4-fluoro-N-[(1S)-1-{3-[3-fluoro-4-(trifluoromethyl)phenyl]-1,2,4-oxadiazol-5-yl}-2-hydroxyethyl]benzamide (Compound No. 217),

[218] N-[(1S)-1-[3-(3,5-difluorophenyl)-1,2,4-oxadiazol-5-yl]-2-hydroxyethyl]-4-fluorobenzamide (Compound No. 218),

[219] N-[(1S)-1-[3-(2-chloro-4-fluorophenyl)-1,2,4-oxadiazol-5-yl]-2-hydroxyethyl]-4-fluorobenzamide (Compound No. 219),

[220] N-[(1S)-2-hydroxy-1-{3-[3-(trifluoromethyl)phenyl]-1,2,4-oxadiazol-5-yl}ethyl]-4-(morpholin-4-yl)benzamide (Compound No. 220),

[221] N-[(1S)-2-hydroxy-1-{3-[3-(trifluoromethyl)phenyl]-1,2,4-oxadiazol-5-yl}ethyl]-4-(pyrrolidin-1-yl)benzamide (Compound No. 221),

[222] 3-chloro-5-fluoro-N-[(1S)-2-hydroxy-1-{3-[3-(trifluoromethyl)phenyl]-1,2,4-oxadiazol-5-yl}ethyl]benzamide (Compound No. 222),

[223] N-[(1S)-2-hydroxy-1-{3-[3-(trifluoromethyl)phenyl]-1,2,4-oxadiazol-5-yl}ethyl]-1H-indole-2-carboxamide (Compound No. 223),

[224] 4-fluoro-N-[(1S)-2-hydroxy-1-{3-[4-(trimethylsilyl)phenyl]-1,2,4-oxadiazol-5-yl}ethyl]benzamide (Compound No. 224),

[225] 4-fluoro-N-[(1S)-2-hydroxy-1-[3-(quinolin-2-yl)-1,2,4-oxadiazol-5-yl]ethyl]benzamide (Compound No. 225),

[226] 4-fluoro-N-[(1S)-2-hydroxy-1-[3-(isoquinolin-11-yl)-1,2,4-oxadiazol-5-yl]ethyl]benzamide (Compound No. 226),

[227] N-[(1S)-1-[3-(5-chlorothiophen-3-yl)-1,2,4-oxadiazol-5-yl]-2-hydroxyethyl]-4-fluorobenzamide (Compound No. 227),

[228] N-[(1S)-1-[3-(5-chlorofuran-2-yl)-1,2,4-oxadiazol-5-yl]-2-hydroxyethyl]-4-fluorobenzamide (Compound No. 228),

[229] 4-fluoro-N-[(1S)-2-hydroxy-1-(3-{1H-pyrrolo[2,3-b]pyridin-3-yl}-1,2,4-oxadiazol-5-yl)ethyl]benzamide (Compound No. 229),

[230] N-[(1S)-1-[3-(1-benzothiophen-3-yl)-1,2,4-oxadiazol-5-yl]-2-hydroxyethyl]-4-fluorobenzamide (Compound No. 230),

[231] N-[(1S)-1-[3-(2,5-dichlorothiophen-3-yl)-1,2,4-oxadiazol-5-yl]-2-hydroxyethyl]-4-fluorobenzamide (Compound No. 231),

[232] N-[(1S)-1-[3-(1-benzothiophen-2-yl)-1,2,4-oxadiazol-5-yl]-2-hydroxyethyl]-4-fluorobenzamide (Compound No. 232),

[233] N-[(1S)-1-[3-(5-chloro-1H-indol-3-yl)-1,2,4-oxadiazol-5-yl]-2-hydroxyethyl]-4-fluorobenzamide (Compound No. 233),

[234] 4-fluoro-N-[(1S)-1-[3-(5-fluoro-1H-indol-3-yl)-1,2,4-oxadiazol-5-yl]-2-hydroxyethyl]benzamide (Compound No. 234),

[235] 4-fluoro-N-[(1S)-2-hydroxy-1-[3-(6-methoxy-1,3-benzothiazol-2-yl)-1,2,4-oxadiazol-5-yl]ethyl]benzamide (Compound No. 235),

[236] 4-chloro-2-fluoro-N-[(1S)-2-hydroxy-1-{3-[4-(trifluoromethyl)phenyl]-1,2,4-oxadiazol-5-yl}ethyl]benzamide (Compound No. 236),

[237] 3-chloro-4-fluoro-N-[(1S)-2-hydroxy-1-{3-[4-(trifluoromethyl)phenyl]-1,2,4-oxadiazol-5-yl}ethyl]benzamide (Compound No. 237),

[238] N-[(1S)-2-hydroxy-1-{3-[4-(trifluoromethyl)phenyl]-1,2,4-oxadiazol-5-yl}ethyl]-1H-1,2,3-benzotriazole-5-carboxamide (Compound No. 238),

[239] 5-chloro-N-[(1S)-2-hydroxy-1-{3-[4-(trifluoromethyl)phenyl]-1,2,4-oxadiazol-5-yl}ethyl]pyridine-2-carboxamide (Compound No. 239),

[240] N-[(1S)-2-hydroxy-1-{3-[4-(trifluoromethyl)phenyl]-1,2,4-oxadiazol-5-yl}ethyl]imidazo[1,2-a]pyridine-2-carboxamide (Compound No. 240),

[241] (2S)-2-amino-N-[(1S)-2-hydroxy-1-{3-[4-(trifluoromethyl)phenyl]-1,2,4-oxadiazol-5-yl}ethyl]-3-(1H-indol-3-yl)propanamide (Compound No. 241),

[242] 3-chloro-4-fluoro-N-[(1S)-2-hydroxy-1-{3-[3-(trifluoromethyl)phenyl]-1,2,4-oxadiazol-5-yl}ethyl]benzamide (Compound No. 242),

[243] N-[(1S)-2-hydroxy-1-{3-[3-(trifluoromethyl)phenyl]-1,2,4-oxadiazol-5-yl}ethyl]-1H-indole-3-carboxamide (Compound No. 243),

[244] N-[(1S)-2-hydroxy-1-{3-[3-(trifluoromethyl)phenyl]-1,2,4-oxadiazol-5-yl}ethyl]imidazo[1,2-a]pyridine-2-carboxamide (Compound No. 244),

[245] 4-fluoro-N-[(1S)-2-hydroxy-1-[3-(1-methyl-1H-indol-3-yl)-1,2,4-oxadiazol-5-yl]ethyl]benzamide (Compound No. 245),

[246] 4-fluoro-N-[(1S)-2-hydroxy-1-[3-(pyrimidin-2-yl)-1,2,4-oxadiazol-5-yl]ethyl]benzamide (Compound No. 246),

[247] N-[(1S)-1-[3-(5-bromo-1H-indol-3-yl)-1,2,4-oxadiazol-5-yl]-2-hydroxyethyl]-4-fluorobenzamide (Compound No. 247),

[248] 4-fluoro-N-[(1S)-2-hydroxy-1-[3-(5-phenylthiophen-2-yl)-1,2,4-oxadiazol-5-yl]ethyl]benzamide (Compound No. 248),

[249] N-[(1S)-1-[3-(4,5-dichloro-1H-pyrrol-2-yl)-1,2,4-oxadiazol-5-yl]-2-hydroxyethyl]-4-fluorobenzamide (Compound No. 249),

[250] 4-fluoro-N-[(1S)-2-hydroxy-1-[3-(1H-indol-6-yl)-1,2,4-oxadiazol-5-yl]ethyl]benzamide (Compound No. 250),

[251] N-[(1S)-1-[3-(5-chloro-1H-pyrrol-2-yl)-1,2,4-oxadiazol-5-yl]-2-hydroxyethyl]-4-fluorobenzamide (Compound No. 251),

[252] 4-chloro-N-[(1S)-1-[3-(5-chloro-1H-indol-3-yl)-1,2,4-oxadiazol-5-yl]-2-hydroxyethyl]-2-fluorobenzamide (Compound No. 252),

[253] N-[(1S)-1-[3-(5-chloro-1H-indol-3-yl)-1,2,4-oxadiazol-5-yl]-2-hydroxyethyl]-4-(pyrrolidin-1-yl)benzamide (Compound No. 253),

[254] 5-chloro-N-[(1S)-1-[3-(5-chloro-1H-indol-3-yl)-1,2,4-oxadiazol-5-yl]-2-hydroxyethyl]pyridine-2-carboxamide (Compound No. 254),

[255] N-[(1S)-1-[3-(2-chlorofuran-3-yl)-1,2,4-oxadiazol-5-yl]-2-hydroxyethyl]-4-fluorobenzamide (Compound No. 255),

[256] 4-fluoro-N-[(1S)-2-hydroxy-1-{3-[3-(2,2,2-trifluoroacetyl)-1H-indol-6-yl]-1,2,4-oxadiazol-5-yl}ethyl]benzamide (Compound No. 256),

[257] N-[(1S)-1-[3-(3-amino-1H-pyrazol-4-yl)-1,2,4-oxadiazol-5-yl]-2-hydroxyethyl]-4-fluorobenzamide (Compound No. 257),

[258] N-[(1S)-1-[3-(5-amino-1H-imidazol-4-yl)-1,2,4-oxadiazol-5-yl]-2-hydroxyethyl]-4-fluorobenzamide (Compound No. 258),

[259] 4-fluoro-N-[(1S)-2-hydroxy-1-[3-(6-hydroxy-1,3-benzothiazol-2-yl)-1,2,4-oxadiazol-5-yl]ethyl]benzamide (Compound No. 259),

[260] 4-fluoro-N-[(1S)-1-[3-(6-fluoro-1H-indol-3-yl)-1,2,4-oxadiazol-5-yl]-2-hydroxyethyl]benzamide (Compound No. 260),

[261] 4-fluoro-N-[(1S)-2-hydroxy-1-[3-(5-methoxy-1H-indol-3-yl)-1,2,4-oxadiazol-5-yl]ethyl]benzamide (Compound No. 261),

[262] 4-fluoro-N-[(1S)-2-hydroxy-1-{3-[5-(trifluoromethyl)-H-indol-3-yl]-1,2,4-oxadiazol-5-yl}ethyl]benzamide (Compound No. 262),

[263] N-[(1S)-1-[3-(6-chloro-1H-indol-3-yl)-1,2,4-oxadiazol-5-yl]-2-hydroxyethyl]-4-fluorobenzamide (Compound No. 263),

[264] 4-fluoro-N-[(1S)-2-hydroxy-1-{3-[1-(2-hydroxyethyl)-1H-indol-3-yl]-1,2,4-oxadiazol-5-yl}ethyl]benzamide (Compound No. 264),

[265] 4-fluoro-N-[(1S)-2-hydroxy-1-[3-(1H-indazol-3-yl)-1,2,4-oxadiazol-5-yl]ethyl]benzamide (Compound No. 265),

[266] 4-fluoro-N-[(1S)-2-hydroxy-1-[3-(1H-indol-2-yl)-1,2,4-oxadiazol-5-yl]ethyl]benzamide (Compound No. 266), and

[267] 4-fluoro-N-[(1S)-1-[3-(5-fluoro-1H-indol-2-yl)-1,2,4-oxadiazol-5-yl]-2-hydroxyethyl]benzamide (Compound No. 267).

The compound used in the present embodiment is more preferably selected from the group consisting of Compound Nos. 2, 5 to 7, 9, 11 to 13, 17 to 20, 23 to 28, 32 to 34, 38 to 43, 45, 46, 48 to 50, 52 to 55, 58, 61 to 69, 71 to 78, 80, 81, 83 to 85, 87, 89 to 94, 96, 97, 99 to 104, 106, 107, 110, 112, 114, 116 to 119, 121, 125 to 133, 142 to 148, 150 to 153, 156 to 158, 161 to 170, 172, 175 to 179, 181 to 212, 214, 215, 217, 218, 220 to 227, 229 to 239, 242, and 245 to 267. The above compounds have strong inhibitory effect against amyloid fibril formation.

The compound used in the present embodiment is particularly preferably selected from the group consisting of Compound Nos. 18, 25, 32, 39, 40, 63, 69, 72, 73, 78, 80, 83, 92 to 94, 101, 114, 116, 125, 129, 130, 132, 133, 143, 144, 146, 150, 157, 164, 165, 167, 168, 172, 175 to 177, 183, 188, 192, 195, 196, 198, 199, 201, 203, 207, 209 to 211, 220 to 222, 224, 232, 236, 237, 266 and 267. The above compounds have particularly strong inhibitory effect against amyloid fibril formation.

The compounds of compound numbers 1 to 133 and 142 to 267 can be synthesized by methods of chemical synthesis described in Examples below and other methods of chemical synthesis corresponding thereto in combination with various methods conventionally known, as appropriate, as Compounds (I) to (III) in the first embodiment can. Alternatively, when they are selected from commercially available compounds, such commercially available compounds may be purchased.

The amyloid fibril formation inhibitor of this embodiment may encompass those comprising particular compounds listed above as well as those comprising pharmaceutically acceptable salts of compounds listed above or solvates thereof. "Pharmaceutically acceptable salts" and "solvates" in this embodiment are as defined in the first embodiment.

The amyloid fibril formation inhibitor of this embodiment may be prepared in the same way as the amyloid fibril formation inhibitor of the first embodiment is prepared except that the particular compounds listed above are used for Compounds (I) to (III) in the first embodiment. Here, Compounds 23, 24, 26 to 28, 32, 33, 34, 41 to 45, 47, 48 to 56, 58 to 62, 64 to 67, 72 to 74, 77, 79, 82, 84, 85, 90, 103, 121 to 124, and 131 are compounds having a structure represented by the general formula (I), Compounds 1 to 17, 19 to 22, 29 to 31, 35 to 36, 39, 46, 57, 63, 68 to 71, 75, 76, 78, 80, 81, 83, 86 to 88, 91 to 100, 102, 104 to 109, 112, 113, 115 to 120, 125 to 130, 132, 133, and 142 to 267 are compounds having a structure represented by the general formula (II), and Compounds 18, 25, 37, 38, 40, 89, 101, 110, 111, and 114 are compounds having a structure represented by the general formula (III).

According to the third embodiment, the present invention is a therapeutic or preventive agent for a neurodegenerative disease, comprising the aforementioned amyloid fibril formation inhibitor. The therapeutic or preventive agent for a neurodegenerative disease according to this embodiment comprises an amyloid fibril formation inhibitor comprising a single compound or a mixture of 2 or more compounds chosen from compounds represented by Compounds (I) to (III) or compounds selected from compound numbers 1 to 133 and 142 to 267 or pharmaceutically acceptable salts thereof or solvates thereof and an optional component. The optional component here may be a usual pharmaceuticals component and the agent may be prepared in forms usually used, for example, a tablet, a capsule, a powder, a granule, a solution, or the like. The therapeutic or preventive agent for a neurodegenerative disease according to this embodiment may further comprise another active ingredient for treatment or prevention of a neurodegenerative disease as an optional component.

In this embodiment, "treatment" may mean preventing or mitigating progression and exacerbation of the disease condition in an animal with a neurodegenerative disease and includes not only complete curing of the disease but also mitigation of symptoms of the disease. "Prevention" may mean preventing an animal that is at risk of a neurodegenerative disease from being affected by the disease.

In this embodiment, "neurodegenerative diseases" may mean diseases associated with degeneration of neural tissue in connection with (or caused by) the formation of aggregation of Aβ and amyloid fibrils in general. The neurodegenerative diseases are not particularly limited, but examples thereof include Alzheimer's disease, Parkinson's disease, Down's syndrome, cerebral amyloid angiopathy, and Huntington's disease.

The neurodegenerative disease targeted by the therapeutic or preventive agent of this embodiment is preferably Alzheimer's disease. "Alzheimer's disease" encompasses not only what is called Alzheimer's disease (sporadic Alzheimer's disease), but also familial (hereditary) Alzheimer's disease.

The animal targeted by the therapeutic or preventive agent of this embodiment may be, for example, a mammal, such as a mouse, a rat, a rabbit, a dog, a cow, a pig, a sheep, a nonhuman primate, and a human, and preferably a human.

The therapeutic or preventive agent for a neurodegenerative disease according to this embodiment is useful for radical treatment or prevention of neurodegenerative diseases associated with the formation of amyloid fibrils.

According to the fourth embodiment, the present invention is compounds selected from the group consisting of compounds of compound numbers 1 to 133 and 142 to 267 or pharmaceutically acceptable salts thereof or solvates thereof.

The compounds of this embodiment are preferably selected from the group consisting of compound numbers 1, 3 to 6, 9, 11 to 22, 25, 29 to 41, 45 to 49, 51 to 58, 60, 62, 63, 65 to 76, 78 to 133, and 142 to 267.

The compounds of this embodiment can be synthesized by methods of chemical synthesis described in Examples below and other methods of chemical synthesis corresponding thereto in combination with various methods conventionally known to be appropriate.

"Pharmaceutically acceptable salts" and "solvates" in this embodiment are as defined in the first embodiment.

The compounds according to this embodiment or pharmaceutically acceptable salts thereof or solvates thereof can inhibit polymerization of Aβ onto GAβ and suppress the formation of amyloid fibrils. Therefore, it is useful for applications such as treatment or prevention of diseases related to the formation of amyloid fibrils.

EXAMPLES

The present invention is further described by way of Examples below. Such Examples are not intended to limit the present invention.

<1. Screening for Compounds that Suppress Formation of Amyloid Fibrils>

To find compounds that specifically recognize GAβ and suppress formation of amyloid fibrils, virtual screening with a molecular docking simulation program DOCK4 (http://dock.compbio.ucsf.edu/) was conducted. For conducting virtual screening, a GAβ complex model was first constructed by molecular dynamics simulation. Structures of sugar chain regions in the GM1 molecule, which are considered to be involved in the binding with Aβ, were optimized based on a molecular orbital calculation, and partial electric charges were assigned for respective atoms. The three-dimensional coordinate data and the values of the partial electric charges of respective atoms in these optimized structures were incorporated into the ff99 parameter set of an empirical force field used in AMBER, and a 5-ns molecular dynamics calculation was conducted in a molecule system in which water molecules were placed. A molecular dynamics calculation of the sugar chain regions in GM1 was conducted and trajectory poses were sampled. Using the obtained trajectory poses, docking with the 3D structure of Aβ40 registered in Protein Data Bank (PDB ID: 1AML) was conducted. As a result of the docking, 2,000,000 docking poses were obtained. Among these, docking poses that have little structural distortion and are energetically most stable were extracted and used as an atomic model of GAβ. A 20-ns molecular dynamics calculation was conducted using the above atomic model of GAβ as an initial structure, structure clustering was conducted based on the positional information of the main chain Ca atoms of Aβ, and promising structures for the pocket to which the compound bind were extracted from the obtained representative structures. Meanwhile, compounds that are not preferable in molecular weight or physical property and those that fit certain conditions, such as having a highly reactive substituent, were excluded and a database of 400,000 compounds was constructed. This database was virtually screened by the docking technique using the 3D structure of GAβ obtained as described above. As a result, 321 virtual hit compounds were obtained.

Compounds narrowed down from commercially available compounds as described above were evaluated for their activity to inhibit the GAβ-dependent amyloid fibril formation in an in vitro reconstituted system described below. As a result, it was suggested that compounds represented by the following general formula (I):

[Formula 7]

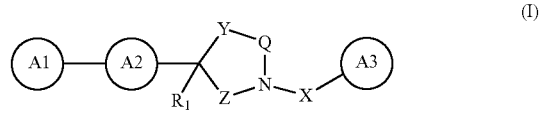

(I)

a general formula (II):

[Formula 8]

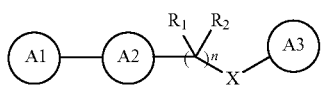

and a general formula (III):

[Formula 9]

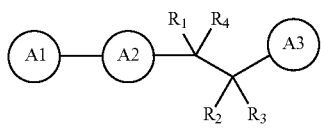

were hit compounds of highest preference among a series of hit compounds and have activity to inhibit the GAβ-dependent amyloid fibril formation. Subsequently, a similarity search for compounds having the inhibitory activity was conducted and the activity to inhibit the GAβ-dependent amyloid fibril formation was evaluated. As a result, it was revealed that compounds represented by the general formula (I) to (III) have the activity to inhibit the GAβ-dependent amyloid fibril formation.

<2. Selection of the Commercially Available Compounds (Compounds 2, 7, 8, 10, 23, 24, 26 to 28, 42 to 44, 50, 59, 61, 64 and 77)>

The commercially available compounds having the structures depicted by general expressions (I) to (III) were purchased from Enamine, UORSY, Ambinter, and others.

<3. The Synthesis of the Novel Compounds (Compounds 1, 3 to 6, 9, 11 to 22, 25, 29 to 41, 45 to 49, 51 to 58, 60, 62, 63, 65 to 76, 78 to 133, and 142 to 267)>

Then, the novel compounds having the structures depicted by general expressions (I) to (III) were synthesized. The instruments and the measurement conditions were adopted for the synthesis as follows.

$^1$H NMR spectra was measured by using Bruker Avance or Bruker Varian (400 MHz or 500 MHz). TMS (tetramethyl silane) was used as an internal standard.

LC/MS analysis was performed by using LCMS-2010 (Shimazu Seisakusho) equipped with ESI (+) ion mode and APCI (+) ion mode and (−) ion mode. Column: Shim-pack XR-ODS (3.0×30 mm, 2.2 m), flow rate: 0.3 to 0.8 mL/min, run time: 3 to 5 minutes, detection wavelength: 220 nm, oven temperature: 40 to 50° C.

Prep-HPLC was carried out under the following conditions. Silica gel column: Fuji C 18 (300×25), YMC 250×20; wavelength: 220 nm; mobile phase A: acetonitrile (0.1% HCl); mobile layer B: water; flow rate condition: 25 mL/min, injection volume: 2 mL, run time: 20 minutes; equilibration time: 3 minutes.

The melting point was measured by using a melting point measuring instrument SMP-300 (manufactured by Synix Corporation).

Abbreviations used in the following examples are as follows.
DIEA: Diisopropylethylamine
HATU: 2-(1H-7-azabenzotriazol-1-yl)-1,1,3,3-tetramethyluronium hexafluorophosphate
DCM: dichloromethane
DMF: N,N-dimethylformamide
TFA: trifluoroacetic acid
THF: tetrahydrofuran
CDI: 1,1'-carbonyldiimidazole
TBS: tert-butyldimethylsilyl
TBAF: tetrabutylammonium fluoride
Pd(Ac)$_2$: palladium acetate
BINAP: 2,2'-bis (diphenylphosphino) 1,1'-binaphthyl
DMP: Dess Martin Periodinane
DMT-MM: 4-(4,6-dimethoxy-1,3,5-triazin-2-yl)-4-methylmorpholinium chloride
DAIB: diacetoxyiodobenzene
DMAP: 4-(N,N-dimethylamino) pyridine
HOBt: 1-hydroxybenzotriazole Synthesis of N-(3-chlorophenyl)-2-{3-(4-methoxyphenyl)-1,2,4-oxadiazol-5-yl}-N-propylacetamide (Compound 1)

[Formula 10]

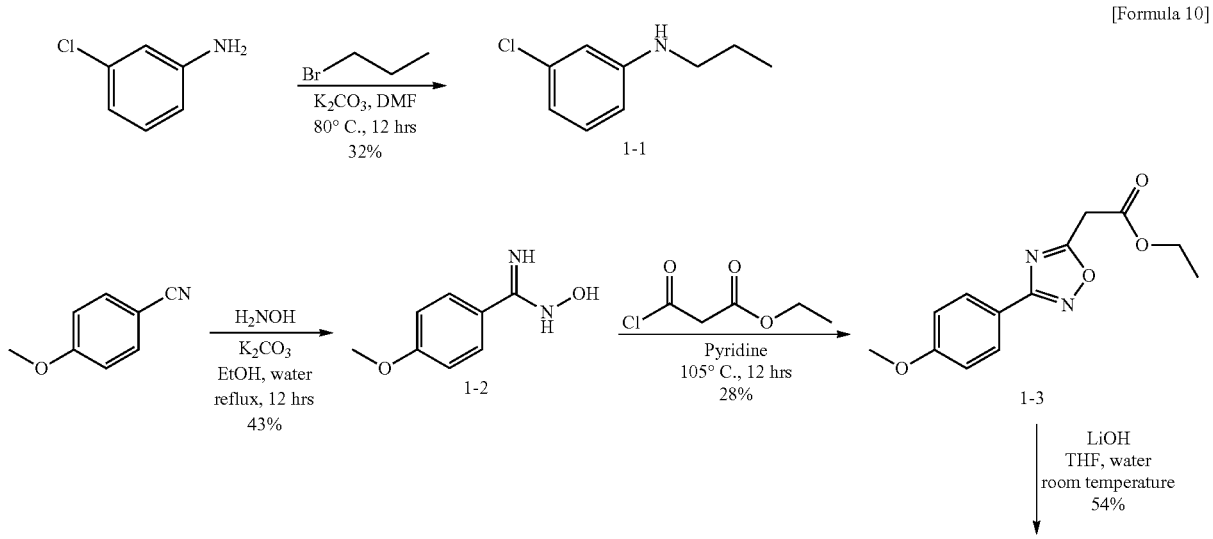

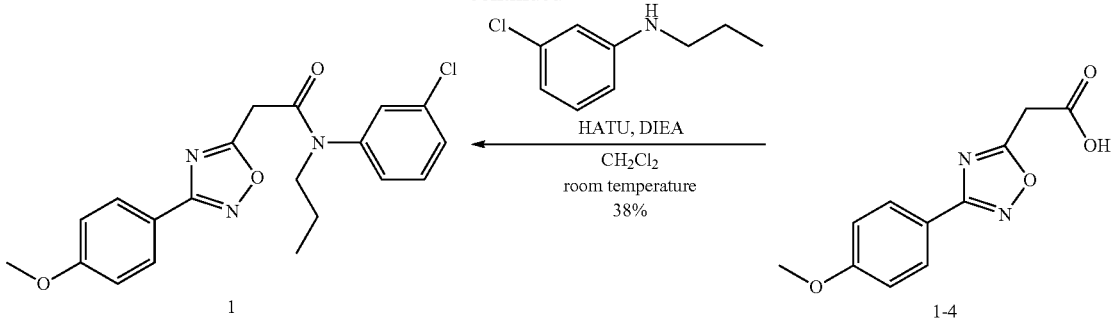

(1-1) Synthesis of 3-chloro-N-propylaniline (Compound 1-1)

To a stirred solution of 3-chloroaniline (1 mL) and bromopropane (1 mL) in DMF (20 mL) was added potassium carbonate (3.9 g), and the mixture was stirred at 80° C. for 12 hours. After cooling to room temperature, the mixture was diluted by ethyl acetate (20 mL) and the whole was washed with saturated brine (20 mL×2) and dried over anhydrous sodium sulfate. The filtrate was evaporated in vacuo and the resulting residue was purified by silica gel column chromatography eluting with hexane and ethyl acetate to give 3-chloro-N-propyl aniline (500 mg, yield 32%).

(1-2) Synthesis of N-hydroxy-4-methoxybenzimidamide (Compound 1-2)

To a stirred solution of 4-methoxybenzonitrile (1 g) in ethanol (20 mL) was added hydroxylamine HCl salt (2.3 g), and then aqueous solution (15 mL) of potassium carbonate (6.26 g) at room temperature. The solution was heated under reflux for 12 hours. After cooling to room temperature, ethyl acetate (20 mL) was added and the whole was washed with saturated brine (20 mL×2), dried over anhydrous sodium sulfate. The filtrate was evaporated in vacuo, and the residue was purified by silica gel column chromatography eluting with hexane-ethyl acetate to give the title compound (650 mg, yield 43%).

(1-3) Synthesis of ethyl 2-[3-(4-methoxyphenyl)-1,2,4-oxadiazole-5-yl] acetate (Compound 1-3)

To a stirred solution of N-hydroxy-4-methoxybenzimidamide (500 mg) in pyridine (20 mL) was added ethyl 3-chloro-3-oxopropionate (0.7 mL) at room temperature. The solution was heated at 105° C. for 12 hours. After cooling to room temperature, ethyl acetate (40 mL) was added and the whole was washed with saturated aqueous solution of ammonium chloride (20 mL×3), dried over anhydrous sodium sulfate. The filtrate was evaporated in vacuo, and the residue was purified by silica gel column chromatography eluting with hexane-ethyl acetate to give the title compound (270 mg, yield 28%).

(1-4) Synthesis of 2-[3-(4-methoxyphenyl)-1,2,4-oxadiazole-5-yl] acetic acid (Compound 1-4)

To a stirred solution of ethyl 2-[3-(4-methoxyphenyl)-1,2,4-oxadiazole-5-yl] acetate (270 mg) in THF (5 mL) was added aqueous solution (2 mL) of LiOH (820 mg). After stirring overnight at room temperature, the precipitate was filtered off. To the filtrate was added 10% aqueous solution of NaOH (20 mL), and the solution was washed with ethyl acetate (20 mL×2). The aqueous layer was acidified (less than or equal to pH 2) with 10% aqueous HCl solution, and the whole was extracted with ethyl acetate (20 mL×3). The ethyl acetate layer was dried over anhydrous sodium sulfate. The filtrate was evaporated in vacuo to obtain the title compound (130 mg, yield 54%).

(1-5) Synthesis of N-(3-chlorophenyl)-2-[3-(4-methoxyphenyl)-1,2,4-oxadiazole-5-yl]-N-propyl acetamide (Compound 1)

To a stirred solution of 2-[3-(4-methoxyphenyl)-1,2,4-oxadiazole-5-yl] acetic acid (66 mg), 3-chloro-N-propyl aniline (40 mg) and DIEA (0.12 mL) in methylene chloride (3 mL) was added HATU (134 mg) at room temperature. After stirring overnight at room temperature, the reaction mixture was diluted with methylene chloride (20 mL), and the whole was washed with saturated brine (20 mL×3). The organic layer was dried over anhydrous sodium sulfate, and the filtrate was evaporated in vacuo. The residue was purified by silica gel chromatography eluting with hexane-ethyl acetate to obtain the title compound (30 mg, yield 33%).

The compounds 3 to 6, 9, 11 to 17, 19, 70, and 71 were prepared by the same method as described above.

Synthesis of 4-chloro-N-methyl-N-(2-{3-[4-(trifluoromethoxy)phenyl]-1,2,4-oxadiazole-5-yl}propan-2-yl)benzamide (Compound 21)

[Formula 11]

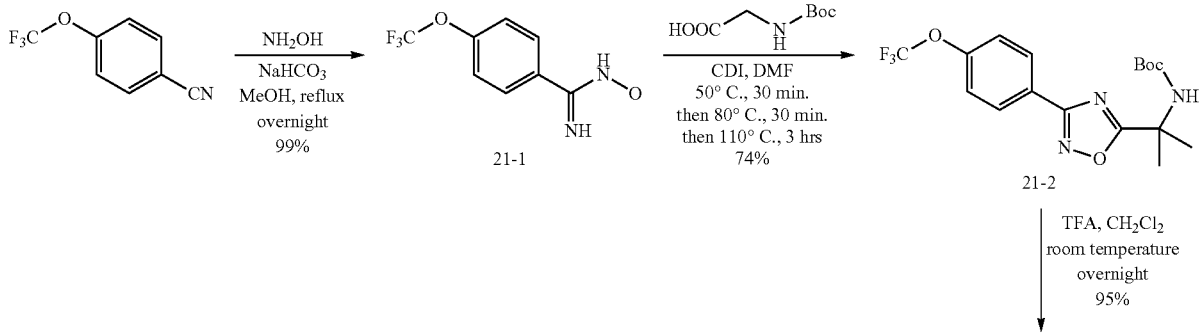

-continued

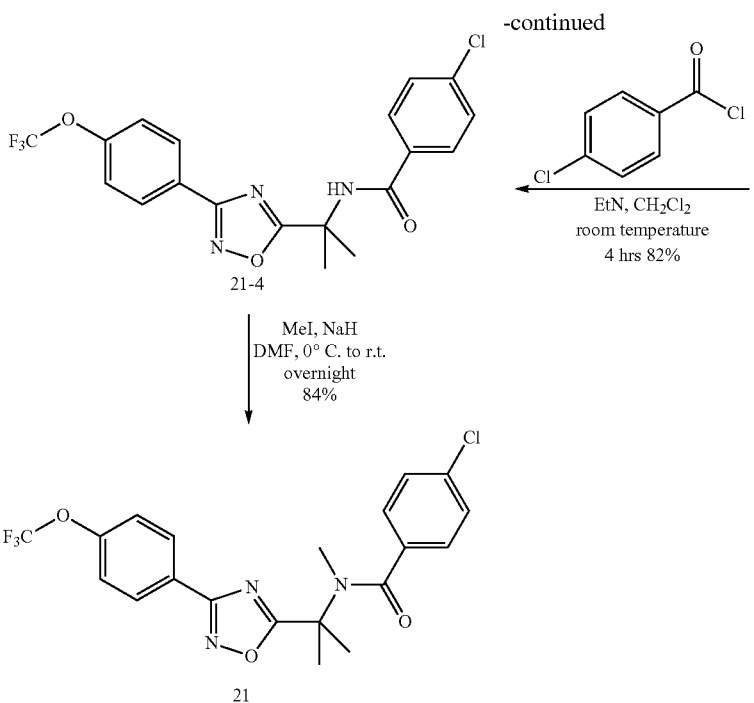
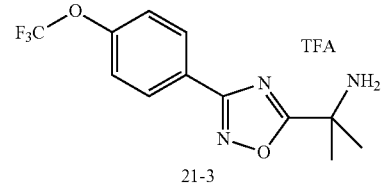

(21-1) Synthesis of N'-hydroxy-4-(trifluoromethoxy)benzimidamide (Compound 21-1)

To a stirred solution of 4-trifluoromethoxybenzonitrile (5 g) in methanol (50 mL) was added potassium carbonate (3.4 g) and hydroxylamine HCl salt (2.04 g) at room temperature. The solution was heated under reflux for 18 hours. After cooling to room temperature, methanol was evaporated in vacuo, and water (50 mL) was added to the residue. The precipitates were collected by filtration and dried thoroughly to obtain the title compound (6.2 g, yield 99%).

(21-2) Synthesis of tert-butyl(2-{3-[4-(trifluoromethoxy)phenyl]-1,2,4-oxadiazole-5-yl}propan-2-yl)carbamate (Compound 21-2)

To a stirred solution of N'-hydroxy-4-(trifluoromethoxy)benzimidamide (1 g) and 2-[(tert-butoxycarbonyl)amino]-2-methylpropionic acid (0.92 g) in DMF (20 mL) was added 1,1'-carbonyldiimidazole (0.81 g) at room temperature. The reaction mixture was heated at 80° C. for 30 minutes, and at 110° C. for 3 hours. After cooling to room temperature, water (50 mL) was added to the mixture. The whole was extracted with ethyl acetate (30 mL×3), and the organic layer was washed with saturated brine (50 mL). The organic layer was dried over anhydrous sodium sulfate, and the filtrate was evaporated in vacuo. The obtained residue was purified by silica gel column chromatography eluting with hexane-ethyl acetate to obtain the title compound (1.3 g, yield 74%).
Ms m/z (APCI) [M−H]−=386.

(21-3) Synthesis of 2-{3-[4-(trifluoromethoxy)phenyl]-1,2,4-oxadiazole-5-yl}propan-2-amine trifluoroacetic acid salt (Compound 21-3)

To a stirred solution of tert-butyl(2-{3-[4-(trifluoromethoxy)phenyl]-1,2,4-oxadiazole-5-yl}propan-2-yl)carbamate (4 g) in methylene chloride (40 mL) was added trifluoroacetic acid (4 mL) at room temperature. After stirring for 18 hours at room temperature, volatiles were evaporated in vacuo to obtain the title compound, which was used for the next reaction without further purification.

(21-4) Synthesis of 4-chloro-N-(2-{3-[4-(trifluoromethoxy)phenyl]-1,2,4-oxadiazole-5-yl}propan-2-yl)benzamide (Compound 21-4)

To a stirred solution of 2-{3-[4-(trifluoromethoxy)phenyl]-1,2,4-oxadiazole-5-yl}propan-2-amine trifluoroacetic acid salt (4 g) in methylene chloride (30 mL) was added trimethylamine (5.7 mL), followed by 4-chlorobenzoyl chloride (1.44 mL) under ice cooling. After stirring for 4 hours at room temperature, saturated aqueous solution of sodium hydrogen carbonate (50 mL) was added to the reaction mixture and then partitioned. The aqueous layer was extracted with methylene chloride (30 mL×2), and the combined organic layer was washed with saturated brine (50 mL). The organic layer was dried over anhydrous sodium sulfate, and the filtrate was evaporated in vacuo. The residue was purified by silica gel column chromatography eluting with hexane-ethyl acetate to obtain the title compound (2 g, yield 46%).
Ms m/z (APCI) [M+H]+=346.

(21-5) Synthesis of 4-chloro-N-methyl-N-(2-{3-[4-(trifluoromethoxy)phenyl]-1,2,4-oxadiazole-5-yl}propan-2-yl)benzamide (Compound 21)

To a stirred solution of sodium hydride (643 mg, 60% mineral oil dispersion) in dehydrated DMF (10 ML) was added a solution of 4-chloro-N-(2-{3-[4-(trifluoromethoxy)phenyl]-1,2,4-oxadiazole-5-yl}propan-2-yl)benzamide (3.8 g) in dehydrated DMF (40 mL) at room temperature in a dropwise manner. After stirring for 18 hours at room temperature, water (100 mL) was poured into the reaction mixture to stop the reaction. The whole was extracted with ethyl acetate (50 mL×3), the combined organic layer was washed with saturated brine (30 mL×2), and then dried over anhydrous sodium sulfate. The filtrate was evaporated in vacuo to obtain the crude product, and it was recrystallized from ethyl acetate/hexane to obtain the title compound (3.28 g, yield 84%).

The compounds 20, 22, 29 to 31, 35, and 36 were prepared by the same method as described above.

Synthesis of (S)-2-(1H-indole-3-yl)-1-[3-(4-trifluoromethoxyphenyl)-1,2,4-oxadiazole-5-yl]ethane-1-amine (Compound 25)

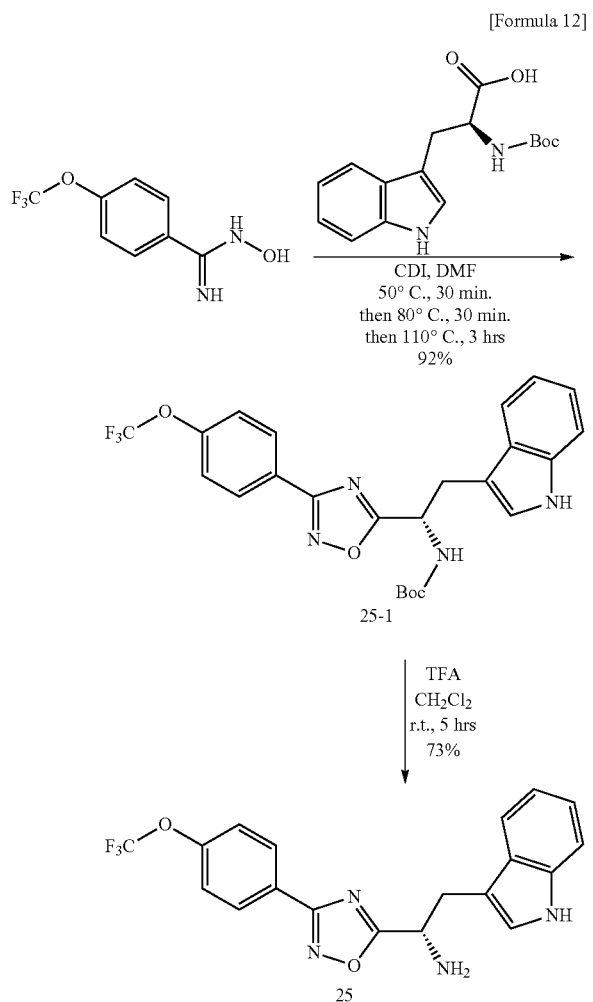

(25-1) Synthesis of tert-butyl (S)-2-(1H-indole-3-yl)-1-{3-[4-(trifluoromethoxyphenyl)-1,2,4-oxadiazole-5-yl]ethyl}carbamate (Compound 25-1)

To a stirred solution of N'-hydroxy-4-(trifluoromethoxy)benzimidamide (440 mg) and Boc-L-tryptophan (608 mg) in DMF (6 mL) was added 1,1'-carbonyldiimidazole (357 mg) at room temperature. The reaction mixture was heated at 50° C. for 30 minutes, 80° C. for 30 minutes, and then 110° C. for 3 hours. After cooling to room temperature, water (50 mL) was poured into the reaction mixture, and the whole was extracted with ethyl acetate (40 mL×3). The combined organic layer was washed with saturated brine (50 mL), dried over anhydrous sodium sulfate. The filtrate was evaporated in vacuo and the residue was purified by silica gel column chromatography eluting with hexane-ethyl acetate to obtain the title compound (916 mg, yield 92%).

(25-2) Synthesis of (S)-2-(1H-indole-3-yl)-1-[3-(4-trifluoromethoxy)phenyl]-1,2,4-oxadiazole-5-yl]ethane-1-amine (Compound 25)

To a stirred solution of tert-butyl (S)-2-(1H-indole-3-yl)-1-{3-[4-(trifluoromethoxyphenyl)-1,2,4-oxadiazole-5-yl]ethyl}carbamate (916 mg) in methylene chloride (7 mL) was added trifluoroacetic acid (1.5 mL) at room temperature. After stirring for 5 hours at room temperature, volatiles were removed in vacuo, and the residue was recrystallized from ethyl acetate to obtain the title compound (519 mg, yield 73%).

The compounds 37, 38 and 40 were prepared by the same method as described above.

Synthesis of 1-(3-chlorophenyl)-4-{3-[4-(trifluoromethoxy)phenyl]-1,2,4-oxadiazole-5-yl}pyrrolidin-2-one (Compound 27)

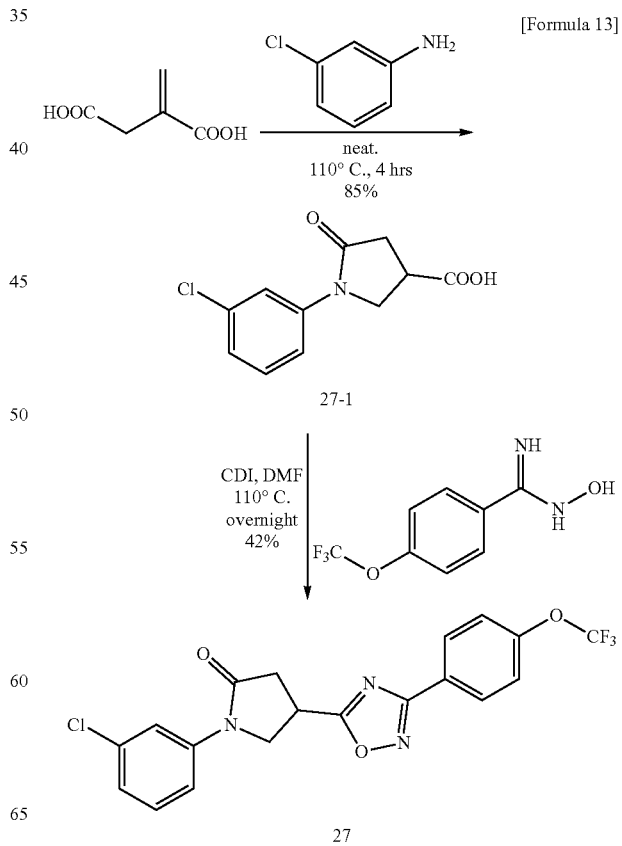

(27-1) Synthesis of 1-(3-chlorophenyl)-5-oxopyrrolidine-3-carboxylic acid (Compound 27-1)

The mixture of itaconic acid (520 mg, 4 mmol) and 3-chloroaniline (418 μL, 4 mmol) was heated at 120° C. overnight. After removal of the solvent in vacuo, the residue was purified by silica gel column chromatography eluting with hexane-ethyl acetate to obtain the title compound (877 mg, yield 92%).

(27-2) Synthesis of 1-(3-chlorophenyl)-4-{3-[4-(trifluoromethoxy)phenyl]-1,2,4-oxadiazol-5-yl}pyrrolidin-2-one (Compound 27)

To a stirred solution of 1-(3-chlorophenyl)-5-oxopyrrolidine-3-carboxylic acid (566 mg, 2.4 mmol) in N,N-dimethylformamide (7.1 mL) was added 1,1'-carbonyldiimidazole (423 mg, 2.6 mmol), and the mixture was heated at 50° C. for 30 minutes. Then N'-hydroxy-4-(trifluoromethoxy)benzene-1-carboxyimidamide (573 mg, 2.6 mmol) was added to the mixture, and the whole was heated and stirred at 110° C. overnight. After cooling to room temperature, water was added to the mixture to stop the reaction, and the whole was extracted with ethyl acetate. The combined extract was washed with saturated brine, dried over anhydrous magnesium sulfate. The filtrate was evaporated in vacuo, and the residue was purified by silica gel column chromatography eluting with hexane-ethyl acetate to obtain the title compound, which was recrystallized from diethyl ether-hexane (9:1) to obtain the title compound (420 mg, yield 42%).

The compounds 32, 33, 45, 48, 49, 51, 52, 54, 65 to 67, 74 and 79 were prepared by the same method as described above.

Synthesis of (4-Chlorophenyl)((2S,4R)-4-hydroxy-2-[3-{4-(trifluoromethoxy)phenyl}-1,2,4-oxazol-5-yl]pyrrolidin-1-yl)methanone (Compound 34)

[Formula 14]

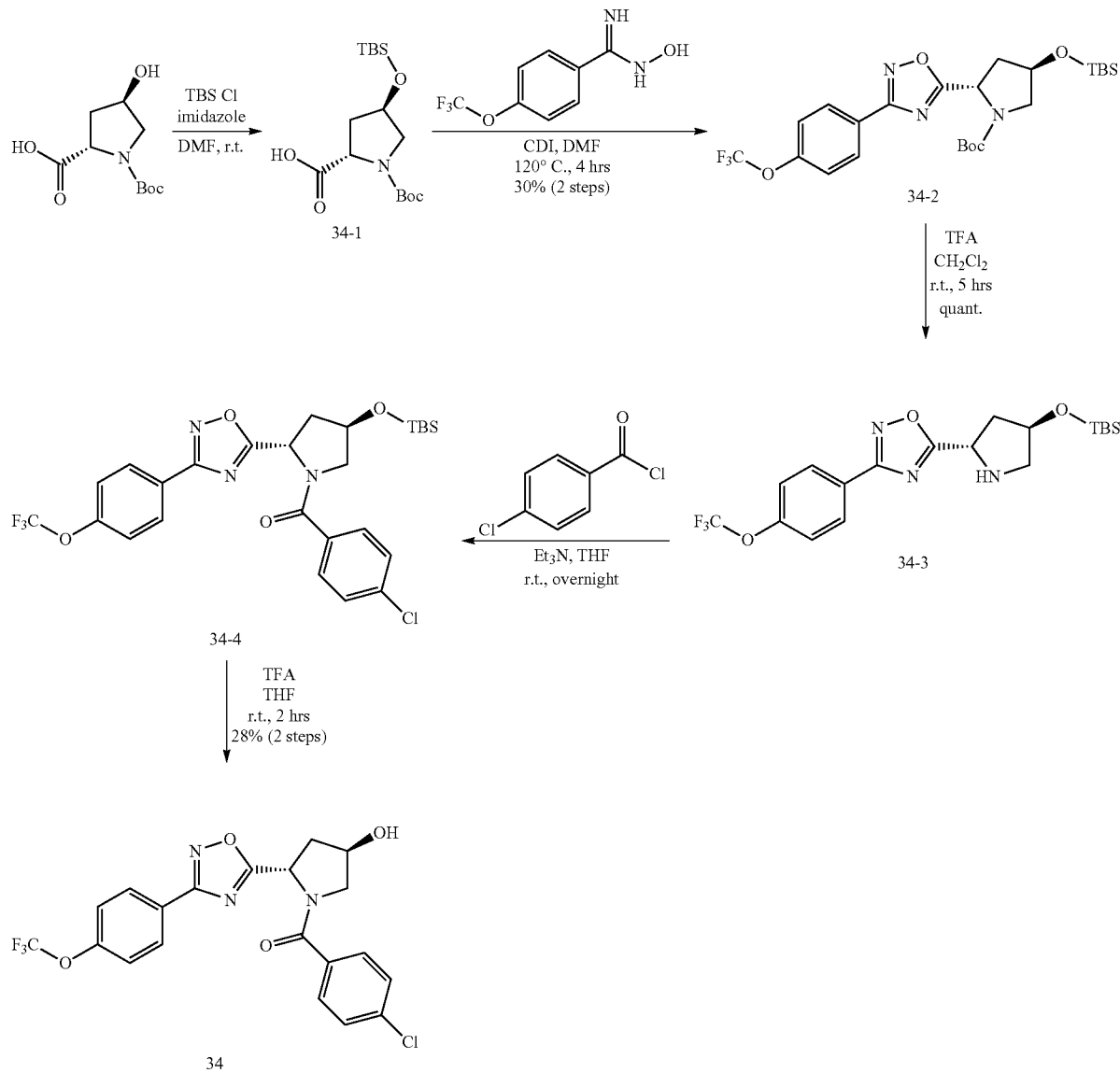

(34-1) Synthesis of N-[(tert-butoxy)carbonyl]-(4R)-4-[(tert-butyldimethylsilyl)oxy]-L-proline (Compound 34-1)

To a stirred solution obtained by dissolving a mixture containing N-[(tert-butoxy)carbonyl]-(4R)-4-hydroxy-L-proline (less than or equal to 15.2 mmol) in N,N-dimethylformamide (10 mL), was added imidazole (2.0 g, 29.4 mmol) and tert-butyldimethylsilyl chloride (2.9 g, 19.2 mmol), followed by stirring at room temperature overnight. Aqueous solution of ammonium chloride was added to the reaction mixture, and the whole was extracted with ethyl acetate. The combined extract was washed with saturated brine, dried over anhydrous magnesium sulfate. The filtrate was evaporated in vacuo to obtain the title compound as a crude product.

(34-2) Synthesis of tert-butyl (2S,4R)-4-[(tert-butyldimethylsilyl)oxy]-2-{3-[4-(trifluoromethoxy)phenyl]-1,2,4-oxadiazol-5-yl}pyrrolidine-1-carboxylate (Compound 34-2)

To a stirred solution of crude N-[(tert-butoxy)carbonyl]-(4R)-4-[(tert-butyldimethylsilyl)oxy]-L-proline obtained above in N,N-dimethylformamide (50 mL) was added 1,1'-carbonyldiimidazole (1.1 g, 6.6 mmol). After stirring for 30 minutes at 50° C., N'-hydroxy-4-(trifluoromethoxy)benzene-1-carboxyimidamide (1.9 g, 8.6 mmol) was added to the mixture, and stirred at 120° C. for 3.5 hours. Then, N-[(tert-butoxy)carbonyl]-(4R)-4-[(tert-butyldimethylsilyl)oxy]-L-proline (310 mg, 0.9 mmol) and 1,1'-carbonyldiimidazole (143 mg, 6.6 mmol) was added to the reaction mixture and the whole was heated and stirred at 120° C. for 1.5 hours. After cooling to room temperature, water was added to the reaction mixture to stop the reaction, and the whole was extracted with ethyl acetate. The combined extract was washed with saturated brine, dried over anhydrous magnesium sulfate. The filtrate was evaporated in vacuo, and the residue was purified by silica gel column chromatography eluting with hexane-ethyl acetate to obtain the title compound (1.9 g, yield 42%).

Ms m/z (APCI) [M+H]+=530, Ms m/z (APCI) [M−H]−=528.

(34-3) Synthesis of 5-{(2S,4R)-4-[(tert-butyldimethylsilyl)oxy]pyrrolidin-2-yl}-3-[4-(trifluoromethoxy)phenyl]-1,2,4-oxadiazole (Compound 34-3)

To a stirred solution of tert-butyl (2S,4R)-4-[(tert-butyldimethylsilyl)oxy]-2-{3-[4-(trifluoromethoxy)phenyl]-1,2,4-oxadiazol-5-yl}pyrrolidine-1-carboxylate (1.8 g, 3.4 mmol) in dichloromethane (36 mL) was added trifluoroacetic acid (4 mL) in a dropwise manner under ice cooling. The mixture was stirred at the same temperature for 1 hour, and then at room temperature for 4 hours. Aqueous solution of sodium hydrogen carbonate was added to the mixture, to stop the reaction and the whole was extracted with dichloromethane. The combined extract was dried over anhydrous magnesium sulfate, and concentrated in vacuo to obtain the title product (1.45 g, quantitative yield).

Ms m/z (APCI) [M+H]+=430, Ms m/z (APCI) [M−H]−=428.

(34-4) Synthesis of 5-{(2S,4R)-4-[(tert-butyldimethylsilyl)oxy]-1-(4-chlorobenzoyl)pyrrolidin-2-yl}-3-[4-(trifluoromethoxy)phenyl]-1,2,4-oxadiazole (Compound 34-4)

To a stirred solution of the crude 5-{(2S,4R)-4-[(tert-butyldimethylsilyl)oxy]pyrrolidin-2-yl}-3-[4-(trifluoromethoxy)phenyl]-1,2,4-oxadiazole obtained above in tetrahydrofuran (8 mL) was added trimethylamine (167 μL, 1.2 mmol) and 4-chlorobenzoyl chloride (128 μL, 1 mmol), and the mixture was stirred overnight at room temperature. Aqueous solution of ammonium chloride was added to the mixture to stop the reaction, and the whole was extracted with ethyl acetate. The combined extract was washed with saturated brine, dried over anhydrous magnesium sulfate, and concentrated in vacuo. The obtained residue was purified by silica gel column chromatography eluting with hexane-ethyl acetate to obtain the title compound as a crude product.

(34-5) Synthesis of (3R,5S)-1-(4-chlorobenzoyl)-5-{3-[4-(trifluoromethoxy)phenyl]-1,2,4-oxadiazol-5-yl}pyrrolidin-3-ol (Compound 34)

The crude 5-{(2S,4R)-4-[(tert-butyldimethylsilyl)oxy]-1-(4-chlorobenzoyl)pyrrolidin-2-yl}-3-[4-(trifluoromethoxy)phenyl]-1,2,4-oxadiazole obtained above was dissolved in 1 mol/L tetrahydrofuran solution of tetrabutylammonium fluoride (2.4 mL), and the mixture was stirred at room temperature for 2 hours. Water was added to the mixture to stop the reaction, and the whole was extracted with ethyl acetate. The combined extract was washed with saturated brine, dried over anhydrous magnesium sulfate, and concentrated in vacuo. The obtained residue was purified by silica gel column chromatography eluting with hexane-ethyl acetate followed by recrystallization to obtain the title product (100 mg, yield 28% via 2 steps).

The compounds 47, 55, 56, 58, 60, 82, 84, 85 and 131 were prepared by the same method as described above.

Synthesis of (S)-4-chloro-N-(2-hydroxy-1-{3-[4-(trifluoromethoxy)phenyl]-1,2,4-oxadiazol-5-yl}ethyl)benzamide (Compound 39)

[Formula 15]

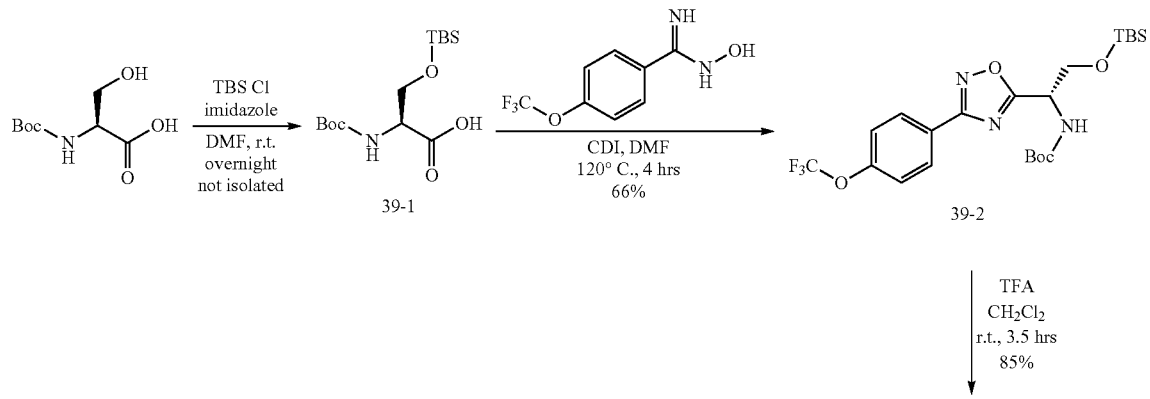

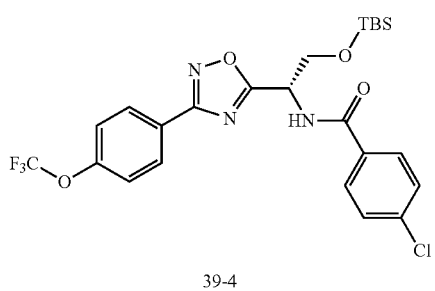
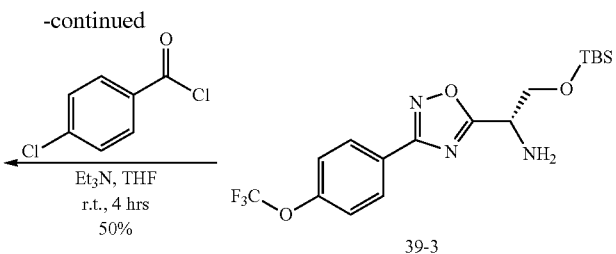

39-4

39-3

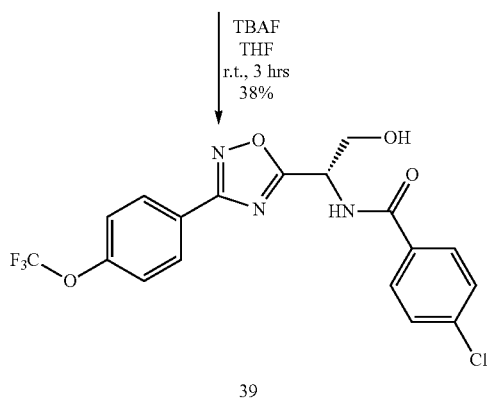

39

(39-1) Synthesis of (2S)-2-{[(tert-butoxy)carbonyl]amino}-3-[(tert-butyldimethylsilyl)oxy]propionic acid (Compound 39-1)

To a stirred solution of N-[(tert-butoxy)carbonyl]-L-serine (2.1 g, 10 mmol) in N,N-dimethylformamide (25 mL) was added imidazole (2.1 g, 30 mmol) and tert-butyldimethylsilyl chloride (3.6 g, 24 mmol). After stirring overnight at room temperature, aqueous solution of ammonium chloride was added to stop the reaction, and the whole was extracted with ethyl acetate. The combined extract was washed with saturated brine, dried over anhydrous magnesium sulfate, and concentrated in vacuo to obtain the title compound as a crude product.
Ms m/z (APCI) [M−H]−=318.

(39-2) Synthesis of tert-butyl N-[(1S)-2-[(tert-butyldimethylsilyl)oxy]-1-{3-[4-(trifluoromethoxy)phenyl]-1,2,4-oxadiazol-5-yl}ethyl] carbamate (Compound 39-2)

To a stirred solution of the crude (2S)-2-{[(tert-butoxy)carbonyl]amino}-3-[(tert-butyldimethylsilyl)oxy]propionic acid obtained above in N,N-dimethylformamide (40 mL) was added carbonyldiimidazole (1.1 g, 10 mmol). After stirring at 50° C. for 30 minutes, N'-hydroxy-4-(trifluoromethoxy)benzene-1-carboxyimidamide (1.8 g, 8.0 mmol) was added to the mixture. After stirring at 120° C. for 3.5 hours, the mixture was cooled down to room temperature and water was added to the mixture to stop the reaction. The whole was extracted with ethyl acetate, and the combined extract was washed with saturated brine, dried over anhydrous magnesium sulfate, and concentrated in vacuo. The resulting residue was purified by silica gel column chromatography eluting with hexane-ethyl acetate to obtain the title compound (2.7 g, yield 66%).
Ms m/z (APCI) [M−H]−=502.

(39-3) Synthesis of 5-[(1S)-1-amino-2[(tert-butyldimethylsilyl)oxy]ethyl]-3-[4-(trifluoromethoxy)phenyl]-1,2,4-oxadiazole (Compound 39-3)

To a stirred solution of tert-butyl N-[(1S)-2-[(tert-butyldimethylsilyl)oxy]-1-{3-[4-(trifluoromethoxy)phenyl]-1,2,4-oxadiazol-5-yl}ethyl]carbamate (2.7 g, 5.3 mmol) in dichloromethane (36 mL) was added trifluoroacetic acid (4 mL) in a dropwise manner under ice cooling. After stirring at the same temperature for 1.5 hours, the mixture was warmed up to room temperature and stirred for additional 2 hours. After quenching by the addition of aqueous solution of sodium hydrogen carbonate, the whole was extracted with dichloromethane. The combined extract was dried over anhydrous magnesium sulfate, and concentrated in vacuo to give the title compound (1.82 g, yield 85%).
Ms m/z (APCI) [M+H]+=404, Ms m/z (APCI) [M−H]−=402.

(39-4) Synthesis of N-[(1S)-2-[(tert-butyldimethylsilyl)oxy]-1-{3-[4-(trifluoromethoxy)phenyl]-1,2,4-oxadiazol-5-yl}ethyl]-4-chlorobenzamide (Compound 39-4)

To a stirred solution of 5-[(1S)-1-amino-2[(tert-butyldimethylsilyl)oxy]ethyl]-3-[4-(trifluoromethoxy)phenyl]-1,2,4-oxadiazole (242 mg, 0.6 mmol) in tetrahydrofuran (6 mL) was added trimethylamine (125 µL, 0.9 mmol) and 4-chlorobenzoyl chloride (96 µL, 0.75 mmol), and the mixture was stirred at room temperature for 4 hours. After terminating the reaction by the addition of aqueous solution of ammonium chloride, the whole was extracted with ethyl acetate. The combined extract was dried over anhydrous magnesium sulfate, and concentrated in vacuo. The resulting residue was purified by silica gel column chromatography eluting with hexane-ethyl acetate to obtain the title compound (163 mg, yield 50%).

Ms m/z (APCI) [M+H]+=542, Ms m/z (APCI) [M−H]−=540.

(39-5) Synthesis of (S)-4-Chloro-N-(2-hydroxy-1-{3-[4-(trifluoromethoxy)phenyl]-1,2,4-oxadiazol-5-yl}ethyl)benzamide (Compound 39)

To a stirred solution of N-[(1S)-2-[(tert-butyldimethylsilyl)oxy]-1-{3-[4-(trifluoromethoxy)phenyl]-1,2,4-oxadiazol-5-yl}ethyl]-4-chlorobenzamide (109 mg, 0.2 mmol) in tetrahydrofuran (3.4 mL) was added 1 mol/L solution of tetrabutylammonium fluoride in tetrahydrofuran (600 μL), and the mixture was stirred at room temperature for 3 hours. After terminating the reaction by the addition of water to the mixture, the whole was extracted with ethyl acetate. The combined extract was washed with saturated brine, dried over anhydrous magnesium sulfate, and concentrated in vacuo. The resulting residue was purified by silica gel column chromatography eluting with hexane-ethyl acetate and by recrystallization to obtain the title compound (32 mg, yield 38%).

The compounds 46, 63, 69, 75, 76, 92 to 95, 97 to 100, 129, 130, 131 and 142 to 267 were prepared by the same method as described above.

Synthesis of 1-(4-chlorophenyl)-4-{3-(4-hydroxyphenyl)-1,2,4-oxadiazol-5-yl}pyrrolidin-2-one (Compound 41)

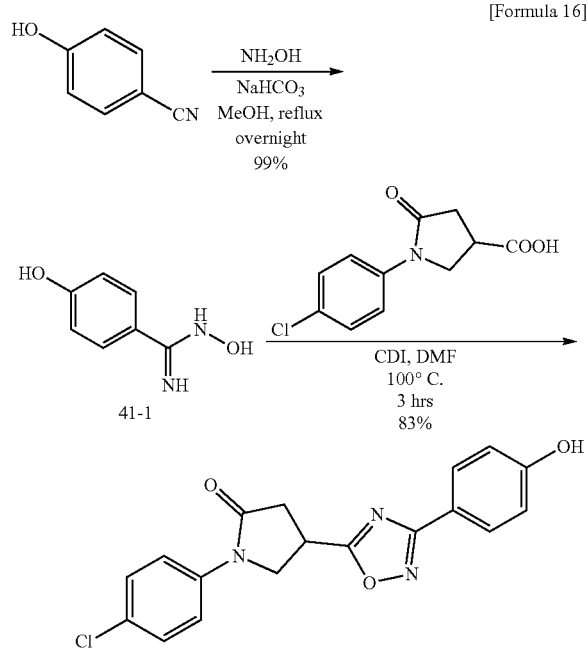

[Formula 16]

(41-1) Synthesis of N,4-dihydroxybenzene-1-carboxyimidamide (Compound 41-1)

A mixture of 4-hydroxybenzonitrile (5.95 g, 50 mmol), hydroxylamine hydrochloride (5.21 g, 75 mmol), and sodium hydrogen carbonate (6.30 g, 75 mmol) in methanol (100 mL) was heated under reflux for 22 hours. After cooling to room temperature, volatiles were evaporated off under reduced pressure. Water (60 mL) was added to the mixture, and the insoluble were collected by filtration, and washed with water, to obtain the title compound (7.5 g, yield 99%).

Ms m/z (APCI) [M+H]+=153.

(41-2) Synthesis of 1-(4-chlorophenyl)-4-{3-(4-hydroxyphenyl)-1,2,4-oxadiazol-5-yl}pyrrolidin-2-one (Compound 41)

A mixture of 1-(4-chlorophenyl)-5-oxopyrrolidin-3-carboxylic acid (132 mg, 0.55 mmol) and carbonyldiimidazole (89 mg, 0.55 mmol) in DMF (10 mL) was stirred at 50° C. for 15 minutes, and N,4-dihydroxybenzene-1-carboxyimidamide (77 mg, 0.50 mmol) was added to the mixture, and heated and stirred at 100° C. for 3 hours. After cooling to the room temperature, water was added to the mixture. The whole was extracted with ethyl acetate, and the combined organic layer was washed with saturated brine, dried over anhydrous sodium sulfate, and concentrated in vacuo. The resulting residue was purified by silica gel column chromatography eluting with hexane-ethyl acetate to obtain the title compound (148 mg, yield 83%). The obtained product was recrystallized from ethanol.

Synthesis of 1-(4-chlorophenyl)-4-{5-[4-(trifluoromethoxy)phenyl]-1,2,4-oxadiazol-3-yl}pyrrolidin-2-one (Compound 45)

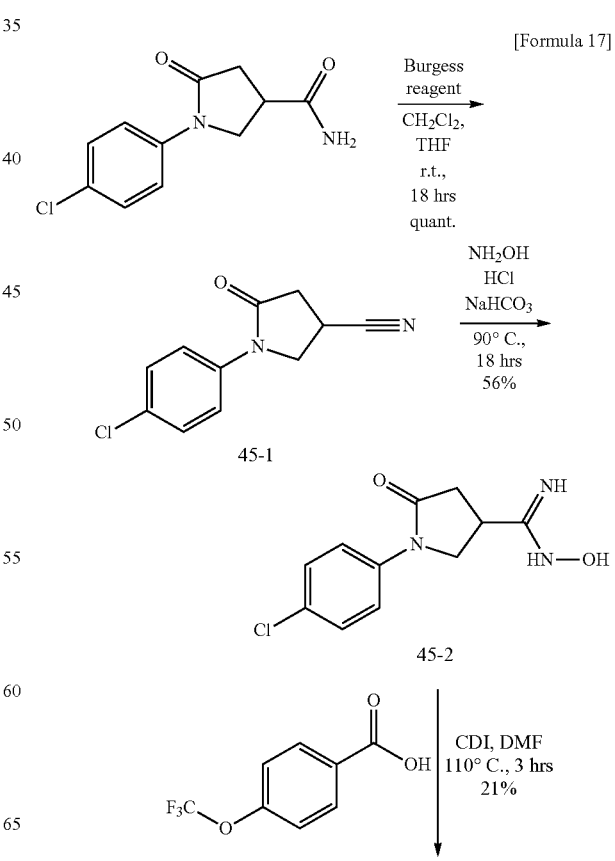

[Formula 17]

-continued

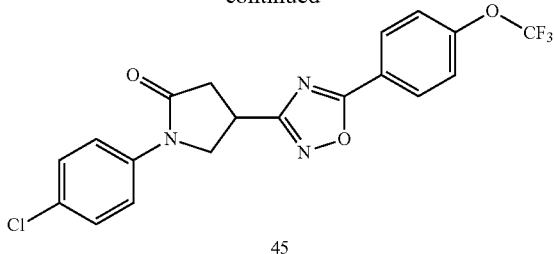

45

(45-1) Synthesis of 1-(4-chlorophenyl)-5-oxopyrrolidine-3-carbonitrile (Compound 45-1)

To a stirred solution of 1-(4-chlorophenyl)-5-oxopyrrolidine-3-carboxamide (200 mg) in dehydrated dichloromethane (10 mL) was added Burgess reagent (260 mg), and the mixture was stirred at room temperature for 18 hours. After completion of the reaction, water (30 mL) was added to the mixture to stop the reaction, and the whole was extracted with ethyl acetate (30 mL×2). The combined organic layer was washed with saturated brine (30 mL), dried over anhydrous sodium sulfate, and concentrated in vacuo. The residue was purified by silica gel column chromatography eluting with hexane-ethyl acetate to obtain the title compound (200 mg, yield 99%).
Ms m/z (APCI) [M+H]+=221.

(45-2) Synthesis of 1-(4-chlorophenyl)-N'-hydroxy-5-oxopyrrolidine-3-carboxyimidamide (Compound 45-2)

To a stirred solution of 1-(4-chlorophenyl)-5-oxopyrrolidine-3-carbonitrile (200 mg) and hydroxylamine hydrochloride (70 mg) in methanol (20 mL) was added sodium hydrogen carbonate (114 mg) at room temperature, and the mixture was heated under reflux for 18 hours. After cooling to the room temperature, methanol was evaporated off under reduced pressure. Water was added to the mixture, and the insolubles were collected by filtration. The solid was dried thoroughly to obtain the title compound (150 mg, yield 65%).

(45-3) Synthesis of 1-(4-chlorophenyl)-4-{5-[4-(trifluoromethoxy)phenyl]-1,2,4-oxadiazol-3-yl}pyrrolidin-2-one (Compound 45)

A mixture of 4-(trifluoromethoxy)benzoic acid (89 mg) and 1,1'-carbonyldiimidazole (104 mg) in DMF (5 mL) was stirred at 50° C. for 30 minutes. 1-(4-chlorophenyl)-N'-hydroxy-5-oxopyrrolidine-3-carboxyimidamide (100 mg) was added to the mixture, and heated at 80° C. for 30 minutes and then at 110° C. for 3 hours. After cooling to room temperature, water (30 mL) was added to the mixture to stop the reaction. The whole was extracted with ethyl acetate (30 mL×2), and the combined organic layer was washed with saturated brine (30 mL), dried over anhydrous sodium sulfate, and concentrated in vacuo. The resulting residue was purified by silica gel column chromatography eluting with hexane-ethyl acetate to obtain the title compound (35 mg, yield 21%).

The compound 128 was prepared by the same method as described above.

Synthesis of 1-(4-chlorophenyl)-4-[3-{4-(fluoromethoxy)phenyl}-1,2,4-oxadiazol-5-yl]pyrrolidin-2-one (Compound 53)

[Formula 18]

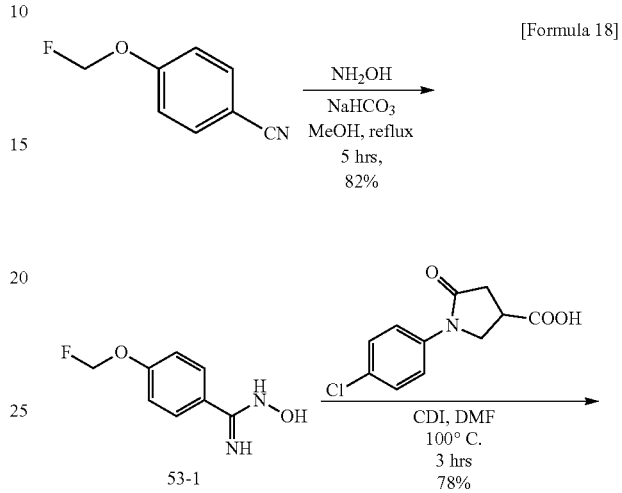

53

(53-1) Synthesis of 4-(fluoromethoxy)-N-hydroxybenzene-1-carboximidamide (Compound 53-1)

A mixed solution of 4-fluoromethoxybenzonitrile (1.51 g, 10 mmol), hydroxyamine hydrochloride (0.76 g, 11 mmol) and sodium hydrogen carbonate (1.26 g, 15 mmol) in methanol (20 mL) was stirred under heating reflux for 4 hours. After cooling to room temperature, the solvent was evaporated off under reduced pressure, and water (30 mL) was added to the obtained residue, followed by filtration and washing with water to obtain the title compound (1.48 g, yield 82%).

(53-2) Synthesis of 1-(4-chlorophenyl)-4-[3-{4-(fluoromethoxy)phenyl}-1,2,4-oxadiazol-5-yl]pyrrolidin-2-one (Compound 53)

A mixed solution of 1-(4-chlorophenyl)-5-oxopyrrolidine-3-carboxylic acid (132 mg, 0.55 mmol) and carbonyldiimidazole (89 mg, 0.55 mmol) in DMF (10 mL) was stirred at 50° C. for 15 minutes, then 4-(fluoromethoxy)-N-hydroxybenzene-1-carboximidamide (92 mg, 0.05 mmol) was added, and the mixture was stirred at 100° C. for 3

Synthesis of (S)-1-(4-chlorobenzoyl)-5-{3-[4-(trifluoromethoxy)phenyl]-1,2,4-oxadiazol-5-yl}pyrrolidin-3-one (Compound 57)

[Formula 19]

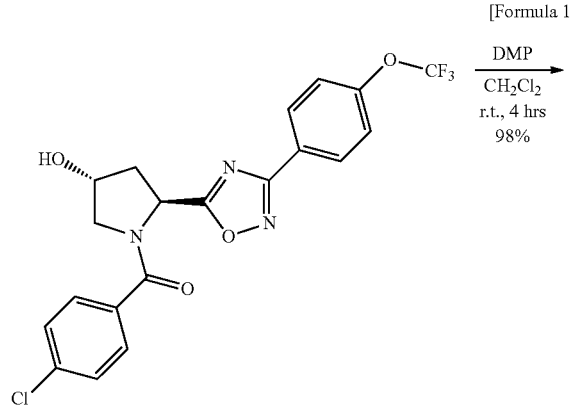

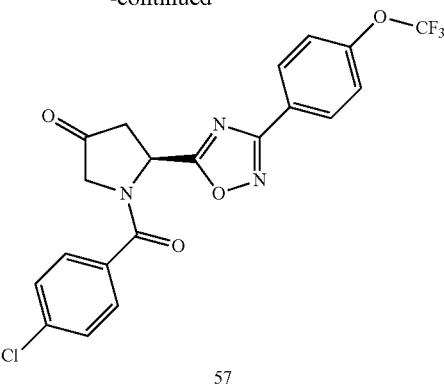

(57-1) Synthesis of (S)-1-(4-chlorobenzoyl)-5-{3-[4-(trifluoromethoxy)phenyl]-1,2,4-oxadiazol-5-yl}pyrrolidin-3-one (Compound 57)

To a solution of (3R,5S)-1-(4-chlorobenzoyl)-5-{3-[4-(trifluoromethoxy)phenyl]-1,2,4-oxadiazol-5-yl}pyrrolidin-3-ol (65 mg, 0.14 mmol) in dichloromethane (3 mL) was added Dess-Martin periodinane (151 mg, 0.35 mmol) and the mixture was stirred at room temperature for 4 hours. Then, saturated aqueous solution of sodium hydrogen carbonate was added, water was added to the mixture, and the mixture was extracted with dichloromethane. The combined extract was dried over anhydrous magnesium sulfate. The solvent was evaporated off under reduced pressure, and the obtained residue was purified by silica gel column chromatography (hexane-ethyl acetate) to obtain the title compound 63 mg (yield 98%).

Synthesis of 1-(5-chloropyridin-2-yl)-4-{3-[4-(difluoromethoxy)phenyl]-1,2,4-oxadiazol-5-yl}pyrrolidin-2-one (Compound 62)

[Formula 20]

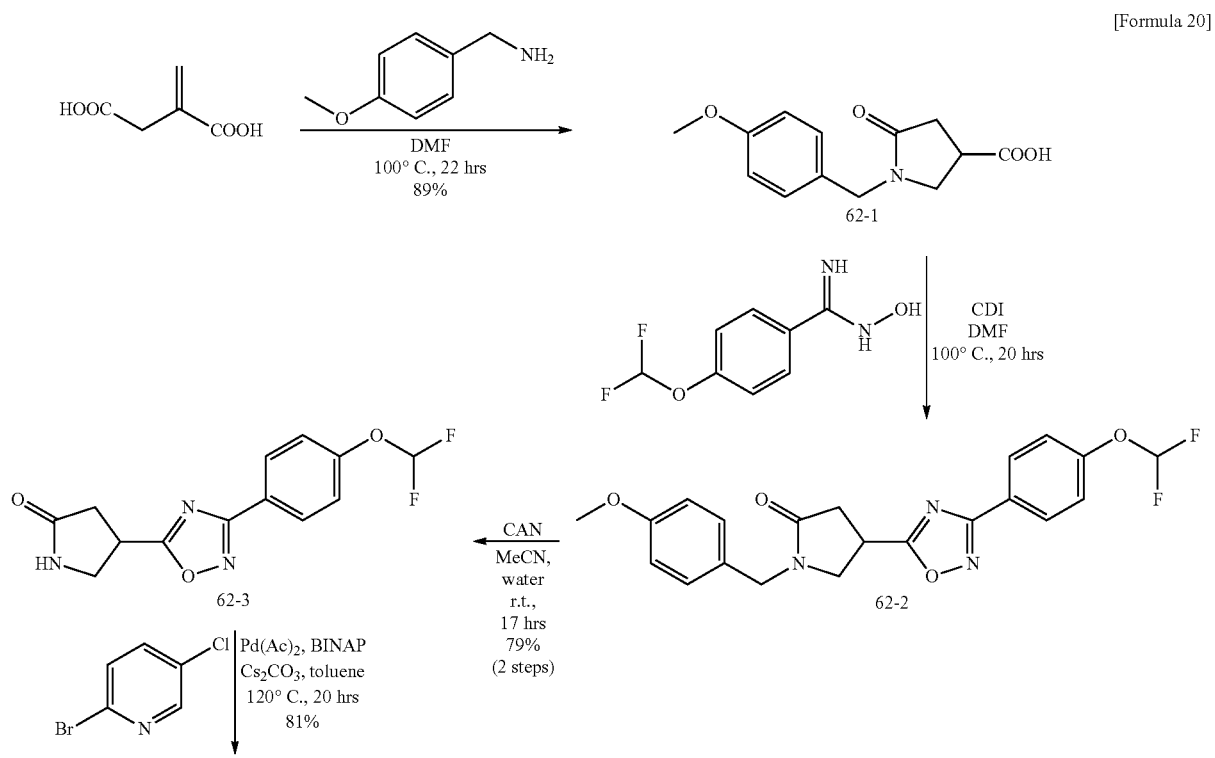

hours. After cooling to room temperature, water was added to the reaction solution, and the mixture was extracted with ethyl acetate. The organic layer was washed with saturated brine and dried over anhydrous sodium sulfate. The solvent was evaporated off under reduced pressure, and the obtained residue was purified using silica gel column chromatography (hexane/ethyl acetate) to obtain the title compound 151 mg (yield 78%). The obtained compound was recrystallized from ethanol.

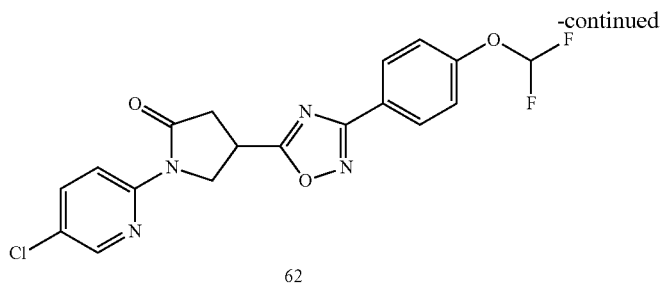

62

(62-1) Synthesis of 1-[(4-methoxyphenyl)methyl]-5-oxopyrrolidine-3-carboxylic acid (Compound 62-1)

A mixed solution of itaconic acid (2.6 g, 20 mmol) and (4-methoxyphenyl)methanamine (2.7 g, 20 mmol) in DMF (3 mL) was stirred at 100° C. for 22 hours. After cooling to room temperature, the solvent was evaporated off under reduced pressure, water (30 mL) was added to the obtained residue, and the mixture was stirred for 20 minutes to crystallize. The insolubles were collected by filtration followed by washing with water to obtain 4.5 g (yield 89%) of the title compound.

(62-2) Synthesis of 4-{3-[4-(difluoromethoxy)phenyl]-1,2,4-oxadiazol-5-yl}-1-[(4-methoxyphenyl)methyl]pyrrolidin-2-on (Compound 62-2)

After stirring a mixed solution of 1-[(4-methoxyphenyl)methyl]-5-oxopyrrolidine-3-carboxylic acid (548 mg, 2.2 mmol) and carbonyldiimidazole (357 mg, 2.2 mmol) in DMF (20 mL) at 50° C. for 15 minutes, 4-(difluoromethoxy)-N-hydroxybenzene-1-carboximidamide (404 mg, 2.0 mmol) was added and the mixture was stirred at 100° C. for 20 hours. After cooling to room temperature, water was added to the reaction solution, and the mixture was extracted with ethyl acetate. The organic layer was washed with saturated brine and dried over anhydrous sodium sulfate. The solvent was evaporated off under reduced pressure to obtain the title compound as a crude product.

Ms m/z (APCI) [M+H+MeCN]+=457.

(62-3) Synthesis of 4-{3-[4-(difluoromethoxy)phenyl]-1,2,4-oxadiazol-5-yl}pyrrolidin-2-on (Compound 62-3)

To a mixed solution of 4-{3-[4-(difluoromethoxy)phenyl]-1,2,4-oxadiazol-5-yl}-1-[(4-methoxyphenyl)methyl]pyrrolidine-2-one obtained above as a crude product in acetonitrile (4 mL) and water (0.1 mL) was added ammonium hexanitratocerate (IV) (4.4 g, 8.0 mmol) and the mixture was stirred at room temperature for 17 hours. Water was added to the reaction solution, and the mixture was extracted with dichloromethane. The organic layer was washed with saturated brine and dried over anhydrous sodium sulfate. The solvent was evaporated off under reduced pressure, and the obtained residue was purified using silica gel column chromatography (dichloromethane/ethanol) to obtain 465 mg (yield 79% (two steps)) of the title compound.

Ms m/z (APCI) [M+H]−=294.

(62-4) Synthesis of 1-(5-chloropyridin-2-yl)-4-{3-[4-(difluoromethoxy)phenyl]-1,2,4-oxadiazol-5-yl}pyrrolidin-2-one (Compound 62)

To a mixture of 4-{3-[4-(difluoromethoxy)phenyl]-1,2,4-oxadiazol-5-yl}pyrrolidin-2-one (148 mg, 0.50 mmol), 2-bromo-5-chloropyridine (96 mg, 0.50 mmol), palladium (II) acetate (11 mg, 0.05 mmol), BINAP (47 mg, 0.08 mmol), cesium carbonate (244 mg, 0.75 mmol) was added toluene (5 mL) under a nitrogen atmosphere, and the mixture was stirred at 120° C. for 20 hours. After cooling to room temperature, the mixture was filtered through Celite, washed with ethyl acetate, and the solvent was evaporated off under reduced pressure. The obtained residue was purified by silica gel column chromatography (hexane/ethyl acetate) to obtain 160 mg (yield 81%) of the title compound. The obtained compound was recrystallized from ethanol.

Synthesis of 1-(4-chlorobenzyl)-4-{3-[4-(trifluoromethoxy)phenyl]-1,2,4-oxadiazol-5-yl}pyrrolidin-2-one (Compound 64)

[Formula 21]

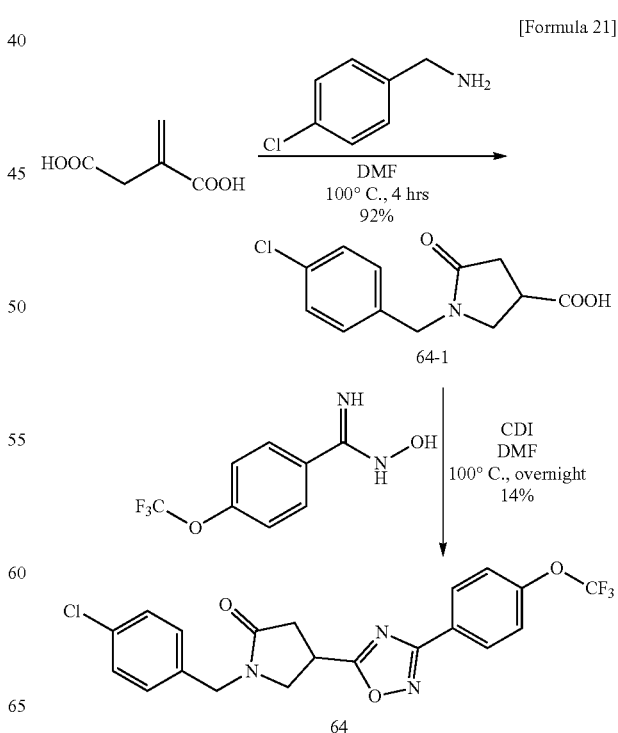

64

(64-1) Synthesis of 1-[(4-chlorophenyl)methyl]-5-pyrrolidine-3-carboxylic acid (Compound 64-1)

A mixture of itaconic acid (1.3 g, 10 mmol) and p-chlorobenzylamine (1.28 ml, 11 mmol) was stirred at 120° C. for 4 hours. Thereafter, the solvent was evaporated off under reduced pressure, and the obtained crystals were washed with a mixed solution of acetic acid and hexane (1:9) to obtain the title compound (2.3 g, yield 92%).

(64-2) Synthesis of 1-(4-chlorobenzyl)-4-{3-[4-(trifluoromethoxy)phenyl]-1,2,4-oxadiazol-5-yl}pyrrolidin-2-one (Compound 64)

To a stirred solution of 1-[(4-Chlorophenyl)methyl]-5-pyrrolidine-3-carboxylic acid (177 mg, 0.8 mmol) in N,N-dimethylformamide (8 mL) was added carbonyldiimidazole (160 mg, 0.9 mmol), and the mixture was stirred at 50° C. for 30 min. Thereafter, N'-hydroxy-4-(trifluoromethoxy)benzene-1-carboximidamide (231 mg, 0.9 mmol) was added and the mixture was stirred overnight at 120° C. After cooling down to room temperature, water was added to stop the reaction. The mixture was extracted with ethyl acetate, and the combined extract was washed with saturated brine, and then dried over anhydrous magnesium sulfate. The solvent was evaporated off under reduced pressure, and the resulting residue was purified by silica gel column chromatography (hexane-ethyl acetate). Further, the obtained crystal was washed with a mixed solution of diethyl ether-hexane (1:9) to obtain the title compound 48 mg (yield 14%).

Synthesis of 1-(4-chlorophenyl)-4-[3-(2,2-difluorobenzo[d][1,3]dioxol-5-yl)-1,2,4-oxadiazol-5-yl]-4-(hydroxymethyl)pyrrolidin-2-one (Compound 73)

[Formula 22]

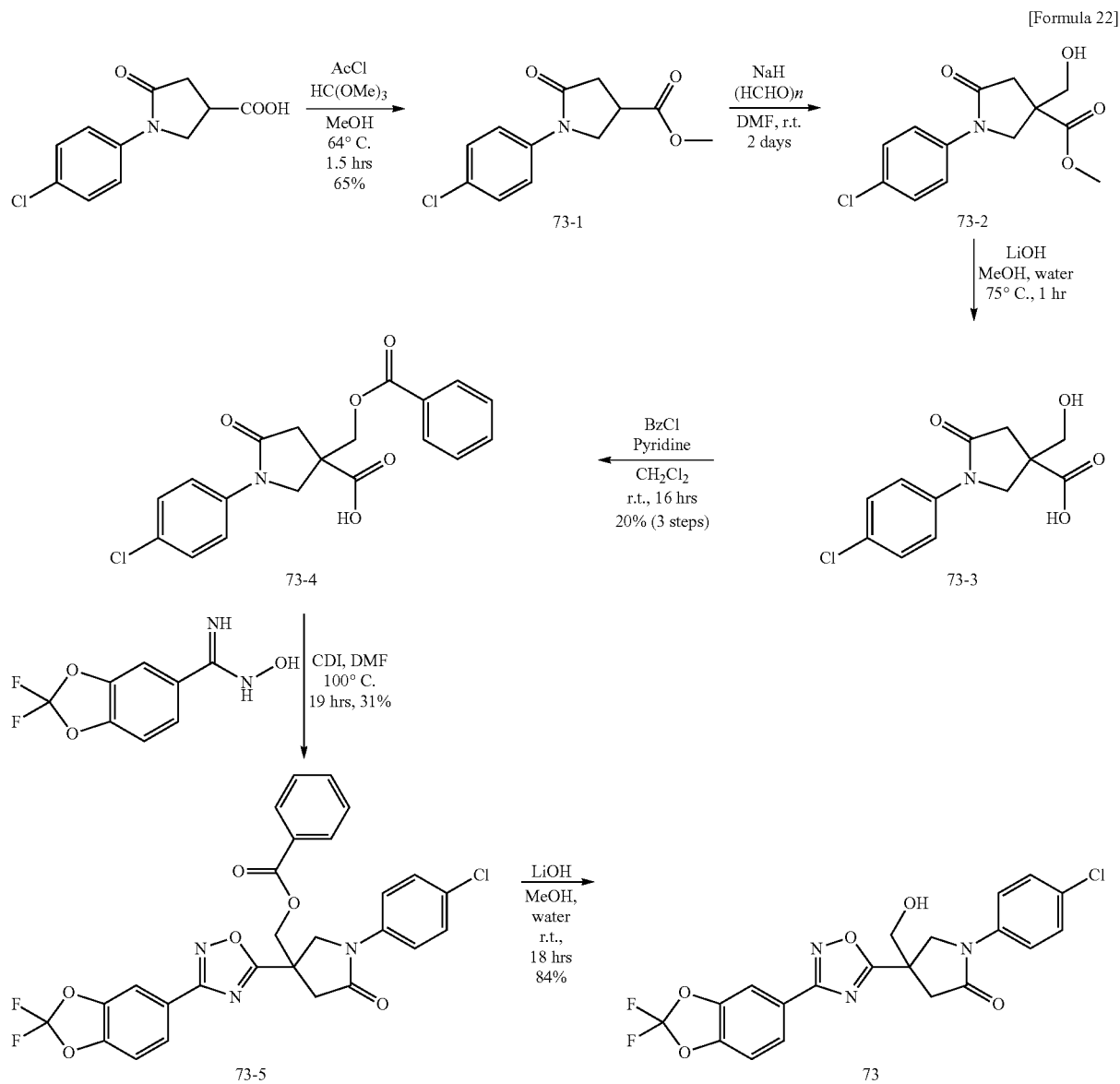

(73-1) Synthesis of 1-(4-chlorophenyl)-5-oxopyrrolidine-3-carboxylic acid methyl ester (Compound 73-1)

To a solution of acetyl chloride (0.2 g, 2.5 mmol) in methanol (30 mL) was added 1-(4-chlorophenyl)-5-oxopyrrolidine-3-carboxylic acid (12 g, 50 mmol) and methyl orthoformate (5.3 g, 50 mmol), and the mixture was stirred at 64° C. for 1.5 hours. After cooling to room temperature, the solvent was evaporated off under reduced pressure, and the obtained residue was recrystallized from ethanol to obtain the title compound 8.2 g (yield 65%).
Ms m/z (APCI) [M+H]+=254.

(73-2) Synthesis of 1-(4-chlorophenyl)-3-(hydroxymethyl)-5-oxopyrrolidine-3-carboxylic acid methyl ester (Compound 73-2)

To a mixed solution of 1-(4-chlorophenyl)-5-oxopyrrolidine-3-carboxylic acid methyl ester (1.3 g, 5.1 mmol) and paraformaldehyde (0.3 g, 10.2 mmol) in DMF (15 mL) was added sodium hydride (60%) (0.2 g, 5.1 mmol), and the mixture was stirred at room temperature for 2 days. After cooling the reaction solution to 0° C., 2N hydrochloric acid was added and the mixture was extracted with ethyl acetate. The organic layer was washed with saturated brine and dried over anhydrous sodium sulfate. The solvent was evaporated off under reduced pressure to obtain the title compound as a crude product.
Ms m/z (APCI) [M+H]+=284.

(73-3) Synthesis of 1-(4-chlorophenyl)-3-(hydroxymethyl)-5-oxopyrrolidine-3-carboxylic acid (Compound 73-3)

To a mixed solution of methyl 1-(4-chlorophenyl)-3-(hydroxymethyl)-5-oxopyrrolidine-3-carboxylate obtained as a crude product in methanol (10 mL) in water (10 mL) was added lithium hydroxide monohydrate (1.3 g, 31 mmol), and the mixture was stirred at 75° C. for 1 hour. After cooling to room temperature, 2N hydrochloric acid was added and the mixture was extracted with ethyl acetate. The organic layer was washed with saturated brine and dried over anhydrous sodium sulfate. The solvent was evaporated off under reduced pressure to obtain the title compound as a crude product.
Ms m/z (APCI) [M-H]-=268.

(73-4) Synthesis of 3-[(benzoyloxy)methyl]-1-(4-chlorophenyl)-5-oxopyrrolidine-3-carboxylic acid (Compound 73-4)

To a solution of 1-(4-chlorophenyl)-3-(hydroxymethyl)-5-oxopyrrolidine-3-carboxylic acid obtained as a crude product in dichloromethane (5 mL) was added benzoyl chloride (3.0 mL, 26 mmol) and pyridine (5 mL), and the mixture was stirred at room temperature. 2N hydrochloric acid was added to the reaction solution and the mixture was extracted with ethyl acetate. The organic layer was washed with saturated brine and dried over anhydrous sodium sulfate. The solvent was evaporated off under reduced pressure, and the obtained residue was purified by silica gel column chromatography (dichloromethane/ethanol ethanol) to obtain the title compound 373 mg (yield 20% (3 steps)).
Ms m/z (APCI) [M-H]-=372.

(73-5) Synthesis of {1-(4-chlorophenyl)-3-[3-(2,2-difluoro-2H-1,3-benzodioxol-5-yl)-1,2,4-oxadiazol-5-yl]-5-oxopyrrolidin-3-yl}methyl benzoate (Compound 73-5)

A solution of 3-[(benzoyloxy)methyl]-1-(4-chlorophenyl)-5-oxopyrrolidine-3-carboxylic acid (112 mg, 0.3 mmol) and carbonyl diimidazole (49 mg, 0.3 mmol) in DMF (6 mL) was stirred at 50° C. for 15 minutes, then 2,2-difluoro-N-hydroxy-2H-1,3-benzodioxole-5-carboximidamide (65 mg, 0.3 mmol) was added, and the mixture was stirred at 100° C. for 19 hours. After cooling to room temperature, water was added to the reaction solution, and the mixture was extracted with ethyl acetate. The organic layer was washed with saturated brine and dried over anhydrous sodium sulfate. The solvent was evaporated off under reduced pressure, and the obtained residue was purified by silica gel column chromatography (hexane/ethyl acetate) to obtain the title compound 51 mg (yield 31%).
Ms m/z (APCI) [M-H]-=552.

(73-6) Synthesis of 1-(4-chlorophenyl)-4-[3-(2,2-difluorobenzo[d][1,3]dioxol-5-yl)-1,2,4-oxadiazol-5-yl]-4-(hydroxymethyl)pyrrolidin-2-one (Compound 73)

A mixed solution of {1-(4-chlorophenyl)-3-[3-(2,2-difluoro-2H-1,3-benzodioxol-5-yl)-1,2,4-oxadiazol-5-yl]-5-oxopyrrolidin-3-yl}methyl benzoate (51 mg, 0.09 mmol), lithium hydroxide monohydrate (23 mg, 0.56 mmol) in methanol (2.5 mL) and water (2.5 mL) was stirred at room temperature for 18 hours. 1N hydrochloric acid was added to the reaction solution, and the mixture was extracted with dichloromethane. The organic layer was washed with saturated brine and dried over anhydrous sodium sulfate. The solvent was evaporated off under reduced pressure, and the obtained residue was purified by silica gel column chromatography (hexane/ethyl acetate) to obtain the title compound 34 mg (yield 84%).

Compounds 72 and 90 were synthesized in the same manner as described above.

Synthesis of 4-chloro-N-{2-hydroxy-1-[3-(4-hydroxyphenyl)-1,2,4-oxadiazol-5-yl]ethyl}benzamide (Compound 78)

[Formula 23]

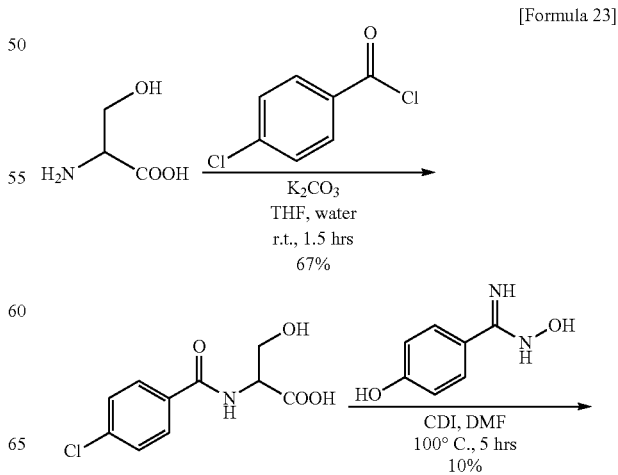

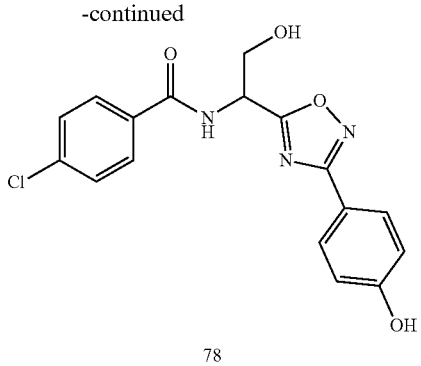

78

(78-1) Synthesis of 2-[(4-chlorophenyl)formamide]-3-hydroxypropionic acid (Compound 78-1)

Water (100 mL) was added to DL-serine (10 g, 95 mmol) and potassium carbonate (13.2 g, 95 mmol), and the mixture was stirred at room temperature for 1 hour, then a THF (20 mL) solution of 4-chlorobenzoyl chloride (12.2 mL, 95 mmol) was added dropwise over 30 minutes, and the mixture was stirred at room temperature for 1 hour. The reaction solution was extracted with ethyl acetate, the aqueous layer was acidified with concentrated hydrochloric acid, and stirred at 0° C. to precipitate crystals. The obtained crystals were collected by filtration and washed with water to obtain the title compound (15.4 g, yield 67%).

Ms m/z (APCI) [M+H]+=244.

(78-2) Synthesis of 4-chloro-N-{2-hydroxy-1-[3-(4-hydroxyphenyl)-1,2,4-oxadiazol-5-yl]ethyl}benzamide (Compound 78)

After a mixed solution of 2-[(4-chlorophenyl)formamide]-3-hydroxypropionic acid (840 mg, 3.45 mmol) and carbonyl diimidazole (615 mg, 3.80 mmol) in DMF (30 mL) was stirred at 50° C. for 15 minutes, N,4-dihydroxybenzene-1-carboximidamide (525 mg, 3.45 mmol) was added and the mixture was stirred at 100° C. for 24 hours. After cooling to room temperature, water was added to the reaction solution, and the mixture was extracted with ethyl acetate. The organic layer was washed with saturated brine and dried over anhydrous sodium sulfate. The solvent was evaporated off under reduced pressure, and the obtained residue was purified by silica gel column chromatography (hexane/ethyl acetate) and recrystallized from hexane/ethyl acetate to obtain 120 mg (yield 10%) of the title compound.

Synthesis of (S)-3-(4-chlorobenzamide)-3-{3-[4-(trifluoromethoxy)phenyl]-1,2,4-oxadiazol-5-yl}propanoic acid (Compound 81)

[Formula 24]

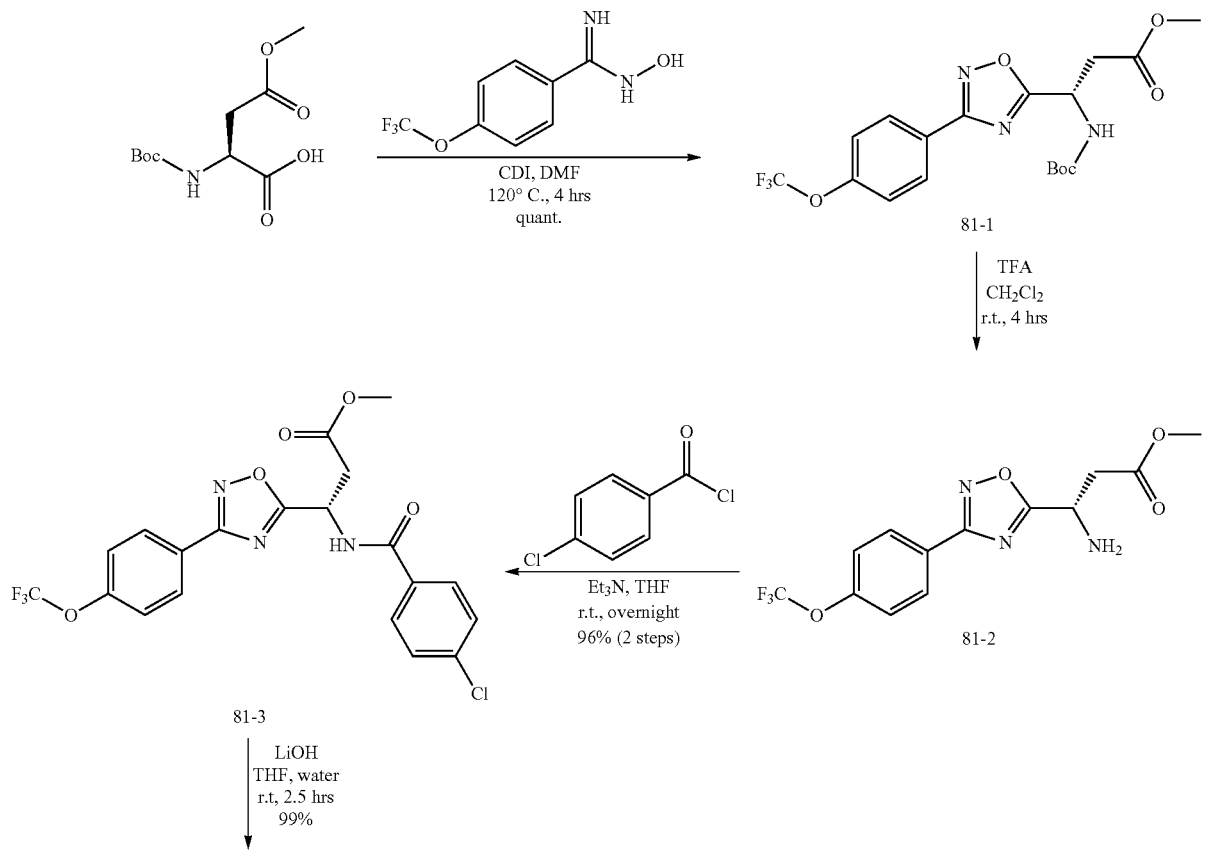

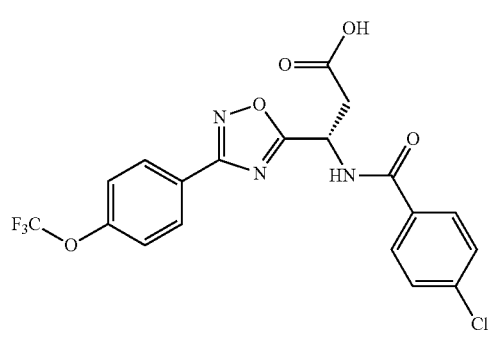

81

(81-1) Synthesis of 3-{[(tert-butoxy)carbonyl]amino}-3-{3-[4-(trifluoromethoxy)phenyl]-1,2,4-oxadiazol-5-yl}propionic acid methyl ester (Compound 81-1)

To a solution of N-{[(tert-butoxy)carbonyl]amino}-L-aspartic acid methylester (2.04 g, 8.3 mmol) in N,N-dimethylformamide (20 mL) was added carbonyldiimidazole (1.46 g, 9 mmol), and the mixture was stirred at 50° C. for 30 minutes. Thereafter, N'-hydroxy-4-(trifluoromethoxy)benzene-1-carboximidamide (1.65 g, 7.5 mmol) was added and the mixture was stirred at 120° C. for 3 hours. After cooling to room temperature, water was added to stop the reaction, and the mixture was extracted with ethyl acetate. The extracts were mixed, washed with saturated brine, and then dried over anhydrous magnesium sulfate. The solvent was evaporated off under reduced pressure, and the obtained residue was purified by silica gel column chromatography (hexane-ethyl acetate) to give the title compound 3.29 g (yield quant.).

(81-2) Synthesis of 3-amino-3-{3-[4-(trifluoromethoxy)phenyl]-1,2,4-oxadiazol-5-yl}propionic acid methyl ester (Compound 81-2)

To a solution of 3-{[(tert-butoxy)carbonyl]amino}-3-{3-[4-(trifluoromethoxy)phenyl]-1,2,4-oxadiazol-5-yl}propionic acid methyl ester (1.29 g, 3 mmol) in dichloromethane (8.5 mL) was added trifluoroacetic acid (1.5 ml) dropwise under ice cooling and the mixture was stirred at the same temperature for 30 minutes. Thereafter, the reaction solution was warmed to room temperature and stirred for 3.5 hours. The reaction solution was cooled to 0° C., and the reaction was terminated by adding saturated aqueous sodium hydrogen carbonate solution, and the mixture was extracted with dichloromethane. The extracts were mixed, dried over anhydrous magnesium sulfate, and the solvent was evaporated off under reduced pressure to give the title compound as a crude product.

(81-3) Synthesis of 3-[(4-chlorophenyl)formamide]-3-{3-[4-(trifluoromethoxy)phenyl]-1,2,4-oxadiazol-5-yl}propionic acid methyl ester (Compound 81-3)

The 3-amino-3-{3-[4-(trifluoromethoxy)phenyl]-1,2,4-oxadiazol-5-yl}propionic acid methyl ester obtained above as a crude product was dissolved in dichloromethane (14.5 mL), and parachlorobenzoic acid (511 mg, 3.3 mmol), 1-ethyl-3-(3-dimethylaminopropyl)carbodiimide monohydrochloride (681 g, 3.6 mmol) and dimethylaminopyridine (69 mg, 0.57 mmol) were added sequentially. The mixture was stirred overnight at room temperature. Thereafter, a saturated aqueous solution of sodium bicarbonate was added to stop the reaction, and the mixture was extracted with dichloromethane. The extract was mixed and dried over anhydrous magnesium sulfate. The solvent was evaporated off under reduced pressure, and the resulting residue was purified by silica gel column chromatography (hexane-ethyl acetate) to obtain the title compound (1.28 g, yield 96%).

(81-4) Synthesis of (S)-3-(4-chlorobenzamide)-3-{3-[4-(trifluoromethoxy)phenyl]-1,2,4-oxadiazol-5-yl}propionic acid (Compound 81)

3-[(4-Chlorophenyl)formamide]-3-{3-[4-(trifluoromethoxy)phenyl]-1,2,4-oxadiazol-5-yl}propionic acid methyl ester (671 mg, 1.4 mmol) was dissolved in a mixture of tetrahydrofuran-water (2:1, 9 mL), and lithium hydroxide monohydrate (150 mg, 3.6 mmol) was added to the resulting solution, and then the mixture was stirred at room temperature for 2.5 hours. Thereafter, 1 mol/L solution of hydrochloric acid was added to stop the reaction, water was added to the mixture, and the mixture was extracted with ethyl acetate. The extracts were mixed, washed with saturated brine, and then dried over anhydrous magnesium sulfate. The solvent was evaporated off under reduced pressure to obtain the title compound (643 mg, yield 99%).

Synthesis of (S)-N-(3-amino-3-oxo-1-{3-[4-(trifluoromethoxy)phenyl]-1,2,4-oxadiazol-5-yl}propyl)-4-chlorobenzamide (Compound 86)

[Formula 25]

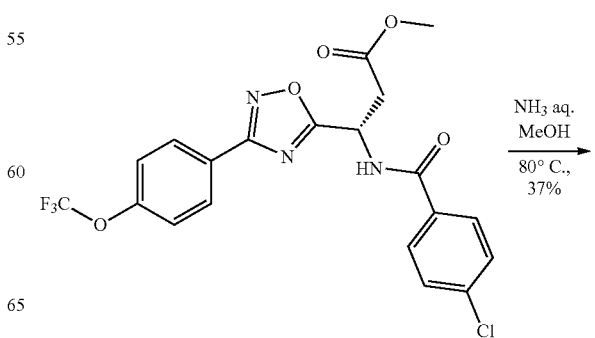

117

-continued

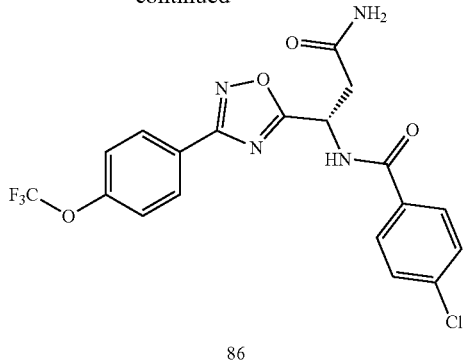

86

(86-1) Synthesis of (S)-N-(3-amino-3-oxo-1-{3-[4-(trifluoromethoxy)phenyl]-1,2,4-oxadiazol-5-yl}propyl)-4-chlorobenzamide (Compound 86)

To a solution of 3-[(4-chlorophenyl)formamide]-3-{3-[4-(trifluoromethoxy)phenyl]-1,2,4-oxadiazol-5-yl}propionic acid methyl ester (130 mg, 0.28 mmol) in methanol (6 mL) was added to a 28% aqueous ammonia solution (600 µl) and the solution was stirred overnight at room temperature. Thereafter, a 28% aqueous ammonia solution (400 µl) was added again and the mixture was stirred at room temperature for 18 hours. The reaction solution was heated to 80° C. and stirred overnight as it was. After the reaction solution was cooled to room temperature, water was added and the mixture was extracted with dichloromethane. The extracts were mixed and the solvent was evaporated off under reduced pressure. The obtained residue was purified by silica gel column chromatography (hexane-ethyl acetate), and the resulting crystals were washed with a mixed solution of ethyl acetate-hexane (1:4) to obtain the title compound 28 mg (yield 37%).

Compounds 87 and 88 were synthesized in the same manner as described above.

Synthesis of 4-[5-{1-hydroxy-2-(1H-indol-3-yl)ethyl}-1,2,4-oxadiazol-3-yl]phenol (Compound 89)

[Formula 26]

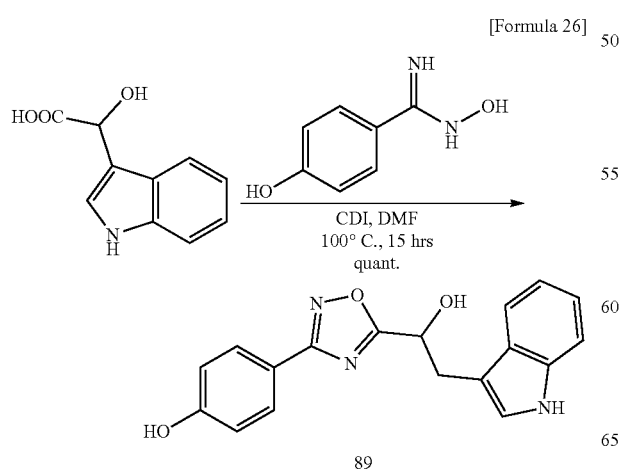

89

(89-1) Synthesis of 4-[5-{1-hydroxy-2-(1H-indol-3-yl)ethyl}-1,2,4-oxadiazol-3-yl]phenol (Compound 89)

A mixed solution of indole-3-lactic acid (113 mg, 0.55 mmol) and carbonyldiimidazole (89 mg, 0.55 mmol) in DMF (10 mL) was stirred at 50° C. for 15 minutes and then to the mixture was added N,4-dihydroxybenzene-1-carboxyimidamide (77 mg, 0.50 mmol), and the mixture was stirred at 100° C. for 15 hours. After cooling to room temperature, water was added to the reaction solution, and the mixture was extracted with ethyl acetate. The organic layer was washed with saturated brine and dried over anhydrous sodium sulfate. The solvent was evaporated off under reduced pressure, and the resulting residue was purified by silica gel column chromatography (hexane/ethyl acetate) to obtain the title compound 160 mg (yield quant.).

Synthesis of (S)-3-chloro-N-(2-hydroxy-1-[3-{4-(trifluoromethoxy)phenyl}-1,2,4-oxadiazol-5-yl]ethyl)benzenesulfonamide (Compound 91)

[Formula 27]

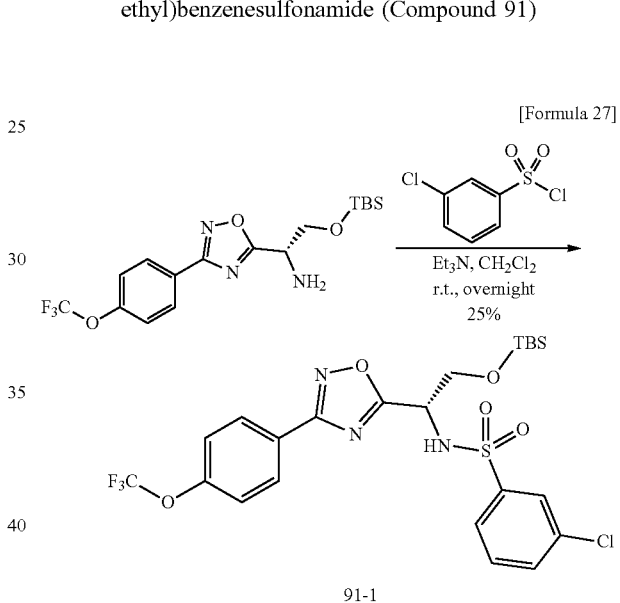

91

(91-1) Synthesis of N-{2-[(tert-butyldimethylsilyl)oxy]-1-{3-[4-(trifluoromethoxy)phenyl]-1,2,4-oxadiazol-5-yl}ethyl}-3-chlorobenzene-1-sulfonamide (Compound 91-1)

Triethylamine (250 µl, 1.8 mmol) and 3-chlorobenzene-1-sulfonyl chloride (245 mg, 1.17 mmol) were added to a solution of 5-{1-amino-2-[(tert-butyldimethylsilyl)oxy]

ethyl}-3-[4-(trifluoromethoxy)phenyl]-1,2,4-oxadiazole (314 mg, 0.78 mmol) in dichloromethane (8 mL), and the mixture was stirred overnight at room temperature. After addition of saturated aqueous ammonium chloride solution to stop the reaction, water was added and the whole was extracted with dichloromethane. The combined extract was dried over anhydrous magnesium sulfate. The solvent was evaporated off under reduced pressure, and the obtained residue was purified by silica gel column chromatography (hexane-ethyl acetate) to obtain the title compound 114 mg (yield 25%).

(91-2) Synthesis of (S)-3-chloro-N-(2-hydroxy-1-[3-{4-(trifluoromethoxy)phenyl}-1,2,4-oxadiazol-5-yl]ethyl)benzenesulfonamide (Compound 91)

A solution (500 µl) of 1 mol/L tetrabutylammonium fluoride in tetrahydrofuran was added to a solution of N-{2-[(tert-butyldimethylsilyl)oxy]-1-{3-[4-(trifluoromethoxy)phenyl]-1,2,4-oxadiazol-5-yl}ethyl}-3-chlorobenzene-1-sulfonamide (114 mg, 0.2 mmol) in tetrahydrofuran (4 mL), and the mixture was stirred overnight at room temperature. Thereafter, water was added to stop the reaction, and the mixture was extracted with ethyl acetate. The extracts were mixed, washed with saturated brine, and then dried over anhydrous magnesium sulfate. The solvent was evaporated off under reduced pressure, and the obtained residue was purified by silica gel column chromatography (hexane-ethyl acetate) followed by recrystallization to obtain the title compound 51 mg (yield 55%).

Synthesis of (S)-4-chloro-N-(2-hydroxy-1-{3-[4-(trifluoromethoxy)phenyl]-1,2,4-oxadiazol-5-yl}ethyl)-N-(2-hydroxyethyl)benzamide (Compound 96)

(96-1) Synthesis of 2-({(1S)-2-[(tert-butyldimethylsilyl)oxy]-1-{3-[4-(trifluoromethoxy)phenyl]-1,2,4-oxadiazol-5-yl}ethyl}amino)ethan-1-ol (Compound 96-1)

2-Iodoethanol (87 µl, 1.1 mmol) and cesium carbonate (391 mg, 1.2 mmol) were added to a solution of 5-{1-amino-2-[(tert-butyldimethylsilyl)oxy]ethyl}-3-[4-(trifluoromethoxy)phenyl]-1,2,4-oxadiazole (408 mg, 1.0 mmol) in N,N-dimethylformamide (5 mL), and the mixture was stirred overnight at 60° C. Thereafter, water was added to the mixture, and the mixture was extracted with ethyl acetate. The extracts were mixed, washed with a saturated aqueous sodium chloride solution, and then dried over anhydrous magnesium sulfate. The solvent was evaporated off under reduced pressure to obtain the title compound as a crude product.

(96-2) Synthesis of N-{(1S)-2-[(tert-butyldimethylsilyl)oxy]-1-{3-[4-(trifluoromethoxy)phenyl]-1,2,4-oxadiazol-5-yl}ethyl}-4-chloro-N-(2-hydroxyethyl)benzamide (Compound 96-2)

Parachlorobenzoic acid (240 mg, 1.5 mmol), 4-(4,6-dimethoxy-1,3,5-triazin-2-yl)-4-methylmorpholinium chloride n-hydrate (484 mg, 1.75 mmol) and water (200 µl) were added to a solution of 2-({(1S)-2-[(tert-butyldimethylsilyl)oxy]-1-{3-[4-(trifluoromethoxy)phenyl]-1,2,4-oxadiazol-5-yl}ethyl}amino)ethan-1-ol obtained above as a crude product in a mixed solution (9 ml) of N,N-dimethylformamide and tetrahydrofuran (1:2), and the mixture was stirred over-

[Formula 28]

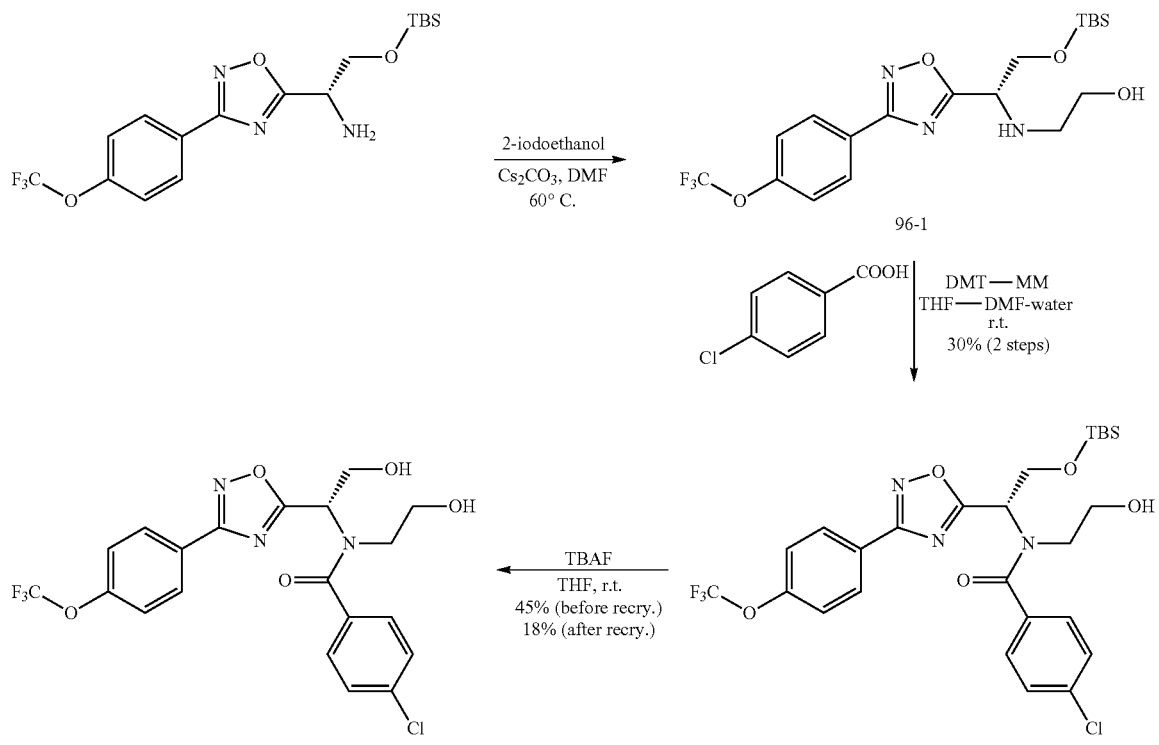

night at night room temperature. Then water was added and the mixture was extracted with ethyl acetate. The extracts were mixed, washed with saturated brine, and then dried over anhydrous magnesium sulfate. The solvent was evaporated off under reduced pressure, and the obtained residue was purified by silica gel column chromatography (hexane-ethyl acetate) to obtain the title compound 176 mg (yield 30% (two steps)).

(96-3) Synthesis of (S)-4-chloro-N-(2-hydroxy-1-{3-[4-(trifluoromethoxy)phenyl]-1,2,4-oxadiazol-5-yl}ethyl)-N-(2-hydroxyethyl)benzamide (Compound 96)

To a solution of N-{(1S)-2-[(tert-butyldimethylsilyl)oxy]-1-{3-[4-(trifluoromethoxy)phenyl]-1,2,4-oxadiazol-5-yl}ethyl}-4-chloro-N-(2-hydroxyethyl)benzamide (176 mg, 0.3 mmol) in tetrahydrofuran (4 mL) was added a solution (900 µl) of 1 mol/L tetrabutylammonium fluoride in tetrahydrofuran and the mixture was stirred overnight at room temperature. Thereafter, water was added to stop the reaction, and the mixture was extracted with ethyl acetate. The extracts were mixed, washed with a saturated aqueous sodium chloride solution, and then dried over anhydrous magnesium sulfate. The solvent was evaporated off under reduced pressure, and the obtained residue was purified by silica gel column chromatography followed by washing with a mixed solution of diethyl ether-hexane (1:9) to obtain the title compound 26 mg (yield 18%).

Synthesis of 2-(1H-indol-3-yl)-1-{3-[4-(trifluoromethoxy)phenyl]-1,2,4-oxadiazol-5-yl}ethan-1-ol (Compound 101)

[Formula 29]

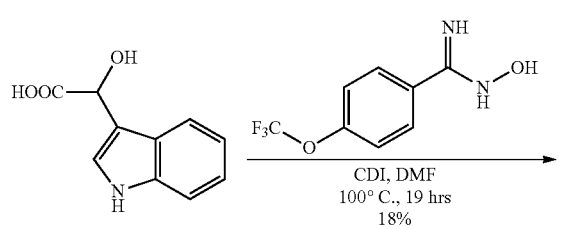

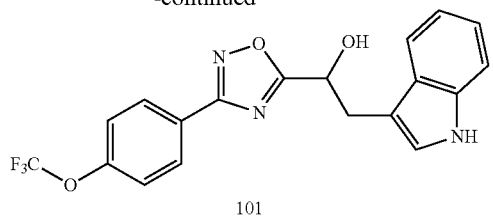
101

(101-1) Synthesis of 2-(1H-indol-3-yl)-1-{3-[4-(trifluoromethoxy)phenyl]-1,2,4-oxadiazol-5-yl}ethan-1-ol (Compound 101)

A mixed solution of indole-3-lactic acid (103 mg, 0.50 mmol) and carbonyldiimidazole (89 mg, 0.55 mmol) in DMF (5 mL) was stirred at 50° C. for 20 minutes, and then N-hydroxy-4-(trifluoromethoxy)benzene-1-carboximidamide (110 mg, 0.50 mmol) was added to the mixture. The mixture was stirred at 120° C. for 19 hours. After cooling to room temperature, water was added to the reaction solution, and the mixture was extracted with ethyl acetate. The organic layer was washed with saturated brine and dried over anhydrous sodium sulfate. The solvent was evaporated off under reduced pressure, and the obtained residue was purified using silica gel column chromatography (hexane/ethyl acetate) and then recrystallization from hexane/ethyl acetate to obtain 35 mg (yield 18%) of the title compound.

Synthesis of 4-chloro-N-(1,3-dihydroxy-2-{3-[4-(trifluoromethoxy)phenyl]-1,2,4-oxadiazol-5-yl}propan-2-yl)benzamide (Compound 102)

[Formula 30]

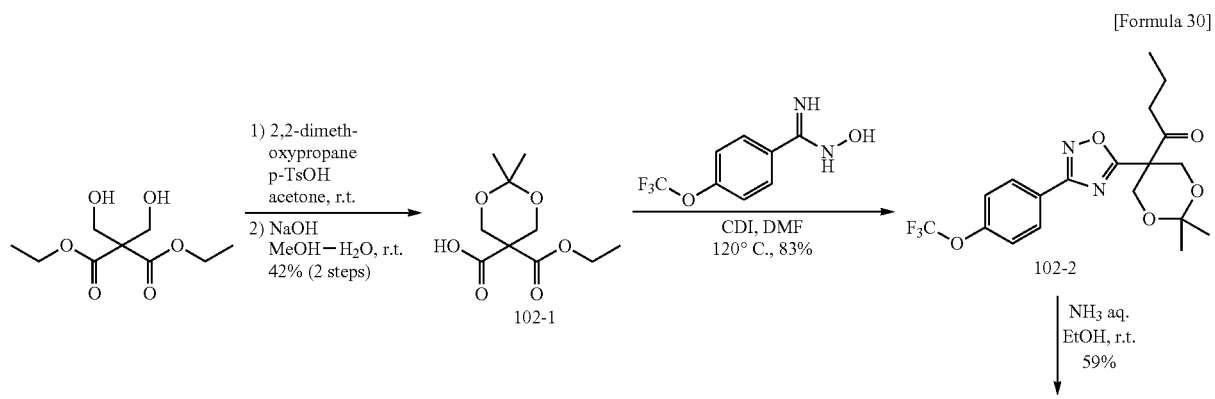

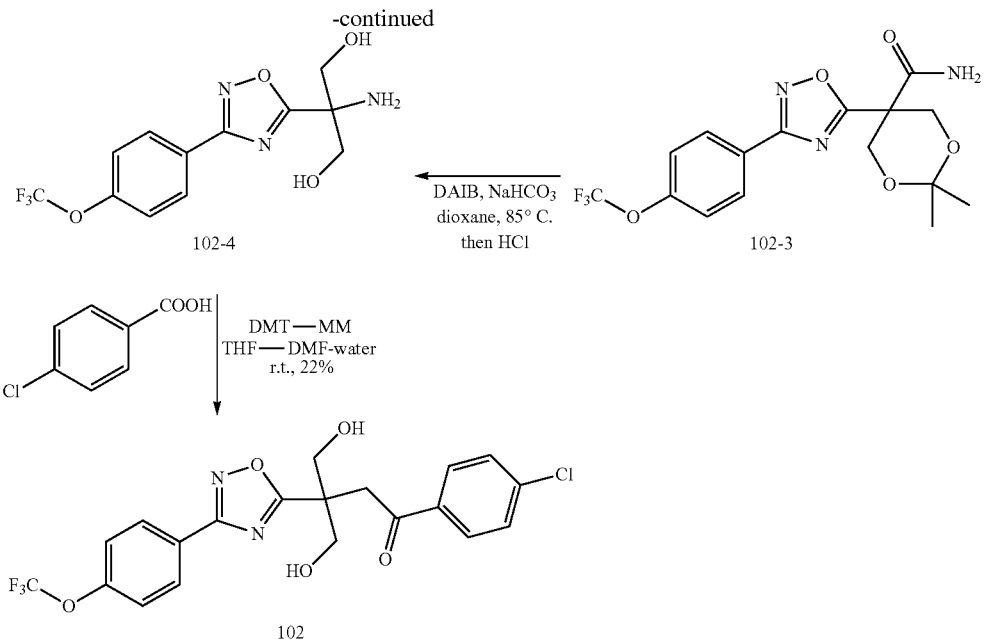

(102-1) Synthesis of 5,5-diethyl 2,2-dimethyl 1,3-dioxan-5,5-dicarboxylate

To a solution of 1,3-diethyl 2,2-bis(hydroxymethyl)propanedioate (4.4 g, 20 mmol) in acetone (25 mL) were added 2,2-dimethoxypropane (3.7 ml, 30 mmol), paratoluenesulfonic acid monohydrate (3.8 g, 20 mmol) and anhydrous magnesium sulfate (1.0 g) and the mixture was stirred overnight at room temperature. Thereafter, triethylamine was added to stop the reaction, and the precipitate was removed by filtration, and the filtrate was concentrated under reduced pressure. The obtained residue was dissolved in diethyl ether, and water was added and the whole was extracted with diethyl ether. The combined extract was dried over anhydrous magnesium sulfate. The solvent was evaporated off under reduced pressure to give the title compound as a crude product.

Ms m/z (APCI) [M+H]+=261.10.

(102-2) Synthesis of 5-(ethoxycarbonyl)-2,2-dimethyl 1,3-dioxan-5-carboxylic acid (Compound 102-1)

Water (18 ml) and sodium hydroxide (834 mg, 20.9 mmol) were added to a solution of 5,5-diethyl 2,2-dimethyl 1,3-dioxane-5,5-dicarboxylate obtained above as a crude product in ethanol (18 ml), and the mixture was stirred overnight at room temperature. Thereafter, an aqueous solution of citric acid was added to stop the reaction, and the mixture was extracted with ethyl acetate. The extracts were mixed, washed with saturated brine, and then dried over anhydrous magnesium sulfate. The solvent was evaporated off under reduced pressure to obtain the title compound as a crude product.

(102-3) Synthesis of 2,2-dimethyl 5-{3-[4-(trifluoromethoxy)phenyl]-1,2,4-oxadiazol-5-yl}-1,3-dioxan-5-carboxylic acid ethyl ester (Compound 102-2)

To a solution of 5-(ethoxycarbonyl)-2,2-dimethyl 1,3-dioxane-5-carboxylic acid obtained above as a crude product in N,N-dimethylformamide (40 ml) was added carbonyldiimidazole (1.51 g, 9.2 mmol), and the mixture was stirred at 50° C. for 20 minutes. Then N'-hydroxy-4-(trifluoromethoxy)benzene-1-carboxyimidamide (1.55 g, 7.1 mmol) was added, and the mixture was stirred at 120° C. for 3 hours. After the reaction solution was cooled to room temperature, the reaction was stopped by adding water, and the mixture was extracted with ethyl acetate. The extracts were mixed, washed with saturated brine, and then dried over anhydrous magnesium sulfate. The solvent was evaporated off under reduced pressure, and the resulting residue was purified by silica gel column chromatography (hexane-ethyl acetate) to obtain the title compound (2.45 g, yield 83%).

Ms m/z (APCI) [M+H]+=417.

(102-4) Synthesis of 2,2-dimethyl 5-{3-[4-(trifluoromethoxy)phenyl]-1,2,4-oxadiazol-5-yl}-1,3-dioxane-5-carboxamide (Compound 102-3)

A 28% aqueous solution of ammonia (4 ml) was added to a solution of 2,2-dimethyl 5-{3-[4-(trifluoromethoxy)phenyl]-1,2,4-oxadiazol-5-yl}-1,3-dioxan-5-carboxylic acid ethyl ester (801 mg, 1.9 mmol) in ethanol (8 mL), and the mixture was stirred overnight at room temperature. Thereafter, a 28% aqueous solution of ammonia (1 ml) was additionally added, and the mixture was stirred at 50° C. for 5 hours. After the reaction solution was cooled to room temperature, water was added and the mixture was extracted with dichloromethane. The extracts were mixed and dried over anhydrous magnesium sulfate, and then the solvent was evaporated off under reduced pressure. The obtained residue was purified by silica gel column chromatography (hexane-ethyl acetate) to obtain the title compound 439 mg (yield 59%).

Ms m/z (APCI) [M+H]+=388.05.

(102-5) Synthesis of 2-amino-2-{3-[4-(trifluoromethoxy)phenyl]-1,2,4-oxadiazol-5-yl}propane-1,3-diol hydrochloride (Compound 102-4)

2,2-Dimethyl 5-{3-[4-(trifluoromethoxy)phenyl]-1,2,4-oxadiazol-5-yl}-1,3-dioxane-5-carboxamide (74.2 mg, 0.19 mmol) was dissolved in dioxane (8 mL), sodium hydrogen carbonate (36.5 mg, 0.42 mmol) and diacetoxyiodobenzene (68.2 mg, 0.21 mmol) were added to the resulting solution, and the mixture was stirred at 85° C. for 40 minutes. Thereafter, hydrochloric acid was added to make the solution acidic, and the mixture was further stirred at 85° C. for 1.5 hours. After the reaction solution was cooled to room temperature, the solvent was evaporated off under reduced pressure to give the title compound as a crude product.

(102-6) Synthesis of 4-chloro-N-(1,3-dihydroxy-2-{3-[4-(trifluoromethoxy)phenyl]-1,2,4-oxadiazol-5-yl}propan-2-yl)benzamide (Compound 102)

Parachlorobenzoic acid (43.2 mg, 0.28 mmol), 4-(4,6-dimethoxy-1,3,5-triazin-2-yl)-4-methylmorpholinium chloride n-hydrate (72 mg, 0.26 mmol) and water (200 μl) were added to the solution of 2-amino-2-{3-[4-(trifluoromethoxy)phenyl]-1,2,4-oxadiazol-5-yl}propane-1,3-diol hydrochloride obtained above as the crude product in a mixed solution (3.6 mL) of N,N-dimethylformamide and tetrahydrofuran (4:5), and the solution was stirred at room temperature for 4.5 hours. Then, a saturated aqueous solution of ammonium chloride was added to stop the reaction, and the mixture was extracted with ethyl acetate. The extracts were mixed, washed with saturated brine, and then dried over anhydrous magnesium sulfate. The solvent was evaporated off under reduced pressure, and the obtained residue was purified by silica gel column chromatography (hexane-ethyl acetate) to obtain 19 mg (yield 22% (two steps)) of the title compound.

Synthesis of 1-(4-chlorophenyl)-4-{5-[4-(trifluoromethoxy)phenyl]-1,3,4-oxadiazol-2-yl}pyrrolidin-2-one (Compound 103)

(103-1) Synthesis of 1-(4-chlorophenyl)-5-oxo-N'-[4-(trifluoromethoxy)benzoyl]pyrrolidin-3-carbohydrazide (Compound 103-1)

DMT-MM (262 mg) was added to a solution of 1-(4-chlorophenyl)-5-oxopyrrolidin-3-carbohydrazide (0.2 g) and 4-(trifluoromethoxy)benzoic acid (0.16 g) in ethanol (10 mL) at room temperature with stirring. The reaction was carried out at room temperature for 18 hours. After the reaction completed, the reaction solution was diluted with ethyl acetate (30 mL), and washed with saturated aqueous solution of sodium hydrogen carbonate (30 mL), followed by saturated brine (30 mL). The organic layer was dried over anhydrous sodium sulfate and evaporated under reduced pressure, and the resulting residue was purified by silica gel column chromatography (hexane-ethyl acetate) to obtain 350 g (yield 99%) of the title compound.

Ms m/z (APCI) [M+H]+=442.

(103-2) Synthesis of 1-(4-chlorophenyl)-4-{5-[4-(trifluoromethoxy)phenyl]-1,3,4-oxadiazol-2-yl}pyrrolidin-2-one (Compound 103)

To a solution of 1-(4-chlorophenyl)-5-oxo-N'-[4-(trifluoromethoxy)benzoyl]pyrrolidin-3-carbohydrazide (100 mg) in anhydrous THF (5 mL) was added the Burgess reagent (70 mg) with stirring at room temperature. The reaction was carried out at room temperature for 4 hours. After the reaction completed, water was added to the reaction solution to stop the reaction. The reaction solution was diluted with ethyl acetate (30 mL) and washed with saturated brine (30 mL×2). The organic layer was dried over anhydrous sodium sulfate and evaporated under reduced pressure, and the resulting residue was purified by silica gel column chromatography (hexane-ethyl acetate) to obtain the title compound (60 g, yield 63%).

[Formula 31]

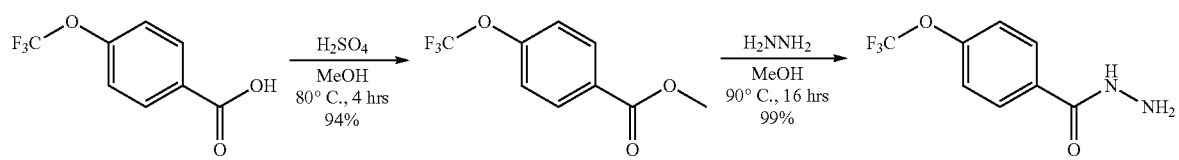

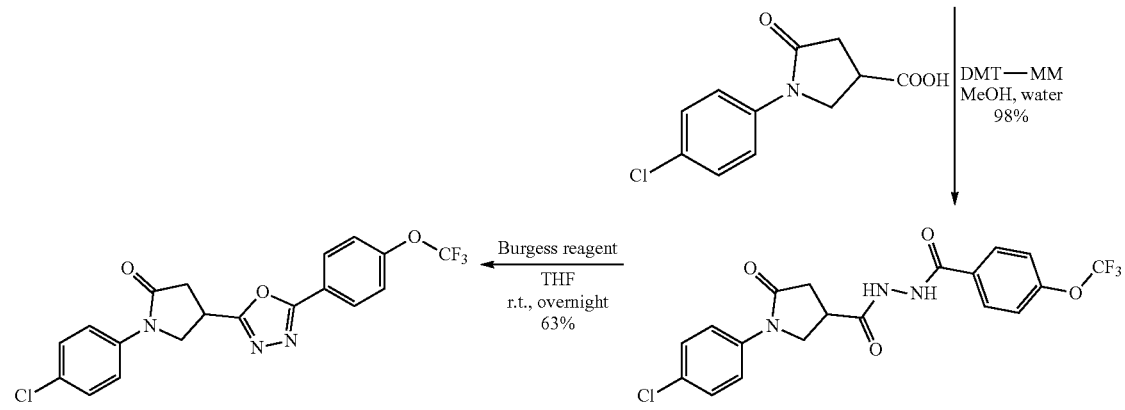

Synthesis of (S)-4-chloro-N-(2-hydroxy-1-{5-[4-(trifluoromethoxy)phenyl]-1,3,4-oxadiazol-2-yl}ethyl)benzamide (Compound 104)

[Formula 32]

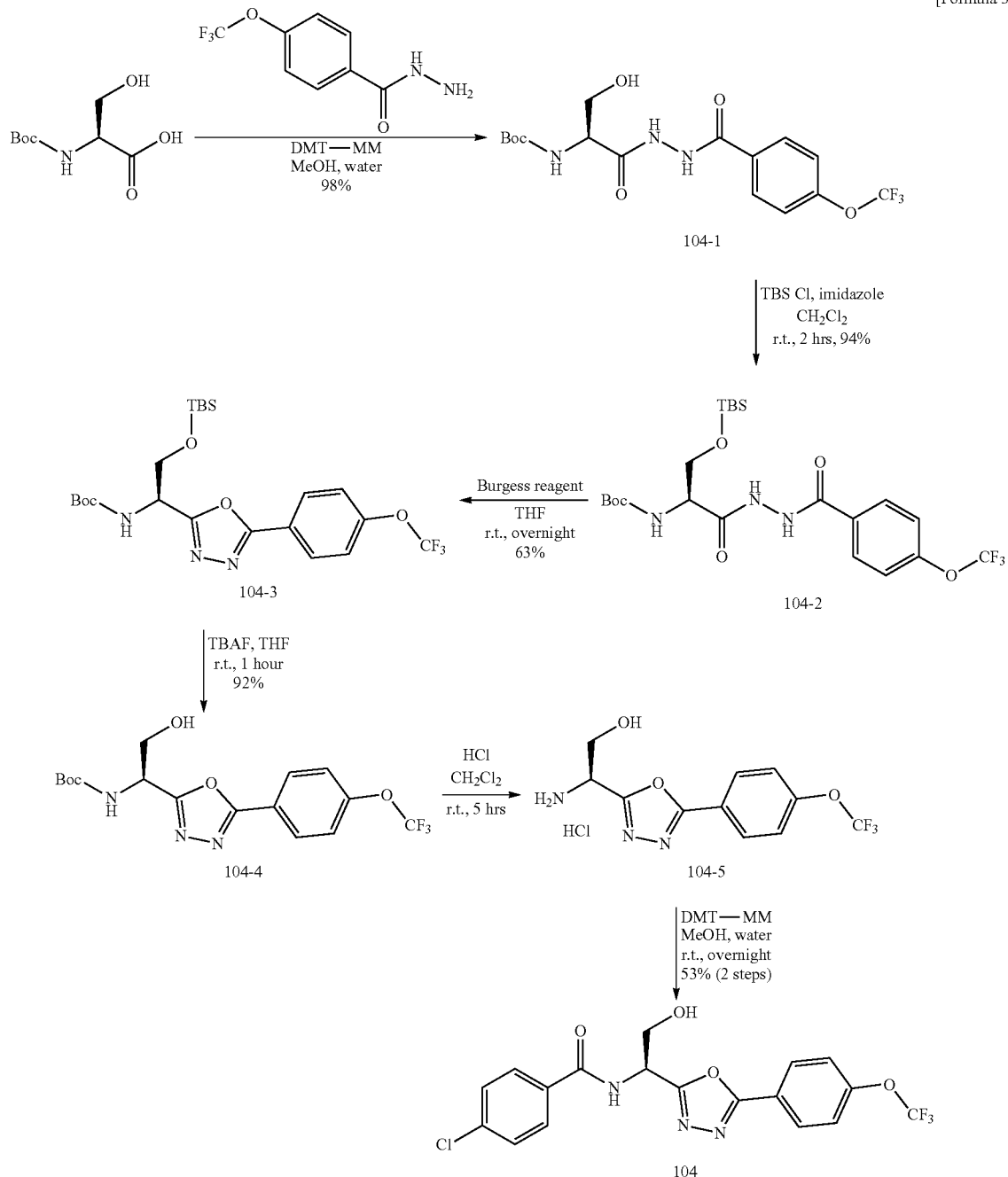

(104-1) Synthesis of tert-butyl (3-hydroxy-1-oxo-1-{2-[4-(trifluoromethoxy)benzoyl]hydrazinyl}propan-2-yl)carbamate (Compound 104-1)

DMT-MM (809 mg) was added to a solution of Boc-L-serine (500 mg) and 4-(trifluoromethoxy)benzohydrazide (536 mg) in ethanol/water (10 mL/10 mL) with stirring at room temperature. The reaction was carried out at room temperature for 18 hours. After completion of the reaction, the reaction solution was diluted with ethyl acetate (50 mL) and washed with saturated brine (30 mL×2). The ethyl acetate layer was dried over anhydrous sodium sulfate and evaporated under reduced pressure, and the resulting residue was purified by silica gel column chromatography (hexane-ethyl acetate) to obtain 1 g of the title compound (yield 99%).

(104-2) Synthesis of tert-butyl {3-[(tert-butyldimethylsilyl)oxy]-1-oxo-1-{2-[4-(trifluoromethoxy)benzoyl]hydrazinyl}propan-2-yl}carbamate (Compound 104-2)

To a solution of tert-butyl (3-hydroxy-1-oxo-1-{2-[4-(trifluoromethoxy)benzoyl]hydrazinyl}propan-2-yl)carbamate (1 g) and imidazole (836 mg) in dichloromethane (50 mL) was added tert-butyldimethylsilyl chloride (740 mg) with stirring at room temperature and the mixture was stirred for 18 hours. After completion of the reaction, the reaction solution was washed with saturated brine (30 mL×2), and the organic layer was dried with anhydrous sodium sulfate. The solvent was evaporated off under reduced pressure, and the resulting residue was purified by silica gel column chromatography (hexane-ethyl acetate) to obtain the title compound (1.2 g, yield 94%).

(104-3) Synthesis of tert-butyl {2-[(tert-butyldimethylsilyl)oxy]-1-{5-[4[(trifluoromethoxy)phenyl]-1,3,4-oxadiazol-2-yl]ethyl}carbamate (Compound 104-3)

The Burgess reagent (1.1 g) was added to a solution of tert-butyl {3-[(tert-butyldimethylsilyl)oxy]-1-oxo-1-{2-[4-(trifluoromethoxy)benzoyl]hydrazinyl}propan-2-yl}carbamate (1.2 g) in dehydrated dichloromethane (15 mL) with stirring at room temperature and the mixture was stirred for 4 hours. After the reaction completed, water was added to the reaction solution to stop the reaction. The reaction solution was diluted with dichloromethane (30 mL) and washed with saturated brine (30 mL×2). The organic layer was dried over anhydrous sodium sulfate and evaporated under reduced pressure, and the obtained residue was purified by silica gel column chromatography (hexane-acetone) to obtain the title compound 700 mg (yield 60%).

(104-4) Synthesis of tert-butyl (2-hydroxy-1-{5-[4-(trifluoromethoxy)phenyl]-1,3,4-oxadiazol-2-yl}ethyl)carbamate (Compound 104-4)

To a solution of tert-butyl {2-[(tert-butyldimethylsilyl)oxy]-1-{5-[4[(trifluoromethoxy)phenyl]-1,3,4-oxadiazol-2-yl]ethyl}carbamate (700 mg) in THF (10 mL) was added TBAF (1 mL) with stirring at room temperature. The reaction was carried out at room temperature for 1 hour. After completion of the reaction, the reaction solution was diluted with ethyl acetate (50 mL) and washed with saturated brine (50 mL×2). The organic layer was dried over anhydrous sodium sulfate and evaporated under reduced pressure, and the obtained residue was purified by silica gel column chromatography (hexane-acetone) to obtain the title compound (500 mg, yield 92%).

(104-5) Synthesis of 2-amino-2-{5-[4-(trifluoromethoxy)phenyl]-1,3,4-oxadiazol-2-yl}ethan-1-ol hydrochloride (Compound 104-5)

To a solution of tert-butyl (2-hydroxy-1-{5-[4-(trifluoromethoxy)phenyl]-1,3,4-oxadiazol-2-yl}ethyl)carbamate (0.5 g) in dichloromethane (5 mL) was added 4M solution of hydrochloric acid in dichloromethane (5 mL) with stirring at room temperature. The reaction was carried out at room temperature for 5 hours. After completion of the reaction, dichloromethane and residual hydrochloric acid were evaporated off under reduced pressure. The obtained residue was used for the next reaction without purification.

(104-6) Synthesis of (S)-4-chloro-N-(2-hydroxy-1-{5-[4-(trifluoromethoxy)phenyl]-1,3,4-oxadiazol-2-yl}ethyl)benzamide (Compound 104)

2-Amino-2-{5-[4-(trifluoromethoxy)phenyl]-1,3,4-oxadiazol-2-yl}ethan-1-ol hydrochloride (230 mg) and 4-chlorobenzoic acid (111 mg) were dissolved in a mixture of ethanol/saturated aqueous solution of sodium hydrogen carbonate (5 mL/2 mL), and DMT-MM (234 mg) was added to the mixture. The reaction was carried out at room temperature overnight. After the reaction completed, the reaction solution was diluted with ethyl acetate (50 mL) and washed with a saturated aqueous solution of sodium bicarbonate (30 mL), followed by saturated brine (30 mL). The organic layer was dried over anhydrous sodium sulfate and evaporated under reduced pressure, and the obtained residue was purified by silica gel column chromatography (hexane-acetone) to obtain the title compound 160 mg (yield 53%).

Compounds 105 to 114, 120, 125 and 127 were synthesized in the same manner as described above.

Synthesis of 4-chloro-N-(1-(5-(4-(trifluoromethoxy)phenyl)-1,3,4-oxadiazol-2-yl)vinyl)benzamide (Compound 115)

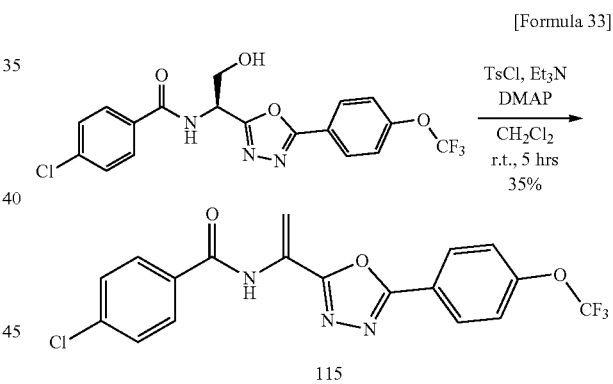

[Formula 33]

(115-1) Synthesis of 4-chloro-N-(1-(5-(4-(trifluoromethoxy)phenyl)-1,3,4-oxadiazol-2-yl)vinyl)benzamide (Compound 115)

Triethylamine (0.59 mL) and p-toluenesulfonyl chloride (348 mg) were added to a solution of (S)-4-chloro-N-(2-hydroxy-1-{5-[4-trifluoromethoxy]phenyl}-1,3,4-oxadiazol-2-yl)ethyl)benzamide (600 mg) and DMAP (51 mg) in dichloromethane (50 mL) with stirring under ice cooling. The reaction was carried out at room temperature for 18 hours. After completion of the reaction, the reaction solution was washed with a saturated aqueous solution of ammonium chloride (30 mL×2) and dried over anhydrous sodium sulfate. The solvent was evaporated off under reduced pressure, and the resulting residue was purified by silica gel column chromatography (hexane-ethyl acetate) to give the title compound (200 mg, yield 35%).

Synthesis of N-(2-amino-1-{5-[4-(trifluoromethoxy)phenyl]-1,3,4-oxadiazol-2-yl}ethyl)-4-chlorobenzamide (Compound 116)

[Formula 34]

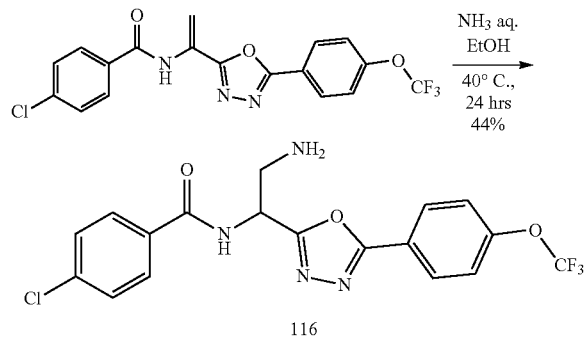

(116-1) Synthesis of N-(2-amino-1-{5-[4-(trifluoromethoxy)phenyl]-1,3,4-oxadiazol-2-yl}ethyl)-4-chlorobenzamide (Compound 116)

To a stirred solution of 4-chloro-N-(1-{5-[4-(trifluoromethoxy)phenyl]-1,3,4-oxadiazol-2-yl}vinyl)benzamide (50 mg) in ethanol (5 mL) was added 28% aqueous solution of ammonia (1 mL) at room temperature. The reaction was carried out at 40° C. for 18 hours. After completion of the reaction, the reaction solution was cooled to room temperature, and ethanol was evaporated off under reduced pressure. The obtained residue was purified by silica gel column chromatography (dichloromethane-ethanol) to obtain the title compound 23 mg (yield 44%).

Compounds 117 to 119 were synthesized in the same manner as described above.

Synthesis of 1-(4-chlorophenyl)-4-{3-[4-(trifluoromethoxy)phenyl]-1,2,4-thiadiazol-5-yl}pyrrolidin-2-one (Compound 121)

[Formula 35]

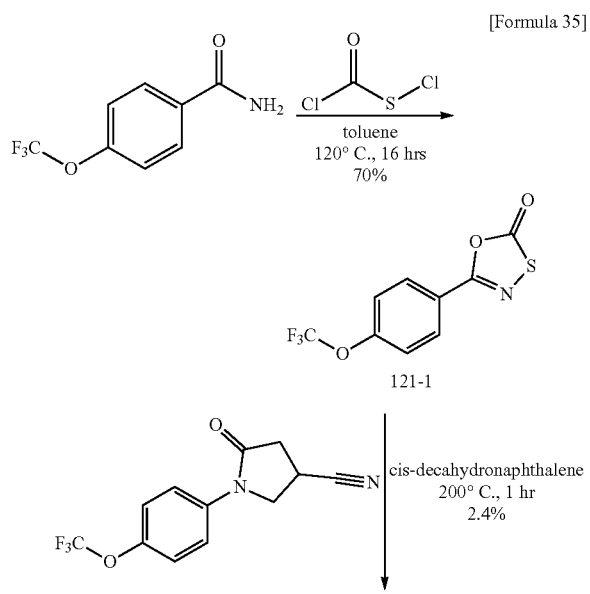

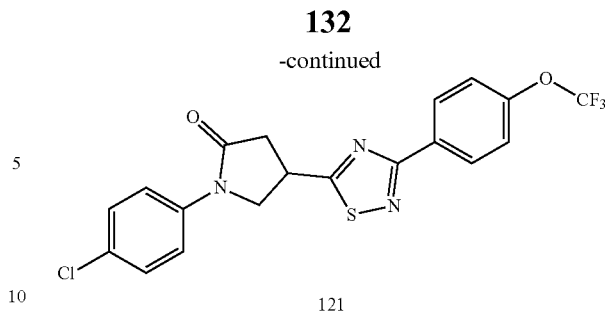

(121-1) Synthesis of 5-[4-(trifluoromethoxy)phenyl]-1,3,4-oxathiazol-2-one (Compound 121-1)

Chlorocarbonylsulfenyl chloride (0.25 mL) was added to a suspension of 4-(trifluoromethoxy)benzamide (500 mg) in toluene (30 mL) with stirring at room temperature. The reaction was carried out at 120° C. for 16 hours. After cooling to room temperature, a saturated aqueous solution of sodium hydrogen carbonate (50 mL) was added to the reaction solution to terminate the reaction. The mixture was extracted with ethyl acetate (30 mL×2). The combined organic layer was washed with saturated brine (50 mL) and dried over anhydrous sodium sulfate. The solvent was evaporated off under reduced pressure, and the resulting residue was purified by silica gel column chromatography (hexane-ethyl acetate) to obtain the title compound 450 mg (yield 70%).

(121-1) Synthesis of 1-(4-chlorophenyl)-4-{3-[4-(trifluoromethoxy)phenyl]-1,2,4-thiadiazol-5-yl}pyrrolidin-2-one (Compound 121)

A solution of 5-[4-(trifluoromethoxy)phenyl]-1,3,4-oxathiazol-2-one (270 mg) and 1-(4-chlorophenyl)-5-oxopyrrolidine-3-carbonitrile (226 mg) in cis-decahydronaphthalene (5 mL) was stirred at 200° C. for 1 hour. After cooling to room temperature, the reaction solution was directly purified by silica gel column chromatography (hexane-ethyl acetate) to give the title compound 20 mg (yield 4.4%).

Synthesis of 1-(4-chlorophenyl)-4-{2-[4-(trifluoromethoxy)phenyl]-2H-tetrazol-5-yl}pyrrolidin-2-one (Compound 122)

[Formula 36]

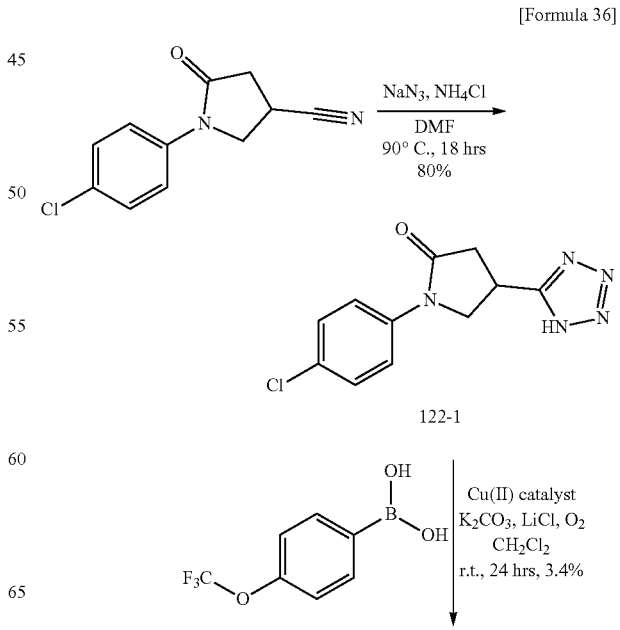

-continued

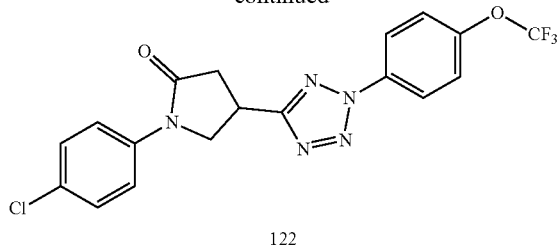

122

(122-1) Synthesis of 1-(4-chlorophenyl)-4-(1H-tetrazol-5-yl)pyrrolidin-2-one (Compound 122-1)

A suspension of 1-(4-chlorophenyl)-5-oxopyrrolidin-3-carbonitrile (200 mg), ammonium chloride (58 mg) and sodium azide (65 mg) in DMF (5 mL) was stirred at 90° C. for 24 hours. After cooling the reaction solution to room temperature, 5% aqueous solution of hydrochloric acid (30 mL) was added to the reaction solution to terminate the reaction. The mixture was extracted with dichloromethane (30 mL×3). The combined organic layer was washed with saturated brine (50 mL) and dried over anhydrous sodium sulfate. The solvent was evaporated off under reduced pressure, and the resulting residue was purified by silica gel column chromatography (hexane-acetone) to obtain 190 mg (yield 80%) of the title compound.
Ms m/z (APCI) [M+H]+=264.

(122-2) Synthesis of 1-(4-chlorophenyl)-4-{2-[4-(trifluoromethoxy)phenyl]-2H-tetrazol-5-yl}pyrrolidin-2-one (Compound 122)

A suspension of 1-(4-Chlorophenyl)-4-(1H-tetrazol-5-yl)pyrrolidin-2-one (190 mg), [4-(trifluoromethoxy)phenyl] boronic acid (237 mg), potassium carbonate (110 mg), lithium chloride (15 mg) and di-μ-hydroxo-bis[(N,N,N',N'-tetramethylethylenediamine) copper (II)]chloride (41 mg) in dichloromethane (3 mL) was stirred at room temperature under an oxygen atmosphere for 24 hours. After stirring for 24 hours, the reaction was stopped by adding a 10% aqueous ammonia solution (15 mL). The mixture was extracted with dichloromethane (30 mL×2), and the combined organic layer was washed with saturated brine (30 mL) and dried over anhydrous sodium sulfate. The solvent was evaporated off under reduced pressure, and the resulting residue was purified by silica gel column chromatography (hexane-ethyl acetate) to obtain the title compound 13 mg (yield 3.4%).

Synthesis of 1-(4-chlorophenyl)-4-{5-[4-(trifluoromethoxy)phenyl]-4H-1,2,4-triazol-3-yl}pyrrolidin-2-one (Compound 123)

[Formula 37]

-continued

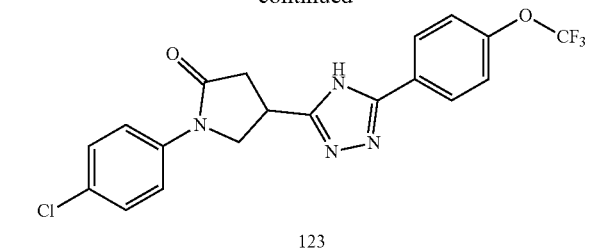

123

(123-1) Synthesis of 1-(4-chlorophenyl)-4-{5-[4-(trifluoromethoxy)phenyl]-4H-1,2,4-triazol-3-yl}pyrrolidin-2-one (Compound 123)

1-(4-Chlorophenyl)-5-oxopyrrolidin-3-carbonitrile (327 mg), 4-(trifluoromethoxy)benzimidamide hydrochloride (200 mg), cesium carbonate (886 mg) and copper (I) iodide (10 mg) were suspended in dehydrated DMSO (5 mL). The reaction was carried out at 120° C. for 24 hours. After cooling to room temperature, ethyl acetate (50 mL) was added followed by washing with 5% aqueous solution of sodium bicarbonate (50 mL) and saturated brine (50 mL). After drying the ethyl acetate layer with anhydrous sodium sulfate, the solvent was distilled off, and the obtained residue was purified by silica gel column chromatography (hexane-acetone) to obtain the title compound 4 mg (yield 1%).

Synthesis of 1-(4-chlorophenyl)-4-{5-[4-(trifluoromethoxy)phenyl]-1H-imidazol-2-yl}pyrrolidin-2-one (Compound 124)

[Formula 38]

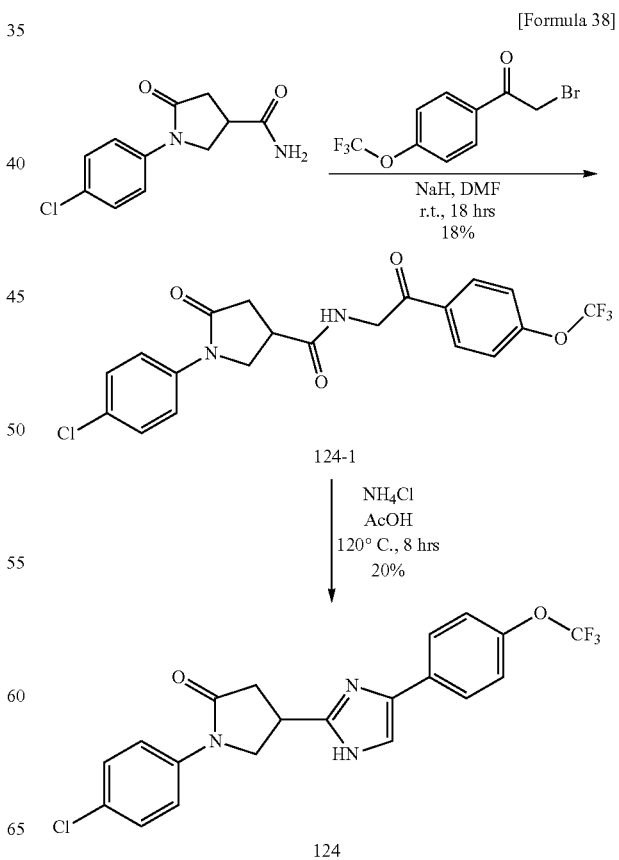

124

(124-1) Synthesis of 1-(4-chlorophenyl)-4-{5-[4-(trifluoromethoxy)phenyl]-1H-imidazol-2-yl}pyrrolidin-2-on (Compound 124-1)

To a solution of 1-(4-chlorophenyl)-5-oxopyrrolidin-3-carboxamide (300 mg) in dry DMF (5 mL) was added NaH (60% mineral oil dispersion, 75 mg) with stirring under ice cooling. After stirring at room temperature for 30 minutes, 4-trifluoromethoxyphenacyl bromide (391 mg) was added. The reaction was carried out at 110° C. for 3 hours, followed by at room temperature for 18 hours. After cooling to room temperature, water (30 mL) was added to stop the reaction. The mixture was extracted with ethyl acetate (30 mL×3). The combined ethyl acetate layer was washed with saturated brine (50 mL) and dried over anhydrous sodium sulfate. The solvent was evaporated off under reduced pressure, and the resulting residue was purified by silica gel column chromatography (hexane-acetone) to obtain the title compound 100 mg (yield 18%).

(124-2) Synthesis of 1-(4-chlorophenyl)-4-{5-[4-(trifluoromethoxy)phenyl]-1H-imidazol-2-yl}pyrrolidin-2-one (Compound 124)

A solution of 1-(4-chlorophenyl)-4-{5-[4-(trifluoromethoxy)phenyl]-1H-imidazol-2-yl}pyrrolidin-2-one (100 mg) and ammonium acetate (52 mg) in acetic acid (5 mL) was stirred at 120° C. for 8 hours. Thereafter, the reaction solution was cooled to room temperature, the mixture was diluted with ethyl acetate (30 mL). The solution was washed with saturated aqueous solution of sodium hydrogen carbonate (30 mL×3). The organic layer was dried over anhydrous sodium sulfate, the solvent was evaporated off under reduced pressure, and the residue obtained was purified by silica gel column chromatography (hexane-ethyl acetate) to obtain the title compound 20 mg (yield 20%).

Synthesis of (R)-4-chloro-N-(2-hydroxy-1-(5-(4-(trifluoromethoxy)phenyl)-1,2,4-oxadiazol-3-yl)ethyl)benzamide (Compound 126)

[Formula 39]

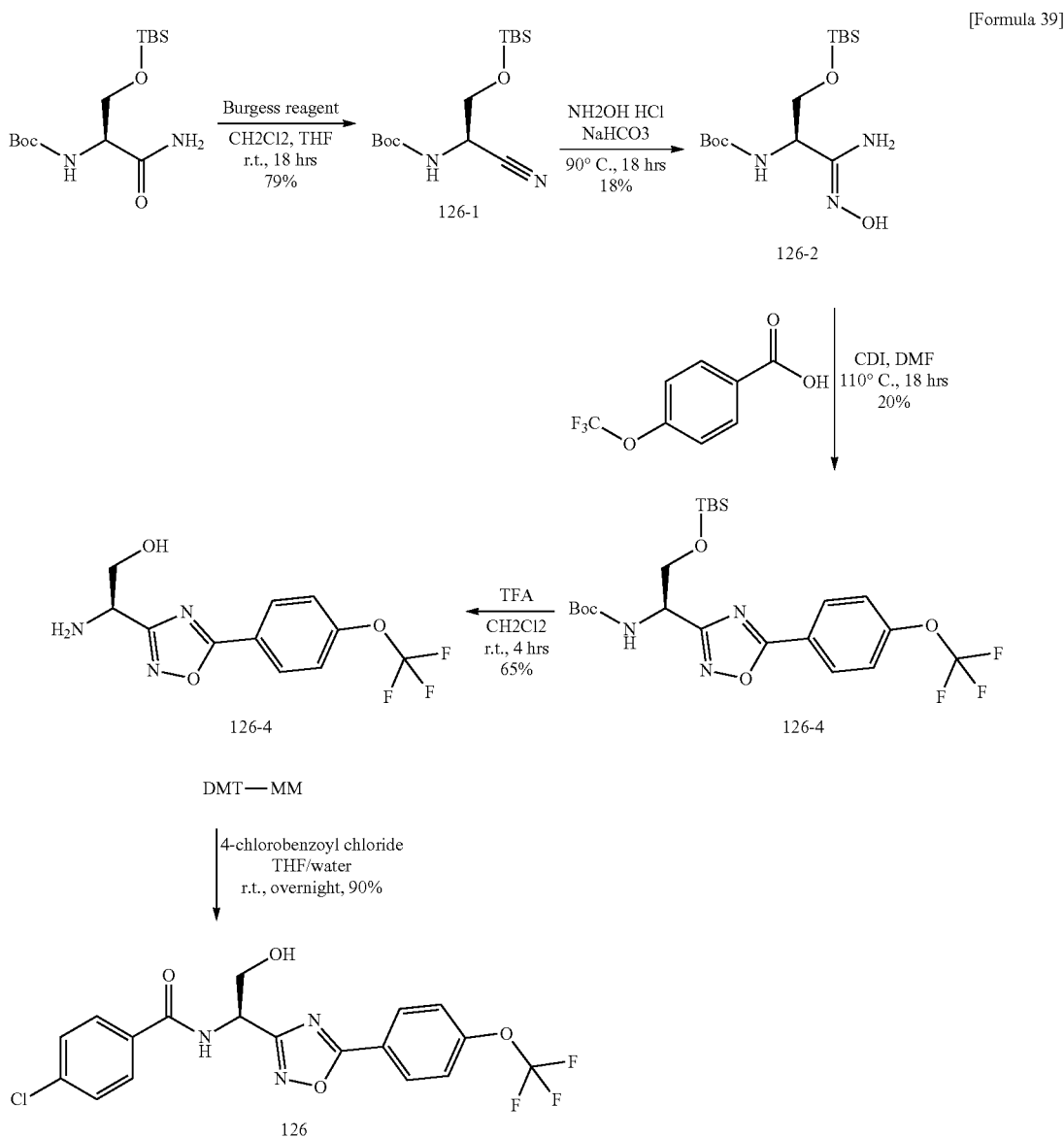

(126-1) Synthesis of tert-butyl (R)-(2-((tert-butyldimethylsilyl)oxy)-1-cyanoethyl)carbamate (Compound 126-1)

The Burgess reagent (1.2 g) was added to a stirred solution of tert-butyl (S)-(1-amino 3-((tert-butyldimethylsilyl)oxy)-1-oxypropan-2-yl)carbamate (800 mg) in dry THF (50 mL) at room temperature. After the reaction completed, water (10 mL) was added to stop the reaction. Saturated brine (50 mL) was added to the mixture, and the mixture was extracted three times with ethyl acetate (50 mL). The combined ethyl acetate layer was washed with saturated brine (50 mL) and dried over anhydrous sodium sulfate. The solvent was evaporated off under reduced pressure, and the resulting residue was purified by silica gel column chromatography (hexane-ethyl acetate) to obtain the title compound (600 mg, yield 79%).

(126-2) Synthesis of tert-butyl (R)-(1-amino-3-((tert-butyldimethylsilyl)oxy)-1-hydroxyamino)propan-2-yl)carbamate (Compound 126-2)

Sodium bicarbonate (252 mg) was added to a solution of tert-butyl (R)-(2-((tert-butyldimethylsilyl)oxy-1-cyanoethyl)carbamate (600 mg) and hydroxylamine hydrochloride (167 mg) in methanol (20 mL) with stirring at room temperature. The reaction was heated to reflux for 18 hours. After cooling to room temperature, methanol was evaporated off under reduced pressure, and the obtained residue was suspended in water to precipitate crystals. These crystals were collected by filtration and dried thoroughly to obtain 120 mg (yield 18%) of the title compound.

(126-3) Synthesis of tert-butyl (R)-(2-((tert-butyldimethylsilyl)oxy)-1-(5-(4-(trifluoromethoxy)phenyl)-1,2,4-oxadiazol-3-yl)ethyl)carbamate (Compound 126-3)

After stirring a mixed solution of tert-butyl (R)-(1-amino-3-((tert-butyldimethylsilyl)oxy)-1-hydroxyamino)propan-2-yl)carbamate (400 mg), 4-(trifluoromethoxy)benzoic acid (247 mg) and HOBt (162 mg) in DMF (15 mL) at 50° C. for 20 minutes, N-hydroxy-4-(trifluoromethoxy)benzene-1-carboximidamide (110 mg, 0.5 mmol) was added and the mixture was stirred at 110° C. for 18 hours. After the reaction completed, the reaction solution was cooled to room temperature, and saturated brine (50 mL) was added thereto to stop the reaction. The mixture was extracted three times with ethyl acetate (30 mL), and the combined ethyl acetate layer was washed with saturated brine (50 mL) and dried over anhydrous sodium sulfate. The solvent was evaporated off under reduced pressure, and the resulting residue was purified using silica gel column chromatography (hexane/ethyl acetate) to obtain the title compound 120 mg (yield 20%).

(126-4) Synthesis of (R)-2-amino-2-(5-(4-trifluoromethoxy)phenyl)-1,2,4-oxadiazol-3-yl)ethan-1-ol (Compound 126-4)

To a stirred solution of tert-butyl (R)-(2-((tert-butyldimethylsilyl)oxy)-1-(5-(4-(trifluoromethoxy)phenyl)-1,2,4-oxadiazol-3-yl)ethyl)carbamate (120 mg) in dichloromethane (5 mL) was added trifluoroacetic acid (1 mL) at room temperature. The reaction was carried out at room temperature for 4 hours. After the reaction completed, the reaction solution was diluted with dichloromethane (30 mL), and extracted three times with 10% solution of hydrochloric acid (30 mL) from this solution. The combined aqueous layer was neutralized with aqueous solution of sodium hydroxide and extracted three times with dichloromethane (30 mL). The combined organic layer was washed with saturated brine (30 mL) and dried over anhydrous sodium sulfate. The solvent was evaporated off under reduced pressure to give 45 mg (65%) of the title compound as a crude product. The crude product obtained above was used for the next reaction without further purification.

(126-5) Synthesis of ((R)-4-chloro-N-(2-hydroxy-1-(5-(4-(trifluoromethoxy)phenyl)-1,2,4-oxadiazol-3-yl)ethyl)benzamide (Compound 126)

(R)-2-amino-2-(5-(4-trifluoromethoxy)phenyl)-1,2,4-oxadiazol-3-yl)ethan-1-ol (45 mg) and 4-chlorobenzoic acid (32 mg) were dissolved in a mixture of THF/water (10 mL/2 mL) and DMT-MM (86 mg) was added to this solution with stirring at room temperature. The reaction was carried out at room temperature overnight. After the reaction completed, water was added to the reaction solution to stop the reaction. The mixture was diluted with ethyl acetate (50 mL) and washed with saturated aqueous sodium bicarbonate solution (30 mL) followed by saturated brine (30 mL). The organic layer was dried over anhydrous sodium sulfate and evaporated under reduced pressure, and the obtained residue was purified by silica gel column chromatography (hexane-ethyl acetate) to obtain the title compound 60 mg (yield 90%).

Compound 128 was synthesized in the same manner as described above.

Compounds 1 to 133 and 142 to 267 are shown in Table 2.

TABLE 2A

| Compound no. | Structural formula | Name | NMR | MS | Melting point (° C.) |
|---|---|---|---|---|---|
| 1 | | N-(3-chlorophenyl)-2-{3-(4-methoxyphenyl)-1,2,4-oxadiazol-5-yl}-N-propylacetamide | 1H NMR (500 MHz, CHLOROFORM-d) d 7.91-8.08 (m, 2H), 7.35-7.45 (m, 2H), 7.29 (s, 1H), 7.10-7.22 (m, 1H), 6.84-7.04 (m, 2H), 3.86 (s, 3H), 3.77 (s, 2H), 3.63-3.74 (m, 2H), 1.47-1.69 (m, 3H), 0.92 (t, J = 7.40 Hz, 3H). | Ms m/z (APCI) [M + H]+ = 386 | 108 |

TABLE 2A-continued

| Compound no. | Structural formula | Name | NMR | MS | Melting point (° C.) |
|---|---|---|---|---|---|
| 2 | | N-(3-chlorophenyl)-3-{3-(4-methoxyphenyl)-1,2,4-oxadiazol-5-yl}-N-propylpropanamide | 1H NMR (495 MHz, CHLOROFORM-d) d 7.97 (d, J = 8.73 Hz, 2H), 7.32-7.43 (m, 2H), 7.13 (td, J = 2.17, 6.62 Hz, 1H), 6.92-7.01 (m, 2H), 3.86 (s, 3H), 3.61-3.70 (m, 2H), 3.22 (t, J = 7.14 Hz, 2H), 2.59 (t, J = 7.13 Hz, 2H), 1.47-1.55 (m, 2H), 0.88 (t, J = 7.37 Hz, 3H). | Ms m/z (APCI) [M + H]+ = 400 | 85 |
| 3 | | N-(3-chlorophenyl)-N-(2-hydroxyethyl)-3-{3-(4-methoxyphenyl)-1,2,4-oxadiazol-5-yl}propanamide | 1H NMR (400 MHz, CHLOROFORM-d) d 7.98 (d, J = 6.8 Hz, 2H), 7.05 (t, J = 8.0 Hz, 1H), 6.95 (dd, J = 2.8, 1.6 Hz, 2H), 6.67 (dd, J = 1.6, 8.0 Hz, 1H), 6.58 (t, J = 2.0 Hz, 1H), 6.46 (dd, J = 2.4, 8.4 Hz, 1H), 4.34 (t, J = 5.2 Hz, 2H), 4.03 (br s, 1H), 3.86 (s, 3H), 3.39 (s, 2H), 3.25 (t, J = 6.4 Hz, 2H), 2.96 (t, J = 5.8 Hz, 2H). | Ms m/z (ESAPI) [M + H]+ = 402.2 | 95 |
| 4 | | N-(4-chloropyridin-2-yl)-3-{3-(4-methoxyphenyl)-1,2,4-oxadiazol-5-yl}propanamide | 1H NMR (400 MHz, CHLOROFORM-d) d 8.38 (s, 1H), 8.28 (s, 1H), 8.18 (d, J = 5.2 Hz, 1H), 8.01 (d, J = 8.8 Hz, 2H), 7.06 (dd, J = 1.2, 5.2 Hz, 1H), 6.97 (d, J = 8.8 Hz, 2H), 3.87 (s, 3H), 3.36 (t, J = 7.2 Hz, 2H), 3.04 (t, J = 7.2 Hz, 2H). | Ms m/z (ESAPI) [M + H]+ = 359.3 | 167 |
| 5 | | N-(5-chloropyridin-3-yl)-3-{3-(4-methoxyphenyl)-1,2,4-oxadiazol-5-yl}-N-propylpropanamide | 1H NMR (400 MHz, CHLOROFORM-d) d 8.62 (s, 1H), 8.46 (s, 1H), 8.00 (d, J = 8.8 Hz, 2H), 7.66 (s, 1H), 6.98 (d, J = 8.8 Hz, 2H), 3.87 (s, 3H), 6.68 (t, J = 7.2 Hz, 2H), 3.25 (t, J = 7.2 Hz, 2H), 2.60 (s, 2H), 1.65-1.71 (m, 2H), 0.90 (t, J = 6.8 Hz, 3H). | Ms m/z (ESAPI) [M + H]+ = 401.2 | Amorphous |
| 6 | | N-(3-chlorophenyl)-N-(3-hydroxypropyl)-3-{3-(4-methoxyphenyl)-1,2,4-oxadiazol-5-yl}propanamide | 1H NMR (400 MHz, CHLOROFORM-d) d 7.99 (dd, J = 2.0, 7.2 Hz, 3H), 7.05 (t, J = 8.0 Hz, 1H), 6.96 (dd, J = 2.0, 6.8 Hz, 2H), 6.65 (dd, J = 1.6, 7.6 Hz, 1H), 6.55 (t, J = 2.0 Hz, 1H), 6.44 (dd, J = 2.4, 8.4 Hz, 1H), 4.25 (t, J = 6.0 Hz, 1H), 3.86 (s, 3H), 3.26 (t, J = 7.2 Hz, 2H), 3.19 (t, J = 6.8 Hz, 2H), 2.96 (t, J = 7.2 Hz, 2H), 1.92-1.96 (m, 2H), 1.56 (s, 1H). | Ms m/z (ESAPI) [M + H]+ = 416.2 | 80 |

TABLE 2B

| | Structure | Name | 1H NMR | MS | |
|---|---|---|---|---|---|
| 7 | 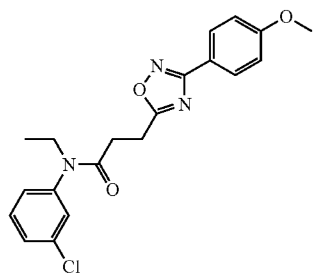 [SMILES: CCN(C(=O)CCc1nc(-c2ccc(OC)cc2)no1)c1cccc(Cl)c1] | N-(3-chlorophenyl)-N-ethyl-3-{3-(4-methoxyphenyl)-1,2,4-oxadiazol-5-yl}propanamide | 1H NMR (400 MHz, CHLOROFORM-d) d 7.97 (d, J = 8.8 Hz, 2H), 7.38-7.40 (m, 2H), 7.27 (s, 1H), 7.13-7.15 (m, 1H), 6.97 (d, J = 8.8 Hz, 2H), 3.85 (s, 3H), 3.75 (q, J = 7.2 Hz, 2H), 3.23 (t, J = 7.2 Hz, 2H), 2.60 (t, J = 7.2 Hz, 2H), 1.12 (t, J = 7.2 Hz, 2H). | Ms m/z (ESAPI) [M + H]+ = 386.2 | 74 |
| 8 | 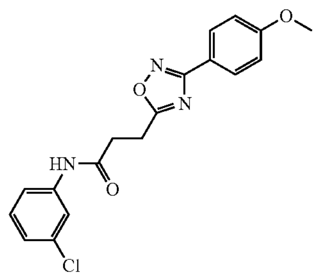 [SMILES: COc1ccc(-c2noc(CCC(=O)Nc3cccc(Cl)c3)n2)cc1] | N-(3-chlorophenyl)-3-{3-(4-methoxyphenyl)-1,2,4-oxadiazol-5-yl}propanamide | 1H NMR (400 MHz, CHLOROFORM-d) d 7.99 (d, J = 8.8 Hz, 2H), 7.69 (s, 1H), 7.65 (s, 1H), 7.34 (d, J = 8.0 Hz, 1H), 7.23 (d, J = 8.4 Hz, 1H), 7.09 (d, J = 8.0 Hz, 1H), 6.98 (d, J = 8.8 Hz, 2H), 3.87 (s, 3H), 3.36 (t, J = 6.8 Hz, 2H), 2.98 (t, J = 6.8 Hz, 2H). | Ms m/z (ESAPI) [M + H]+ = 358.1 | 136 |
| 9 | 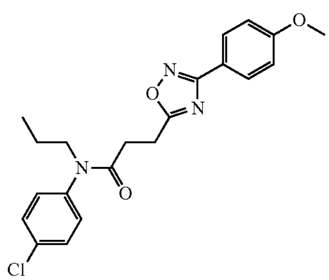 | N-(3-chlorobenzyl)-3-{3-(4-methoxyphenyl)-1,2,4-oxadiazol-5-yl}-N-propylpropanamide | 1H NMR (400 MHz, CHLOROFORM-d) d 7.99 (dd, J = 2.0, 6.8 Hz, 2H), 7.29-7.31 (m, 1H), 7.09-7.20 (m, 3H), 6.97 (dd, J = 2.0, 6.8 Hz, 2H), 4.59 (s, 2H), 3.87 (s, 3H), 3.36 (t, J = 7.2 H, 2H), 3.25-3.31 (m, 2H), 3.02 (t, J = 7.2 Hz, 2H), 1.56-1.68 (m, 2H), 0.95 (t, J = 7.2 Hz, 3H). | Ms m/z (ESAPI) [M + H]+ = 414.2 | Amorphous |
| 10 | 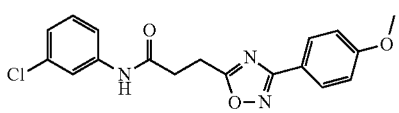 [SMILES: COc1ccc(-c2noc(CCC(=O)Nc3cccc(Cl)c3)n2)cc1] | N-(3-chlorophenyl)-3-{3-(4-methoxyphenyl)-1,2,4-oxadiazol-5-yl}propanamide | 1H NMR (600 MHz, CDCl3) d 7.99 (d, J = 8.54 Hz, 2H), 7.78 (br. s., 1H), 7.64 (s, 1H), 7.33 (d, J = 8.12 Hz, 1H), 7.23 (t, J = 8.05 Hz, 1H), 7.08 (d, J = 7.89 Hz, 1H), 6.98 (d, J = 8.56 Hz, 2H), 3.87 (s, 3H), 3.35 (t, J = 7.01 Hz, 2H), 2.97 (t, J = 7.02 Hz, 2H), | Ms m/z (ESAPI) [M + H]+ = 358 | 137 |
| 11 | 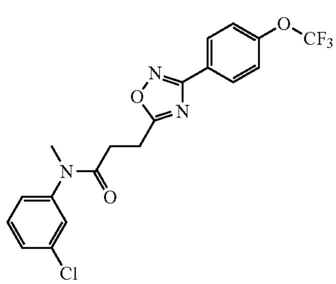 [SMILES: CN(C(=O)CCc1nc(-c2ccc(OC(F)(F)F)cc2)no1)c1cccc(Cl)c1] | N-(3-chlorophenyl)-N-methyl-3-[3-{4-(trifluoromethoxy)phenyl}-1,2,4-oxadiazol-5-yl]propanamide | 1H NMR (400 MHz, CHLOROFORM-d) d 8.09 (d, J = 8.8 Hz, 2H), 7.30-7.38 (m, 5H), 7.16 (d, J = 7.2 Hz, 1H), 3.24-3.28 (m, 5H), 2.68 (s, 2H). | Ms m/z (ESAPI) [M + H]+ = 425.9 | 79 |
| 12 | 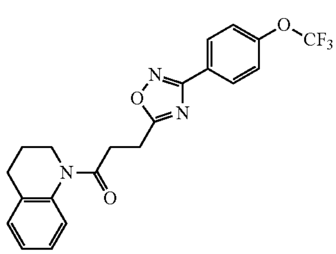 [SMILES: O=C(CCc1nc(-c2ccc(OC(F)(F)F)cc2)no1)N1CCCc2ccccc21] | 1-{3,4-dihydroquinolin-1(2H)-yl}-3-[3-{4-(trifluoromethoxy)phenyl}-1,2,4-oxadiazol-5-yl]propan-1-one | 1H NMR (400 MHz, CHLOROFORM-d) d 8.07 (d, J = 8.8 Hz, 2H), 7.26-7.31 (m, 6H), 3.82 (t, J = 6.8 Hz, 2H), 3.31 (t, J = 6.8 Hz, 2H), 3.10 (t, J = 6.8 Hz, 2H), 2.74 (t, J = 6.8 Hz, 2H), 2.01 (m, 2H). | Ms m/z (ESAPI) [M + H]+ = 418.1 | 76 |

TABLE 2C

| 13 | 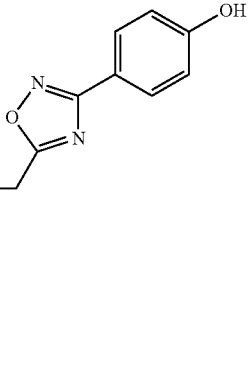 | N-(3-chloropbenyl)-3-{3-(4-hydroxyphenyl)-1,2,4-oxadiazol-5-yl}-N-methylpropanamide | 1H NMR (400 MHz, CHLOROFORM-d) d 8.09 (d, J = 8.8 Hz, 2H), 7.38-7.40 (m, 2H), 7.30-7.32 (m, 3H), 7.15-7.18 (m, 1H), 3.24-3.28 (m, 5H), 2.65 (s, 2H). | Ms m/z (ESAPI) [M + H]+ = 358.1 | 186 |
| --- | --- | --- | --- | --- | --- |
| 14 | 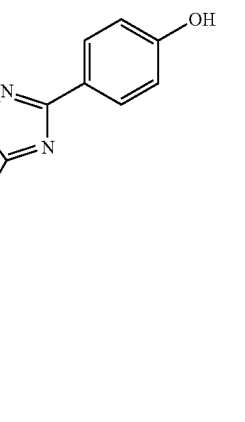 | N-(3-fluorobenzyl)-3-{3-(4-hydroxyphenyl)-1,2,4-oxadiazol-5-yl}-N-methylpropanamide | 1H NMR (400 MHz, DMSO-d6) d 10.09 (s, 1H), 7.80-7.84 (m, 2H), 7.28-7.34 (m, 1H), 6.99-7.16 (m, 3H), 6.68-6.93 (m, 2H), 4.53 (s, 2H), 3.15-3.21 (m, 2H), 3.03 (s, 3H), 2.96-3.01 (m, 2H). | Ms m/z (ESAPI) [M + H]+ = 356.1 | 164 |
| 15 | 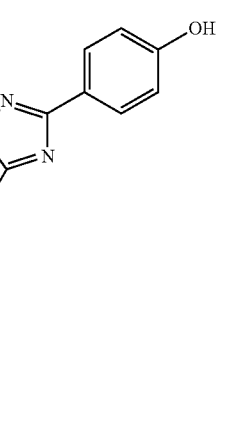 | N-(3-fluorobenzyl)-3-{3-(4-hydroxyphenyl)-1,2,4-oxadiazol-5-yl}propanamide | 1H NMR (400 MHz, DMSO-d6) d 8.54 (s, 1H), 7.80 (dd, J = 2.0, 6.8 Hz, 2H), 7.24-7.27 (m, 2H), 7.04 (t, J = 8.8 Hz, 2H), 6.91 (dd, J = 2.0, 6.8 Hz, 2H), 4.25 (d, J = 6.4 Hz, 2H), 3.18 (t, J = 6.8 Hz, 2H), 2.74 (t, J = 6.8 Hz, 2H). | Ms m/z (ESAPI) [M + H]+ = 364.0 | 144 |
| 16 | 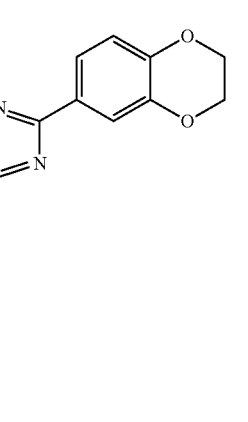 | N-benzyl-3-{3-(2,3-dihydrobenzo[b][1,4]dioxin-6-yl)-1,2,4-oxadiazol-5-yl}-N-methylpropanamide | 1H NMR (400 MHz, CHLOROFORM-d) d 7.58-7.59 (m, 2H), 7.22-739 (m, 5H), 6.92-6.95 (m, 1H), 4.61 (d, J = 6.8 Hz, 2H), 4.31 (s, 4H), 3.30-3.35 (m, 2H), 2.96-3.01 (m, 5H). | Ms m/z (ESAPI) [M + H]+ = 380.0 | 86 |

TABLE 2C-continued

| | | | | | |
|---|---|---|---|---|---|
| 17 | | 3-{3-(2,3-dihydrobenzo[b][1,4]dioxin-6-yl)-1,2,4-oxadiazol-5-yl}-1-{3,4-dihydroisoquinolin-2(1H)-yl}propan-1-one | 1H NMR (400 MHz, CHLOROFORM-d) d 7.57 (s, 1H), 7.51-7.54 (m, 1H), 7.14-7.23 (m, 4H), 6.92 (d, J = 8.4 Hz, 1H), 4.67 (s, 2H), 4.30 (s, 4H), 3.75 (t, J = 6.0 Hz, 2H), 3.21 (t, J = 7.2 Hz, 2H), 2.99-3.04 (m, 2H), 2.95 (t, J = 6.0 Hz, 2H). | Ms m/z (ESAPI) [M + H]+ = 392.0 | 97 |
| 18 | | (S)-2-(1H-indol-3-yl)-1-{3-(4-methoxyphenyl)-1,2,4-oxadiazol-5-yl}ethan-1-amine | 1H NMR (500 MHz, CHLOROFORM-d) d 8.07 (br. s., 1H), 7.98-8.04 (m, 2H), 7.63 (d, J = 7.91 Hz, 1H), 7.32-7.38 (m, 1H), 7.20 (dt, J = 1.18, 7.59 Hz, 1H), 7.12 (ddd, J = 1.04, 7.01, 7.94 Hz, 1H), 7.04 (d, J = 2.40 Hz, 1H), 6.93-7.01 (m, 2H), 4.59 (dd, J = 5.33, 7.65 Hz, 1H), 3.86 (s, 3H), 3.51 (dd, J = 5.17, 14.29 Hz, 1H), 3.30 (dd, J = 7.67, 14.50 Hz, 1H). | Ms m/z (APCI) [M + H]+ = 335 | 110 |

TABLE 2D

| | | | | | |
|---|---|---|---|---|---|
| 19 | | N-(3-chlorophenyl)-3-{3-(4-hydroxyphenyl)-1,2,4-oxadiazol-5-yl}-N-propylpropanamide | 1H NMR (500 MHz, CHLOROFORM-d) d 7.99 (d, J = 8.33 Hz, 2H), 7.39-7.50 (m, 3H), 7.31 (s, 1H), 6.95 (d, J = 8.33 Hz, 2H), 3.54-3.73 (m, 2H), 3.36 (br. s., 2H), 2.96 (br. s., 2H), 1.54 (d, J = 7.92 Hz, 2H), 0.88 (t, J = 7.34 Hz, 3H). | Ms m/z (APCI) [M + H]+ = 386 | 147 |
| 20 | | 4-chloro-N-(2-[3-{4-(trifluoromethoxy)phenyl}-1,2,4-oxadiazol-5-yl]propan-2-yl)benzamide | 1H NMR (500 MHz, CHLOROFORM-d) d 8.06-8.15 (m, 2H), 7.67-7.76 (m, 2H), 7.38-7.47 (m, 2H), 7.30 (d, J = 8.37 Hz, 2H), 6.73 (s, 1H), 1.93 (s, 3H). | Ms m/z (APCI) [M + H]+ = 426 | 173 |
| 21 | | 4-chloro-N-methyl-N-(2-[3-{4-(trifluoromethoxy)phenyl}-1,2,4-oxadiazol-5-yl]propan-2-yl)benzamide | 1H NMR (600 MHz, CHLOROFORM-d) d 8.10-8.14 (m, 2H), 7.42-7.47 (m, 2H), 7.36-7.41 (m, 2H), 7.27-7.31 (m, 2H), 3.12 (s, 3H), 1.86 (s, 6H). | Ms m/z (APCI) [M + H]+ = 440 | 137 |
| 22 | | 4-chloro-N-[2-{3-(4-methoxyphenyl)-1,2,4-oxadiazol-5-yl}propan-2-yl]-N-methyl-benzamide | 1H NMR (500 MHz, CHLOROFORM-d) d 7.94-8.06 (m, 2H), 7.41-7.50 (m, 2H), 7.32-7.41 (m, 2H), 6.89-7.03 (m, 2H), 3.85 (s, 3H), 3.10 (s, 3H), 1.85 (s, 6H). | Ms m/z (APCI) [M + H]+ = 386 | 135 |
| 23 | | 1-(4-chlorophenyl)-4-[3-{4-(trifluoromethoxy)phenyl}-1,2,4-oxadiazol-5-yl]pyrrolidin-2-one | 1H NMR (600 MHz, CHLOROFORM-d) d 8.11-8.17 (m, 2H), 7.56-7.61 (m, 2H), 7.36-7.40 (m, 2H), 7.32-7.36 (m, 2H), 4.32 (dd, J = 1.33, 7.48 Hz, 2H), 4.08 (dq, J = 6.82, 8.35 Hz, 1H), 3.18 (d, J = 8.52 Hz, 2H). | Ms m/z (APCI) [M + H]+ = 424 | 124 |
| 24 | | 1-(4-chlorophenyl)-4-{3-(4-methoxyphenyl)-1,2,4-oxadiazol-5-yl}pyrrolidin-2-one | 1H NMR (600 MHz, CHLOROFORM-d) d 7.97-8.06 (m, 2H), 7.55-7.64 (m, 2H), 7.31-7.39 (m, 2H), 6.91-7.06 (m, 2H), 4.30 (dd, J = 2.02, 7.52 Hz, 2H), 4.00-4.10 (m, 1H), 3.87 (s, 3H), 3.16 (dd, J = 1.47, 8.44 Hz, 2H). | Ms m/z (APCI) [M + H]+ = 370 | 141 |

TABLE 2D-continued

| # | Structure | Name | 1H NMR | MS | |
|---|---|---|---|---|---|
| 25 | 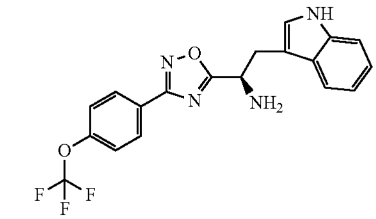 [SMILES: N[C@H](Cc1c[nH]c2ccccc12)c1nc(-c2ccc(OC(F)(F)F)cc2)no1] | (S)-2-(1H-indol-3-yl)-1-[3-{4-(trifluoromethoxy)phenyl}-1,2,4-oxadiazol-5-yl]ethan-1-amine | 1H NMR (600 MHz, CHLOROFORM-d) d 8.13-8.17 (m, 2H), 8.11 (br. s., 1H), 7.65 (dd, J = 1.10, 7.98 Hz, 1H), 7.39 (td, J = 0.91, 8.14 Hz, 1H), 7.32-7.36 (m, 2H), 7.23 (ddd, J = 1.15, 7.00, 8.11 Hz, 1H), 7.13-7.17 (m, 1H), 7.08 (d, J = 2.40 Hz, 1H), 4.65 (dd, J = 5.35, 7.67 Hz, 1H), 3.54 (ddd, J = 0.85, 5.38, 14.48 Hz, 1H), 3.29-3.38 (m, 1H), 1.84 (br. s., 2H), 1.63 (s, 1H). | Ms m/z (APCI) [M + H]+ = 389 | 108 |
| 26 | 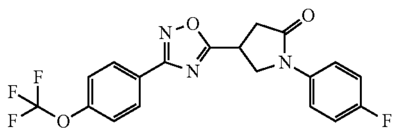 [SMILES: O=C1CC(c2nc(-c3ccc(OC(F)(F)F)cc3)no2)CN1c1ccc(F)cc1] | 1-(4-fluorophenyl)-4-[3-{4-(trifluoromethoxy)phenyl}-1,2,4-oxadiazol-5-yl]pyrrolidin-2-one | 1H NMR (CHCl3-d, 600 MHz): δ 8.15 (d, 2H, J = 9.2 Hz), 7.61-7.58 (m, 2H), 7.36 (d, 2H, J = 8.1 Hz), 7.14-7.10 (m, 2H), 4.32 (d, 1H, J = 1.1 Hz), 4.30 (s, 1H), 4.12-4.07 (m, 1H), 3.19 (dd, 2H, J = 8.6, 0.9 Hz) | Ms m/z (ESI) [M + H]+ = 408.05 [M + H]− = 406.00 | 119 |

TABLE 2E

| # | Structure | Name | 1H NMR | MS | |
|---|---|---|---|---|---|
| 27 | 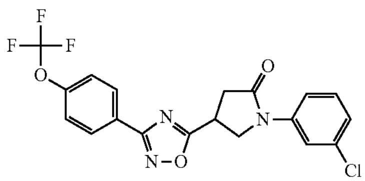 [SMILES: O=C1CC(c2nc(-c3ccc(OC(F)(F)F)cc3)no2)CN1c1cccc(Cl)c1] | 1-(3-chlorophenyl)-4-{3-{4-(trifluoromethoxy)phenyl}-1,2,4-oxadiazol-5-yl]pyrrolidin-2-one | 1H NMR (CHCl3-d, 600 MHz): δ 8.17-8.14 (m, 2H), 7.70 (t, 1H, J = 2.0 Hz), 7.56 (ddd, 1H, J = 8.3, 2,2, 0.9 Hz), 7.37-7.34 (m, 4H), 7.2 (ddd, 1H, J = 8.1, 2,0, 0,9 Hz), 4.34 (dd, 2H, J = 7.3, 2.2 Hz), 4.12-4.07 (m, 1H), 3.21 (d, 1H, J = 0.7 Hz), 3.19 (s, 1H). | Ms m/z (ESI) [M + H]+ = 424.00 [M + H]− = 421.95 | 93 |
| 28 | 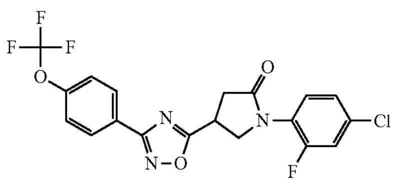 [SMILES: O=C1CC(c2nc(-c3ccc(OC(F)(F)F)cc3)no2)CN1c1ccc(Cl)cc1F] | 1-(4-chloro-2-fluorophenyl)-4-[3-{4-(trifluoromethoxy)phenyl}-1,2,4-oxadiazol-5-yl]pyrrolidin-2-one | 1H NMR (CHCl3-d, 600 MHz): δ 8.17-8.15 (m, 2H), 7.47-7.45 (m, 1H), 7.37 (dd, J = 8.8, 1,1 Hz), 7.25-7.22 (m, 2H), 4.33-4.30 (m, 1H), 4.27-4.24 (m, 1H), 4.17-4.12 (m, 1H), 3.21 (d, 1H, J = 0.7 Hz), 3.15 (dd, 2H, J = 6.6, 2,2 Hz) | Ms m/z (ESI) [M + H]+ = 442.00 [M + H]− = 439.95 | 111 |
| 29 | 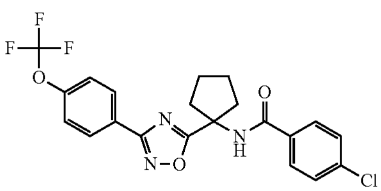 [SMILES: O=C(NC1(c2nc(-c3ccc(OC(F)(F)F)cc3)no2)CCCC1)c1ccc(Cl)cc1] | 4-chloro-N-(1-[3-{4-(trifluoromethoxy)phenyl}-1,2,4-oxadiazol-5-yl]cyclopentyl)benzamide | 1H NMR (CHCl3-d, 600 MHz): δ 8.14-8.12 (m, 2H), 7.76-7.74 (m, 2H), 7.46-7.44 (m, 2H), 7.25-7.22 (m, 2H), 7.32 (dd, 2H, J = 8.1, 0.7 Hz), 6.67 (s, 1H), 2.62-2.57 (m, 2H), 2.42-2.38 (m, 2H), 2.07-1.94 (m, 4H). | Ms m/z [M + H]+ = 452.05 [M + H]− = 450.00 | 177 |
| 30 | 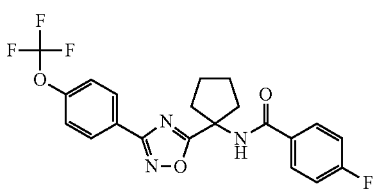 [SMILES: O=C(NC1(c2nc(-c3ccc(OC(F)(F)F)cc3)no2)CCCC1)c1ccc(F)cc1] | 4-fluoro-N-(1-[3-{4-(trifluoromethoxy)phenyl}-1,2,4-oxadiazol-5-yl]cyclopentyl)benzamide | 1H NMR (CHCl3-d, 600 MHz): δ 8.14-8.12 (m, 2H), 7.84-7.81 (m, 2H), 7.32 (d, 2H, J = 8.1 Hz), 7.17-7.13 (m, 2H), 6.63 (s, 1H), 2.62-2.58 (m, 2H), 2.43-2.38 (m, 2H), 2.04-1.96 (m, 4H) | Ms m/z [M + H]+ = 436.05 [M + H]− = 434.00 | 152 |
| 31 | 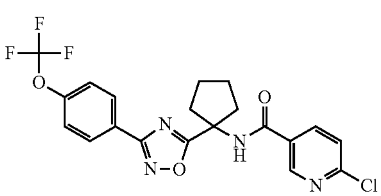 [SMILES: O=C(NC1(c2nc(-c3ccc(OC(F)(F)F)cc3)no2)CCCC1)c1ccc(Cl)nc1] | 6-chloro-N-(1-[3-{4-(trifluoromethoxy)phenyl}-1,2,4-oxadiazol-5-yl]cyclopentyl)nicotinamide | 1H NMR (CHCl3-d, 600 MHz): δ 8.81 (dd, 1H, J = 2.6, 07 Hz), 8.14-8.11 (m, 2H), 8.10 (dd, 1H, J = 8.1, 2.6 Hz), 7.46 (dd, J = 8.1, 0.7 Hz), 7.33 (dd, 2H, J = 8.1, 0.7 Hz), 6.72 (s, 1H), 2.64-2.59 (m, 2H), 2.44-2.39 (m, 2H), 2.06-1.98 (m, 4H) | Ms m/z [M + H]+ = 453.05 [M + H]− = 450.95 | 164 |
| 32 | 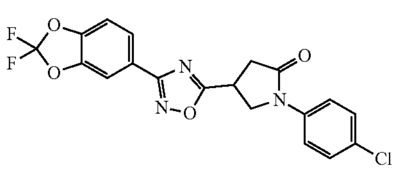 [SMILES: O=C1CC(c2nc(-c3ccc4c(c3)OC(F)(F)O4)no2)CN1c1ccc(Cl)cc1] | 1-(4-chlorophenyl)-4-{3-(2,2-difluoro-benzo[d][1,3]dioxol-5-yl)-1,2,4-oxadiazol-5-yl}pyrrolidin-2-one | 1H NMR (600 MHz, CHLOROFORM-d) Shift 7.89 (dd, J = 1.47, 8.44 Hz, 1H), 7.79 (d, J = 1.50 Hz, 1H), 7.58 (d, J = 8.80 Hz, 2H), 7.37 (d, J = 8.80 Hz, 2H), 7.18 (d, J = 8.07 Hz, 1H), 4.26-4.34 (m, 2H), 4.06 (quin, J = 7.90 Hz, 1H), 3.08-3.22 (m, 2H) | Ms m/z (ESI) [M + H]+ = 420 | 125.1 |

TABLE 2E-continued

| # | Structure | Name | 1H NMR | MS | |
|---|---|---|---|---|---|
| 33 | 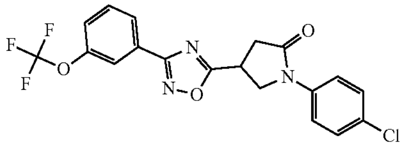 [SMILES: O=C1CC(c2nc(-c3cccc(OC(F)(F)F)c3)no2)CN1c1ccc(Cl)cc1] | 1-(4-chlorpheny])-4-[3-{3-(trifluoro-methoxy)phenyl}-1,2,4-oxadiazol-5-yl]pyrrolidin-2-one | 1H NMR (600 MHz, CHLOROFORM-d) Shift 8.03 (d, J = 7.70 Hz, 1H), 7.95 (s, 1H), 7.58 (d, J = 8.80 Hz, 2H), 7.50-7.57 (m, 2H), 7.37 (d, J = 9.17 Hz, 2H), 4.32 (d, J = 7.70 Hz, 2H), 4.08 (quin, J = 8.10 Hz, 1H), 3.12-3.25 (m, 2H) | Ms m/z (ESI) [M + H]+ = 424 | Oil |
| 34 | 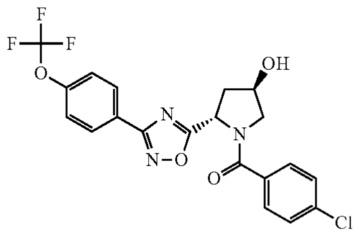 [SMILES: O=C(c1ccc(Cl)cc1)N1C[C@H](O)C[C@H]1c1nc(-c2ccc(OC(F)(F)F)cc2)no1] | (4-chlorophenyl)((2S,4R)-4-hydroxy-2-[3-{4-(trifluoromethoxy)phenyl}-1,2,4-oxadiazol-5-yl]pyrrolidin-1-yl)methanone | 1H NMR (CHCl3-d, 600 MHz); δ 8.13 (d, 2H, J = 6.6 Hz), 7.59 (d, 2H, J = 3.7 Hz), 7.44 (d, 2H, J = 5.1 Hz), 7.33 (dd, 2H, J = 9.0, 0.9 Hz), 5.76 (br, 1H), 4.70 (br, 1H), 4.03 (dd, 1H, J = 11.4, 3.7 Hz), 3.67 (d, 1H, J = 11.4 Hz), 2.61 (dd, 1H, J = 13.8, 7.9 Hz), 2.40 (ddd, 1H, J = 13.5, 8.7, 4.2 Hz), 1.93 (br, 1H) | Ms m/z (ESI) [M + H]+ = 454.05 [M + H]− = 431.95 | 171 |

TABLE 2F

| # | Structure | Name | 1H NMR | MS | |
|---|---|---|---|---|---|
| 35 | 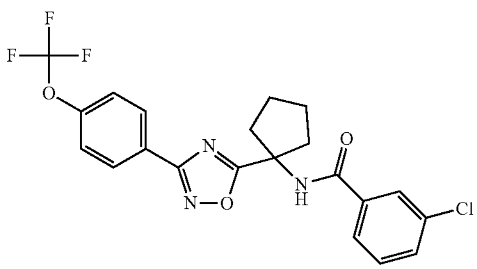 [SMILES: O=C(NC1(c2nc(-c3ccc(OC(F)(F)F)cc3)no2)CCCC1)c1cccc(Cl)c1] | 3-chloro-N-(1-[3-{4-(trifluoromethoxy)phenyl}-1,2,4-oxadiazol-5-yl]cyclopentyl)benzamide | 1H NMR (CHCl3-d, 600 MHz): δ 8.14-8.12 (m, 2H), 7.79 (s, 1H), 7.68 (d, 1H, J = 7.7 Hz), 7.53 (d, 1H, J = 8.1 Hz), 7.42 (t, 1H, J = 8.1 Hz), 7.32 (d, 2H, J = 8.1 Hz), 6.67 (s, 1H), 2.62-2.58 (m, 2H), 2.43-2.39 (m, 2H), 2.03-1.99 (m, 4H) | Ms m/z [M + H]+ = 452.05 [M + H]− = 450.00 | 155 |
| 36 | 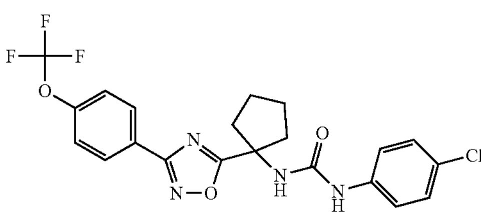 [SMILES: O=C(Nc1ccc(Cl)cc1)NC1(c2nc(-c3ccc(OC(F)(F)F)cc3)no2)CCCC1] | 1-(4-chlorophenyl)-3-(1-[3-{4-(trifluoromethoxy)phenyl}-1,2,4-oxadiazol-5-yl]cyclopentyl)urea | 1H NMR (CHCl3-d, 600 MHz): δ 8.07 (br, 2H), 7.32-7.28 (m, 2H), 7.20 (br, 4H), 6.86 (br, 1H), 5.56 (br, 1H), 2.48-2.47 (m, 2H), 2.25 (m, 2H), 1.93-1.88 (m, 4H) | Ms m/z [M + H]+ = 4367.05 [M + H]− = 465.00 | 176 |
| 37 | 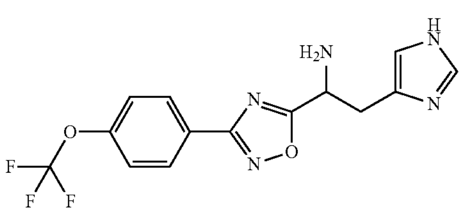 [SMILES: NC(Cc1c[nH]cn1)c1nc(-c2ccc(OC(F)(F)F)cc2)no1] | 2-(1H-imidazol-4-yl)-1-[3-{4-(trifluoromethoxy)phenyl}-1,2,4-oxadiazol-5-yl]ethan-1-amine | 1H NMR (600 MHz, CHLOROFORM-d) d 8.11-8.20 (m, 2H), 7.63 (s, 1H), 7.34 (d, J = 8.34 Hz, 2H), 7.28 (s, 1H), 6.86-6.96 (m, 1H), 4.61 (dd, J = 4.76, 8.04 Hz, 1H), 3.35 (dd, J = 4.77, 14.79 Hz, 2H), 3.11-3.24 (m, 2H). | Ms m/z (APCI) [M + H]+ = 340 | Oil |
| 38 | 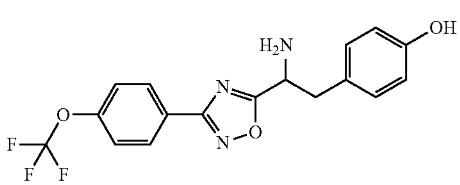 [SMILES: NC(Cc1ccc(O)cc1)c1nc(-c2ccc(OC(F)(F)F)cc2)no1] | 4-(2-amino-2-[3-{4-(trifluoromethoxy)phenyl}-1,2,4-oxadiazol-5-yl]ethyl)phenol | 1H NMR (600 MHz, CHLOROFORM-d) d 8.03-8.20 (m, J = 8.67 Hz, 2H), 7.28-7.38 (m, J = 8.34 Hz, 2H), 6.98-7.09 (m, J = 7.86 Hz, 2H), 6.66-6.79 (m, J = 7.95 Hz, 2H), 4.47 (dd, J = 5.65, 7.72 Hz, 1H), 3.25 (dd, J = 5.64, 13.84 Hz, 1H), 3.08 (dd, J = 7.72, 13.84 Hz, 1H). | Ms m/z (APCI) [M + H]+ = 366 | 75 |

TABLE 2F-continued

| | | Name | 1H NMR | Ms m/z | |
|---|---|---|---|---|---|
| 39 | | (S)-4-chloro-N-(2-hydroxy-1-[3-{4-(trifluoromethoxy)phenyl}-1,2,4-oxadiazol-5-yl]ethyl)benzamide | 1H NMR (CHCl3-d, 600 MHz): δ 8.15-8.13 (m, 2H), 7.85-7.13 (m, 2H), 7.50-7.47 (m, 2H), 7.35 (d, 2H, J = 8.4 Hz), 7.19 (br, 1H), 5.73-5.71 (m, 1H), 4.37-4.35 (m, 1H), 4.20-4.17 (m, 1H), 2.62 (br, 1H) | Ms m/z (ESI) [M + H]+ = 427.95 [M + H]− = 425.95 | 140 |
| 40 | | 1-{3-(2,2-difluorobenzo[d][1,3]dioxol-5-yl)-1,2,4-oxadiazol-5-yl}-2-(1H-indol-3-yl)ethan-1-amine | 1H NMR (600 MHz, CHLOROFORM-d) Shift 8.08 (br, s., 1H), 7.88 (dd, J = 1.65, 8.25 Hz, 1H), 7.79 (d, J = 1.47 Hz, 1H), 7.61 (d, J = 7.70 Hz, 1H), 7.37 (d, J = 8.07 Hz, 1H), 7.09-7.24 (m, 3H), 7.06 (d, J = 2.20 Hz, 1H), 4.61 (dd, J = 5.32, 7.52 Hz, 1H), 3.51 (dd, J = 5.32, 14.49 Hz, 1H), 3.31 (dd, J = 7.70, 14.67 Hz, 1H) | Ms m/z (ESI) [M + H]+ = 385 | 103.7 |
| 41 | | 1-(4-chlorophenyl)-4-{3-(4-hydroxyphenyl)-1,2,4-oxadiazol-5-yl}pyrrolidin-2-one | 1H NMR (600 MHz, CHLOROFORM-d) Shift 7.98 (d, J = 8.07 Hz, 2H), 7.58 (d, J = 8.44 Hz, 2H), 7.37 (d, J = 8.80 Hz, 2H), 6.93 (d, J = 8.07 Hz, 2H), 5.13 (s, 1H), 4.30 (d, J = 7.70 Hz, 2H), 4.05 (quin, J = 8.10 Hz, 1H), 3.16 (d, J = 8.44 Hz, 2H) | Ms m/z (APCl) [M + H]+ = 356 | 198.0 |
| 42 | | 1-(4-chlorophenyl)-4-{3-(3-fluoro-4-methoxyphenyl)-1,2,4-oxadiazol-5-yl}pyrrolidin-5-one | 1H NMR (600 MHz, CHLOROFORM-d) Shift 7.83 (d, J = 8.80 Hz, 1H), 7.80 (dd, J = 1.83, 11.74 Hz, 1H), 7.58 (d, J = 9.17 Hz, 2H), 7.37 (d, J = 9.20 Hz, 2H), 6.99-7.11 (m, J = 8.44, 8.44 Hz, 1H), 4.30 (d, J = 7.34 Hz, 2H), 4.05 (quin, J = 7.98 Hz, 1H), 3.96 (s, 3H), 3.16 (d, J = 8.80 Hz, 2H) | Ms m/z (APCl) [M + H]+ = 388 | 158.3 |

TABLE 2G

| | | Name | 1H NMR | Ms m/z | |
|---|---|---|---|---|---|
| 43 | | 1-(4-chlorophenyl)-4-(3-phenyl-1,2,4-oxadiazol-5-yl)pyrrolidin-2-one | 1H NMR (600 MHz, CHLOROFORM-d) Shift 8.08 (d, J = 6.97 Hz, 2H), 7.56-7.64 (m, J = 8.80 Hz, 2H), 7.45-7.56 (m, 3H), 7.33-7.40 (m, J = 8.80 Hz, 2H), 4.23-4.37 (m, 2H), 4.07 (quin, J = 8.07 Hz, 1H), 3.17 (d, J = 8.44 Hz, 2H) | Ms m/z (APCl) [M + H]+ = 340 | 119.0 |
| 44 | | 1-(4-chlorophenyl)-4-{3-(pyridin-4-yl)-1,2,4-oxadiazol-5-yl}pyrrolidin-2-one | 1H NMR (600 MHz, CHLOROFORM-d) Shift 8.78-8.87 (m, 2H), 7.86-8.02 (m, 2H), 7.51-7.65 (m, 2H), 7.30-7.44 (m, 2H), 4.23-4.41 (m, 2H), 4.10 (quin, J = 7.89 Hz, 1H), 3.12-3.24 (m, 2H) | Ms m/z (APCl) [M + H]+ = 341 | 145.4 |

TABLE 2G-continued

| | | | | | |
|---|---|---|---|---|---|
| 45 | | 1-(4-chlorophenyl)-4-[5-{4-(trifluoromethyl)phenyl}-1,2,4-oxadiazol-3-yl]pyrrolidin-2-one | 1H NMR (600 MHz, CDCl3): δ 8.17-8.20 (m, 2H), 7.57-7.62 (m, 2H), 7.37-7.40 (m, 2H), 7.33-7.36 (m, 2H), 4.18-4.27 (m, 2H), 3.97 (dq, J = 6.83, 8.50 Hz, 1H), 3.09 (dd, J = 1.18, 8.58 Hz, 2H) | Ms m/z (APCl) [M + H]+ = 424 | 112 |
| 46 | | N-(2-hydroxy-1-[3-{4-(trifluoromethoxy)phenyl}-1,2,4-oxadiazol-5-yl]ethyl)-1H-indole-3-carboxamide | 1H NMR (CHCl3-d, 600 MHz): δ 8.59 (br, 1H), 8.18-8.16 (m, 2H), 8.12-8.11 (m, 1H), 7.94 (d, 1H, J = 2.9 Hz), 7.51-7.49 (m, 1H), 7.36-7.34 (m, 3H), 7.11-7.08 (m, 1H), 5.84-5.81 (m, 1H), 4.38-4.35 (m, 1H), 4.25 (ddd, 1H, J = 11.2, 7.2, 4.0 Hz), 2.73-2.71 (m, 1H) | Ms m/z [M + H]+ = 433.05 [M + H]− = 430.95 | 166 |
| 47 | | ((2S,4R)-4-hydroxy-2-[3-{4-(trifluoromethoxy)phenyl}-1,2,4-oxadiazol-5-yl]pyrrolidin-1-yl)(1H-indol-3-yl)methanone | 1H NMR (CHCl3-d, 600 MHz): δ 8.49 (br, 1H), 8.14--8.11 (m, 3H), 7.63 (d, 1H, J = 2.9 Hz), 7.43 (d, 1H, J = 8.1 Hz), 7.32-7.24 (m, 3H), 4.78-4.75 (m, 1H), 4.22 (dd, 1H, J = 11.2, 4.2 Hz), 3.99-3.96 (m, 1H), , 2.63-2.58 (m, 1H), 2.44-2.40 (ddd, 1H, J = 13.3, 8.3, 4.4 Hz) 1.78 (d, 1H, J = 3.7 Hz) | Ms m/z (ESI) [M + H]+ = 459.05 [M + H]− = 457.00 | 201 |
| 48 | | 1-(6-chloropyridin-3-yl)-4-[3-{4-(trifluoromethoxy)phenyl}-1,2,4-oxadiazol-5-yl]pyrrolidin-2-one | 1H NMR (CHCl3-d, 600 MHz): δ 8.51 (dd, 1H, J = 2.2, 0.7 Hz), 8.32 (dd, 1H, J = 8.8, 2.9 Hz) 8.16-8.14 (m, 2H), 7.40 (dd, 1H, J = 8.1, 0.7 Hz), 7.36 (dd, 2H, J = 9.0, 0.9 Hz), 4.40-4.35 (m, 2H), 4.18-4.12 (m, 1H), 4.12-4.07 (m, 1H), 3.21 (dd, 2H, J = 8.4, 2.2 Hz) | Ms m/z [M + H]+ = 425.00 [M + H]− = 422.90 | 152 |
| 49 | | 1-(5-chloropyridin-2-yl)-4-[3-{4-(trifluoromethoxy)phenyl}-1,2,4-oxadiazol-5-yl]pyrrolidin-2-one | 1H NMR (CHCl3-d, 600 MHz): δ 8.42 (dd, 1H, J = 8.8, 0.7 Hz), 8.34 (dd, 1H, J = 2.6, 0.7 Hz), 8.16-8.14 (m, 2H), 7.72 (dd, 1H, J = 9.2, 2.6 Hz), 7.36 (dd, 2H, J = 8.1, 0.7 Hz), 4.64 (dd, 1H, J = 11.0, 8.4 Hz), 4.50 (dd, 1H, J = 11.6, 6.4 Hz), 4.09-4.04 (m, 1H), 3.29-3.21 (m, 2H) | Ms m/z [M + H]+ = 425.00 [M + H]− = 422.95 | 125 |
| 50 | | 1-(4-methoxybenzyl)-4-[3-{4-(trifluoromethoxy)phenyl}-1,2,4-oxadiazol-5-yl]pyrrolidin-2-one | 1H NMR (CHCl3-d, 600 MHz): δ 8.12-8.10 (m, 2H), 7.35 (dd, 2H, J = 9.0, 0.9 Hz), 7.24-7.21 (m, 2H), 6.90-6.87 (m, 2H), 4.52-4.46 (m, 2H), 3.93-3.87 (m, 1H), 3.81 (s, 3H), 3.77-3.74 (m, 1H), 3.69-3.66 (m, 1H), 3.05-2.97 (m, 2H) | Ms m/z (ESI) [M + H]+ = 434.05 [M + H]− = 432.00 | 81 |

TABLE 2H

| # | Structure | Name | 1H NMR | MS | m/z |
|---|---|---|---|---|---|
| 51 | 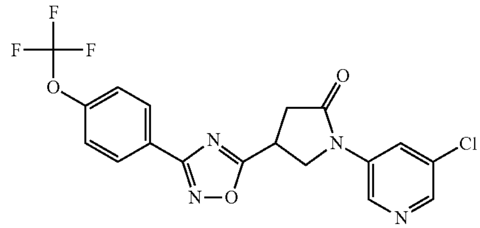 [SMILES: O=C1CC(c2nc(-c3ccc(OC(F)(F)F)cc3)no2)CN1c1cncc(Cl)c1] | 1-(5-chloropyridin-3-yl)-4-[3-{4-(trifluoromethoxy)phenyl}-1,2,4-oxadiazol-5-yl]pyrrolidin-2-one | 1H NMR (CHCl3-d, 600 MHz): δ 7.68 (dd, 2H, J = 7.7, 1.1 Hz), 7.45 (br, 1H), 7.21-7.28 (m, 2H), 7.13-7.10 (m, 2H), 4.15 (dd, 1H, J = 7.3, 7.3 Hz), 3.50 (dd, 1H, J = 7.0, 7.0 Hz), 1.30-1.27 (m, 1H), 1.25-1.22 (m, 1H), 0.92-0.90 (m, 1 Hz) | Ms m/z [M + H]+ = 425.00 [M + H]− = 422.90 | 189 |
| 52 | 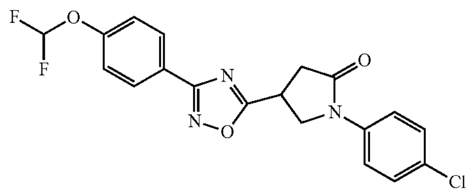 | 1-(4-chlorophenyl)-4-[3-{4-(difluoromethoxy)phenyl}-1,2,4-oxadiazol-5-yl]pyrrolidin-2-one | 1H NMR (600 MHz, CHLOROFORM-d) Shift 8.10 (d, J = 8.80 Hz, 2H), 7.52-7.66 (m, 2H), 7.31-7.45 (m, 2H), 7.23 (d, J = 8.80 Hz, 2H), 6.47-6.72 (m, 1H), 4.31 (d, J = 7.34 Hz, 2H), 4.07 (quin, J = 8.00 Hz, 1H), 3.17 (d, J = 8.80 Hz, 2H) | Ms m/z (APCI) [M + H]− = 404 | 132.7 |
| 53 | 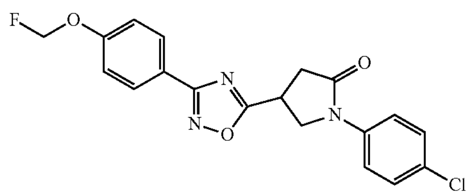 [SMILES: O=C1CC(c2nc(-c3ccc(OCF)cc3)no2)CN1c1ccc(Cl)cc1] | 1-(4-chlorophenyl)-4-[3-{4-(fluoromethoxy)phenyl}-1,2,4-oxadiazol-5-yl]pyrrolidin-2-one | 1H NMR (600 MHz, CHLOROFORM-d) Shift 8.03-8.10 (m, 2H), 7.54-7.62 (m, 2H), 7.34-7.41 (m, 2H), 7.18 (d, J = 8.80 Hz, 2H), 5.71-5.87 (m, 2H), 4.30 (d, J = 7.70 Hz, 2H), 4.06 (quin, J = 7.90 Hz, 1H), 3.16 (d, J = 8.80 Hz, 2H) | Ms m/z (APCI) [M + H]+ = 388 | 132.0 |
| 54 | 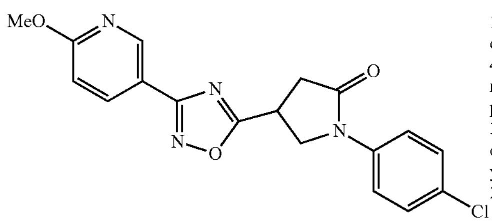 | 1-(4-chlorophenyl)-4-{3-(6-methoxypyridin-3-yl)-1,2,4-oxadiazol-5-yl}pyrrolidin-2-one | 1H NMR (600 MHz, CHLOROFORM-d) Shift 8.88 (d, J = 1.83 Hz, 1H), 8.20 (dd, J = 2.38, 8.62 Hz, 1H), 7.52-7.66 (m, 2H), 7.32-7.44 (m, J = 9.17 Hz, 2H), 6.85 (d, J = 8.80 Hz, 1H), 4.31 (d, J = 7.34 Hz, 2H), 4.06 (quin, J = 7.90 Hz, 1H), 4.01 (s, 3H), 3.16 (d, J = 8.44 Hz, 2H) | Ms m/z (APCI) [M + H]+ = 371 | 123.5 |
| 55 | 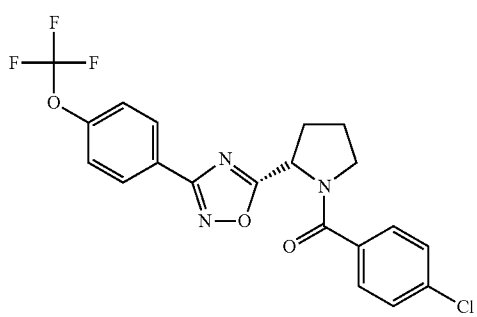 | (S)-(4-chlorophenyl)(2-[3-{4-(trifluoromethoxy)phenyl)-1,2,4-oxadiazol-5-yl}pyrrolidin-1-yl)methanone | 1H NMR (CHCl3-d, 600 MHz): δ 8.14 (d, 2H, J = 8.1 Hz), 7.57 (d, 2H, J = 8.1 Hz), 7.42 (d, 2H, J = 8.1 Hz), 7.33 (d, 2H, J = 8.1 Hz), 5.57 (dd, 1H, J = 7.2, 4.6 Hz), 3.86-3.83 (m, 1H), 3.68-3.64 (m, 1H), 2.53-2.51 (m, 1H), 2.24-2.19 (m, 2H), 2.09-2.03 (m, 1H) | Ms m/z [M + H]+ = 438.05 [M + H]− = 435.95 | Amorphous |
| 56 | 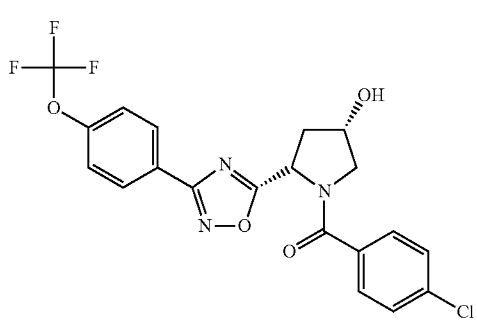 | (4-chlorophenyl)((2S,4S)-4-hydroxy-2-[3-{4-(trifluoromethoxy)phenyl}-1,2,4-oxadiazol-5-yl]pyrrolidin-1-yl)methanone | 1H NMR (CHCl3-d, 600 MHz): δ 8.13 (d, 2H, J = 7.0 Hz), 7.60 (d, 2H, J = 6.2 Hz), 7.44 (d, 2H, J = 6.2 Hz), 7.33 (dd, 2H, J = 9.0, 0.9 Hz), 5.76 (br, 1H), 4.70 (br, 1H), 4.03 (dd, 1H, J = 11.4, 3.7 Hz), 3.68 (d, 1H, J = 12.1 Hz), 2.61 (dd, 1H, J = 13.6, 7.7 Hz), 2.41 (ddd, 1H, J = 13.4, 8.8, 4.2 Hz), 1.93 (br, 1H) | Ms m/z [M + H]+ = 454.00 | 171 |

TABLE 2H-continued

| 57 | (structure) | (S)-1-(4-chlorobenzoyl)-5-[3-{4-(trifluoromethoxy)phenyl}-1,2,4-oxadiazol-5-yl]pyrrolidin-3-one | 1H NMR (CHCl3-d, 600 MHz): δ 8.14-8.11 (m, 2H), 7.53 (br, 2H), 7.47 (m, 2H), 7.35 (d, 2H, J = 8.1 Hz), 6.32 (br, 1H), 4.24 (d, 1H, J = 13.6 Hz), 4.08 (br, 1H), 3.21 (dd, 1H, J = 18.7, 9.9 Hz), 2.97 (d, 1H, J = 18.7 Hz) | Ms m/z [M + H]+ = 452.00 [M + H]− = 449.95 | Amorphous |

TABLE 2I

| 58 | (structure) | (3-chlorophenyl)((2S,4R)-4-hydroxy-2-[3-{4-(trifluoromethoxy)phenyl}-1,2,4-oxadiazol-5-yl]pyrrolidin-1-yl)methanone | 1H NMR (CHCl3-d, 600 MHz): δ 8.14 (d, 2H, J = 8.1 Hz), 7.62 (br, 1H), 7.53-7.52 (m, 1H), 7.48-7.47 (m, 1H), 7.40 (t, 1H, J = 7.5 Hz), 7.34 (dd, 2H, J = 9.0, 0.9 Hz), 5.77-5.74 (m, 1H), 4.67 (br, 1H), 4.01 (dd, 1H, J = 11.4, 3.3 Hz), 3.66-3.64 (m, 1H), 2.59 (dd, 1H, J = 13.6, 8.1 Hz), 2.39 (ddd, 1H, J = 13.4, 8.8, 4.2 Hz), 1.91 (br, 1H) | Ms m/z [M + H]+ = 454.05 | 159 |
| 59 | (structure) | 1-(4-chlorophenyl)-4-{3-(4-chlorophenyl)-1,2,4-oxadiazol-5-yl}pyrrolidin-2-one | 1H NMR (600 MHz, CHLOROFORM-d) Shift 8.02 (d, J = 8.80 Hz, 2H), 7.54-7.64 (m, 2H), 7.42-7.54 (m, J = 8.44 Hz, 2H), 7.33-7.42 (m, 2H), 4.30 (d, J = 7.34 Hz, 2H), 4.07 (quin, J = 8.10 Hz, 1H), 3.16 (d, J = 8.44 Hz, 2H) | Ms m/z (ESI) [M + H]+ = 374 | 153.2 |
| 60 | (structure) | (5-chloropyridin-2-yl)((2S,4R)-4-hydroxy-2-[3-{4-(trifluoromethoxy)phenyl}-1,2,4-oxadiazol-5-yl]pyrrolidin-1-yl)methanone | 1H NMR (CHCl3-d, 600 MHz): δ 5.58 (dd, 1H, J = 1.8, 0.7 Hz), 8.13-8.11 (m, 2H), 7.94 (dd, 1H, J = 8.4, 0.7 Hz), 7.79 (dd, 1H, J = 8.4, 2.2 Hz), 7.31 (dd, 2H, J = 9.0, 0.9 Hz), 5.74-5.71 (m, 1H), 4.39 (dd, 1H, J = 12.7, 4.2 Hz), 4.21-4.18 (m, 1H), 2.59-2.54 (m, 1H), 2.58 (br, 1H), 2.36 (ddd, 1H, J = 13.3, 8.7 4.4 Hz), 1.88 (br, 1H)<br>1H NMR (rotamer): δ 8.30 (dd, 1H, J = 1.8, 0.7 Hz), 8.04-8.02 (m, 2H), 7.98 (dd, 1H, J = 8.4, 0.7 Hz), 7.71 (dd, 1H, J = 8.4, 2.2 Hz), 7.31 (dd, 1H, J = 9.0, 0.9 Hz), 6.25 (dd, 1H, J = 8.1, 6.6 Hz), 4.16-4.13 (m, 1H), 4.08 (dd, 1H, J = 12.7, 4.2 Hz), 2.72 (br, 1H), 2.70-2.65 (m, 1H), 2.42 (ddd, 1H, J = 13.3, 6.3, 5.0 Hz), 1.88 (br, 1H) | Ms m/z [M + H]+ = 455.05 | Amorphous |
| 61 | (structure) | 1-(4-chlorophenyl)-4-{3-(4-fluorophenyl)-1,2,4-oxadiazol-5-yl}pyrrolidin-2-one | 1H NMR (600 MHz, CHLOROFORM-d) Shift 7.98-8.17 (m, 2H), 7.52-7.67 (m, 2H), 7.30-7.44 (m, 2H), 7.12-7.23 (m, 2H), 4.30 (d, J = 7.70 Hz, 2H), 4.06 (quin, J = 7.70 Hz, 1H), 3.16 (d, J = 8.80 Hz, 2H) | Ms m/z (APCI) [M + H]+ = 358 | 159.2 |

TABLE 2I-continued

| | | | | | |
|---|---|---|---|---|---|
| 62 | (structure) | 1-(5-chloropyridin-2-yl)-4-[3-{4-(difluoromethoxy)phenyl}-1,2,4-oxadiazol-5-yl]pyrrolidin-2-one | 1H NMR (600 MHz, CHLOROFORM-d) Shift 8.40 (d, J = 8.80 Hz, 1H), 8.31 (d, J = 2.57 Hz, 1H), 8.03-8.14 (m, J = 8.80 Hz, 2H), 7.69 (dd, J = 2.57, 8.80 Hz, 1H), 7.19-7.24 (m, J = 8.80 Hz, 2H), 6.59 (t, J = 73.00 Hz, 1H), 4.62 (dd, J = 8.62, 11.55 Hz, 1H), 4.47 (dd, J = 6.42, 11.55 Hz, 1H), 3.96-4.11 (m, 1H), 3.14-3.31 (m, 2H) | Ms m/z (APCl) [M + H]+ = 407 | 129.8 |
| 63 | (structure) | (S)-3-chloro-N-(2-hydroxy-1-[3-{4-(trifluoromethoxy)phenyl}-1,2,4-oxadiazol-5-yl]ethyl)benzamide | 1H NMR (CHCl3-d, 600 MHz): δ 8.16-8.13 (m, 2H), 7.89 (t, 1H, J = 1.8 Hz), 7.77 (dt, 1H, J = 7.7, 1.3 Hz), 7.57 (ddd, 1H, J = 8.1, 2.2, 1.1 Hz), 7.36-7.35 (m, 2H), 7.22 (d, 1H, J = 8.4 Hz), 5.75-5.72 (m, 1H), 4.37 (ddd, 1H, J = 11.6, 5.1, 3.1 Hz), 4.19 (ddd, 1H, J = 11.5, 7.2, 3.7 Hz), 2.58 (dd, 1H, J = 7.3, 5.1 Hz) | Ms m/z [M + H]+ = 428.00 [M + H]− = 425.95 | 154 |
| 64 | (structure) | 1-(4-chlorobenzyl)-4-[3-{4-(trifluoromethoxy)phenyl}-1,2,4-oxadiazol-5-yl]pyrrolidin-2-one | 1H NMR (CHCl3-d, 600 MHz): δ 8.12-8.09 (m, 2H), 7.36-7.33 (m, 4H), 7.25-7.23 (m, 2H), 7.14-7.10 (m, 2H), 4.56-4.49 (m, 2H), 3.95-3.90 (m, 1H), 3.76 (dd, 1H, J = 10.1, 8.3 Hz), 3.71-3.69 (m, 1H), 3.06-2.98 (m, 2H) | Ms m/z (ESI) [M + H]+ = 438.00 [M + H]− = 435.95 | 61 |

TABLE 2J

| | | | | | |
|---|---|---|---|---|---|
| 65 | (structure) | N-(4-[5-{1-(4-chlorophenyl)-5-oxopyrrolidin-3-yl}-1,2,4-oxadiazol-3-yl]phenyl)methanesulfonamide | 1H NMR (600 MHz, CHLOROFORM-d) Shift 8.08 (d, J = 8.44 Hz, 2H), 7.54-7.64 (m, J = 8.80 Hz, 2H), 7.34-7.42 (m, J = 8.80 Hz, 2H), 7.31 (d, J = 8.80 Hz, 2H), 6.58 (br, s, 1H), 4.31 (d, J = 7.70 Hz, 2H), 4.07 (quin, J = 7.90 Hz, 1H), 3.17 (d, J = 8.44 Hz, 2H), 3.10 (s, 3H) | Ms m/z (APCl) [M + H]+ = 433 | 195.8 |
| 66 | (structure) | 1-(4-chlorophenyl)-4-[3-{3-(difluoromethoxy)phenyl}-1,2,4-oxadiazol-5-yl]pyrrolidin-2-one | 1H NMR (600 MHz, CHLOROFORM-d) Shift 7.94 (d, J = 7.70 Hz, 1H), 7.84 (s, 1H), 7.55-7.62 (m, 2H), 7.50 (t, J = 8.10 Hz, 1H), 7.33-7.41 (m, 2H), 7.30 (dd, J = 2.02, 8.25 Hz, 1H), 6.37-6.79 (m, 1H), 4.31 (d, J = 7.70 Hz, 2H), 4.08 (quin, J = 8.07 Hz, 1H), 3.17 (d, J = 8.44 Hz, 2H) | Ms m/z (APCl) [M + H]+ = 404 | 102.8 |

TABLE 2J-continued

| # | Structure | Name | 1H NMR | MS |
|---|---|---|---|---|
| 67 | | 1-(4-chloro-phenyl)-4-[3-{2-(trifluoro-methoxy)phenyl}-1,2,4-oxadiazol-5-yl]pyrrolidin-2-one | 1H NMR (600 MHz, CHLOROFORM-d) Shift 8.10 (dd, J = 1.28, 7.89 Hz, 1H), 7.51-7.65 (m, 3H), 7.41-7.51 (m, 2H), 7.37 (d, J = 9.17 Hz, 2H), 4.31 (d, J = 8.07 Hz, 2H), 4.09 (quin, J = 7.30 Hz, 1H), 3.18 (d, J = 8.80 Hz, 2H) | Ms m/z (ESI) [M + H]+ = 424 80.2 |
| 68 | | (4-chloro-phenyl)(3-[3-{4-(trifluoro-methoxy)phenyl}-1,2,4-oxadiazol-5-yl]azetidin-1-yl)methanone | 1H NMR (CHCl3-d, 600 MHz): δ 8.18-8.15 (m, 2H), 7.67-7.64 (m, 2H), 7.46-7.44 (m, 2H), 7.37 (dd, 2H, J = 9.0, 0.9 Hz), 4.73 (br, 3H), 4.59 (br, 1H), 4.25 (ddd, 2H, J = 15.1, 8.3, 6.6 Hz) | Ms m/z (ESI) [M + H]+ = 424.00 [M + H]− = 421.95 120 |
| 69 | | (S)-4-fluoro-N-(2-hydroxy-1-[3-{4-(trifluoro-methoxy)phenyl}-1,2,4-oxadiazol-5-yl]ethyl)benzamide | 1H NMR (CHCl3-d, 600 MHz): δ 8.16-8.14 (m, 2H), 7.94-7.91 (m, 2H), 7.36 (dd, 2H, J = 8.8, 0.7 Hz), 7.21-7.17 (m, 2H), 7.15 (d, 1H, J = 8.4 Hz), 5.75-5.72 (m, 1H), 4.37 (ddd, 1H, J = 11.5, 4.9, 3.1 Hz), 4.19 (ddd, 1H, J = 11.4, 7.3, 3.7 Hz), 2.51 (dd, 1H, J = 7.3, 5.1 Hz) | Ms m/z (ESI) [M + H]+ = 412.05 [M + H]− = 410.00 113 |
| 70 | | N-[2-{3-(1H-indol-3-yl)-1,2,4-oxadiazol-5-yl}ethyl]-2-(7-methoxy-1H-indol-3-yl)acetamide | 1H NMR (CHCl3-d, 400 MHz): 11.82 (s, 1H), 10.96 (s, 1H), 8.14 (t, J = 6.8 Hz, 1H), 8.04-8.06 (m, 2H), 7.51 (d, J = 7.2 Hz, 1H), 7.18-7.26 (m, 2H), 7.07-7.10 (m, 2H), 6.83 (t, J = 7.6 Hz, 1H), 6.59 (d, J = 7.6 Hz, 1H), 3.88 (s, 3H), 3.51-3.56 (m, 2H), 3.48 (s, 2H), 3.11 (t, J = 6.8 Hz, 2H). | Ms m/z (ES-API) [M + H]+ = 416.3 224 |
| 71 | | N-[2-{3-(1H-indol-3-yl)-1,2,4-oxadiazol-5-yl}ethyl]-4-chloro-benzamide | 1H NMR (CHCl3-d, 400 MHz): 11.82 (s, 1H), 8.85 (t, J = 5.6 Hz, 1H), 8.01-8.56 (m, 2H), 7.85 (d, J = 8.8 Hz, 2H), 7.54 (d, J = 8.4 Hz, 2H), 7.50 (d, J = 8.0 Hz, 1H), 7.16-7.25 (m, 2H), 3.72-3.76 (m, 2H), 3.25 (t, J = 6.8 Hz, 2H). | Ms m/z (ES-API) [M + H]+ = 367.2 163 |

TABLE 2J-continued

| | | | | | |
|---|---|---|---|---|---|
| 72 | [structure] | 1-(4-chloro-phenyl)-4-(hydroxy-methyl)-4-{3-(4-hydroxy phenyl)-1,2,4-oxadiazol-5-yl} pyrrolidin-2-one | 1H NMR (600 MHz, DMSO-d6) Shift 10.16 (br, s., 1H), 7.85 (d, J = 8.44 Hz, 2H), 7.69-7.78 (m, J = 9.17 Hz, 2H), 7.42-7.50 (m, J = 8.80 Hz, 2H), 6.92 (d, J = 8.44 Hz, 2H), 5.58 (br. s., 1H), 4.37 (d, J = 9.90 Hz, 1H), 4.16 (d, J = 10.27 Hz, 1H), 3.87 (s, 2H), 3.18 (d, J = 17.24 Hz, 1H), 2.95 (d, J = 17.24 Hz, 1H) | Ms m/z (APCI) [M + H]+ = 386 | 189.6 |

TABLE 2K

| | | | | | |
|---|---|---|---|---|---|
| 73 | [structure] | 1-(4-chloro-phenyl)-4-{3-(2,2-difluoro-benzo[d][1,3]dioxol-5-yl)-1,2,4-oxadiazol-5-yl}-4-(hydroxymethyl) pyrrolidin-2-one | 1H NMR (600 MHz, CHLOROFORM-d) Shift 7.89 (dd, J = 1.47, 8.07 Hz, 1H), 7.79 (d, J = 1.10 Hz, 1H), 7.54-7.65 (m, 2H), 7.31-7.42 (m, J = 8.80 Hz, 2H), 7.19 (d, J = 8.44 Hz, 1H), 4.36 (d, J = 10.27 Hz, 1H), 4.22 (d, J = 10.27 Hz, 1H), 4.15 (d, J = 11.37 Hz, 1H), 4.03 (d, J = 11.00 Hz, 1H), 3.24 (d, J = 17.61 Hz, 1H), 2.94 (d, J = 17.24 Hz, 1H) | Ms m/z (ESI) [M + H]+ = 450 | 60.7 |
| 74 | [structure] | 1-(4-chloro-phenyl)-4-{3-(3-fluoro-4-hydroxyphenyl)-1,2,4-oxadiazol-5-yl}pyrrolidin-2-one | 1H NMR (600 MHz, CHLOROFORM-d) Shift 7.76-7.85 (m, 2H), 7.54-7.61 (m, J = 8.80 Hz, 2H), 7.33-7.40 (m, J = 8.80 Hz, 2H), 7.03-7.19 (m, J = 8.60, 8.60 Hz, 1H), 5.74 (br. s., 1H), 4.30 (d, J = 7.34 Hz, 2H), 4.05 (quin, J = 7.90 Hz, 1H), 3.16 (d, J = 8.44 Hz, 2H) | Ms m/z (ESI) [M + H]+ = 374 | 172.9 |
| 75 | [structure] | (S)-4-chloro-N-(3-hydroxy-1-[3-{4-(trifluoro-methoxy)phenyl}-1,2,4-oxadiazol-5-yl]propyl) benzamide | 1H NMR (CHCl3-d, 600 MHz): δ 8.16-8.13 (m, 2H), 7.85-7.83 (m, 2H), 7.59 (d, 1H, J = 7.3 Hz), 7.50-7.48 (m, 2H), 7.35 (d, 2H, J = 8.1 Hz), 5.83-5.80 (m, 1H), 3.95 (dt, 1H, J = 11.4, 4.2 Hz), 3.85 (dt, 1H, J = 10.8, 2.6 Hz), 2.74 (br, 1H), 2.48 (ddt, 1H, 14.5, 10.1, 4.4), 2.18 (dddd, 1H, J = 14.8, 8.3, 4.3, 2.8 Hz) | Ms m/z (ESI) [M + H]+ = 442.00 [M + H]− = 439.95 | 98 |
| 76 | [structure] | (S)-6-chloro-N-(2-hydroxy-1-[3-{4-(trifluoro-methoxy)phenyl}-1,2,4-oxadiazol-5-yl]ethyl)-1H-indole-3-carboxamide | | Ms m/z (ESI) [M + H]+ = 467.00 [M + H]− = 464.95 | 218 |
| 77 | [structure] | (3R,5S)-1-(4-chlorobenzyl)-5-[3-{4-(trifluoro-methoxy)phenyl}-1,2,4-oxadiazol-5-yl]pyrrolidin-3-ol | 1H NMR (CHCl3-d, 600 MHz): δ 8.12-8.10 (m, 2H), 7.32 (d, 2H, J = 7.8 Hz), 7.24-7.21 (m, 4H), 4.63 (br, 1H), 4.39 (m, 1H), 3.85 (d, 1H, J = 13.3 Hz), 3.66 (d, 1H, J = 13.3 Hz), 3.40 (dd, 1H, J = 10.5, 5.5 Hz), 2.59 (dd, 1H, J = 10.3, 3,4 Hz), 2.54-2.49 (m, 1H), 2.31 (ddd, 1H, J = 13.4, 7.4, 3.0 Hz), 1.77 (br, 1H) | Ms m/z [M + H]+ = 440.05 | Amorphous |

TABLE 2K-continued

| # | Structure | Name | 1H NMR | MS |
|---|---|---|---|---|
| 78 | (structure) | 4-chloro-N-[2-hydroxy-1-{3-(4-hydroxyphenyl)-1,2,4-oxadiazol-5-yl}ethyl]benzamide | 1H NMR (600 MHz, DMSO-d6) Shift 10.15 (br, s., 1H), 9.21 (br. d, J = 7.30 Hz, 1H), 7.90-8.05 (m, J = 8.44 Hz, 2H), 7.77-7.90 (m, J = 8.80 Hz, 2H), 7.60 (d, J = 8.44 Hz, 2H), 6.91 (d, J = 8.80 Hz, 2H), 5.28-5.43 (m, 2H), 3.92-4.08 (m, 2H) | Ms m/z (APCI) [M + H]+ = 360 | 167.5 |
| 79 | (structure) | 4-[4-{3-(4-hydroxyphenyl)-1,2,4-oxadiazol-5-yl}-2-oxopyrrolidin-1-yl]benzonitrile | 1H NMR (500 MHz, CHLOROFORM-d) Shift 7.96 (d, J = 8.71 Hz, 2H), 7.80 (d, J = 8.71 Hz, 3H), 7.64 (d, J = 8.71 Hz, 2H), 6.94 (d, J = 8.25 Hz, 2H), 4.35 (d, J = 7.79 Hz, 2H), 4.02-4.10 (m, 1H), 3.20 (d, J = 8.71 Hz, 2H) | Ms m/z (ESI) [M + H]+ = 347 | 202.9 |
| 80 | (structure) | 4-chloro-N-((1S,2R)-2-hydroxy-1-[3-{4-(trifluoromethoxy)phenyl}-1,2,4-oxadiazol-5-yl]propyl)benzamide | 1H NMR (CHCl3-d, 600 MHz): δ 8.14-8.12 (m, 2H), 7.86-7.84 (m, 2H), 7.50-7.48 (m, 2H), 7.35 (dd, 2H, J = 9.0, 0.9 Hz), 7.08 (d, 1H, J = 9.2 Hz), 5.62 (dd, 1H, J = 8.8, 2.2 Hz), 4.65 (qd, 1H, J = 6.4 × 3, 1.8 Hz), 2.66 (br, 1H), 1.43 (d, 3H, J = 6.2 Hz) | Ms m/z (ESI) [M + H]+ = 442.00 | 140 |

TABLE 2L

| # | Structure | Name | 1H NMR | MS |
|---|---|---|---|---|
| 81 | (structure) | (S)-3-(4-chlorobenzamido)-3-[3-{4-(trifluoromethoxy)phenyl}-1,2,4-oxadiazol-5-yl]propanoic acid | 1H NMR (CHCl3-d, 600 MHz): δ 8.12-8.10 (m, 2H), 7.82-7.79 (m, 2H), 7.47-7.45 (m, 2H), 7.14-7.10 (m, 2H), 7.31 (d, 2H, J = 7.9 Hz), 5.94-5.91 (m, 1H), 3.45 (dd, 1H, J = 17.9, 4.3 Hz), 3.22 (dd, 1H, J = 17.6, 4.5 Hz) | Ms m/z (ESI) [M + H]+ = 456.00 [M + H]− = 453.95 | 195 |
| 82 | (structure) | (4-chlorophenyl)((2S,4R)-4-hydroxy-2-[3-{4-(trifluoromethoxy)phenyl}-1,2,4-oxadiazol-5-yl]pyrrolidin-1-yl)methanone | 1H NMR (CHCl3-d, 600 MHz): δ 8.09 (d, 2H, J = 8.8 Hz), 7.52 (d, 2H, J = 7.0 Hz), 7.42 (d, 2H, J = 7.0 Hz), 7.34 (d, 2H, J = 8.1 Hz), 5.62 (d, 1H, J = 8.1 Hz), 4.58 (br, 1H), 3.86 (br, 2H), 2.68-2.64 (m, 1H), 2.38 (d, 1H, J = 13.6 Hz), 1.93 (br, 1H) | Ms m/z [M + H]+ = 454.00 | |

TABLE 2L-continued

| | | | | |
|---|---|---|---|---|
| 83 | | (R)-4-chloro-N-(2-hydroxy-1-[3-{4-(trifluoromethoxy)phenyl}-1,2,4-oxadiazol-5-yl]ethyl)benzamide | 1H NMR (CHCl3-d, 600 MHz): δ 8.16-8.13 (m, 2H), 7.86-7.84 (m, 2H), 7.50-7.48 (m, 2H), 7.35 (dd, 2H, J = 9.0, 0.9 Hz), 7.21 (d, 1H, J = 8.1 Hz), 5.75-5.72 (m, 1H), 4.38-4.35 (m, 1H), 4.19 (ddd, 1H, J = 11.3, 7.2, 3.9 Hz), 2.58-2.56 (m, 1H) | Ms m/z (ESI) [M + H]+ = 428.00 [M + H]− = 425.90 | 141 |
| 84 | | (S)-1-(4-chlorobenzoyl)-5-[3-{4-(trifluoromethoxy)phenyl}-1,2,4-oxadiazol-5-yl]pyrrolidin-2-one | 1H NMR (CHCl3-d, 600 MHz): δ 8.13-8.11 (m, 2H), 7.68-7.65 (m, 2H), 7.46-7.44 (m, 2H), 7.34 (dd, 2H, J = 8.8, 1.1 Hz), 5.82-5.80 (m, 1H), 3.01-2.94 (m, 1H), 2.79-2.70 (m, 2H), 2.41-2.35 (m, 1H) | Ms m/z (ESI) [M + H]+ = 452.00 [M + H]− = 449.95 | 115 |
| 85 | | (4-chlorophenyl)((2S,4S)-4-hydroxy-2-[3-{4-(trifluoromethoxy)phenyl}-1,2,4-oxadiazol-5-yl]pyrrolidin-1-yl)methanone | 1H NMR (CHCl3-d, 600 MHz): δ 8.13 (d, 2H, J = 7.7 Hz), 7.59 (d, 2H, J = 6.2 Hz), 7.44 (d, 2H, J = 6.2 Hz), 7.33 (d, 2H, J = 9.2 Hz), 5.76 (br, 1H), 4.69 (br, 1H), 4.03 (dd, 1H, J = 11.4, 3.7 Hz), 3.67 (d, 1H, J = 11.0 Hz), 2.63-2.59 (m, 1H), 2.40 (ddd, 1H, J = 13.5, 8.9, 4.4 Hz), 1.97 (br, 1H) | Ms m/z (ESI) [M + H]+ = 454.05 | 171 |
| 86 | | (S)-N-(3-amino-3-oxo-1-[3-{4-(trifluoromethoxy)phenyl}-1,2,4-oxadiazol-5-yl]propyl)-4-chlorobenzamide | 1H NMR (CHCl3-d, 600 MHz): δ 8.14-8.11 (m, 3H), 7.87-7.85 (m, 2H), 7.49-7.47 (m, 2H), 7.33 (d, 2H, J = 8.4 Hz), 5.92-5.89 (m, 1H), 5.68 (s, 1H), 5.46 (s, 1H), 3.35 (dd, 1H, J = 16.5, 4.0 Hz), 3.11 (dd, 2H, J = 16.5, 4.4 Hz) | Ms m/z (ESI) [M + H]+ = 455.05 [M + H]− = 452.95 | 240 |
| 87 | | (S)-4-chloro-N-(3-(dimethylamino)-3-oxo-1-[3-{4-(trifluoromethoxy)phenyl}-1,2,4-oxadiazol-5-yl]propyl)benzamide | 1H NMR (CHCl3-d, 600 MHz): δ 8.19 (d, 1H, J = 9.2 Hz), 8.12 (d, 2H, J = 8.4 Hz), 7.87 (d, 2H, J = 8.4 Hz), 7.48 (d, 2H, J = 8.4 Hz), 7.32 (d, 2H, J = 8.4 Hz), 5.94-5.91 (m, 1H), 3.56 (dd, 1H, J = 17.1, 3.5 Hz), 3.11-3.08 (m, 4H), 2.95 (s, 3H) | Ms m/z (ESI) [M + H]+ = 483.05 [M + H]− = 481.00 | 64 |

TABLE 2L-continued

| 88 | (S)-4-chloro-N-(3-(methylamino)-3-oxo-1-[3-{4-(trifluoromethoxy)phenyl}-1,2,4-oxadiazol-5-yl]propyl)benzamide | 1H NMR (CHCl3-d, 600 MHz): δ 8.38 (d, 1H, J = 8.4 Hz), 8.13-8.11 (m, 2H), 7.89-7.87 (m, 2H), 7.49-7.47 (m, 2H), 7.33 (d, 2H, J = 8.1 Hz), 5.89-5.86 (m, 1H), 5.72 (d, 1H, J = 4.4 Hz), 3.23 (dd, 1H, J = 16.1, 4.0 Hz), 3.04 (dd, 1H, J = 16.0, 4.6 Hz), 2.83 (d, 3H, J = 4.8 Hz) | Ms m/z (ESI) [M + H]+ = 469.05 [M + H]− = 467.00 | 214 |

TABLE 2M

| 89 | 4-[5-{1-hydroxy-2-(1H-indol-3-yl)ethyl}-1,2,4-oxadiazol-3-yl]phenol | 1H NMR (500 MHz, CHLOROFORM-d) Shift 8.10 (br. s, 1H), 7.92-8.04 (m, J = 8.71 Hz, 2H), 7.62 (d, J = 7.79 Hz, 1H), 7.38 (d, J = 7.79 Hz, 1H), 7.18-7.24 (m, 1H), 7.07-7.18 (m, 2H), 6.85-6.97 (m, J = 8.71 Hz, 2H), 5.26-5.35 (m, 1H), 5.21 (s, 1H), 3.57 (dd, J = 4.81, 14.89 Hz, 1H), 3.43 (dd, J = 7.33, 14.66 Hz, 1H), 2.66 (d, J = 6.42 Hz, 1H) | Ms m/z (ESI) [M + H]+ = 322 | Oil |
| 90 | 1-(4-chlorophenyl)-4-{3-(3-fluoro-4-hydroxyphenyl)-1,2,4-oxadiazol-5-yl}-4-(hydroxymethyl)pyrrolidin-2-one | 1H NMR (600 MHz, DMSO-d6) Shift 10.70 (br. s., 1H), 7.68-7.76 (m, 4H), 7.40-7.51 (m, 2H), 7.07-7.19 (m, 1H), 5.52-5.66 (m, 1H), 4.32-4.45 (m, 1H), 4.12-4.21 (m, 1H), 3.84-3.89 (m, 2H), 3.10-3.27 (m, 1H), 2.90-3.04 (m, 1H) | Ms m/z (ESI) [M + H]+ = 404 | 195.1 |
| 91 | (S)-3-chloro-N-(2-hydroxy-1-[3-{4-(trifluoromethoxy)phenyl}-1,2,4-oxadiazol-5-yl]ethyl)benzenesulfonamide | 1H NMR (CHCl3-d, 600 MHz): δ 8.01-7.99 (m, 2H), 7.88 (t, 1H, J = 1.8 Hz), 7.74 (dd, 1H, J = 7.9, 0.9 Hz), 7.45-7.44 (m, 1H), 7.40-7.37 (m, 1H), 7.33 (d, 2H, J = 8.4 Hz), 5.90 (br, 1H), 4.94 (br, 1H), 4.18-4.14 (m, 1H), 4.11-4.08 (m, 1H), 2.44 (br, 1H) | Ms m/z (ESI) [M + H]+ = 463.95 [M + H]− = 461.95 | 131 |
| 92 | (S)-N-(2-hydroxy-1-[3-{4-(trifluoromethoxy)phenyl}-1,2,4-oxadiazol-5-yl]ethyl)benzamide | 1H NMR (CHCl3-d, 600 MHz): δ 8.16 (d, 2H, J = 8.8 Hz), 7.91 (dd, 2H, J = 7.0, 1.5 Hz), 7.62-7.58 (m, 1H), 7.53-7.51 (m, 2H), 7.36-7.35 (m, 2H), 7.21 (d, 1H, J = 7.7 Hz), 5.77-5.75 (m, 1H), 4.38-4.35 (m, 1H), 4.20 (ddd, 1H, J = 11.4, 7.3, 4.0 Hz), 2.52-2.50 (m, 1H) | Ms m/z (ESI) [M + H]+ = 394.05 [M + H]− = 361.95 | 130 |

TABLE 2M-continued

| # | Structure | Name | 1H NMR | MS | Ref |
|---|---|---|---|---|---|
| 93 | 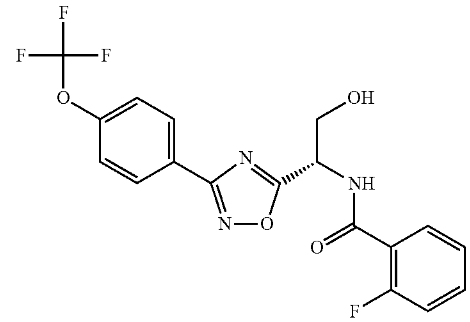 [SMILES: O=C(N[C@@H](CO)c1nc(-c2ccc(OC(F)(F)F)cc2)no1)c1ccccc1F] | (S)-3-fluoro-N-(2-hydroxy-1-[3-{4-(trifluoromethoxy)phenyl}-1,2,4-oxadiazol-5-yl]ethyl)benzamide | 1H NMR (CHCl3-d, 600 MHz): δ 8.18-8.15 (m, 3H), 7.84 (dd, 1H, J = 13.2, 7.7 Hz), 7.59-7.55 (m, 1H), 7.36-7.32 (m, 3H), 7.21 (ddd, 1H, J = 12.2, 8.3, 1.1 Hz), 5.76 (dtd, 1H, J = 7.7, 3.9, 2.2 Hz), 4.36-4.33 (m, 1H), 4.22 (ddd, 1H, J = 11.4, 7.3, 4.0 Hz), 2.59 (t, 1H, J = 5.9 Hz) | Ms m/z (APCI) [M + H]+ = 412.00 [M + H]− = 409.95 | 92 |
| 94 | 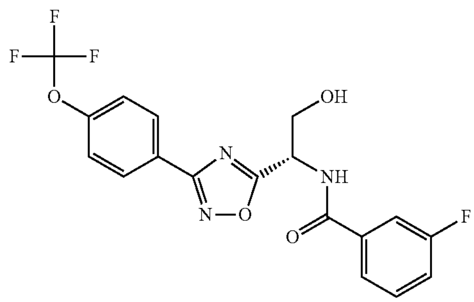 [SMILES: O=C(N[C@@H](CO)c1nc(-c2ccc(OC(F)(F)F)cc2)no1)c1cccc(F)c1] | (S)-3-fluoro-N-(2-hydroxy-1-[3-{4-(trifluoromethoxy)phenyl}-1,2,4-oxadiazol-5-yl]ethyl)benzamide | 1H NMR (CHCl3-d, 600 MHz): δ 8.14-8.12 (m, 2H), 7.66 (dt, 1H, J = 7.7, 1.3 Hz), 7.62-7.60 (m, 1H), 7.48 (td, 1H, J = 8.0, 5.7 Hz), 7.30-7.27 (m, 1H), 7.32 (dd, 2H, J = 9.0, 0.9 Hz), 5.72 (dt, 1H, J = 8.1, 3.5 Hz), 4.36 (ddd, 1H, J = 11.7, 5.1, 3.3 Hz), 4.19 (ddd, 1H, J = 11.4, 7.3, 4.0 Hz), 2.69 (dd, 1H, J = 7.0, 5.1 Hz) | Ms m/z (APCI) [M + H]+ = 412.00 [M + H]− = 409.95 | 117 |
| 95 | 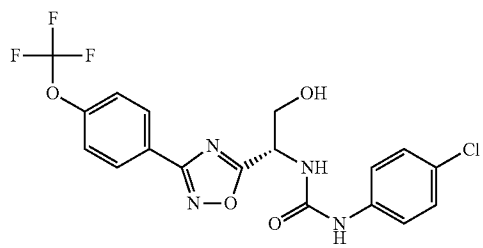 | (S)-1-(4-chlorophenyl)-3-(2-hydroxy-1-[3-{4-(trifluoromethoxy)phenyl}-1,2,4-oxadiazol-5-yl]ethyl)urea | 1H NMR (CHCl3-d, 600 MHz): δ 8.14-8.13 (m, 2H), 7.37-7.29 (m, 6H), 6.55 (br, 1H), 5.81-5.79 (m, 1H), 5.49-5.47 (m, 1H), 4.27 (dd, 1H, J = 11.6, 3.1 Hz), 4.13 (dd, 1H, J = 11.6, 3.9 Hz) | Ms m/z (APCI) [M + H]+ = 443.00 [M + H]− = 449.95 | 187 |
| 96 | 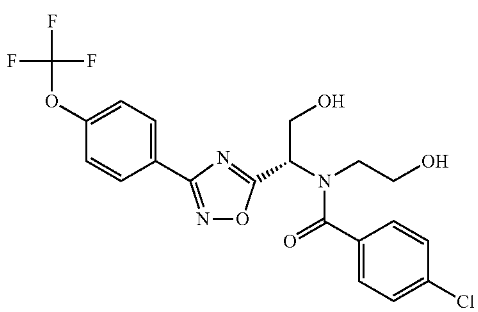 [SMILES: O=C(c1ccc(Cl)cc1)N(CCO)[C@@H](CO)c1nc(-c2ccc(OC(F)(F)F)cc2)no1] | (S)-4-chloro-N-(2-hydroxy-1-[3-{4-(trifluoromethoxy)phenyl}-1,2,4-oxadiazol-5-yl]ethyl)-N-(2-hydroxyethyl)benzamide | 1H NMR (CHCl3-d, 600 MHz): δ 8.10-8.08 (m, 1H), 8.07-8.04 (m, 2H), 8.01-7.98 (m, 1H), 7.48-7.47 (m, 2H), 7.44-7.42 (m, 1H), 7.33 (d, 1H, J = 7.7 Hz), 4.50 (t, 2H, J = 5.1 Hz), 4.27 (dd, 1H, J = 6.8, 4.6 Hz), 4.05 (dd, 1H, J = 11.2, 4.6 Hz), 3.93 (dd, 1H, J = 11.2, 6.8 Hz), 3.27-3.23 (m, 1H), 3.13-3.09 (m, 1H) | Ms m/z (APCI) [M + H]+ = 472.00 [M + H]− = 469.95 | 146 |

TABLE 2N

| # | Structure | Name | 1H NMR | MS | Ref |
|---|---|---|---|---|---|
| 97 | 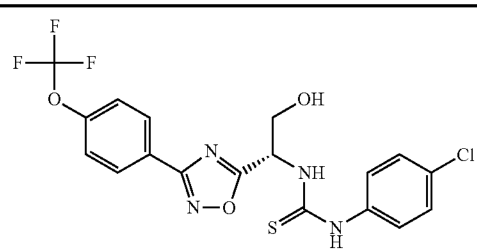 | (S)-1-(4-chlorophenyl)-3-(2-hydroxy-1-[3-{4-(trifluoromethoxy)phenyl}-1,2,4-oxadiazol-5-yl]ethyl)thiourea | | Ms m/z (APCI) [M + H]+ = 458.95 [M + H]− = 456.90 | |

| | | | | | |
|---|---|---|---|---|---|
| 98 | | (S)-3-chloro-4-hydroxy-N-(2-hydroxy-1-[3-{4-(trifluoromethoxy)phenyl}-1,2,4-oxadiazol-5-yl]ethyl)benzamide | 1H NMR (CHCl3-d, 600 MHz): δ 8.16-8.14 (m, 2H), 7.95 (d, 1H, J = 2.2 Hz), 7.74 (dd, 1H, J = 8.4, 2.2 Hz), 7.36 (d, 2H, J = 7.7 Hz), 7.13 (d, 1H, J = 8.1 Hz), 7.10 (d, 1H, J = 8.1 Hz), 5.72 (dt, 1H, J = 8.1, 3.5 Hz), 4.36 (dd, 1H, J = 11.6, 3.1 Hz), 4.18 (dd, 1H, J = 11.6, 3.9 Hz), 3.52 (br, 1H) | Ms m/z (APCI) [M + H]+ = 444.00 [M + H]− = 441.90 | 148 |
| 99 | | (S)-4-chloro-N-(1-(3-(3-fluoro-4-hydroxyphenyl)-1,2,4-oxadiazol-5-yl)-2-hydroxy-ethyl)benzamide | 1H NMR (600 MHz, DMSO-d6) Shift 9.22 (d, J = 6.97 Hz, 1H), 7.90-8.00 (m, J = 8.44 Hz, 2H), 7.63-7.73 (m, 2H), 7.55-7.63 (m, J = 8.44 Hz, 2H), 7.03-7.18 (m, 1H), 5.30-5.43 (m, 2H), 3.90-4.07 (m, 2H) | Ms m/z (APCI) [M + H]+ = 378 | 155.5 |
| 100 | | (S)-4-cyano-N-(1-(3-(3-fluoro-4-hydroxyphenyl)-1,2,4-oxadiazol-5-yl)-2-hydroxy-ethyl)benzamide | 1H NMR (600 MHz, DMSO-d6) Shift 9.42 (d, J = 7.34 Hz, 1H), 8.04-8.19 (m, J = 8.44 Hz, 2H), 7.93-8.04 (m, J = 8.44 Hz, 2H), 7.63-7.73 (m, 2H), 7.00-7.20 (m, 1H), 5.32-5.45 (m, 2H), 3.94-4.06 (m, 2H) | Ms m/z (APCI) [M + H]+ = 369 | 183.5 |
| 101 | | 2-(1H-indol-3-yl)-1-(3-(4-(trifluoro-methoxy)phenyl)-1,2,4-oxadiazol-5-yl)ethan-1-ol | 1H NMR (600 MHz, CHLOROFORM-d) Shift 8.12 (d, J = 8.44 Hz, 3H), 7.61 (d, J = 8.07 Hz, 1H), 7.38 (d, J = 8.44 Hz, 1H), 7.32 (d, J = 8.07 Hz, 2H), 7.22 (t, J = 7.50 Hz, 1H), 7.14 (t, J = 7.50 Hz, 1H), 7.10 (d, J = 1.83 Hz, 1H), 5.29-5.37 (m, 1H), 3.58 (dd, J = 4.77, 14.67 Hz, 1H), 3.45 (dd, J = 7.00, 14.70 Hz, 1H), 2.68 (d, J = 6.60 Hz, 1H) | Ms m/z (APCI) [M + H]+ = 390 | 97.2 |
| 102 | | 4-chloro-N-(1,3-dihydroxy-2-(3-(4-(trifluoro-methoxy)phenyl)-1,2,4-oxadiazol-5-yl)propan-2-yl)benzamide | 1H NMR (CHCl3-d, 600 MHz): δ 8.16-8.13 (m, 2H), 7.83--7.81 (m, 1H), 7.79-7.77 (m, 2H), 7.50-7.48 (m, 1H), 7.47-7.45 (m, 2H), 5.33 (s, 1H), 4.40 (dd, 2H, J = 11.4, 4.4 Hz), 4.27 (dd, 2H, J = 11.4, 6.2 Hz), 3.42 (br, 2H). | Ms m/z (APCI) [M + H]+ = 457.95 | 96 |
| 103 | | 1-(4-chlorophenyl)-4-(5-(4-(trifluoromethoxy)phenyl)-1,3,4-oxadiazol-2-yl)pyrrolidin-2-one | 1H NMR (600 MHz, CHLOROFORM-d) d 8.00-8.19 (m, 2H), 7.52-7.65 (m, 2H), 7.32-7.44 (m, 4H), 4.23-4.42 (m, 2H), 3.99-4.16 (m, 1H), 3.14 (dq, J = 8.54, 17.03 Hz, 2H). | Ms m/z (APCI) [M + H]+ = 424 | 151 |

TABLE 2N-continued

| | | | | | |
|---|---|---|---|---|---|
| 104 | (structure) | Cl | (S)-4-chloro-N-(2-hydroxy-1-(5-(4-(trifluoromethoxy)phenyl)-1,3,4-oxadiazol-2-yl)ethyl)benzamide | 1H NMR (500 MHz, CHLOROFORM-d) d 7.98-8.15 (m, 2H), 7.76-7.85 (m, 2H), 7.39-7.47 (m, 2H), 7.32 (d, J = 8.39 Hz, 2H), 7.29 (d, J = 8.26 Hz, 1H), 5.68 (td, J = 3.35, 8.31 Hz, 1H), 4.37 (ddd, J = 2.95, 5.04, 11.80 Hz, 1H), 4.12 (ddd, J = 3.77, 8.33, 11.90 Hz, 1H), 3.12 (dd, J = 5.04, 8.38 Hz, 1H). | Ms m/z (APCl) [M + H]+ = 428 | 184 |

TABLE 2O

| | | | | | |
|---|---|---|---|---|---|
| 105 | (structure) | Cl | (S)-4-chloro-N-(2-hydroxy-1-(5-(4-(methyl-sulfonamido)phenyl)-1,3,4-oxadiazol-2-yl)ethyl)benzamide | 1H NMR (495 MHz, CHLOROFORM-d) d 7.97-8.08 (m, 2H), 7.75-7.84 (m, 2H), 7.42-7.49 (m, 2H), 7.31 (d, J = 9.07 Hz, 2H), 7.13-7.16 (m, 1H), 7.04 (s, 1H), 5.64-5.70 (m, 1H), 3.49 (d, J = 5.10 Hz, 1H), 3.10 (s, 1H) | Ms m/z (APCl) [M + H]+ = 437. | 196 |
| 106 | (structure) | Cl | (S)-4-chloro-N-(1-(5-(3-cyanophenyl)-1,3,4-oxadiazol-2-yl)-2-hydroxyethyl)benzamide | 1H NMR (495 MHz, CHLOROFORM-d) d 8.34 (d, J = 1.70 Hz, 1H), 8.27-8.32 (m, 1H), 7.80-7.87 (m, 3H), 7.67 (t, J = 7.94 Hz, 1H), 7.45-7.50 (m, 2H), 7.16-7.22 (m, 1H), 5.68-5.74 (m, 1H), 4.41 (dd, J = 1.98, 12.19 Hz, 1H), 4.12-4.18 (m, 1H), 2.70-2.80 (m, 1H). | Ms m/z (APCl) [M + H]+ = 369 | 160 |
| 107 | (structure) | Cl | (R)-4-chloro-N-(2-hydroxy-1-(5-(4-(trifluoro-methoxy)phenyl)-1,3,4-oxzdiazol-2-yl)ethyl)benzamide | 1H NMR (495 MHz, CHLOROFORM-d) d 8.03-8.08 (m, 2H), 7.79-7.84 (m, 2H), 7.41-7.46 (m, 2H), 7.30-7.36 (m, 3H), 5.70 (td, J = 3.35, 8.33 Hz, 1H), 4.38 (ddd, J = 2.99, 5.09, 11.82 Hz, 1H), 4.14 (ddd, J = 3.77, 8.32, 11.92 Hz, 1H), 3.18 (dd, J = 5.10, 8.36 Hz, 1H). | Ms m/z (APCl) [M + H]+ = 428 | 182 |
| 108 | (structure) | Cl | (R)-4-chloro-N-(2-hydroxy-1-(5-(4-(methyl-sulfonamido)phenyl)-1,3,4-oxzdiazol-2-yl)ethyl)benzamide | 1H NMR (495 MHz, CHLOROFORM-d) d 8.03 (d, J = 9.07 Hz, 2H), 7.81 (td, J = 2.05, 8.93 Hz, 2H), 7.43-7.47 (m, 2H), 7.29-7.32 (m, 2H), 7.17 (d, J = 9.64 Hz, 1H), 7.04 (s, 1H), 5.64-5.70 (m, 1H), 4.34-4.39 (m, 1H), 4.09-4.14 (m, 1H), 2.81-2.86 (m, 1H). | Ms m/z (APCl) [M + H]+ = 437. | 192 |
| 109 | (structure) | Cl | (R)-4-chloro-N-(1-(5-(3-cyanophenyl)-1,3,4-oxadiazol-2-yl)-2-hydroxyethyl)benzamide | 1H NMR (500 MHz, CHLOROFORM-d) d 8.21-8.32 (m, 2H), 7.76-7.87 (m, 3H), 7.62-7.71 (m, 1H), 7.38-7.47 (m, 2H), 7.28 (d, J = 8.25 Hz, 1H), 5.69 (td, J = 3.44, 8.25 Hz, 1H), 4.38 (ddd, J = 2.98, 4.81, 11.91 Hz, 1H), 4.14 (ddd, J = 3.90, 8.13, 11.80 Hz, 1H), 3.02 (dd, J = 5.04, 7.79 Hz, 1H) | Ms m/z (APCl) [M + H]+ = 369 | 167 |

TABLE 2O-continued

| 110 | (structure) | (S)-2-(1H-indol-3-yl)-1-(5-(4-(trifluoromethoxy)phenyl)-1,3,4-oxadiazol-2-yl)ethan-1-amine hydrochloride | 1H NMR (600 MHz, DMSO) d 9.09 (br. s., 1H), 8.03-8.08 (m, 2H), 7.67-7.74 (m, 1H), 7.60-7.66 (m, 2H), 7.50-7.55 (m, 1H), 7.32-7.37 (m, 1H), 7.22 (d, J = 2.57 Hz, 1H), 7.03-7.08 (m, 1H), 6.94 (dt, J = 1.10, 7.52 Hz, 1H), 5.08 (br. s., 1H), 3.49-3.54 (m, 2H). | Ms m/z (APCI) [M + H]+ = 389 (HCl free) | 225 (Decomposition) |
|---|---|---|---|---|---|
| 111 | (structure) | (S)-N-(4-(5-(1-amino-2-(1H-indol-3-yl)ethyl)-1,3,4-oxadiazol-2-yl)phenyl)methanesulfonamide hydrochloride | 1H NMR (600 MHz, DMSO-d6) d 11.02-11.08 (m, 1H), 10.44 (s, 1H), 9.19 (s, 2H), 7.86-7.90 (m, 2H), 7.53 (d, J = 7.94 Hz, 1H), 7.38-7.40 (m, 2H), 7.35 (d, J = 8.11 Hz, 1H), 7.20 (d, J = 2.46 Hz, 1H), 7.04-7.08 (m, 1H), 6.91-6.96 (m, 1H), 5.03 (dd, J = 5.24, 8.92 Hz, 1H), 3.58-3.62 (m, 1H), 3.48-3.54 (m, 1H), 3.14 (s, 3H). | Ms m/z (APCI) [M + H]+ = 398 (HCl free) | 210 (Decomposition) |
| 112 | (structure) | (S)-4-fluoro-N-(2-hydroxy-1-(5-(4-(trifluoromethoxy)phenyl)-1,3,4-oxadiazol-2-yl)ethyl)benzamide | 1H NMR (600 MHz, CHLOROFORM-d) d 8.05-8.11 (m, 2H), 7.86-7.92 (m, 2H), 7.34 (d, J = 8.44 Hz, 2H), 7.20 (d, J = 8.11 Hz, 1H), 7.12-7.17 (m, 2H), 5.69 (td, J = 3.30, 8.29 Hz, 1H), 4.38 (d, J = 12.14 Hz, 1H), 4.13 (br. s., 1H), 2.95 (br. s., 1H). | Ms m/z (APCI) [M + H]+ = 412 | 148 |

TABLE 2P

| 113 | (structure) | (S)-4-chloro-N-(1-(5-(3-fluoro-4-methoxyphenyl)-1,3,4-oxadiazol-2-yl)-2-hydroxyethyl)benzamide | 1H NMR (600 MHz, CHLOROFORM-d) d 7.81-7.87 (m, 2H), 7.77-7.80 (m, 1H), 7.74 (dd, J = 2.11, 11.28 Hz, 1H), 7.44-7.50 (m, 2H), 7.06 (t, J = 8.40 Hz, 1H), 5.69 (td, J = 3.30, 8.31 Hz, 1H), 4.39 (ddd, J = 2.91, 4.91, 11.86 Hz, 1H), 4.14 (ddd, J = 3.68, 8.58, 12.02 Hz, 1H), 3.99 (s, 3H), 3.14 (dd, J = 4.87, 8.70 Hz, 1H). | Ms m/z (APCI) [M + H]+ = 392 | 194 |
|---|---|---|---|---|---|
| 114 | (structure) | (R)-2-(1H-indol-3-yl)-1-(5-(4-(trifluoromethoxy)phenyl)-1,3,4-oxadiazol-2-yl)ethan-1-amine | 1H NMR (600 MHz, DMSO-d6) d 10.94 (s, 1H), 9.15 (br. s., 3H), 7.95-8.08 (m, 2H), 7.29-7.40 (m, 1H), 7.17 (s, 1H), 6.99-7.09 (m, 1H), 6.93 (t, J = 7.16 Hz, 1H), 5.01 (s, 1H), 3.61-3.70 (m, 1H), 3.50-3.61 (m, 1H). | Ms m/z (APCI) [M + H]+ = 389 | 210 (Decomposition) |
| 115 | (structure) | 4-chloro-N-(1-(5-(4-(trifluoromethoxy)phenyl)-1,3,4-oxadiazol-2-yl)vinyl)benzamide | 1H NMR (600 MHz, CDCl3) d 8.62 (s, 1H), 8.12-8.21 (m, 2H), 7.84-7.89 (m, 2H), 7.79 (d, J = 8.17 Hz, 2H), 7.48-7.53 (m, 2H), 7.32-7.42 (m, 2H), 7.32-7.37 (m, 3H), 6.81 (d, J = 1.21 Hz, 1H), 5.91 (d, J = 1.25 Hz, 1H). | Ms m/z (APCI) [M + H]+ = 410 | 125 |

TABLE 2P-continued

| # | Structure | Name | NMR | MS |
|---|---|---|---|---|
| 116 | | N-(2-amino-1-(5-(4-(trifluoromethoxy)phenyl)-1,3,4-oxadiazol-2-yl)ethyl)-4-chlorobenzamide | | Ms m/z (APCl) [M + H]+ = 427 | 108 |
| 117 | | 4-chloro-N-(2-morpholino-1-(5-(4-(trifluoromethoxy)phenyl)-1,3,4-oxadiazol-2-yl)ethyl)benzamide | | Ms m/z (APCl) [M + H]+ = 497 | 120 |
| 118 | | 4-chloro-N-(2-(methylamino)-1-(5-(4-(trifluoromethoxy)phenyl)-1,3,4-oxadiazol-2-yl)ethyl)benzamide | 1H NMR (600 MHz, CHLOROFORM-d) d 8.06-8.18 (m, 2H), 7.80-7.90 (m, 2H), 7.56 (d, J = 7.61 Hz, 1H), 7.44-7.50 (m, 2H), 7.34-7.39 (m, 2H), 5.67 (ddd, J = 3.91, 4.99, 7.74 Hz, 1H), 5.33 (s, 1H), 3.47 (dd, J = 3.93, 12.54 Hz, 1H), 3.11 (dd, J = 5.00, 12.55 Hz, 1H), 2.54 (s, 3H). | Ms m/z (APCl) [M + H]+ = 441 | 102 |
| 119 | | 4-chloro-N-(2-((2-hydroxyethyl)amino)-1-(5-(4-(trifluoromethoxy)phenyl)-1,3,4-oxadiazol-2-yl)ethyl)benzamide | | Ms m/z (APCl) [M + H]+ = 471 | 119 |
| 120 | | (S)-4-chloro-N-(1-(5-(3-fluoro-4-hydroxyphenyl)-1,3,4-oxadiazol-2-yl)-2-hydroxyethyl)benzamide | | Ms m/z (APCl) [M + MeOH]+ = 410 | 158 |
| 121 | | 1-(4-chlorophenyl)-4-(3-(4-(trifluoromethoxy)phenyl)-1,2,4-thiadiazol-5-yl)pyrrolidin-2-one | 1H NMR (600 MHz, CHLOROFORM-d) d 8.36 (d, J = 8.56 Hz, 2H), 7.57-7.64 (m, J = 8.71 Hz, 2H), 7.39 (d, J = 8.68 Hz, 2H), 7.33-7.37 (m, J = 8.35 Hz, 2H), 4.35-4.40 (m, 1H), 4.29 (td, J = 7.53, 15.00 Hz, 1H), 4.22-4.26 (m, 1H), 3.23 (dd, J = 8.74, 17.03 Hz, 1H), 3.10 (dd, J = 7.42, 17.02 Hz, 1H). | Ms m/z (APCl) [M + H]+ = 440 | 131 |

TABLE 2Q

| # | Structure | Name | NMR | MS |
|---|---|---|---|---|
| 122 | | 1-(4-chlorophenyl)-4-(2-(4-(trifluoromethoxy)phenyl)-2H-tetrazol-5-yl)pyrrolidin-2-one | 1H NMR (600 MHz, CHLOROFORM-d) d 8.18-8.23 (m, 2H), 7.58-7.64 (m, 2H), 7.42-7.47 (m, J = 8.79 Hz, 2H), 7.36-7.38 (d, J = 7.82 Hz, 2H), 4.27-4.40 (m, 2H), 4.17 (dq, J = 6.53, 8.33 Hz, 1H), 3.20 (d, J = 8.39 Hz, 2H). | Ms m/z (APCl) [M + H]+ = 424 | 110 |

TABLE 2Q-continued

| | | | | | |
|---|---|---|---|---|---|
| 123 | (structure) | 1-(4-chlorophenyl)-4-(5-(4-(trifluoromethoxy)phenyl)-4H-1,2,4-triazol-3-yl)pyrrolidin-2-one | 1H NMR (600 MHz, CHLOROFORM-d) d 8.02 (d, J = 8.40 Hz, 2H), 7.60 (td, J = 2.90, 9.90 Hz, 2H), 7.31-7.39 (m, 4H), 4.28 (ddd, J = 8.07, 9.54, 17.61 Hz, 2H), 3.97 (quin, J = 7.79 Hz, 1H), 3.16 (ddd, J = 8.80, 17.97, 38.88 Hz, 2H). | Ms m/z (APCI) [M + H]+ = 423 | 168 |
| 124 | (structure) | 1-(4-chlorophenyl)-4-(5-(4-(trifluoromethoxy)phenyl)-1H-imidazol-2-yl)pyrrolidin-2-one | 1H NMR (600 MHz, CHLOROFORM-d) d 7.79 (br. s., 1H), 7.54-7.66 (m, 2H), 7.35-7.38 (m, 2H), 7.27-7.29 (m, 2H), 7.25 (d, J = 8.28 Hz, 2H), 4.35 (dd, J = 7.36, 9.65 Hz, 1H), 4.20 (dd, J = 8.27, 9.65 Hz, 1H), 3.82-3.94 (m, 1H), 3.06 (dd, J = 3.32, 8.86 Hz, 2H). | Ms m/z (APCI) [M + H]+ = 422 | 211 |
| 125 | (structure) | (S)-4-chloro-N-(2-hydroxy-1-(3-(4-methoxyphenyl)-1,2,4-oxadiazol-5-yl)ethyl)benzamide | 1H NMR (CHCl3-d, 600 MHz): δ 8.01-7.98 (m, 2H), 7.82-7.80 (d, 2H), 7.46-7.44 (m, 2H), 7.17 (d, 1H, J = 8.1 Hz), 6.99-6.97 (m, 2H), 5.69-5.66 (m, 1H), 4.31 (dd, 1H, J = 11.6, 3.1 Hz), 4.14 (d, 1H, J = 11.0), 3.87 (s, 3H, 2.73 (br, 1H) | Ms m/z (APCI) [M + H]+ = 374.05 [M + H]− = 371.95 | |
| 126 | (structure) | (S)-4-chloro-N-(2-hydroxy-1-(5-(4-(trifluoromethoxy)phenyl)-1,2,4-oxadiazol-3-yl)ethyl)benzamide | 1H NMR (CHCl3-d, 600 MHz): δ 8.16-8.13 (m, 2H), 7.85-7.13 (m, 2H), 7.50-7.47 (m, 2H), 7.35 (d, 2H, J = 8.4 Hz), 7.19 (br, 1H), 5.73-5.71 (m, 1H), 4.38-4.35 (m, 1H), 4.20-4.17 (m, 1H), 2.62 (br, 1H) | Ms m/z (APCI) [M + H]+ = 428 | |
| 127 | (structure) | 4-chloro-N-((1S,2S)-2-hydroxy-1-(3-(4-(trifluoromethoxy)phenyl)-1,2,4-oxadiazol-5-yl)propyl)benzamide | 1H NMR (CHCl3-d, 600 MHz): δ 8.15-8.13 (m, 2H), 7.81-7.79 (m, 2H), 7.47-7.45 (m, 2H), 7.34 (dd, 2H, J = 8.8, 1.1 Hz), 7.17 (d, 1H, J = 8.4 Hz), 5.59 (dd, 1H, J = 8.4, 3.7 Hz), 4.40-4.35 (m, 1H), 2.62 (d, 1H, J = 8.1 Hz), 1.35 (d, 3H, J = 6.2 Hz) | Ms m/z (APCI) [M + H]+ = 442.00 [M + H]− = 439.90 | |

TABLE 2Q-continued

| # | Structure | Name | 1H NMR | MS |
|---|---|---|---|---|
| 128 | 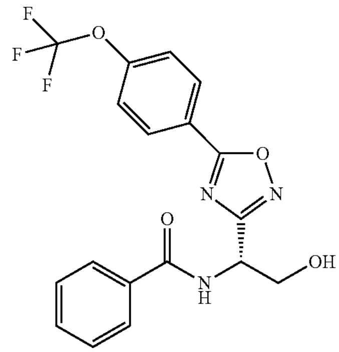 [SMILES: O=C(N[C@@H](CO)c1noc(-c2ccc(OC(F)(F)F)cc2)n1)c1ccccc1] | (R)-N-(2-hydroxy-1-(5-(4-(trifluoromethoxy)phenyl)-1,2,4-oxadiazol-3-yl)ethyl)benzamide | 1H NMR (600 MHz, CDCl3) δ 8.18-8.25 (m, 2H), 7.87-7.93 (m, 2H), 7.55-7.60 (m, 1H), 7.47-7.53 (m, 2H), 7.38-7.43 (m, J = 8.38 Hz, 2H), 7.19 (d, J = 7.91 Hz, 1H), 5.67 (td, J = 3.92, 7.95 Hz, 1H), 4.27 (ddd, J = 3.70, 5.04, 11.47 Hz, 1H), 4.18 (ddd, J = 4.10, 7.48, 11.50 Hz, 1H), 2.64 (dd, J = 5.09, 7.56 Hz, 1H) | Ms m/z (APCI) [M + H]+ = 394 |
| 129 | 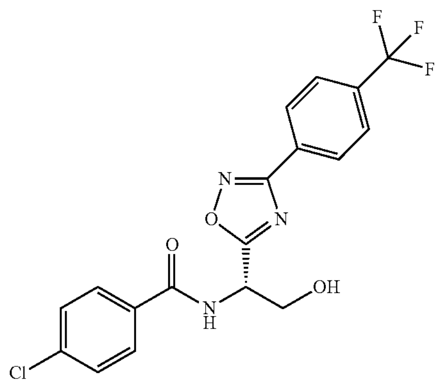 [SMILES: O=C(N[C@@H](CO)c1nc(-c2ccc(C(F)(F)F)cc2)no1)c1ccc(Cl)cc1] | (S)-4-chloro-N-(2-hydroxy-1-(3-(4-(trifluoromethyl)phenyl)-1,2,4-oxadiazol-5-yl)ethyl)benzamide | 1H NMR (600 MHz, CDCl3) δ 8.23 (d, J = 8.14 Hz, 2H), 7.83-7.88 (m, 2H), 7.75-7.81 (m, J = 8.20 Hz, 2H), 7.47-7.52 (m, 2H), 7.18 (d, J = 8.17 Hz, 1H), 5.75 (td, J = 3.47, 8.17 Hz, 1H), 4.33-4.46 (m, 1H), 4.21 (ddd, J = 3.81, 7.26, 11.34 Hz, 1H), 2.47 (dd, J = 4.94, 7.12 Hz, 1H) | Ms m/z (APCI) [M + H]+ = 412 |

TABLE 2R

| # | Structure | Name | 1H NMR | MS | |
|---|---|---|---|---|---|
| 130 | 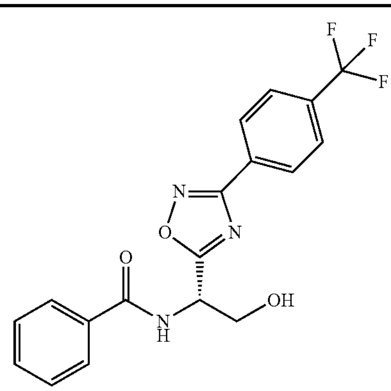 | (S)-N-(2-hydroxy-1-(3-(4-(trifluoromethyl)phenyl)-1,2,4-oxadiazol-5-yl)ethyl)benzamide | 1H NMR (600 MHz, CDCl3 ? - 8.21-8.28 (m, J = 8.13 Hz, 2H), 7.88-7.95 (m, 2H), 7.75-7.81 (m, J = 8.20 Hz, 2H), 7.60 (tt, J = 1.26, 7.43 Hz, 1H), 7.50-7.55 (m, 2H), 7.23 (d, J = 8.03 Hz, 1H), 5.77 (td, J = 3.56, 8.15 Hz, 1H), 4.38 (td, J = 3.97, 11.43 Hz, 1H), 4.22 (ddd, J = 3.85, 7.03, 11.29 Hz, 1H), 2.57 (t, J = 6.00 Hz, 1H) | Ms m/z (APCI) [M + H]+ = 378 | Not provided |
| 131 | 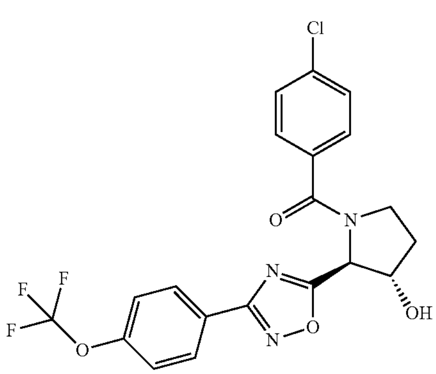 [SMILES: O=C(c1ccc(Cl)cc1)N1CC[C@H](O)[C@H]1c1nc(-c2ccc(OC(F)(F)F)cc2)no1] | (4-chlorophenyl)((2S,3S)-3-hydroxy-2-(3-(4-(trifluoromethoxy)phenyl)-1,2,4-oxadiazol-5-yl)pyrrolidin-1-yl)methanone | 1H NMR (CHCl3-d, 600 MHz): δ 8.12 (d, 2H, J = 8.80 Hz), 7.60 (d, 2H, J = 7.70 Hz), 7.43 (d, 2H, J = 6.24 Hz), 7.32 (d, 2H, J = 8.44 Hz), 5.60 (d, 1H, J = 4.40 Hz), 4.87 (br, 1H), 4.06 (dt, J = 10.45, 7.61 Hz, 1H), 3.69 (br, 1H), 2.42 (br, 1H), 2.28-2.20 (m, 2H) | Ms m/z (APCI) [M + H]+ = 424.00 | Not provided |

TABLE 2R-continued

| # | Structure | Name | NMR | MS | Other |
|---|---|---|---|---|---|
| 132 | (structure: 4-methoxyphenyl-oxadiazole with (1S,2R)-2-hydroxy-propyl, N-H linked to 4-chlorobenzamide) | 4-chloro-N-((1S,2R)-2-hydroxy-1-(3-(4-methoxy-phenyl)-1,2,4-oxadiazol-5-yl)propyl)benzamide | Not provided | Ms m/z (APCl) [M + H]+ = 389 | Not provided |
| 133 | (structure: 4-(trifluoromethyl)phenyl-oxadiazole with (S)-2-hydroxyethyl, N-H linked to 4-fluorobenzamide) | (S)-4-fluoro-N-(2-hydroxy-1-(3-(4-(trifluoromethyl)phenyl)-1,2,4-oxadiazol-5-yl)ethyl)benzamide | Not provided | Ms m/z (APCl) [M + H]+ = 396 | Not provided |

TABLE 2S

| # | Structure | Name | NMR | MS | Other |
|---|---|---|---|---|---|
| 142 | (structure: 2-fluoro-4-hydroxyphenyl-oxadiazole with (1S)-2-hydroxyethyl, N-H linked to benzamide) | N-[(1S)-1-[3-(2-fluoro-4-hydroxyphenyl)-1,2,4-oxadiazol-5-yl]-2-hydroxyethyl]benzamide | Not provided | Ms m/z (APCl) [M + H]+ = 344.05 | Not provided |
| 143 | (structure: 4-methylphenyl-oxadiazole with (1S)-2-hydroxyethyl, N-H linked to benzamide) | N-[(1S)-2-hydroxy-1-[3-(4-methylphenyl)-1,2,4-oxadiazol-5-yl]ethyl]benzamide | 1H NMR (CHCl3-d, 600 MHz): δ 7.91-7.98 (m, 2H), 7.84-7.90 (m, 2H), 7.53-7.59 (m, 1H), 7.45-7.51 (m, 2H), 7.28 (d, 2H, J = 8.1), 7.21 (br, 1H), 5.68-5.73 (m, 1H), 4.27-4.34 (m, 1H), 4.12-4.18 (m, 1H), 2.42 (s, 3H). | Ms m/z (APCl) [M + H]+ = 324.05 | Not provided |

TABLE 2S-continued

| | | | | |
|---|---|---|---|---|
| 144 | (structure) | N-[(1S)-1-[3-(3-fluoro-4-methoxyphenyl)-1,2,4-oxadiazol-5-yl]-2-hydroxyethyl]benzamide | 1H NMR (CHCl3-d, 600 MHz): δ 7.89-7.87 (m, 2H), 7.84 (ddd, 1H, J = 8.5, 1.1, 1.1 Hz), 7.80 (dd, 1H, J = 11.6, 2.0 Hz), 7.59-7.56 (m, 1H), 7.51-7.48 (m, 2H), 7.17 (d, 1H, J = 8.1 Hz), 7.05 (t, 1H, J = 8.4 Hz), 5.72-5.70 (m, 1H), 4.32 (ddd, 1H, J = 11.6, 5.0, 3.3 Hz), 4.17 (ddd, 1H, J = 11.4, 7.5, 3.9 Hz), 3.96 (s, 3H), 2.54 (dd, 1H, J = 7.3, 5.1 Hz). | Ms m/z (APCI) [M + H]+ = 358 Not provided |
| 145 | (structure) | N-[(1S)-2-hydroxy-1-{3-[4-(propan-2-yl)phenyl]-1,2,4-oxadiazol-5-yl}ethyl]benzamide | Not provided | Ms m/z (APCI) [M + H]+ = 352.05 Not provided |

TABLE 2T

| | | | | |
|---|---|---|---|---|
| 146 | (structure) | N-[(1S)-2-hydroxy-1-[3-(4-hydroxyphenyl)-1,2,4-oxadiazol-5-yl]ethyl]benzamide | 1H NMR (CHCl3-d): δ 8.00-7.97 (m, 2H), 7.89-7.87 (m, 2H), 7.57 (tt, 2H, J = 7.4, 1.2 Hz), 7.51-7.48 (m, 2H), 7.08 (s, 1H), 6.94-6.92 (m, 2H), 5.73-5.70 (m, 1H), 5.16 (br, 1H), 4.32 (ddd, 1H, J = 11.6, 5.0, 3.3 Hz), 4.16 (ddd, 1H, J = 11.5, 7.6, 4.0 Hz), 2.58-2.56 (m, 1H). | Ms m/z (APCI) [M + H]+ = 326 |
| 147 | (structure) | 4-{5-[(1S)-1-[(4-fluorophenyl)formamido]-2-hydroxyethyl]-1,2,4-oxadiazol-3-yl}-N-(3-methoxypropyl)benzamide | 1H NMR (600 MHz, CHLOROFORM-d) d 8.04-8.10 (m, J = 8.07 Hz, 2H), 7.89-7.96 (m, 2H), 7.77-7.83 (m, J = 8.07 Hz, 2H), 7.41 (d, J = 5.14 Hz, 1H), 7.16 (t, J = 8.62 Hz, 3H), 5.63-5.78 (m, 1H), 4.31-4.39 (m, 1H), 4.18 (ddd, J = 3.67, 7.24, 11.46 Hz, 1H), 3.55-3.62 (m, 4H), 3.41 (s, 3H), 3.13 (br. s., 1H), 1.91 (td, J = 5.64, 11.83 Hz, 2H). | Ms m/z (APCI) [M + H]+ = 443 |

TABLE 2T-continued

| 148 | 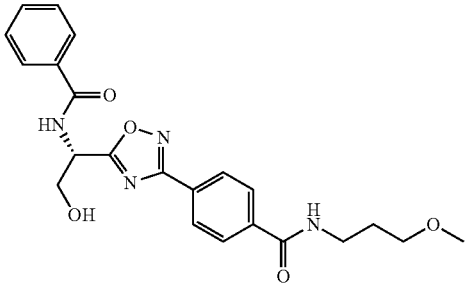 [SMILES: COCCCNC(=O)c1ccc(-c2noc([C@H](CO)NC(=O)c3ccccc3)n2)cc1] | 4-[5-[(1S)-2-hydroxy-1-(phenylformamido)ethyl]-1,2,4-oxadiazol-3-yl)-N-(3-methoxypropyl)benzamide | 1H NMR (600 MHz, CHLOROFORM-d) d 8.03-8.08 (m, 2H), 7.90-7.95 (m, 2H), 7.77-7.81 (m, 2H), 7.56-7.59 (m, 1H), 7.54 (d, J = 8.44 Hz, 1H), 7.47-7.51 (m, 2H), 7.19 (t, J = 4.95 Hz, 1H), 5.74 (td, J = 3.62, 8.16 Hz, 1H), 4.37 (dd, J = 3.30, 11.74 Hz, 1H), 4.20 (dd, J = 3.67, 11.74 Hz, 1H), 3.56-3.65 (m, 4H), 3.40-3.45 (m, 3H), 1.86-1.99 (m, 2H). | Ms m/z (APCl) [M + H]+ = 425 |
| --- | --- | --- | --- | --- |
| 149 | 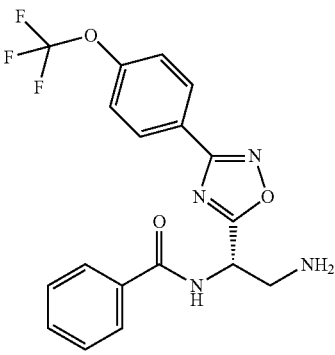 [SMILES: NC[C@H](NC(=O)c1ccccc1)c1nc(-c2ccc(OC(F)(F)F)cc2)no1] | N-[(1S)-2-amino-1-{3-[4-(trifluoromethoxy)phenyl]-1,2,4-oxadiazol-5-yl}ethyl]benzamide | 1H NMR (CHCl3-d): δ 8.02 (d, 1H, J = 8.8 Hz), 7.88-7.82 (m, 3H), 7.57-7.44 (m, 1H), 7.49-7.46 (m, 2H), 7.35-7.30 (m, 2H), 7.89 (d, 1H, J = 5.1 Hz), 4.87 (ddd, 1H, J = 14.4., 7.1, 5.7 Hz), 4.64 (dd, 1H, J = 15.4, 7.2 Hz), 3.54-3.49 (m, 1H). | Ms m/z (APCl) [M + H]+ = 393 |
| 150 | 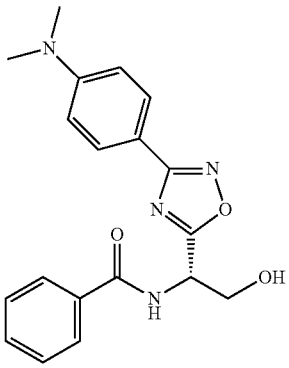 | N-[(1S)-1-{3-[4-(dimethylamino)phenyl]-1,2,4-oxadiazol-5-yl}-2-hydroxyethyl]benzamide | 1H NMR (CHCl3-d): δ 7.92-7.90 (m, 2H), 7.88-7.86 (m, 2H), 7.56-7.53 (m, 1H), 7.49-7.46 (m, 2H), 7.23 (d, 1H, J = 8.4 Hz), 6.73 (d, 2H, J = 9.2 Hz), 5.69-5.66 (m, 1H), 4.28 (dt, 1H, J = 11.5, 54.0 Hz), 4.13 (ddd, 1H, J = 11.5, 7.6, 4.0 Hz), 3.04 (s, 6H), 2.96 (br, 1H). | Ms m/z (APCl) [M + H]+ = 353.05 |
| 151 | 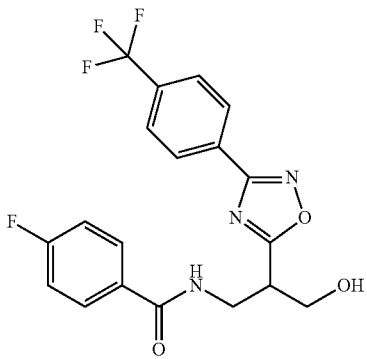 [SMILES: O=C(NCC(CO)c1nc(-c2ccc(C(F)(F)F)cc2)no1)c1ccc(F)cc1] | 4-fluoro-N-(3-hydroxy-2-{3-[4-(trifluoromethyl)phenyl]-1,2,4-oxadiazol-5-yl}propyl)benzamide | 1H NMR (CHLOROFORM-d) d: 8.14-8.28 (m, J = 8.1 Hz, 2H), 7.80-7.85 (m, 2H), 7.74-7.79 (m, J = 8.4 Hz, 2H), 7.12-7.18 (m, 2H), 6.87 (t, J = 6.1 Hz, 1H), 4.35 (ddd, J = 14.5, 7.7, 4.6 Hz, 1H), 4.15 (br. s., 1H), 4.03-4.13 (m, 1H), 3.85-3.97 (m, 2H), 3.56-3.61 (m, 1H). | Ms m/z (APCl) [M + H]+ = 410 |

TABLE 2T-continued

| 152 | (structure) | 4-fluoro-N-[(1R)-2-hydroxy-1-{3-[4-(trifluoromethyl)phenyl]-1,2,4-oxadiazol-5-yl}ethyl]benzamide | 1H NMR (CHLOROFORM-d) d: 8.21 (dd, J = 8.8, 0.7 Hz, 2H), 7.87-7.95 (m, 2H), 7.76 (d, J = 8.1 Hz, 2H), 7.16-7.20 (m, 2H), 7.12-7.16 (m, 1H), 5.73 (dt, J = 8.1, 3.5 Hz, 1H), 4.32-4.42 (m, 1H), 4.19 (ddd, J = 11.3, 7.2, 3.9 Hz, 1H), 2.47 (dd, J = 6.8, 5.0 Hz, 1H). | Ms m/z (APCI) [M + H]+ = 396 |
|---|---|---|---|---|
| 153 | (structure) | N-[(1S)-1-[3-(4-acetylphenyl)-1,2,4-oxadiazol-5-yl]-2-hydroxyethyl]benzamide | 1H NMR (CHCl3-d): δ 8.16 (d, 2H, J = 8.1 Hz), 8.04 (d, 2H, J = 8.1 Hz), 7.89-7.88 (m, 2H), 7.58-7.56 (m, 1H), 7.50-7.48 (m, 2H), 7.25 (br, 1H), 5.75-5.72 (m, 1H), 4.35 (ddd, 1H, J = 11.7, 5.1, 3.3 Hz), 4.18 (ddd, 1H, J = 11.4, 7.3, 4.0 Hz), 2.75-2.73 (m, 1H), 2.65 (s, 3H). | Ms m/z (APCI) [M +H]+ = 352 |

TABLE 2U

| 154 | (structure) | N-[(1S)-2-hydroxy-1-{3-[4-(1-hydroxyethyl)phenyl]-1,2,4-oxadiazol-5-yl}ethyl]benzamide | 1H NMR (CHCl3-d): δ 8.07 (d, 2H, J = 8.1 Hz), 7.89-7.88 (m, 2H), 7.59-7.56 (m, 2H), 7.51-7.48 (m, 4H), 7.18 (d, 1H, J = 7.7 Hz), 5.75-5.72 (m, 1H), 4.98 (qd, 1H, J = 6.4 × (3), 3.9 Hz), 4.33 (ddd, 1H, J = 11.6, 5.0, 3.3 Hz), 4.17 (ddd, 1H, J = 11.6, 7.5, 3.7 Hz), 2.56 (dd, 1H, J = 7.7, 5.1 Hz), 1.86 (d, 1H, J = 3.7 Hz), 1.55 (s, 1H), 1.54 (s, 1H), 1.53 (s, 1H). | Ms m/z (APCI) [M + H]+ = 354.05 | Not provided |
|---|---|---|---|---|---|
| 155 | (structure) | N-[(1S)-2-hydroxy-1-{3-[4-(2-hydroxypropan-2-yl)phenyl]-1,2,4-oxadiazol-5-yl}ethyl]benzamide | 1H NMR (CHCl3-d): δ 7.89 (d, 2H, J = 7.7 Hz), 7.87-7.86 (m, 2H), 7.57-7.53 (m, 3H), 7.47-7.45 (m, 2H), 7.34 (d, 1H, J = 6.6 Hz), 5.69-5.67 (m, 1H), 4.30-4.28 (m, 1H), 4.15-4.13 (m, 1H), 3.13 (br, 1H), 2.12 (br, 1H), 1.59 (s, 6H). | Ms m/z (APCI) [M + H]+ = 368.05 | Not provided |

TABLE 2U-continued

| 156 | | N-[(1S)-2-hydroxy-1-{3-[4-(2-hydroxyethoxy)phenyl]-1,2,4-oxadiazol-5-yl}ethyl]benzamide | 1H NMR (CHCl3-d): δ 8.04-8.01 (m, 2H), 7.88 (dd, 2H, J = 8.1, 1.1 Hz), 7.58-7.55 (m, 1H), 7.51-7.48 (m, 2H), 7.18 (d, 1H, J = 8.4 Hz), 7.03-7.00 (m, 2H), 5.73-5.70 (m, 1H), 4.32 (ddd, 1H, J = 11.4, 5.1, 3.3 Hz), 4.18-4.14 (m, 3H), 4.01 (dt, 2H, J = 6.1, 4.7 Hz), 2.61 (dd, 1H, J = 7.7, 5.1 Hz), 2.01-1.99 (m, 1H). | Ms m/z (APCl) [M + H]+ = 370.05 | Not provided |
| --- | --- | --- | --- | --- | --- |
| 157 | | 6-fluoro-N-[(1S)-2-hydroxy-1-{3-[4-(trifluoromethyl)phenyl]-1,2,4-oxadiazol-5-yl}ethyl]pyridine-3-carboxamide | Not provided | Ms m/z (APCl) [M + H]+ = 397 | Not provided |
| 158 | | N-[(1S)-2-hydroxy-1-(3-{4-[2-(morpholin-4-yl)ethoxy]phenyl}-1,2,4-oxadiazol-5-yl)ethyl]benzamide | 1H NMR (CHCl3-d): δ 8.00-7.98 (m, 2H), 7.88-7.87 (m, 2H), 7.57-7.54 (m, 1H), 7.49-7.46 (m, 2H), 7.24 (br, 1H), 6.99-6.97 (m, 2H), 5.71-5.68 (m, 1H), 4.30 (dd, 1H, J = 11.4, 3.3 Hz), 4.17-4.13 (m, 3H), 3.75-3.73 (m, 4H), 2.83 (t, 2H, J = 5.7 Hz), 2.60-2.59 (m, 4H), 1.65 (br, 1H). | Ms m/z (APCl) [M + H]+ = 439.15 | Not provided |
| 159 | | 4-{5-[(1S)-2-hydroxy-1-(phenylformamido)ethyl]-1,2,3-oxadiazol-3-yl}phenyl N-ethyl-N-methylcarbamate | Not provided | Ms m/z (APCl) [M + H]+ = 411.05 | Not provided |
| 160 | | 4-fluoro-N-[(2S)-1-hydroxy-3-{3-[4-(trifluoromethyl)phenyl]-1,2,4-oxadiazol-5-yl}propan-2-yl]benzamide | Not provided | Ms m/z (APCl) [M + H]+ = 410 | Not provided |

TABLE 2U-continued

| | | | | | |
|---|---|---|---|---|---|
| 161 | 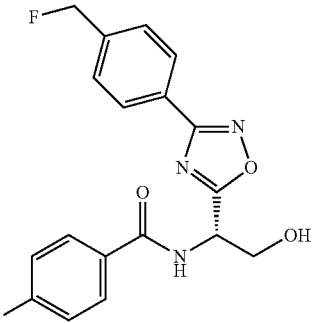 | 4-fluoro-N-[(1S)-1-{3-[4-(fluoromethyl)phenyl]-1,2,4-oxadiazol-5-yl}-2-hydroxyethyl]benzamide | 1H NMR (CHCl3-d): δ 8.11 (d, 2H, J = 7.3 Hz), 7.92-7.89 (m, 2H), 7.49 (d, 2H, J = 7.0 Hz), 7.19-7.15 (m, 2H), 7.14 (d, 1H, J = 8.1 Hz), 5.72 (dt, 1H, J = 8.2, 3.6 Hz), 5.50 (s, 1H), 5.42 (s, 1H), 4.34 (ddd, 1H, J = 11.6, 5.0, 3.3 Hz), 4.17 (ddd, 1H, J = 11.6, 7.5, 3.7 Hz), 2.53 (dd, 1H, J = 7.3, 4.8 Hz). | Ms m/z (APCl) [M + H]+ = 360 | Not provided |

TABLE 2V

| | | | | | |
|---|---|---|---|---|---|
| 162 | 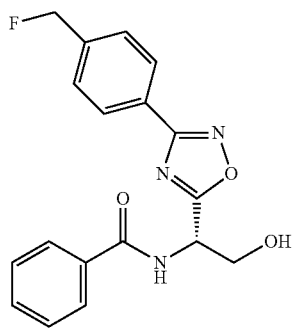 [SMILES: O=C(N[C@@H](CO)c1nc(-c2ccc(CF)cc2)no1)c1ccccc1] | N-[(1S)-1-{3-[4-(fluoromethyl)phenyl]-1,2,4-oxadiazol-5-yl}-2-hydroxyethyl]benzamide | 1H NMR (CHCl3-d): δ 8.12 (d, 2H, J = 7.7 Hz), 7.90-7.88 (m, 2H), 7.59-7.56 (m, 1H), 7.51-7.49 (m, 4H), 7.19 (d, 1H, J = 8.4 Hz), 5.74 (dt, 1H, J = 8.1, 3.5 Hz), 5.50 (s, 1H), 5.42 (s, 1H), 4.34 (ddd, 1H, J = 11.6, 5.0, 3.3 Hz), 4.18 (ddd, 1H, J = 11.4, 7.5, 3.9 Hz), 2.54 (dd, 1H, J = 7.5, 5.0 Hz). | Ms m/z (APCl) [M + H]+ = 360 | Not provided |
| 163 | 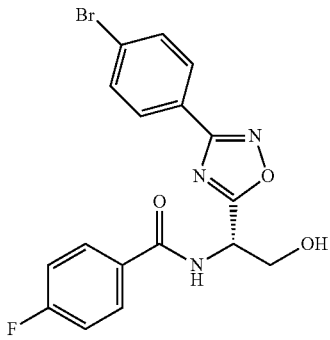 [SMILES: O=C(N[C@@H](CO)c1nc(-c2ccc(Br)cc2)no1)c1ccc(F)cc1] | N-[(1S)-1-[3-(4-bromophenyl)-1,2,4-oxadiazol-5-yl]-2-hydroxyethyl]-4-fluorobenzamide | 1H NMR (CHCl3-d): δ 7.95-7.93 (m, 4H), 7.64-7.61 (m, 4H), 5.58 (d, 1H, J = 5.5 Hz), 5.19 (br, 1H), 4.17 (br, 1H), 4.06 (dd, 1H, J = 11.4, 4.0 Hz), 2.47 (br, 1H). | Ms m/z (APCl) [M + H]+ = 405.9 | Not provided |
| 164 | 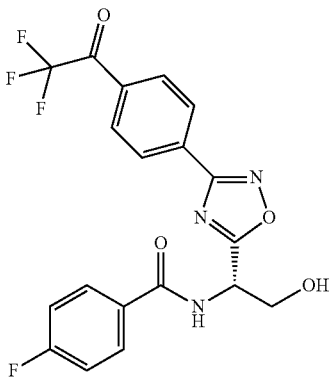 [SMILES: O=C(N[C@@H](CO)c1nc(-c2ccc(C(=O)C(F)(F)F)cc2)no1)c1ccc(F)cc1] | 4-fluoro-N-[(1S)-2-hydroxy-1-{3-[4-(2,2,2-trifluoroacetyl)phenyl]-1,2,4-oxadiazol-5-yl}ethyl]benzamide | 1H NMR (CHCl3-d): δ 8.13-8.10 (m, 2H), 7.92-7.88 (m, 2H), 7.73 (d, 1H, J = 8.2 Hz), 7.19-7.13 (m, 3H), 5.72 (dt, 1H, J = 8.0, 3.5 Hz), 4.16 (ddd, 1H, J = 11.4, 7.4, 3.8 Hz), 2.53 (dd, 1H, J = 7.4, 5.1 Hz). | Ms m/z (APCl) [M + H + C2H6O]+ = 470 | Not provided |

| | | | | | |
|---|---|---|---|---|---|
| 165 | | N-[(1S)-2-hydroxy-1-{3-[4-(2,2,2-trifluoroacetyl)phenyl]-1,2,4-oxadiazol-5-yl}ethyl]benzamide | 1H NMR (CHCl3-d): δ 8.12-8.10 (m, 2H), 7.89-7.87 (m, 2H), 7.72 (d, 1H, J = 8.5 Hz), 7.58-7.55 (m, 1H), 7.50-7.47 (m, 2H), 7.22 (d, 1H, J = 8.2 Hz), 5.73 (dt, 1H, J = 8.0, 3.6 Hz), 4.34-4.31 (m, 1H), 4.19-4.16 (m, 1H), 2.66 (br, 1H). | Ms m/z (APCI) [M + H + C2H6O]+ = 452 | Not provided |
| 166 | | N-[(1S)-1-{3-[4-(difluoromethyl)phenyl]-1,2,4-oxadiazol-5-yl}-2-hydroxyethyl]-4-fluorobenzamide | 1H NMR (CHCl3-d): δ 8.17 (d, 2H, J = 8.8 Hz), 7.92-7.88 (m, 2H), 7.63 (d, 2H, J = 7.9 Hz), 7.19-7.14 (m, 3H), 6.70 (t, 1H, JHF = 69.0 Hz), 5.71 (dt, 1H, J = 8.0, 3.6 Hz), 4.36-4.32 (m, 1H), 4.18 (ddd, 1H, J = 11.4, 7.3, 4.0 Hz), 2.62 (dd, 1H, J = 7.2, 5.2 Hz). | Ms m/z (APCI) [M + H]+ = 378 | Not provided |
| 167 | | 4-chloro-N-[(1S)-1-{3-[4-(difluoromethyl)phenyl]-1,2,4-oxadiazol-5-yl}-2-hydroxyethyl]benzamide | 1H NMR (CHCl3-d): δ 8.17 (d, 2H, J = 8.4 Hz), 7.84-7.81 (m, 2H), 7.64 (d, 2H, J = 8.4 Hz), 7.48-7.46 (m, 2H), 7.14 (d, 1H, J = 8.1 Hz), 6.71 (t, 1H, JHF = 57.0 Hz), 5.72 (dt, 1H, J = 8.1, 3.5 Hz), 4.35 (ddd, 1H, J = 11.6, 5.0, 3.3 Hz), 4.17 (ddd, 1H, J = 11.4, 7.3, 3.7 Hz), 2.47-2.44 (m, 1H). | Ms m/z (APCI) [M + H]+ = 394 | Not provided |
| 168 | | N-[(1S)-1-{3-[4-(difluoromethyl)phenyl]-1,2,4-oxadiazol-5-yl}-2-hydroxyethyl]benzamide | 1H NMR (CHCl3-d): δ 8.18 (d, 2H, J = 8.5 Hz), 7.90-7.87 (m, 2H), 7.63 (d, 2H, J = 8.2 Hz), 7.59-7.55 (m, 1H), 7.51-7.47 (m, 2H), 7.21 (d, 1H, J = 7.9 Hz), 6.70 (t, 1H, JHF = 69.0 Hz), 5.74 (dt, 1H, J = 8.0, 3.6 Hz), 4.34 (ddd, 1H, J = 11.4, 5.0, 3.4 Hz), 4.18 (ddd, 1H, J = 11.3, 7.4, 4.0 Hz), 2.61-2.58 (m, 1H). | Ms m/z (APCI) [M + H]+ = 360.05 | Not provided |

TABLE 2V-continued

| | | | | | |
|---|---|---|---|---|---|
| 169 | 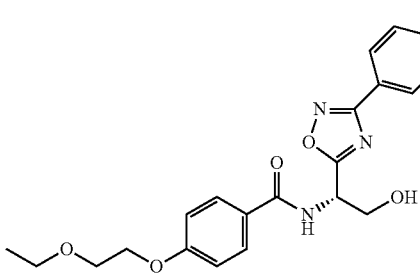 | 4-(2-ethoxyethoxy)-N-[(1S)-2-hydroxy-1-{3-[4-(trifluoromethoxy)phenyl]-1,2,4-oxadiazol-5-yl}ethyl]benzamide | Not provided | Ms m/z (APCI) [M + H]+ = 482.05 | Not provided |

TABLE 2W

| | | | | | |
|---|---|---|---|---|---|
| 170 | | 4-(2-ethoxyethoxy)-N-[(1S)-2-hydroxy-1-{3-[2-(trifluoromethyl)phenyl]-1,2,4-oxadiazol-5-yl}ethyl]benzamide | Not provided | Ms m/z (APCI) [M + H]+ = 466.05 | Not provided |
| 171 | | 4-[2-(diethylamino)ethoxy]-N-[(1S)-2-hydroxy-1-{3-[4-(trifluoromethoxy)phenyl]-1,2,4-oxadiazol-5-yl}ethyl]benzamide | 1H NMR (CHCl3-d): δ 8.12-8.09 (m, 2H), 7.83 (d, 2H, J = 8.7 Hz), 7.31 (d, 2H, J = 8.7 Hz), 7.27-7.26 (m, 1H), 6.94 (d, 2H, J = 8.7 Hz), 5.68-5.65 (m, 1H), 4.28 (dd, 1H, J = 11.3, 3.6 Hz), 4.13 (dd, 1H, J = 11.3, 3.8 Hz), 4.10 (t, 2H, J = 6.2 Hz), 2.33 (q + br, 5H, J = 7.2 Hz), 1.08 (t, 6H, J = 7.1 Hz). | Ms m/z (APCI) [M + H]+ = 509.1 | Not provided |
| 172 | 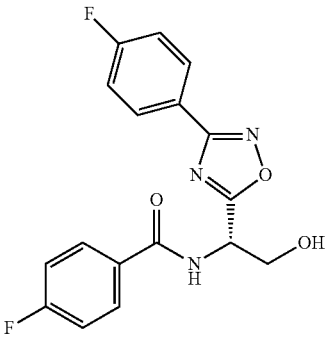 [SMILES: O=C(N[C@@H](CO)c1nc(-c2ccc(F)cc2)no1)c1ccc(F)cc1] | 4-fluoro-N-[(1S)-1-[3-(4-fluorophenyl)-1,2,4-oxadiazol-5-yl]-2-hydroxyethyl]benzamide | Not provided | Ms m/z (APCI) [M + H]+ = 346 | Not provided |

TABLE 2W-continued

| | | | | | |
|---|---|---|---|---|---|
| 173 | | 4-fluoro-N-[(1S)-2-hydroxy-1-[3-(quinolin-3-yl)-1,2,4-oxadiazol-5-yl]ethyl]benzamide | Not provided | Ms m/z (APCl) [M + H]+ = 379 | Not provided |
| 174 | | N-{3-[4-(trifluoromethyl)phenyl]-1,2,4-oxadiazol-5-yl}benzamide | Not provided | Ms m/z (APCl) [M + H]+ = 334 | Not provided |
| 145 | | 4-fluoro-N-[(1S)-2-hydroxy-1-[3-(1H-indol-5-yl)-1,2,4-oxadiazol-5-yl]ethyl]benzamide | Not provided | Ms m/z (APCl) [M + H]+ = 367 | Not provided |
| 176 | | 4-fluoro-N-[(1S)-2-hydroxy-1-{3-[3-(trifluoromethyl)phenyl]-1,2,4-oxadiazol-5-yl}ethyl]benzamide | 1H NMR (CHCl3-d): δ 8.33 (s, 1H), 8.26 (d, 1H, J = 7.7 Hz), 7.91-7.89 (m, 2H), 7.79-7.77 (m, 1H), 7.63 (t, 1H, J = 7.9 Hz), 7.18-7.15 (m, 3H), 5.73-5.70 (m, 1H), 4.36-4.33 (m, 1H), 4.17 (ddd, 1H, J = 11.3, 7.2, 3.9 Hz), 2.60 (t, 1H, J = 6.1 Hz). | Ms m/z (APCl) [M + H]+ = 396.05 | Not provided |
| 177 | | N-[(1S)-2-hydroxy-1-{3-[3-(trifluoromethyl)phenyl]-1,2,4-oxadiazol-5-yl}ethyl]benzamide | 1H NMR (CHCl3-d): δ 8.35 (s, 1H), 8.27 (d, 1H, J = 7.7 Hz), 7.89-7.88 (m, 2H), 7.78 (d, 1H, J = 7.7 Hz), 7.63 (t, 1H, J = 7.7 Hz), 7.59-7.56 (m, 1H), 7.51-7.48 (m, 2H), 7.21 (d, 1H, J = 8.1 Hz), 5.75-5.73 (m, 1H), 4.36-4.33 (m, 1H), 4.18 (ddd, 1H, J = 11.4, 7.2, 3.9 Hz), 2.57 (dd, 1H, J = 7.0, 5.1 Hz). | Ms m/z (APCl) [M + H]+ = 378 | Not provided |

TABLE 2X

| | | | | | |
|---|---|---|---|---|---|
| 178 | 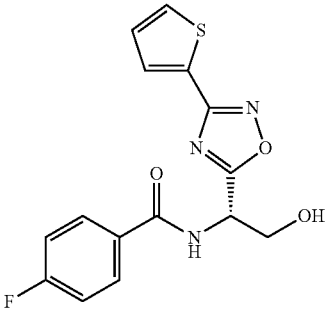 [SMILES: O=C(N[C@@H](CO)c1nc(-c2cccs2)no1)c1ccc(F)cc1] | 4-fluoro-N-[(1S)-2-hydroxy-1-[3-(thiophen-2-yl)-1,2,4-oxadiazol-5-yl]ethyl]benzamide | Not provided | Ms m/z (APCl) [M + H]+ = 334 | Not provided |
| 179 | 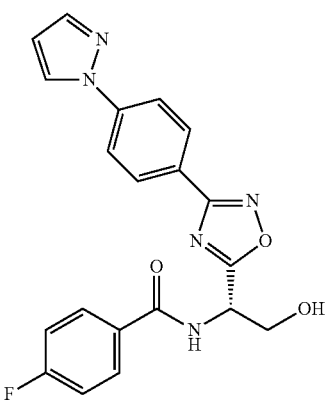 [SMILES: O=C(N[C@@H](CO)c1nc(-c2ccc(-n3cccn3)cc2)no1)c1ccc(F)cc1] | 4-fluoro-N-[(1S)-2-hydroxy-1-{3-[4-(1H-pyrazol-1-yl)phenyl]-1,2,4-oxadiazol-5-yl}ethyl]benzamide | 1H NMR (CHCl3-d): δ 8.20-8.17 (m, 2H), 8.02-8.01 (m, 1H), 7.93-7.90 (m, 2H), 7.86-7.84 (m, 2H), 7.77 {d, 1H, J = 1.7 Hz), 7.19-7.16 (m, 2H), 7.12 (d, 1H, J = 7.9 Hz), 6.52 (dd, 1H, J = 2.4, 1.8 Hz), 5.72 (dt, 1H, J = 8.0, 3.5 Hz), 4.35 (ddd, 1H, J = 11.5, 5.0, 3.4 Hz), 4.18 (ddd, 1H, J = 11.5, 7.5, 3.7 Hz), 2.47 (dd, 1H, J = 7.5, 5.0 Hz). | Ms m/z (APCl) [M + H]+ = 394.1 | Not provided |
| 180 | 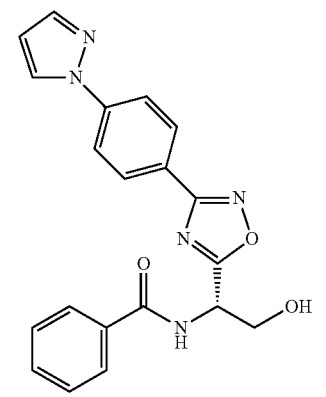 [SMILES: O=C(N[C@@H](CO)c1nc(-c2ccc(-n3cccn3)cc2)no1)c1ccccc1] | N-[(1S)-2-hydroxy-1-{3-[4-(1H)-pyrazol-1-yl)phenyl]-1,2,4-oxadiazol-5-yl}ethyl]benzamide | 1H NMR (CHCl3-d): δ 8.18 (d, 2H, J = 8.5 Hz), 8.01 (d, 1H, J = 2.3 Hz), 7.89 (d, 2H, J = 7.4 Hz), 7.85 (d, 2H, J = 8.5 Hz), 7.77 (s, 1H), 7.59-7.56 (m, 1H), 7.52-7.48 (m, 2H), 7.18 (d, 1H, J = 8.2 Hz), 7.52 (m, 1H), 5.74 (dt, 1H, J = 7.8, 3.5 Hz), 4.37-4.33 (m, 1H), 4.18 (ddd, 1H, J = 11.5, 7.4, 3.8 Hz), 2.53 (dd, 1H, J = 7.5, 5.2 Hz). | Ms m/z (APCl) [M + H]+ = 376.05 | Not provided |
| 181 | 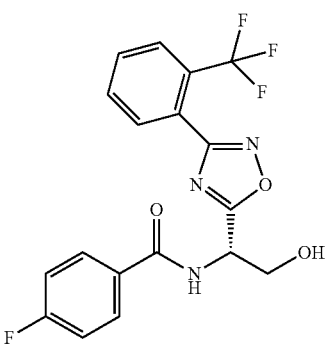 [SMILES: O=C(N[C@@H](CO)c1nc(-c2ccccc2C(F)(F)F)no1)c1ccc(F)cc1] | 4-fluoro-N-[(1S)-2-hydroxy-1-{3-[2-(trifluoromethyl)phenyl]-1,2,4-oxadiazol-5-yl}ethyl]benzamide | 1H NMR (CHCl3-d): δ 7.89-7.84 (m, 3H), 7.82-7.80 (m, 1H), 7.69-7.64 (m, 2H), 7.21 (d, 1H, J = 8.5 Hz), 7.15-7.10 (m, 2H), 5.72 (dt, 1H, J = 8.1, 3.6 Hz), 4.32 (dd, 1H, J = 11.6, 3.4 Hz), 4.14 (dd, 1H, J = 11.6, 3.7 Hz), 2.83 (br, 1H). | Ms m/z (APCl) [M + H]+ = 395.9 | Not provided |

TABLE 2X-continued

| | | | | | |
|---|---|---|---|---|---|
| 182 | | N-(2-hydroxy-1-{3-[4-(trifluoromethyl)phenyl]-1,2,4-oxadiazol-5-yl}ethyl)-1H-indole-2-carboxamide | Not provided | Ms m/z (APCl) [M + H]+ = 417 | Not provided |
| 183 | | N-(2-hydroxy-1-{3-[4-(trifluoromethyl)phenyl]-1,2,4-oxadiazol-5-yl}ethyl)-1H-indole-5-carboxamide | Not provided | Ms m/z (APCl) [M + H]+ = 417 | Not provided |
| 184 | | N-(2-hydroxy-1-{3-[4-(trifluoromethyl)phenyl]-1,2,4-oxadiazol-5-yl}ethyl)-1H-indole-7-carboxamide | Not provided | Ms m/z (APCl) [M + H]+ = 417 | Not provided |
| 185 | | N-(2-hydroxy-1-{3-[4-(trifluoromethyl)phenyl]-1,2,4-oxadiazol-5-yl}ethyl)-2-(1H-indol-3-yl)acetamide | Not provided | Ms m/z (APCl) [M + H]+ = 431 | Not provided |

TABLE 2Y

| | | | | | |
|---|---|---|---|---|---|
| 186 | | N-(2-hydroxy-1-{3-[4-(trifluoromethyl)phenyl]-1,2,4-oxadiazol-5-yl}ethyl)-1H-indazole-3-carboxamide | Not provided | Ms m/z (APCl) [M + H]+ = 418 | Not provided |

TABLE 2Y-continued

| | | | | | |
|---|---|---|---|---|---|
| 187 | (structure) | 2-(4-fluorophenyl)-N-(2-hydroxy-1-{3-[4-(trifluoromethyl)phenyl]-1,2,4-oxadiazol-5-yl}ethyl)acetamide | Not provided | Ms m/z (APCl) [M + H]+ = 410 | Not provided |
| 188 | (structure) | N-(2-hydroxy-1-{3-[4-(trifluoromethyl)phenyl]-1,2,4-oxadiazol-5-yl}ethyl)-4-(trifluoromethyl)benzamide | Not provided | Ms m/z (APCl) [M + H]+ = 446 | Not provided |
| 189 | (structure) | N-[(1S)-2-hydroxy-1-{3-[2-(trifluoromethyl)phenyl]-1,2,4-oxadiazol-5-yl}ethyl]benzamide | 1H NMR (CHCl3-d): δ 7.87-7.84 (m, 3H), 7.83-7.81 (m, 1H), 7.70-7.65 (m, 2H), 7.56-7.53 (m, 1H), 7.48-7.45 (m, 2H), 7.22 (br, 1H) 5.76-5.73 (m, 1H), 4.33-4.30 (m, 1H), 4.16-4.14 (m, 1H), 2.75 (br, 1H). | Ms m/z (APCl) [M + H]+ = 377.95 | Not provided |
| 190 | (structure) | 4-fluoro-N-[(1S)-1-{3-[4-(3-fluorooxetan-3-yl)phenyl]-1,2,4-oxadiazol-5-yl}-2-hydroxyethyl]benzamide | Not provided | Ms m/z (APCl) [M + H]+ = 402 | Not provided |

TABLE 2Y-continued

| | | | | | |
|---|---|---|---|---|---|
| 191 | 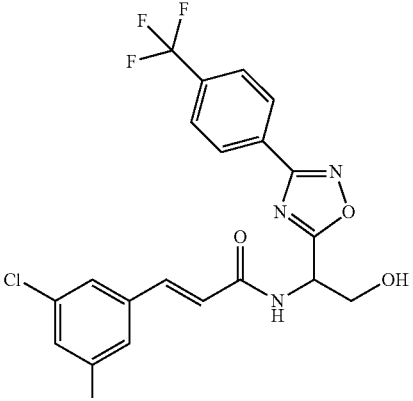 | (2E)-3-(3,5-dichlorophenyl)-N-(2-hydroxy-1-{3-[4-(trifluoromethyl)phenyl]-1,2,4-oxadiazol-5-yl}ethyl)prop-2-enamide | Not provided | Ms m/z (APCI) [M + H]+ = 472 | Not provided |
| 192 | 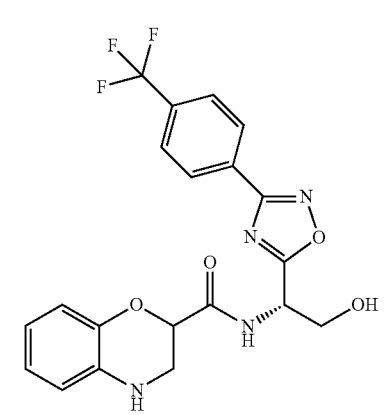 [SMILES: O=C(N[C@@H](CO)c1nc(-c2ccc(C(F)(F)F)cc2)no1)C1CNc2ccccc2O1] | N-[(1S)-2-hydroxy-1-{3-[4-(trifluoromethyl)phenyl]-1,2,4-oxadiazol-5-yl}ethyl]-3,4-dihydro-2H-1,4-benzoxazine-2-carboxamide | Not provided | Ms m/z (APCI) [M + H]+ = 435 | Not provided |
| 193 | 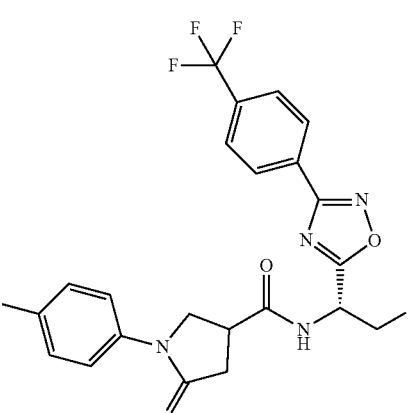 | 1-(4-chlorophenyl)-N-[(1S)-2-hydroxy-1-{3-[4-(trifluoromethyl)phenyl]-1,2,4-oxadiazol-5-yl}ethyl]-5-oxopyrrolidine-3-carboxamide | Not provided | Ms m/z (APCI) [M + H]+ = 495 | Not provided |

TABLE 2Z

| | | | | | |
|---|---|---|---|---|---|
| 194 | 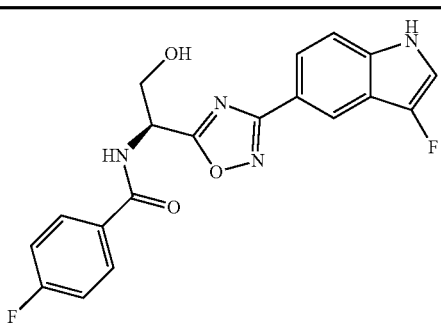 | 4-fluoro-N-[(1S)-1-[3-(3-fluoro-1H-indol-5-yl)-1,2,4-oxadiazol-5-yl]-2-hydroxyethyl]benzamide | Not provided | Ms m/z (APCI) [M + H]+ = 385 | Not provided |

TABLE 2Z-continued

| | | | | | |
|---|---|---|---|---|---|
| 195 | (structure) | 3-chloro-4-fluoro-N-[(1S)-2-hydroxy-1-{3-[4-(trifluoromethyl)phenyl]-1,2,4-oxadiazol-5-yl}ethyl]benzamide | Not provided | Ms m/z (APCl) [M + H]+ = 430 | Not provided |
| 196 | (structure) | 3,5-difluoro-N-[(1S)-2-hydroxy-1-{3-[4-(trifluoromethyl)phenyl]-1,2,4-oxadiazol-5-yl}ethyl]benzamide | Not provided | Ms m/z (APCl) [M + H]+ = 414 | Not provided |
| 197 | (structure) | 2,6-difluoro-N-[(1S)-2-hydroxy-1-{3-[4-(trifluoromethyl)phenyl]-1,2,4-oxadiazol-5-yl}ethyl]benzamide | Not provided | Ms m/z (APCl) [M + H]+ = 414 | Not provided |
| 198 | (structure) | 5-chloro-N-[(1S)-2-hydroxy-1-{3-[4-(trifluoromethyl)phenyl]-1,2,4-oxadiazol-5-yl}ethyl]thiophene-2-carboxamide | Not provided | Ms m/z (APCl) [M + H]+ = 418 | Not provided |

TABLE 2Z-continued

| | | | | | |
|---|---|---|---|---|---|
| 199 | 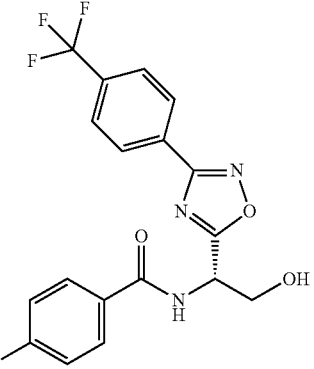 | N-[(1S)-2-hydroxy-1-{3-[4-(trifluoromethyl)phenyl]-1,2,4-oxadiazol-5-yl}ethyl]-4-(trifluoromethoxy)benzamide | Not provided | Ms m/z (APCl) [M + H]+ = 462 | Not provided |
| 200 | 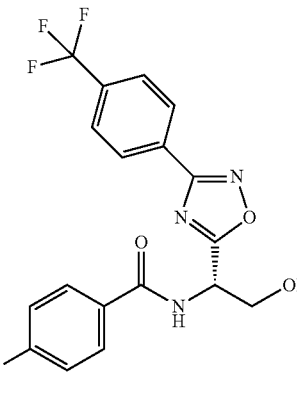 | N-[(1S)-2-hydroxy-1-{3-[4-(trifluoromethyl)phenyl]-1,2,4-oxadiazol-5-yl}ethyl]-4-(morpholin-4-yl)benzamide | Not provided | Ms m/z (APCl) [M + H]+ = 463 | Not provided |
| 201 | 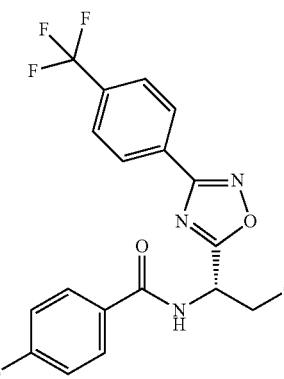 | N-[(1S)-2-hydroxy-1-{3-[4-(trifluoromethyl)phenyl]-1,2,4-oxadiazol-5-yl}ethyl]-4-phenoxybenzamide | Not provided | Ms m/z (APCl) [M + H]+ = 470 | Not provided |

TABLE 2AA

| # | Structure | Name | | MS | |
|---|---|---|---|---|---|
| 202 | 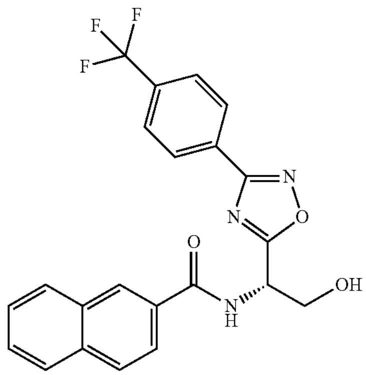 [SMILES: O=C(N[C@@H](CO)c1nc(-c2ccc(C(F)(F)F)cc2)no1)c1ccc2ccccc2c1] | N-[(1S)-2-hydroxy-1-{3-[4-(trifluoromethyl)phenyl]-1,2,4-oxadiazol-5-yl}ethyl]naphthalene-2-carboxamide | Not provided | Ms m/z (APCl) [M + H]+ = 428 | Not provided |
| 203 | 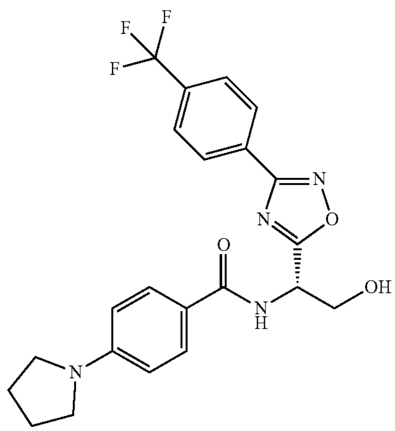 [SMILES: O=C(N[C@@H](CO)c1nc(-c2ccc(C(F)(F)F)cc2)no1)c1ccc(N2CCCC2)cc1] | N-[(1S)-2-hydroxy-1-{3-[4-(trifluoromethyl)phenyl]-1,2,4-oxadiazol-5-yl}ethyl]-4-(pyrrolidin-1-yl)benzamide | Not provided | Ms m/z (APCl) [M + H]+ = 447 | Not provided |
| 204 | 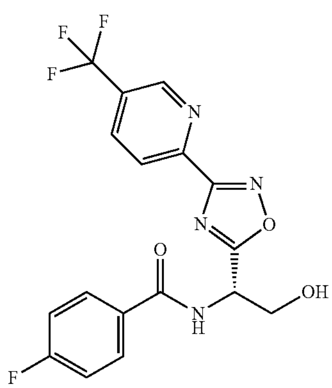 | 4-fluoro-N-[(1S)-2-hydroxy-1-{3-[5-(trifluoromethyl)pyridin-2-yl]-1,2,4-oxadiazol-5-yl}ethyl]benzamide | Not provided | Ms m/z (APCl) [M + H]+ = 396.9 | Not provided |
| 205 | 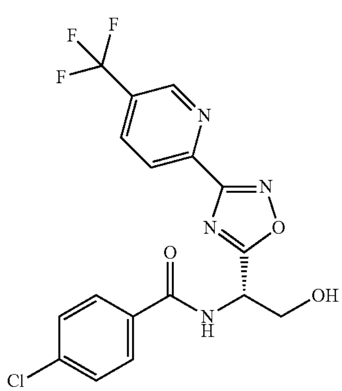 [SMILES: O=C(N[C@@H](CO)c1nc(-c2ccc(C(F)(F)F)cn2)no1)c1ccc(Cl)cc1] | 4-chloro-N-[(1S)-2-hydroxy-1-{3-[5-(trifluoromethyl)pyridin-2-yl]-1,2,4-oxadiazol-5-yl}ethyl]benzamide | Not provided | Ms m/z (APCl) [M + H]+ = 412.9 | Not provided |

TABLE 2AA-continued

| | | | | | |
|---|---|---|---|---|---|
| 206 | 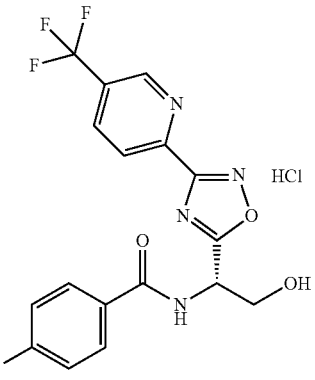 | 4-fluoro-N-[(1S)-2-hydroxy-1-{3-[5-(trifluoromethyl)pyridin-2-yl]-1,2,4-oxadiazol-5-yl}ethyl]benzamide hydrochloride | Not provided | Ms m/z (APCl) [M + H]+ = 396.9 | Not provided |
| 207 | 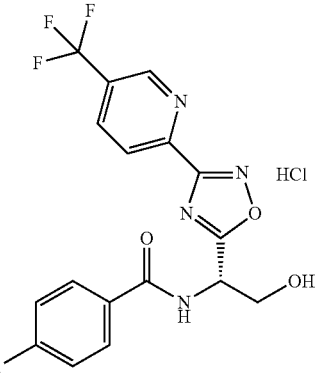 | 4-chloro-N-[(1S)-2-hydroxy-1-{3-[5-(trifluoromethyl)pyridin-2-yl]-1,2,4-oxadiazol-5-yl}ethyl]benzamide hydrochloride | Not provided | Ms m/z (APCl) [M + H]+ = 412.9 | Not provided |
| 208 | 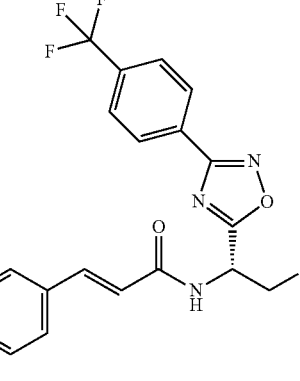 | (2E)-3-(4-fluorophenyl)-N-[(1S)-2-hydroxy-1-{3-[4-(trifluoromethyl)phenyl]-1,2,4-oxadiazol-5-yl}ethyl]prop-2-enamide | Not provided | Ms m/z (APCl) [M + H]+ = 522 | Not provided |
| 209 | 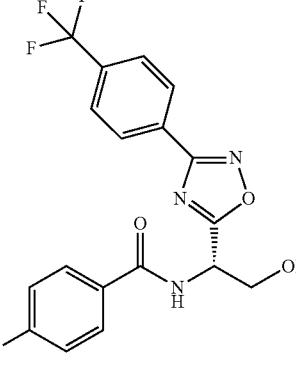 | 4-(dimethylamino)-N-[(1S)-2-hydroxy-1-{3-[4-(trifluoromethyl)phenyl]-1,2,4-oxadiazol-5-yl}ethyl]benzamide | Not provided | Ms m/z (APCl) [M + H]+ = 521 | Not provided |

TABLE 2AB

| | | | | | |
|---|---|---|---|---|---|
| 210 | 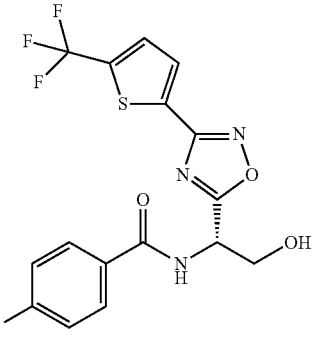 | 4-fluoro-N-[(1S)-2-hydroxy-1-{3-[5-(trifluoromethyl)thiophen-2-yl]-1,2,4-oxadiazol-5-yl}ethyl]benzamide | Not provided | Ms m/z (APCl) [M + H]+ = 401.85 | Not provided |
| 211 | 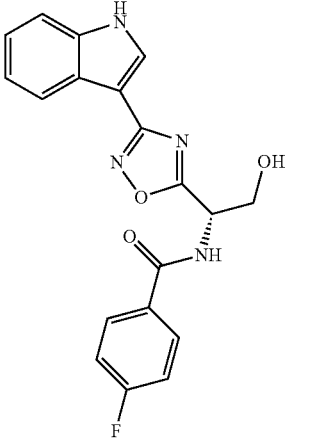 [SMILES: O=C(N[C@@H](CO)c1nc(-c2c[nH]c3ccccc23)no1)c1ccc(F)cc1] | 4-fluoro-N-[(1S)-2-hydroxy-1-[3-(1H-indol-3-yl)-1,2,4-oxadiazol-5-yl]ethyl]benzamide | Not provided | Ms m/z (APCl) [M + H]+ = 367 | Not provided |
| 212 | 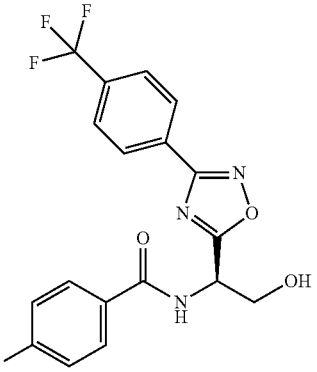 | 4-fluoro-N-[(1R)-2-hydroxy-1-{3-[4-(trifluoromethyl)phenyl]-1,2,4-oxadiazol-5-yl}ethyl]benzamide | 1H NMR (CHCl3-d): δ 8.21 (d, 2H, J = 8.1 Hz), 7.91-7.89 (m, 2H), 7.76 (d, 2H, J = 8.1 Hz), 7.19-7.16 (m, 2H), 7.12 (d, 1H, J = 8.1 Hz), 5.73 (dt, 1H, J = 8.2, 3.6 Hz), 4.36 (ddd, 1H, J = 11.5, 5.0, 3.3 Hz), 4.18 (ddd, 1H, J = 11.4, 7.3, 4.0 Hz), 2.43 (dd, 1H, J = 7.2, 5.0 Hz). | Ms m/z (APCl) [M + H]+ = 395.9 | Not provided |
| 213 | 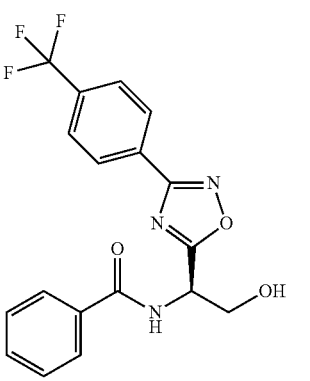 [SMILES: O=C(N[C@H](CO)c1nc(-c2ccc(C(F)(F)F)cc2)no1)c1ccccc1] | N-[(1R)-2-hydroxy-1-{3-[4-(trifluoromethyl)phenyl]-1,2,4-oxadiazol-5-yl}ethyl]benzamide | 1H NMR (CHCl3-d): δ 8.21-8.19 (m, 2H), 7.88-7.87 (m, 2H), 7.74 (d, 2H, J = 8.1 Hz), 7.58-7.55 (m, 1H), 7.50-7.47 (m, 2H), 7.22 (d, 1H, J = 8.1 Hz), 5.74-5.72 (m, 1H), 4.34 (ddd, 1H, J = 11.6, 5.0, 3.3 Hz), 4.18 (ddd, 1H, J = 11.4, 7.3, 4.0 Hz), 2.63 (dd, 1H, J = 7.0, 5.1 Hz). | Ms m/z (APCl) [M + H]+ = 377.9 | Not provided |

TABLE 2AB-continued

| # | Structure | Name | 1H NMR | MS | Other |
|---|---|---|---|---|---|
| 214 | 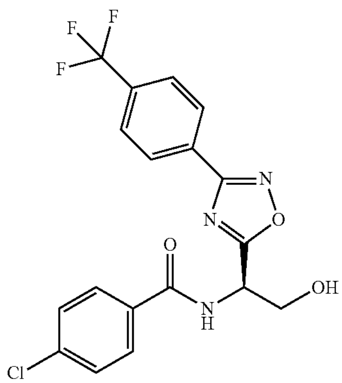 [SMILES: O=C(N[C@H](CO)c1nc(-c2ccc(C(F)(F)F)cc2)no1)c1ccc(Cl)cc1] | 4-chloro-N-[(1R)-2-hydroxy-1-{3-[4-(trifluoromethyl)phenyl]-1,2,4-oxadiazol-5-yl}ethyl]benzamide | 1H NMR (CHCl3-d): δ 8.20-8.19 (m, 2H), 7.83-7.80 (m, 2H), 7.75 (d, 2H, J = 8.4 Hz), 7.47-7.45 (m, 2H), 7.17 (d, 1H, J = 8.1 Hz), 5.71 (dt, 1H, J = 8.1, 3.5 Hz), 4.35 (ddd, 1H, J = 11.6, 5.0, 2.9 Hz), 4.18 (ddd, 1H, J = 11.5, 7.2, 3.7 Hz), 2.54 (dd, 1H, J = 7.3, 5.1 Hz). | Ms m/z (APCI) [M + H]+ = 411.9 | Not provided |
| 215 | 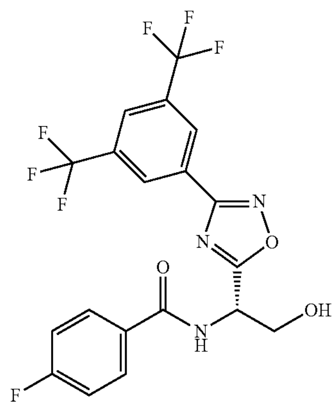 [SMILES: O=C(N[C@@H](CO)c1nc(-c2cc(C(F)(F)F)cc(C(F)(F)F)c2)no1)c1ccc(F)cc1] | N-[(1S)-1-{3-[3,5-bis(trifluoromethyl)phenyl]-1,2,4-oxadiazol-5-yl}-2-hydroxyethyl]-4-fluorobenzamide | Not provided | Ms m/z (APCI) [M + H]+ = 464 | Not provided |
| 216 | 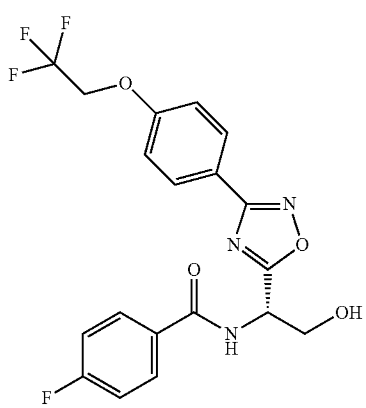 [SMILES: O=C(N[C@@H](CO)c1nc(-c2ccc(OCC(F)(F)F)cc2)no1)c1ccc(F)cc1] | 4-fluoro-N-[(1S)-2-hydroxy-1-{3-[4-(2,2,2-trifluoroethoxy)phenyl]-1,2,4-oxadiazol-5-yl}ethyl]benzamide | Not provided | Ms m/z (APCI) [M + H]+ = 426 | Not provided |
| 217 | 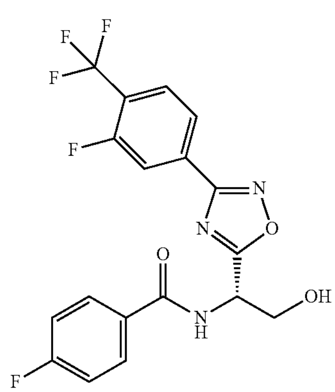 [SMILES: O=C(N[C@@H](CO)c1nc(-c2ccc(C(F)(F)F)c(F)c2)no1)c1ccc(F)cc1] | 4-fluoro-N-[(1S)-1-{3-[3-fluoro-4-(trifluoromethyl)phenyl]-1,2,4-oxadiazol-5-yl}-2-hydroxyethyl]benzamide | Not provided | Ms m/z (APCI) [M + H]+ = 414 | Not provided |

TABLE 2AC

| | | | | | | |
|---|---|---|---|---|---|---|
| 218 | 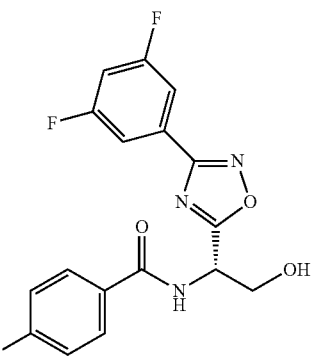 | N-[(1S)-1-[3-[3,5-difluorophenyl)-1,2,4-oxadiazol-5-yl]-2-hydroxyethyl]-4-fluorobenzamide | Not provided | Ms m/z (APCl) [M + H]+ = 364 | Not provided |
| 219 | 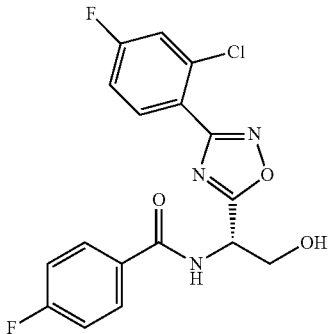 [SMILES: O=C(N[C@@H](CO)c1nc(-c2ccc(F)cc2Cl)no1)c1ccc(F)cc1] | N-[(1S)-1-[3-(2-chloro-4-fluorophenyl)-1,2,4-oxadiazol-5-yl]-2-hydroxyethyl]-4-fluorobenzamide | Not provided | Ms m/z (APCl) [M + H]+ = 380 | Not provided |
| 220 | 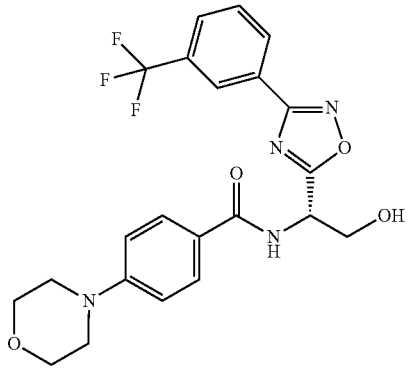 [SMILES: O=C(N[C@@H](CO)c1nc(-c2cccc(C(F)(F)F)c2)no1)c1ccc(N2CCOCC2)cc1] | N-[(1S)-1-hydroxy-1-{3-[3-(trifluoromethyl)phenyl]-1,2,4-oxadiazol-5-yl}ethyl]-4-(morpholin-4-yl)benzamide | Not provided | Ms m/z (APCl) [M + H]+ = 463 | Not provided |
| 221 | 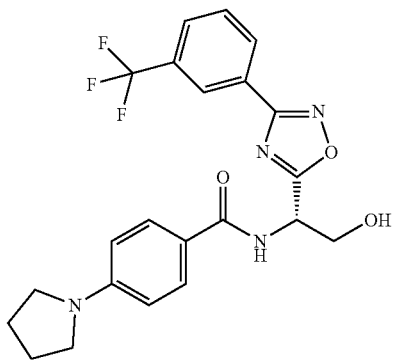 [SMILES: O=C(N[C@@H](CO)c1nc(-c2cccc(C(F)(F)F)c2)no1)c1ccc(N2CCCC2)cc1] | N-[(1S)-2-hydroxy-1-{3-[3-(trifluoromethyl)phenyl]-1,2,4-oxadiazol-5-yl}ethyl]-4-(pyrrolidin-1-yl)benzamide | Not provided | Ms m/z (APCl) [M + H]+ = 447 | Not provided |

TABLE 2AC-continued

| | | | | | |
|---|---|---|---|---|---|
| 222 | 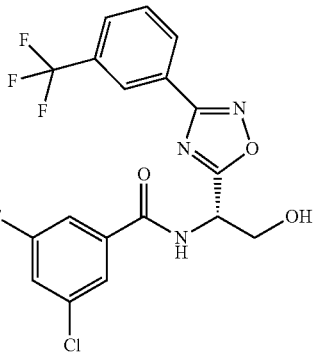 | 3-chloro-5-fluoro-N-[(1S)-2-hydroxy-1-{3-[3-(trifluoromethyl)phenyl]-1,2,4-oxadiazol-5-yl}ethyl]benzamide | Not provided | Ms m/z (APCl) [M + H]+ = 430 | Not provided |
| 223 | 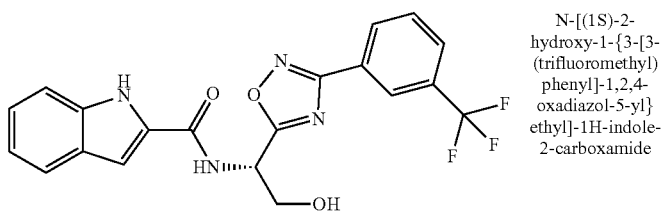 | N-[(1S)-2-hydroxy-1-{3-[3-(trifluoromethyl)phenyl]-1,2,4-oxadiazol-5-yl}ethyl]-1H-indole-2-carboxamide | Not provided | Ms m/z (APCl) [M + H]+ = 417 | Not provided |
| 224 | 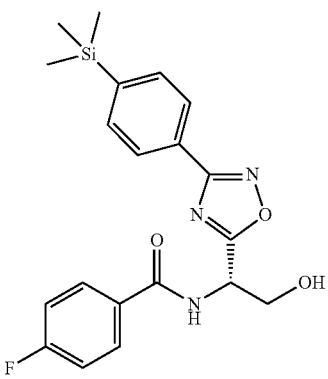 [SMILES: C[Si](C)(C)c1ccc(-c2noc([C@H](CO)NC(=O)c3ccc(F)cc3)n2)cc1] | 4-fluoro-N-[(1S)-2-hydroxy-1-{3-[4-(trimethylsilyl)phenyl]-1,2,4-oxadiazol-5-yl}ethyl]benzamide | Not provided | Ms m/z (APCl) [M + H]+ = 400 | Not provided |
| 225 | 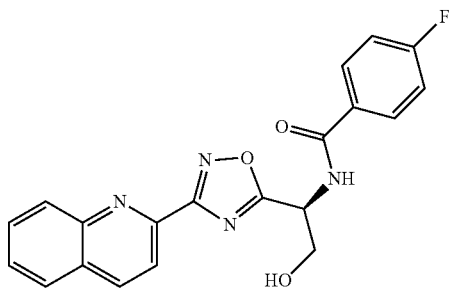 [SMILES: O=C(N[C@@H](CO)c1nc(-c2ccc3ccccc3n2)no1)c1ccc(F)cc1] | 4-fluoro-N-[(1S)-2-hydroxy-1-[3-(quinolin-2-yl)-1,2,4-oxadiazol-5-yl]ethyl]benzamide | Not provided | Ms m/z (APCl) [M + H]+ = 379 | Not provided |

TABLE 2AD

| | | | | | |
|---|---|---|---|---|---|
| 226 | 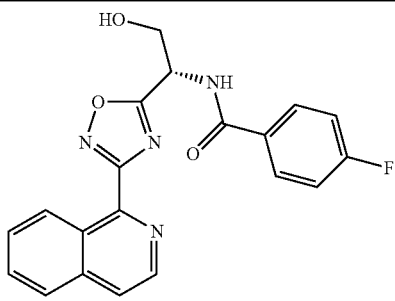 | 4-fluoro-N-[(1S)-2-hydroxy-1-[3-(isoquinolin-1-yl)-1,2,4-oxadiazol-5-yl]ethyl]benzamide | Not provided | Ms m/z (APCl) [M + H]+ = 379 | Not provided |

TABLE 2AD-continued

| | | | | | |
|---|---|---|---|---|---|
| 227 | 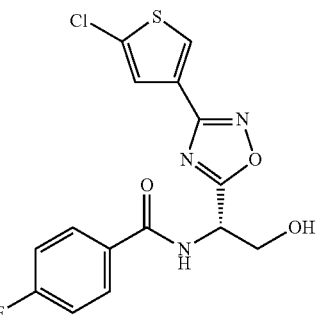 | N-[(1S)-1-[3-(5-chlorothiophen-3-yl)-1,2,4-oxadiazol-5-yl]-2-hydroxyethyl-4-fluorobenzamide | Not provided | Ms m/z (APCI) [M + H]+ = 368 | Not provided |
| 228 | 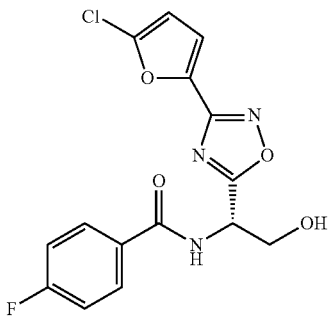 | N-[(1S)-1-[3-(5-chlorofuran-2-yl)-1,2,4-oxadiazol-5-yl]-2-hydroxyethyl]-4-fluorobenzamide | Not provided | Ms m/z (APCI) [M + H]+ = 352 | Not provided |
| 229 | 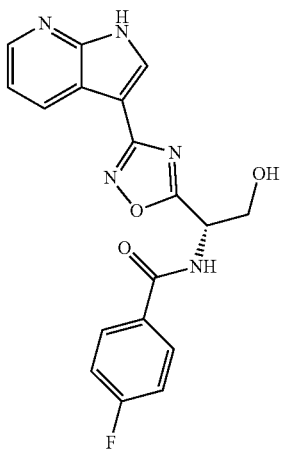 [SMILES: O=C(N[C@@H](CO)c1nc(-c2c[nH]c3ncccc23)no1)c1ccc(F)cc1] | 4-fluoro-N-[(1S)-2-hydroxy-1-(3-{1H-pyrrolo[2,3-b]pyridin-3-yl}-1,2,4-oxadiazol-5-yl)ethyl]benzamide | Not provided | Ms m/z (APCI) [M + H]+ = 368 | Not provided |
| 230 | 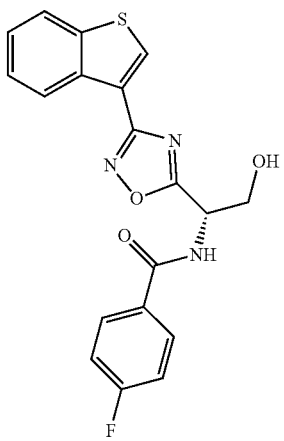 [SMILES: O=C(N[C@@H](CO)c1nc(-c2csc3ccccc23)no1)c1ccc(F)cc1] | N-[(1S)-1-[3-(1-benzothiophen-3-yl)-1,2,4-oxadiazol-5-yl]-2-hydroxyethyl]-4-fluorobenzamide | Not provided | Ms m/z (APCI) [M + H]+ = 384 | Not provided |

TABLE 2AD-continued

| | | | | | |
|---|---|---|---|---|---|
| 231 | 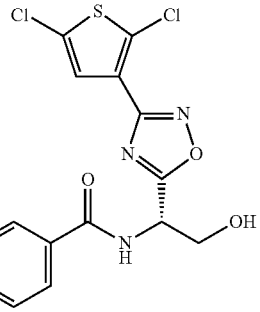 | N-[(1S)-1-[3-(2,5-dichlorothiophen-3-yl)-1,2,4-oxadiazol-5-yl]-2-hydroxyethyl]-4-fluorobenzamide | Not provided | Ms m/z (APCl) [M + H]+ = 401 | Not provided |
| 232 | 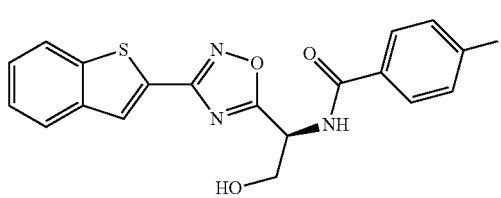 | N-[(1S)-1-[3-(1-benzothiophen-2-yl)-1,2,4-oxadiazol-5-yl]-2-hydroxyethyl]-4-fluorobenzamide | Not provided | Ms m/z (APCl) [M + H]+ = 384 | Not provided |
| 233 | 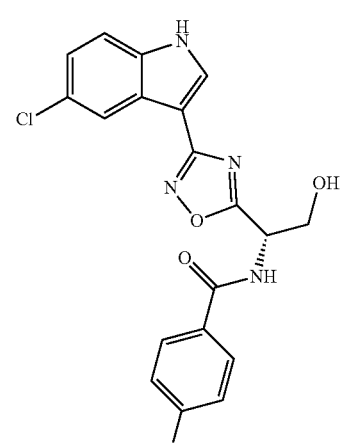 | N-[(1S)-1-[3-(5-chloro-1H-indol-3-yl)-1,2,4-oxadiazol-5-yl]-2-hydroxyethyl]-4-fluorobenzamide | Not provided | Ms m/z (APCl) [M + H]+ = 401 | Not provided |

TABLE 2AE

| | | | | | |
|---|---|---|---|---|---|
| 234 | 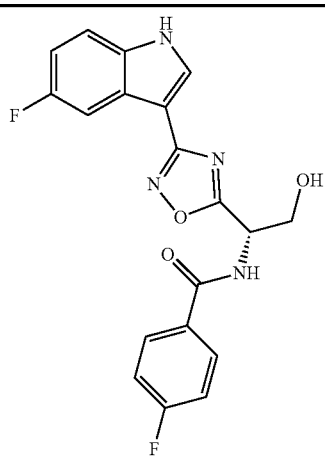 | 4-fluoro-N-[(1S)-1-[3-(5-fluoro-1H-indol-3-yl)-1,2,4-oxadiazol-5-yl]-2-hydroxyethyl benzamide | Not provided | Ms m/z (APCl) [M + H]+ = 385 | Not provided |

TABLE 2AE-continued

| | | | | | |
|---|---|---|---|---|---|
| 235 | 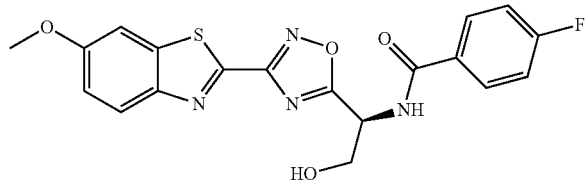 [SMILES: COc1ccc2nc(-c3noc([C@H](CO)NC(=O)c4ccc(F)cc4)n3)sc2c1] | 4-fluoro-N-[(1S)-2-hydroxy-1-[3-(6-methoxy-1,3-benzothiazol-2-yl)-1,2,4-oxadiazol-5-yl]ethyl]benzamide | Not provided | Ms m/z (APCl) [M + H]+ = 415 | Not provided |
| 236 | 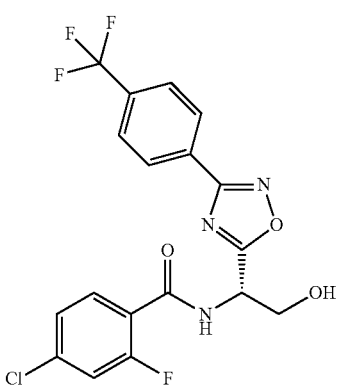 [SMILES: O=C(N[C@@H](CO)c1nc(-c2ccc(C(F)(F)F)cc2)no1)c1ccc(Cl)cc1F] | 4-chloro-2-fluoro-N-[(1S)-2-hydroxy-1-{3-[4-(trifluoromethyl)phenyl]-1,2,4-oxadiazol-5-yl}ethyl]benzamide | Not provided | Ms m/z (APCl) [M + H]+ = 430 | Not provided |
| 237 | 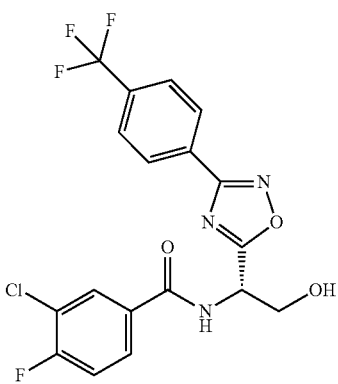 [SMILES: O=C(N[C@@H](CO)c1nc(-c2ccc(C(F)(F)F)cc2)no1)c1ccc(F)c(Cl)c1] | 3-chloro-4-fluoro-N-[(1S)-2-hydroxy-1-{3-[4-(trifluoromethyl)phenyl]-1,2,4-oxadiazol-5-yl}ethyl]benzamide | Not provided | Ms m/z (APCl) [M + H]+ = 430 | Not provided |
| 238 | 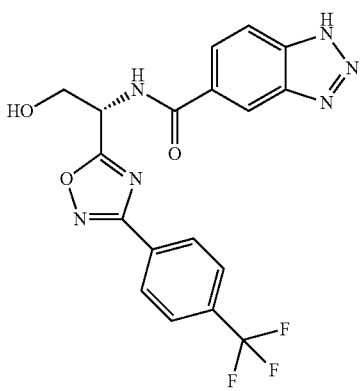 [SMILES: O=C(N[C@@H](CO)c1nc(-c2ccc(C(F)(F)F)cc2)no1)c1ccc2[nH]nnc2c1] | N-[(1S)-2-hydroxy-1-{3-[4-(trifluoromethyl)phenyl]-1,2,4-oxadiazol-5-yl}ethyl]-1H-1,2,3-benzotriazole-5-carboxamide | Not provided | Ms m/z (APCl) [M + H]+ = 419 | Not provided |

TABLE 2AE-continued

| | | | | | |
|---|---|---|---|---|---|
| 239 | 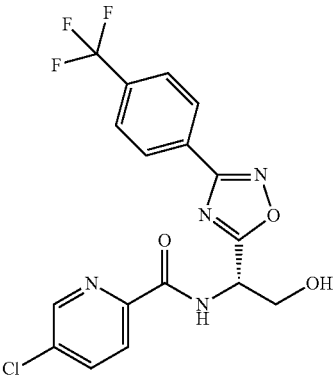 [SMILES: O=C(N[C@@H](CO)c1nc(-c2ccc(C(F)(F)F)cc2)no1)c1ccc(Cl)cn1] | 5-chloro-N-[(1S)-2-hydroxy-1-{3-[4-(trifluoromethyl)phenyl]-1,2,4-oxadiazol-5-yl}ethyl]pyridine-2-carboxamide | Not provided | Ms m/z (APCl) [M + H]+ = 413 | Not provided |
| 240 | 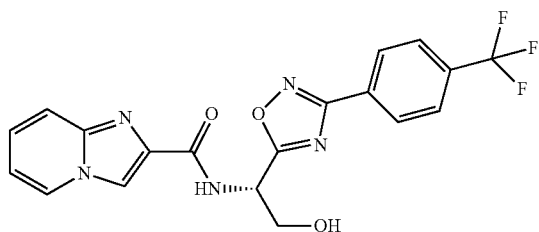 [SMILES: O=C(N[C@@H](CO)c1nc(-c2ccc(C(F)(F)F)cc2)no1)c1cn2ccccc2n1] | N-[(1S)-2-hydroxy-1-{3-[4-(trifluoromethyl)phenyl]-1,2,4-oxadiazol-5-yl}ethyl]imidazo[1,2-a]pyridine-2-carboxamide | Not provided | Ms m/z (APCl) [M + H]+ = 418 | Not provided |
| 241 | 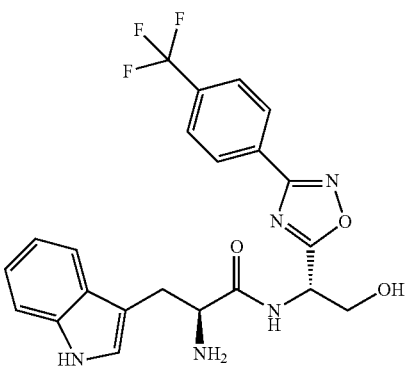 [SMILES: N[C@@H](Cc1c[nH]c2ccccc12)C(=O)N[C@@H](CO)c1nc(-c2ccc(C(F)(F)F)cc2)no1] | (2S)-2-amino-N-[(1S)-2-hydroxy-1-{3-[4-(trifluoromethyl)phenyl]-1,2,4-oxadiazol-5-yl}ethyl]-3-(1H-indol-3-yl)propanamide | Not provided | Ms m/z (APCl) [M + H]+ = 460 | Not provided |

TABLE 2AF

| | | | | | |
|---|---|---|---|---|---|
| 242 | 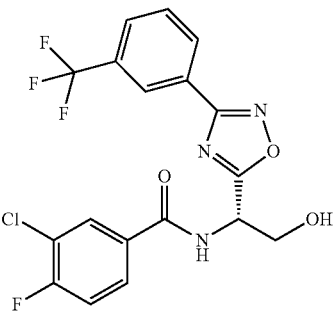 [SMILES: O=C(N[C@@H](CO)c1nc(-c2cccc(C(F)(F)F)c2)no1)c1ccc(F)c(Cl)c1] | 3-chloro-4-fluoro-N-[(1S)-2-hydroxy-1-{3-[3-(trifluoromethyl)phenyl]-1,2,4-oxadiazol-5-yl}ethyl]benzamide | Not provided | Ms m/z (APCl) [M + H]+ = 430 | Not provided |

TABLE 2AF-continued

| | | | | | |
|---|---|---|---|---|---|
| 243 | 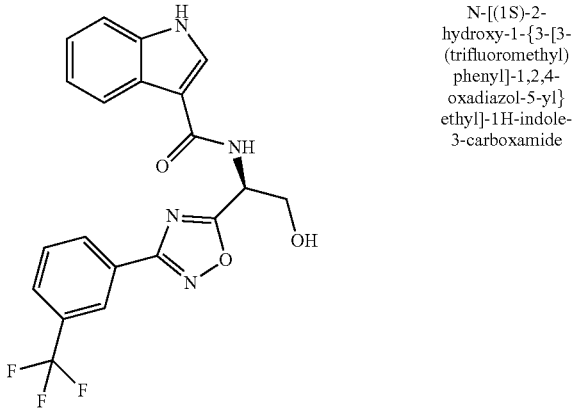 | N-[(1S)-2-hydroxy-1-{3-[3-(trifluoromethyl)phenyl]-1,2,4-oxadiazol-5-yl}ethyl]-1H-indole-3-carboxamide | Not provided | Ms m/z (APCl) [M + H]+ = 417 | Not provided |
| 244 | 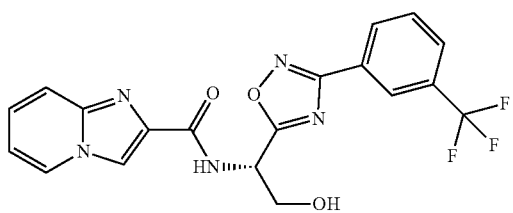 [SMILES: O=C(N[C@@H](CO)c1nc(-c2cccc(C(F)(F)F)c2)no1)c1cn2ccccc2n1] | N-[(1S)-2-hydroxy-1-{3-[3-(trifluoromethyl)phenyl]-1,2,4-oxadiazol-5-yl}ethyl]imidazo[1,2-a]pyridine-2-carboxamide | Not provided | Ms m/z (APCl) [M + H]+ = 418 | Not provided |
| 245 | 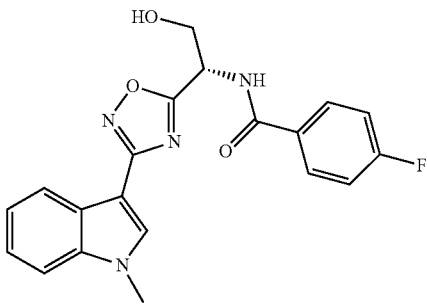 [SMILES: Cn1cc(-c2noc([C@H](CO)NC(=O)c3ccc(F)cc3)n2)c2ccccc21] | 4-fluoro-N-[(1S)-2-hydroxy-1-[3-(1-methyl-1H-3-yl)-1,2,4-oxadiazol-5-yl]ethyl]benzamide | Not provided | Ms m/z (APCl) [M + H]+ = 381 | Not provided |
| 246 | 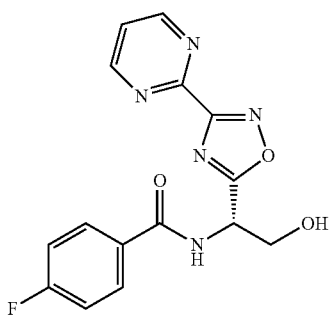 [SMILES: O=C(N[C@@H](CO)c1nc(-c2ncccn2)no1)c1ccc(F)cc1] | 4-fluoro-N-[(1S)-2-hydroxy-1-[3-(pyrimidin-2-yl)-1,2,4-oxadiazol-5-yl]ethyl]benzamide | Not provided | Ms m/z (APCl) [M + H]+ = 330 | Not provided |

TABLE 2AF-continued

| | | | | | |
|---|---|---|---|---|---|
| 247 | (structure) | N-[(1S)-1-[3-(5-bromo-1H-indol-3-yl)-1,2,4-oxadiazol-5-yl]-2-hydroxyethyl]-4-fluorobenzamide | Not provided | Ms m/z (APCI) [M + H]+ = 445 | Not provided |
| 248 | (structure) | 4-fluoro-N-[(1S)-2-hydroxy-1-[3-(5-phenylthiophen-2-yl)-1,2,4-oxadiazol-5-yl]ethyl]benzamide | Not provided | Ms m/z (APCI) [M + H]+ = 410 | Not provided |
| 249 | (structure) | N-[(1S)-1-[3-(4,5-dichloro-1H-pyrrol-2-yl)-1,2,4-oxadiazol-5-yl]-2-hydroxyethyl]-4-fluorobenzamide | Not provided | Ms m/z (APCI) [M + H]+ = 385 | Not provided |

TABLE 2AG

| | | | | | |
|---|---|---|---|---|---|
| 250 | (structure) | 4-fluoro-N-[(1S)-2-hydroxy-1-[3-(1H-indol-6-yl)-1,2,4-oxadiazol-5-yl]ethyl]benzamide | Not provided | Ms m/z (APCI) [M + H]+ = 367 | Not provided |

| | | | | | |
|---|---|---|---|---|---|
| 251 | | N-[(1S)-1-[3-(5-chloro-1H-pyrrol-2-yl)-1,2,4-oxadiazol-5-yl]-2-hydroxyethyl]-4-fluorobenzamide | Not provided | Ms m/z (APCI) [M + H]+ = 351 | Not provided |
| 252 | | 4-chloro-N-[(1S)-1-[3-(5-chloro-1H-indol-3-yl)-1,2,4-oxadiazol-5-yl]-2-hydroxyethyl]-2-fluorobenzamide | Not provided | Ms m/z (APCI) [M + H]+ = 435 | Not provided |
| 253 | | N-[(1S)-1-[3-(5-chloro-1H-indol-3-yl)-1,2,4-oxadiazol-5-yl]-2-hydroxyethyl]-4-(pyrrolidin-1-yl)benzamide | Not provided | Ms m/z (APCI) [M + H]+ = 452 | Not provided |

TABLE 2AG-continued

| # | Structure | Name | | MS | |
|---|---|---|---|---|---|
| 254 | 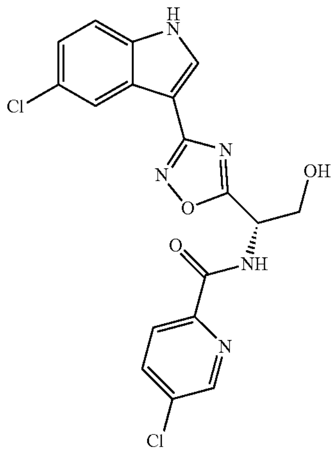 [SMILES: O=C(N[C@@H](CO)c1nc(-c2c[nH]c3ccc(Cl)cc23)no1)c1ccc(Cl)cn1] | 5-chloro-N-[(1S)-1-[3-(5-chloro-1H-indol-3-yl)-1,2,4-oxadiazol-5-yl]-2-hydroxyethyl]pyridine-2-carboxamide | Not provided | Ms m/z (APCl) [M + H]+ = 418 | Not provided |
| 255 | 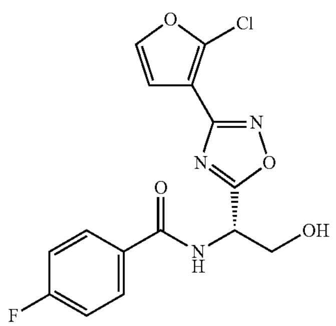 [SMILES: O=C(N[C@@H](CO)c1nc(-c2ccoc2Cl)no1)c1ccc(F)cc1] | N-[(1S)-1-[3-(2-chlorofuran-3-yl)-1,2,4-oxadiazol-5-yl]-2-hydroxyethyl]-4-fluorobenzamide | Not provided | Ms m/z (APCl) [M + H]+ = 352 | Not provided |
| 256 | 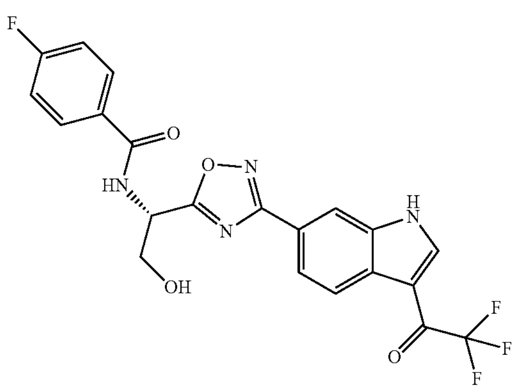 [SMILES: O=C(N[C@@H](CO)c1nc(-c2ccc3c(C(=O)C(F)(F)F)c[nH]c3c2)no1)c1ccc(F)cc1] | 4-fluoro-N-[(1S)-2-hydroxy-1-{3-[3-(2,2,2-trifluoroacetyl)-1H-indol-6-yl]-1,2,4-oxadiazol-5-yl}ethyl]benzamide | Not provided | Ms m/z (APCl) [M + H]+ = 463 | Not provided |
| 257 | 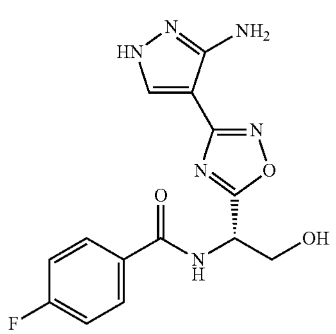 [SMILES: Nc1n[nH]cc1-c1noc([C@H](CO)NC(=O)c2ccc(F)cc2)n1] | N-[(1S)-1-[3-(3-amino-1H-pyrazol-4-yl)-1,2,4-oxadiazol-5-yl]-2-hydroxyethyl]-4-fluorobenzamide | Not provided | Ms m/z (APCl) [M + H]+ = 333 | Not provided |

TABLE 2AH

| | | | | | |
|---|---|---|---|---|---|
| 258 | 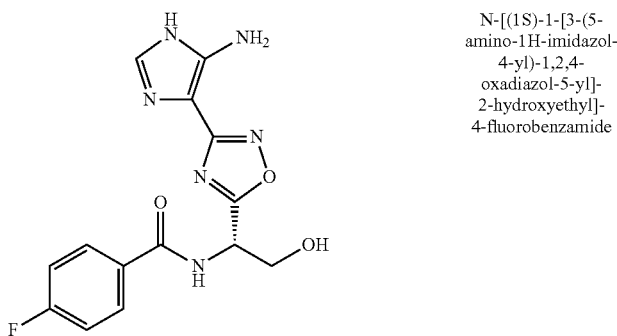 | N-[(1S)-1-[3-(5-amino-1H-imidazol-4-yl)-1,2,4-oxadiazol-5-yl]-2-hydroxyethyl]-4-fluorobenzamide | Not provided | Ms m/z (APCl) [M + H]+ = 333 | Not provided |
| 259 | 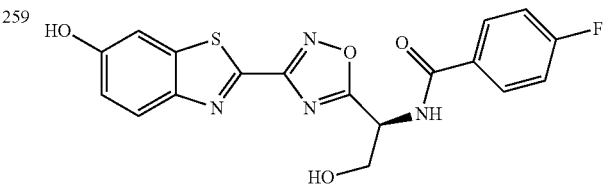 | 4-fluoro-N-[(1S)-2-hydroxy-1-[3-(6-hydroxy-1,3-benzothiazol-2-yl)-1,2,4-oxadiazol-5-yl]ethyl]benzamide | Not provided | Ms m/z (APCl) [M + H]+ = 401.85 | Not provided |
| 260 | 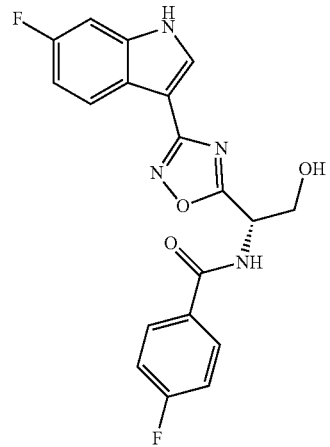 [SMILES: O=C(N[C@@H](CO)c1nc(-c2c[nH]c3cc(F)ccc23)no1)c1ccc(F)cc1] | 4-fluoro-N-[(1S)-1-[3-(6-fluoro-1H-indol-3-yl)-1,2,4-oxadiazol-5-yl]-2-hydroxyethyl]benzamide | Not provided | Ms m/z (APCl) [M + H]+ = 385 | Not provided |
| 261 | 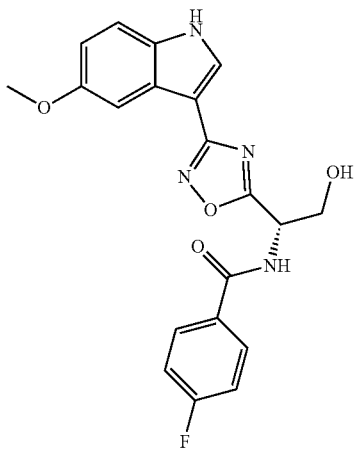 [SMILES: COc1ccc2[nH]cc(-c3noc([C@H](CO)NC(=O)c4ccc(F)cc4)n3)c2c1] | 4-fluoro-N-[(1S)-2-hydroxy-1-[3-(5-methoxy-1H-indol-3-yl)-1,2,4-oxadiazol-5-yl]ethyl]benzamide | Not provided | Ms m/z (APCl) [M + H]+ = 397 | Not provided |

TABLE 2AH-continued

| 262 | 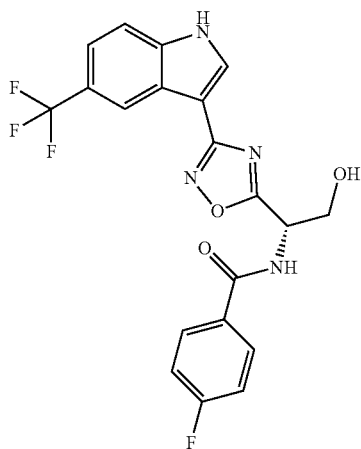 [SMILES: O=C(N[C@@H](CO)c1nc(-c2c[nH]c3ccc(C(F)(F)F)cc23)no1)c1ccc(F)cc1] | 4-fluoro-N-[(1S)-2-hydroxy-1-{3-[5-(trifluoromethyl)-1H-indol-3-yl]-1,2,4-oxadiazol-5-yl}ethyl]benzamide | Not provided | Ms m/z (APCl) [M + H]+ = 435 | Not provided |
| --- | --- | --- | --- | --- | --- |
| 263 | 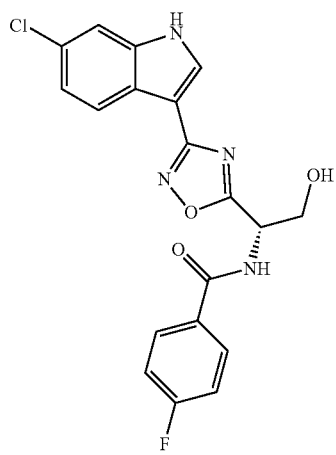 [SMILES: O=C(N[C@@H](CO)c1nc(-c2c[nH]c3cc(Cl)ccc23)no1)c1ccc(F)cc1] | N-[(1S)-1-[3-(6-chloro-1H-indol-3-yl)-1,2,4-oxadiazol-5-yl]-2-hydroxyethyl]-4-fluorobenzamide | Not provided | Ms m/z (APCl) [M + H]+ = 401.85 | Not provided |
| 264 | 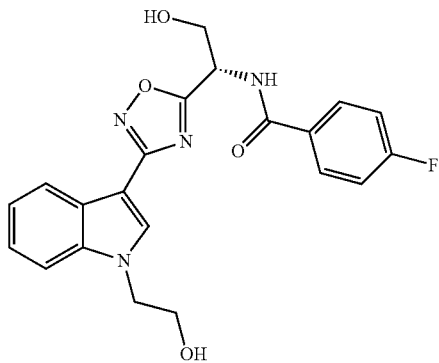 [SMILES: O=C(N[C@@H](CO)c1nc(-c2cn(CCO)c3ccccc23)no1)c1ccc(F)cc1] | 4-fluoro-N-[(1S)-2-hydroxy-1-{3-[1-(2-(hydroxyethyl)-1H-indol-3-yl]-1,2,4-oxadiazol-5-yl}ethyl]benzamide | Not provided | Ms m/z (APCl) [M + H]+ = 411 | Not provided |

TABLE 2AH-continued

| | | | | | |
|---|---|---|---|---|---|
| 265 | (structure) | 4-fluoro-N-[(1S)-2-hydroxy-1-[3-(1H-indazol-3-yl)-1,2,4-oxadiazol-5-yl]ethyl]benzamide | Not provided | Ms m/z (APCl) [M + H]+ = 367 | Not provided |

TABLE 2AI

| | | | | | |
|---|---|---|---|---|---|
| 266 | (structure) | 4-fluoro-N-[(1S)-2-hydroxy-1-[3-(1H-indol-2-yl)-1,2,4-oxadiazol-5-yl]ethyl]benzamide | Not provided | Ms m/z (APCl) [M + H]+ = 367 | Not provided |
| 267 | (structure) | 4-fluoro-N-[(1S)-1-[3-(5-fluoro-1H-indol-2-yl)-1,2,4-oxadiazol-5-yl]-2-hydroxyethyl]benzamide | Not provided | Ms m/z (APCl) [M + H]+ = 385 | Not provided |

<3. Evaluation of the Compounds Based on the Inhibitory Activity Against Amyloid Fibril Formation in Thioflabin T (ThT) Assay>

Inhibitory activity against GAβ-dependent amyloid fibril formation of the above compounds 1 to 133 and 142 to 267 were evaluated in ThT assay.

(1) Preparation of Aβ Solution

Human Aβ1-40 (cat. #4307-v, prepared by Peptide Institute) was dissolved in a 0.02% ammonia solution (400 μM), and the mixture was treated in an ultracentrifuge (S110AT rotor, Hitachi) at 100,000 rpm for 3 hours. Approximately two-thirds of the upper layer of the supernatant was recovered and protein concentration was measured. The Aβ solution was aliquoted and stored at −80° C. until use, was melted immediately before use, and was diluted to 75 μM using phosphate buffer (PBS: cat. #10010, manufactured by Life Technologies).

(2) Preparation of GM1-Containing Liposome

Using a mixed solution of chloroform/methanol (1:1) as a solvent, a mixed solution of 100 mM each of cholesterol and sphingomyelin (both manufactured by Sigma-Aldrich) was prepared. To this mixed solution, GM 1 (cat. #1061, manufactured by Matreya Co.) was dissolved to make a solution of 50 mM concentration. This lipid mixed solution was aliquoted into glass test tubes and stored at −20° C. until use, was melted before use, was mixed with chloroform/methanol mixture (1:1) and mixed, and then the solvent was removed by applying nitrogen gas to the suspension. The dried lipid mixture was resuspended in PBS to be a GM1 concentration of 2.5 mM, and frozen and thawed 5 times with liquid nitrogen. The lipid suspension was centrifuged at 15,000 rpm for 10 minutes and the precipitate was resuspended in PBS to be a GM1 concentration of 2.5 mM. Using an ultrasonic crusher (XL-2000, MISONIX Co., Ltd.) equipped with a microchip, ultrasonic treatment was repeated on ice for 10 seconds until the suspension became transparent, and GM1-containing liposome was prepared. Immediately prior to use, PBS was added and diluted to a GM 1 concentration of 75 μM.

(3) Preparation of Compound Solution

Compounds 1 to 133 and 142 to 267 were prepared as 10 mM and 2 mM solution in DMSO, respectively. And each solution was diluted to 75 μM or 15 μM with PBS immediately prior to use.

(4) GAβ-Dependent Amyloid Fibril Formation

To a 96-well microplate, 5 μl each of the 75 μM Aβ solution prepared above (1), the compound solution prepared in (3) or 0.75% DMSO was mixed and incubated at room temperature for 10 minutes. Then, 5 μl each of 750 μM GM1-containing liposome prepared in (2) was added to each well and incubated at 37° C. for 18 hours.

(5) ThT Assay

ThT (manufactured by Sigma-Aldrich) was adjusted to 5 μM using 50 mM glycine-NaOH buffer (pH 8.5). Immediately before measurement, 10 μl from each well of (4) was transferred to a 96-well black plate. 50 μl of 5 μM ThT solution was added from each injector to each well using a multi-plate reader (ARVO-HTS, manufactured by Perkin Elmer), and then the optimal fluorescence of ThT bound to amyloid fiber (excitation wavelength 430 nm, fluorescence wavelength 490 nm) was measured.

The fluorescence intensity of ThT indicates the degree of amyloid fibrils formation. By calculating the ratio of the ThT fluorescence intensity between addition of the compound and without addition of the compound, the inhibition rate against amyloid fibril formation by the compound was calculated. When the final concentration of the compound was 25 μM, the inhibition rate of less than 40% was evaluated as C, 40% or more and less than 80% were evaluated as B, 80% or more was evaluated as A.

In Table 3, inhibitory activities of compounds 1 to 133 and 142 to 267 against amyloid fibril formation were shown on a scale of A to C. All of the compounds 1 to 133 and 142 to 267 were confirmed to have the inhibitory activities against amyloid fibril formation. In particular, some of the compounds with an A for inhibitory activity (as exemplified by 39, 129, 132, and 133) were identified with having a similar activity to 4396C antibody (Japanese Patent No. 4102850), which is an anti-GAβ monoclonal antibody known to specifically recognize GAβ and suppress the amyloid fibril formation.

TABLE 3A

| Compound number | Inhibitory activity ABC evaluation | ThT Inhibitory activity (% inhibition) |
|---|---|---|
| 1 | C | Not provided |
| 2 | B | Not provided |
| 3 | C | Not provided |
| 4 | C | Not provided |
| 5 | B | Not provided |
| 6 | B | Not provided |
| 7 | B | Not provided |
| 8 | C | Not provided |
| 9 | B | Not provided |
| 10 | C | Not provided |
| 11 | B | Not provided |
| 12 | B | Not provided |
| 13 | B | Not provided |
| 14 | C | Not provided |
| 15 | C | Not provided |
| 16 | C | Not provided |
| 17 | B | Not provided |
| 18 | A | 86% @25 μM |
| 19 | B | Not provided |
| 20 | B | Not provided |
| 21 | C | Not provided |
| 22 | C | Not provided |
| 23 | B | Not provided |
| 24 | B | Not provided |
| 25 | A | Not provided |
| 26 | B | Not provided |
| 27 | B | Not provided |
| 28 | B | Not provided |
| 29 | C | Not provided |
| 30 | C | Not provided |
| 31 | C | Not provided |
| 32 | A | 86% @25 μM |
|   |   | 43% @5 μM |
| 33 | B | Not provided |
| 34 | B | Not provided |
| 35 | C | Not provided |
| 36 | C | Not provided |
| 37 | C | Not provided |
| 38 | B | Not provided |
| 39 | A | 98% @25 μM |
| 40 | A | 80% @25 μM |
|   |   | 38% @5 μm |

TABLE 3B

| Compound number | Inhibitory activity ABC evaluation | ThT Inhibitory activity (% inhibition) |
|---|---|---|
| 41 | B | Not provided |
| 42 | B | Not provided |
| 43 | B | Not provided |
| 44 | C | Not provided |
| 45 | B | Not provided |
| 46 | B | Not provided |
| 47 | C | Not provided |
| 48 | B | Not provided |
| 49 | B | Not provided |
| 50 | B | Not provided |
| 51 | C | Not provided |
| 52 | B | Not provided |
| 53 | B | Not provided |
| 54 | B | Not provided |
| 55 | B | Not provided |
| 56 | C | Not provided |
| 57 | C | Not provided |
| 58 | B | Not provided |
| 59 | C | Not provided |
| 60 | C | Not provided |
| 61 | B | Not provided |
| 62 | B | Not provided |
| 63 | A | 99% @25 μM |
|   |   | 53% @5 μM |
| 64 | B | Not provided |
| 65 | B | Not provided |
| 66 | B | Not provided |
| 67 | B | Not provided |
| 68 | B | Not provided |
| 69 | A | 87% @25 μM |
| 70 | C | Not provided |
| 71 | B | Not provided |
| 72 | A | 81% @25 μM |
|   |   | 47% @5 μM |
| 73 | A | Not provided |
| 74 | B | Not provided |
| 75 | B | Not provided |
| 76 | B | Not provided |
| 77 | B | Not provided |
| 78 | A | 89% @25 μM |
|   |   | 52% @5 μM |
| 79 | C | Not provided |
| 80 | A | 80% @25 μM |

TABLE 3C

| Compound number | Inhibitory activity ABC evaluation | ThT Inhibitory activity (% inhibition) |
|---|---|---|
| 81 | B | Not provided |
| 82 | C | Not provided |
| 83 | A | Not provided |
| 84 | B | Not provided |
| 85 | B | Not provided |
| 86 | C | Not provided |
| 87 | B | Not provided |
| 88 | C | Not provided |
| 89 | B | Not provided |
| 90 | B | Not provided |
| 91 | B | Not provided |
| 92 | A | 81% @25 μM |
|   |   | 51% @5 μM |
| 93 | A | Not provided |
| 94 | A | Not provided |
| 95 | C | Not provided |
| 96 | B | Not provided |
| 97 | B | Not provided |
| 98 | C | Not provided |
| 99 | B | Not provided |
| 100 | B | Not provided |

TABLE 3C-continued

| Compound number | Inhibitory activity ABC evaluation | ThT Inhibitory activity (% inhibition) |
|---|---|---|
| 101 | A | 87% @25 μM |
| 102 | B | Not provided |
| 103 | B | Not provided |
| 104 | B | 75% @25 μM |
| 105 | C | Not provided |
| 106 | B | Not provided |
| 107 | B | Not provided |
| 108 | C | Not provided |
| 109 | C | Not provided |
| 110 | B | Not provided |
| 111 | C | Not provided |
| 112 | B | Not provided |
| 113 | C | Not provided |
| 114 | A | Not provided |
| 115 | C | Not provided |
| 116 | A | Not provided |
| 117 | B | Not provided |
| 118 | B | 72% @25 μM |
| 119 | B | Not provided |
| 120 | C | Not provided |

TABLE 3D

| Compound number | Inhibitory activity ABC evaluation | ThT Inhibitory activity (% inhibition) |
|---|---|---|
| 121 | B | Not provided |
| 122 | C | Not provided |
| 123 | C | Not provided |
| 124 | C | Not provided |
| 125 | A | 88% @25 μM<br>59% @5 μM |
| 126 | B | Not provided |
| 127 | B | Not provided |
| 128 | B | Not provided |
| 129 | A | 86% @25 μM<br>68% @5 μM |
| 130 | A | 85% @25 μM<br>67% @5 μM |
| 131 | B | Not provided |
| 132 | A | Not provided |
| 133 | A | 88% @25 μM |
| Not provided | Not provided | Not provided |
| Not provided | Not provided | Not provided |
| Not provided | Not provided | Not provided |
| Not provided | Not provided | Not provided |
| Not provided | Not provided | Not provided |
| Not provided | Not provided | Not provided |
| Not provided | Not provided | Not provided |
| 142 | B | Not provided |
| 143 | A | Not provided |
| 144 | A | Not provided |
| 145 | B | Not provided |
| 146 | A | 87% @25 μM |
| 147 | B | 53% @25 μM |
| 148 | B | Not provided |
| 149 | C | Not provided |
| 150 | A | Not provided |
| 151 | B | Not provided |
| 152 | B | Not provided |
| 153 | B | 76% @25 μM |
| 154 | Not provided | Not provided |
| 155 | Not provided | Not provided |
| 156 | B | 74% @25 μM |
| 157 | A | Not provided |
| 158 | B | Not provided |
| 159 | C | Not provided |
| 160 | Not provided | Not provided |

TABLE 3E

| Compound number | Inhibitory activity ABC evaluation | ThT Inhibitory activity (% inhibition) |
|---|---|---|
| 161 | B | Not provided |
| 162 | B | Not provided |
| 163 | B | Not provided |
| 164 | A | Not provided |
| 165 | A | Not provided |
| 166 | B | Not provided |
| 167 | A | 98% @25 μM |
| 168 | A | Not provided |
| 169 | B | Not provided |
| 170 | B | Not provided |
| 171 | C | Not provided |
| 172 | A | 91% @25 μM |
| 173 | C | Not provided |
| 174 | C | Not provided |
| 175 | A | Not provided |
| 176 | A | Not provided |
| 177 | A | Not provided |
| 178 | B | 61% @25 μM |
| 179 | B | Not provided |
| 180 | C | Not provided |
| 181 | B | 73% @25 μM |
| 182 | B | 64% @25 μM |
| 183 | A | Not provided |
| 184 | B | Not provided |
| 185 | B | Not provided |
| 186 | B | Not provided |
| 187 | B | Not provided |
| 188 | A | Not provided |
| 189 | B | Not provided |
| 190 | B | 67% @25 μM |
| 191 | B | 73% @25 μM |
| 192 | A | Not provided |
| 193 | B | Not provided |
| 194 | B | Not provided |
| 195 | A | Not provided |
| 196 | A | Not provided |
| 197 | B | 70% @25 μM |
| 198 | A | Not provided |
| 199 | A | Not provided |
| 200 | B | Not provided |

TABLE 3F

| Compound number | Inhibitory activity ABC evaluation | ThT Inhibitory activity (% inhibition) |
|---|---|---|
| 201 | A | Not provided |
| 202 | B | Not provided |
| 203 | A | 81% @25 μM |
| 204 | B | Not provided |
| 205 | B | Not provided |
| 206 | B | 55% @25 μM |
| 207 | A | Not provided |
| 208 | B | Not provided |
| 209 | A | Not provided |
| 210 | A | Not provided |
| 211 | A | 89% @25 μM |
| 212 | B | Not provided |
| 213 | C | Not provided |
| 214 | B | Not provided |
| 215 | B | Not provided |
| 216 | C | Not provided |
| 217 | B | Not provided |
| 218 | B | Not provided |
| 219 | C | Not provided |
| 220 | A | Not provided |
| 221 | A | Not provided |
| 222 | A | Not provided |
| 223 | B | Not provided |
| 224 | A | Not provided |

TABLE 3F-continued

| Compound number | Inhibitory activity ABC evaluation | ThT Inhibitory activity (% inhibition) |
|---|---|---|
| 225 | B | Not provided |
| 226 | B | Not provided |
| 227 | B | Not provided |
| 228 | C | Not provided |
| 229 | B | 71% @25 μM |
| 230 | B | 73% @25 μM |
| 231 | B | Not provided |
| 232 | A | Not provided |
| 233 | B | Not provided |
| 234 | B | Not provided |
| 235 | B | 63% @25 μM |
| 236 | A | Not provided |
| 237 | A | Not provided |
| 238 | B | Not provided |
| 239 | B | 64% @25 μM |
| 240 | C | Not provided |

TABLE 3G

| Compound number | Inhibitory activity ABC evaluation | ThT Inhibitory activity (% inhibition) |
|---|---|---|
| 241 | C | Not provided |
| 242 | B | 59% @25 μM |
| 243 | C | Not provided |
| 244 | C | Not provided |
| 245 | B | Not provided |
| 246 | B | Not provided |
| 247 | B | Not provided |
| 248 | B | Not provided |
| 249 | B | Not provided |
| 250 | B | Not provided |
| 251 | B | Not provided |
| 252 | B | Not provided |
| 253 | B | Not provided |
| 254 | B | Not provided |
| 255 | B | Not provided |
| 256 | B | Not provided |
| 257 | B | Not provided |
| 258 | B | Not provided |
| 259 | B | Not provided |
| 260 | B | Not provided |
| 261 | B | Not provided |
| 262 | B | Not provided |
| 263 | B | Not provided |
| 264 | B | Not provided |
| 265 | B | Not provided |
| 266 | A | Not provided |
| 267 | A | Not provided |

That which is claimed is:

1. An amyloid fibril formation inhibitor comprising a compound of formula (II):

[Formula 2]

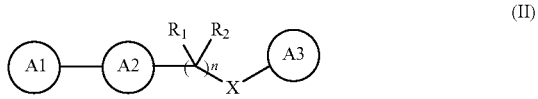

(II)

wherein:
Ring A1 is a substituted or unsubstituted phenyl group, or a substituted or unsubstituted indolyl group;
Ring A2 is 1,2,4-oxadiazolyl or 1,3,4-oxadiazolyl;
Ring A3 is a substituted or unsubstituted phenyl group;
n is 1;
$R_1$ is hydrogen and $R_2$ is a $C_{1-10}$ hydroxyalkyl group; and
X is —NH—C(=O)—;
or a pharmaceutically acceptable salt thereof or a solvate thereof.

2. The amyloid fibril formation inhibitor according to claim 1, wherein
Ring A1 is selected from the group consisting of phenyl, 4-trifluoromethylphenyl, 3-trifluoromethylphenyl, 4-trifluoromethoxyphenyl, 4-hydroxyphenyl, 3-fluoro-4-hydroxyphenyl, 4-methanesulfonylaminophenyl, 3-cyanophenyl, 3-fluoro-4-methoxyphenyl, 4-methoxyphenyl, 2-fluoro-4-hydroxyphenyl, 4-dimethylaminophenyl, 4-acethylphenyl, 4-(1'-hydroxyethyl)phenyl, 4-(1'-hydroxy-1'-methylethyl)phenyl, 4-fluoromethylphenyl, 4-bromophenyl, 4-trifluoromethylcarbonylphenyl, 4-difluoromethylphenyl, 4-fluoromethylphenyl, 2-trifluoromethylphenyl, 3-fluoro-4-trifluoromethylphenyl, 3,5-difluorophenyl, 2-chloro-4-fluorophenyl, 3-indolyl, 5-indolyl, 2-indolyl, 5'-chloro-3-indolyl, 5'-fluoro-3-indolyl, 1'-methyl-3-indolyl, 5'-bromo-3-indolyl, 6-indolyl, 3'-trifluoromethylcarbonyl-6-indolyl, 6'-fluoro-3-indolyl, 5'-methoxy-3-indolyl, 5'-trifluoromethyl-3-indolyl, 6'-chloro-3-indolyl, 1'-hydroxyethyl-3-indolyl, 3'-fluoro-5-indolyl, 7'-fluoro-3-indolyl and 7'-chloro-3-indolyl; and
Ring A3 is selected from the group consisting of phenyl, 4-chlorophenyl, 3-chlorophenyl, 2-fluorophenyl, 3-fluorophenyl, 3-chloro-4-hydroxyphenyl, 4-cyanophenyl, 4-fluorophenyl, 4-chlorophenyl, 4-trifluoromethylphenyl, 3-chloro-4-fluorophenyl, 3,5-difluorophenyl, 2,6-difluorophenyl, 4-trifluoromethoxyphenyl, 4-morpholinophenyl, 4-dimethylaminophenyl, 4-pyrrolidinophenyl, and 3-chloro-5-fluorophenyl.

3. An amyloid fibril formation inhibitor comprising a compound selected from the group consisting of (S)-4-chloro-N-(2-hydroxy-1-[3-{4-(trifluoromethoxy)phenyl}-1,2,4-oxadiazol-5-yl]ethyl)benzamide, (S)-3-chloro-N-(2-hydroxy-1-[3-{4-(trifluoromethoxy)phenyl}-1,2,4-oxadiazol-5-yl]ethyl)benzamide, (S)-4-fluoro-N-(2-hydroxy-1-[3-{4-(trifluoromethoxy)phenyl}-1,2,4-oxadiazol-5-yl]ethyl) benzamide, 4-chloro-N-[2-hydroxy-1-{3-(4-hydroxyphenyl)-1,2,4-oxadiazol-5-yl}ethyl]benzamide, (R)-4-chloro-N-(2-hydroxy-1-[3-{4-(trifluoromethoxy)phenyl}-1,2,4-oxadiazol-5-yl]ethyl)benzamide, (S)-N-(2-hydroxy-1-[3-{4-(trifluoromethoxy)phenyl}-1,2,4-oxadiazol-5-yl]ethyl)benzamide, (S)-2-fluoro-N-(2-hydroxy-1-[3-{4-(trifluoromethoxy)phenyl}-1,2,4-oxadiazol-5-yl]ethyl) benzamide, (S)-3-fluoro-N-(2-hydroxy-1-[3-{4-(trifluoromethoxy)phenyl}-1,2,4-oxadiazol-5-yl] ethyl) benzamide, (S)-3-chloro-4-hydroxy-N-(2-hydroxy-1-[3-{4-(trifluoromethoxy)phenyl}-1,2,4-oxadiazol-5-yl]ethyl) benzamide, (S)-4-chloro-N-(1-(3-(3-fluoro-4-hydroxyphenyl)-1,2,4-oxadiazol-5-yl)-2-hydroxyethyl) benzamide, (S)-4-cyano-N-(1-(3-(3-fluoro-4-hydroxyphenyl)-1,2,4-oxadiazol-5-yl)-2-hydroxyethyl) benzamide, (S)-4-chloro-N-(2-hydroxy-1-(5-(4-(trifluoromethoxy)phenyl)-1,3,4-oxadiazol-2-yl)ethyl) benzamide, (S)-4-chloro-N-(2-hydroxy-1-(5-(4-(methylsulfonamido)phenyl)-1,3,4-oxadiazol-2-yl)ethyl) benzamide, (S)-4-chloro-N-(1-(5-(3-cyanophenyl)-1,3,4-oxadiazol-2-yl)-2-hydroxyethyl)benzamide, (R)-4-chloro-N-(2-hydroxy-1-(5-(4-(trifluoromethoxy)phenyl)-1,3,4-oxadiazol-2-yl)ethyl)benzamide, (R)-4-chloro-N-(2-hydroxy-1-(5-(4-(methylsulfonamido)phenyl)-1,3,4-oxadiazol-2-yl)ethyl)benzamide, (R)-4-chloro-N-(1-(5-(3-cyanophenyl)-1,3,4-oxadiazol-2-yl)-2-hydroxyethyl) benzamide, (S)-4-fluoro-N-(2-hydroxy-1-(5-(4-

(trifluoromethoxy)phenyl)-1,4-oxadiazol-2-yl)ethyl)benzamide, (S)-4-chloro-N-(1-(5-(3-fluoro-4-methoxyphenyl)-1,3,4-oxadiazol-2-yl)-2-hydroxyethyl)benzamide, (S)-4-chloro-N-(1-(5-(3-fluoro-4-hydroxyphenyl)-1,3,4-oxadiazol-2-yl)-2-hydroxyethyl)benzamide, (S)-4-chloro-N-(2-hydroxy-1-(3-(4-methoxyphenyl)-1,2,4-oxadiazol-5-yl)ethyl)benzamide, (R)-4-chloro-N-(2-hydroxy-1-(5-(4-(trifluoromethoxy)phenyl)-1,2,4-oxadiazol-3-yl ethyl)benzamide, (R)-N-(2-hydroxy-1-(5-(4-(trifluoromethoxy)phenyl)-1,2,4-oxadiazol-3-yl)ethyl)benzamide, (S)-4-chloro-N-(2-hydroxy-1-(3-(4-(trifluoromethyl)phenyl)-1,2,4-oxadiazol-5-yl)ethyl)benzamide, (S)-N-(2-hydroxy-1-(3-(4-(trifluoromethyl)phenyl)-1,2,4-oxadiazol-5-yl)ethyl)benzamide, (S)-4-fluoro-N-(2-hydroxy-1-(3-(4-(trifluoromethyl)phenyl)-1,2,4-oxadiazol-5-yl)ethyl)benzamide, N-[(1S)-1-[3-(2-fluoro-4-hydroxyphenyl)-1,2,4-oxadiazol-5-yl]-2-hydroxyethyl]benzamide, N-[(1S)-2-hydroxy-1-[3-(4-methylphenyl)-1,2,4-oxadiazol-5-yl]ethyl]benzamide, N-[(1S)-1-[3-(3-fluoro-4-methoxyphenyl)-1,2,4-oxadiazol-5-yl]-2-hydroxyethyl]benzamide, N-[(1S)-2-hydroxy-1-{3-[4-(propan-2-yl)phenyl]-1,2,4-oxadiazol-5-yl}ethyl]benzamide, N-[(1S)-2-hydroxy-1-[3-(4-hydroxyphenyl)-1,2,4-oxadiazol-5-yl]ethyl]benzamide, 4-{5-[(1S)-1-[(4-fluorophenyl)formamido]-2-hydroxyethyl]-1,2,4-oxadiazol-3-yl}-N-(3-methoxypropyl)benzamide, 4-{5-[(1S)-2-hydroxy-1-(phenylformamido)ethyl]-1,2,4-oxadiazol-3-yl}-N-(3-methoxypropyl)benzamide, N-[(1S)-1-{3-[4-(dimethylamino)phenyl]-1,2,4-oxadiazol-5-yl}-2-hydroxyethyl]benzamide, 4-fluoro-N-[(1R)-2-hydroxy-1-{3-[4-(trifluoromethyl)phenyl]-1,2,4-oxadiazol-5-yl}ethyl]benzamide, N-[(1S)-1-[3-(4-acetylphenyl)-1,2,4-oxadiazol-5-yl]-2-hydroxyethyl]benzamide, N-[(1S)-2-hydroxy-1-{3-[4-(1-hydroxyethyl)phenyl]-1,2,4-oxadiazol-5-yl}ethyl]benzamide, N-[(1S)-2-hydroxy-1-{3-[4-(2-hydroxypropan-2-yl)phenyl]-1,2,4-oxadiazol-5-yl}ethyl]benzamide, N-[(1S)-2-hydroxy-1-{3-[4-(2-hydroxyethoxy)phenyl]-1,2,4-oxadiazol-5-yl}ethyl]benzamide, N-[(1S)-2-hydroxy-1-(3-{4-[2-morpholin-4-yl)ethoxy]phenyl}-1,2,4-oxadiazol-5-yl)ethyl]benzamide, 4-{(5-[(1S)-2-hydroxy-1-(phenylformamido)ethyl]-1,2,4-oxadiazol-3-yl}phenyl N-ethyl-N-methylcarbamate, 4-fluoro-N-[(1S) 1-{(3-[4-fluoromethyl)phenyl]-1,2,4-oxadiazol-5-yl}-2-hydroxyethyl]benzamide, N-[(1S)-1-{3-[4-(fluoromethyl)phenyl]-1,2,4-oxadiazol-5-yl}-2-hydroxyethyl]benzamide, N-[(1S)-1-[3-(4-bromophenyl)-1,2,4-oxadiazol-5-yl]-2-hydroxyethyl]-4-fluorobenzamide, 4-fluoro-N-[(1S)-2-hydroxy-1-{3-[4-(2,2,2-trifluoroacetyl)phenyl]-1,2,4-oxadiazol-5-yl}ethyl]benzamide, N-[(1S)-2-hydroxy-1-{3-[4-(2,2,2-trifluoroacetyl)phenyl]-1,2,4-oxadiazol-5-yl}ethyl]benzamide, N-[(1S)-1-{3-[4-(difluoromethyl)phenyl]-1,2,4-oxadiazol-5-yl}-2-hydroxyethyl]-4-fluorobenzamide, 4-chloro-N-[(1S)-1-{3-[4-(difluoromethyl)phenyl]-1,2,4-oxadiazol-5-yl}-2-hydroxyethyl]benzamide, N-[(1S)-1-{3-[4-(difluoromethyl)phenyl]-1,2,4-oxadiazol-5-yl}-2-hydroxyethyl]benzamide, 4-(2-ethoxyethoxy)-N-[(1S)-2-hydroxy-1-{3-[4-(trifluoromethoxy)phenyl]-1,2,4-oxadiazol-5-yl}ethyl]benzamide, 4-(2-ethoxyethoxy)-N-[(1S)-2-hydroxy-1-{3-[4-(trifluoromethyl)phenyl]-1,2,4-oxadiazol-5-yl}ethyl]benzamide, 4-[2-(diethylamino)ethoxy]-N-[(1S)-2-hydroxy-1-{3-[4-(trifluoromethoxy)phenyl]-1,2,4-oxadiazol-5-yl}ethyl]benzamide, 4-fluoro-N-[(1S)-1-[3-(4-fluorophenyl)-1,2,4-oxadiazol-5-yl]-2-hydroxyethyl]benzamide, 4-fluoro-N-[(1S)-2-hydroxy-1-[3-(1H-indol-5-yl)-1,2,4-oxadiazol-5-yl]ethyl]benzamide, 4-fluoro-N-[(1S)-2-hydroxy-1-{3-[3-(trifluoromethyl)phenyl]-1,2,4-oxadiazol-5-yl}ethyl]benzamide, N-[(1S)-2-hydroxy-1-{3-[3-(trifluoromethyl)phenyl]-1,2,4-oxadiazol-5-yl}ethyl]benzamide, 4-fluoro-N-[(1S)-2-hydroxy-1-{3-[4-(1H-pyrazol-1-yl)phenyl]-1,2,4-oxadiazol-5-yl]ethyl]benzamide, N-[(1S)-2-hydroxy-1-{3-[4-(1H-pyrazol-1-yl)phenyl]-1,2,4-oxadiazol-5-yl}ethyl]benzamide, 4-fluoro-N-[(1S)-2-hydroxy-1-{(3-[2-(trifluoromethyl)phenyl]-1,2,4-oxadiazol-5-yl}ethyl]benzamide, N-(2-hydroxy-1-{3-[4-(trifluoromethyl)phenyl]-1,2,4-oxadiazol-5-yl}ethyl)-4-(trifluoromethyl)benzamide, N-[(1S)-2-hydroxy-1-{3-[2-(trifluoromethyl)phenyl]-1,2,4-oxadiazol-5-yl}ethyl]benzamide, 4-fluoro-N-[(1S)-1-{3-[4-(3-fluorooxetan-3-yl)phenyl]-1,2,4-oxadiazol-5-yl}-2-hydroxyethyl]benzamide, 4-fluoro-N-[(1S)-1-[3-(3-fluoro-1H-indol-5-yl)-1,2,4-oxadiazol-5-yl]-2-hydroxyethyl]benzamide, 3-chloro-4-fluoro-N-[(1S)-2-hydroxy-1-{3-[4-(trifluoromethyl)phenyl]-1,2,4-oxadiazol-5-yl}ethyl]benzamide, 3,5-difluoro-N-[(1S)-2-hydroxy-1-{3-[4-(trifluoromethyl)phenyl]-1,2,4-oxadiazol-5-yl}ethyl]benzamide, 2,6-difluoro-N-[(1S)-2-hydroxy-1-{(3-[4-(trifluoromethyl)phenyl]-1,2,4-oxadiazol-5-yl}ethyl]benzamide, N-[(1S)-2-hydroxy-1-{3-[4-(trifluoromethyl)phenyl]-1,2,4-oxadiazol-5-yl}ethyl]-4-(trifluoromethoxy)benzamide, N-[(1S)-2-hydroxy-1-{3-[4-(trifluoromethyl)phenyl]-1,2,4-oxadiazol-5-yl}ethyl]-4-(morpholin-4-yl)benzamide, N-[(1S)-2-hydroxy-1-{3-[4-(trifluoromethyl)phenyl]-1,2,4-oxadiazol-5-yl}ethyl]-4-phenoxybenzamide, N-[(1S)-2-hydroxy-1-{3-[4-(trifluoromethyl)phenyl]-1,2,4-oxadiazol-5-yl}ethyl]-4-(pyrrolidin-1-yl)benzamide, 4-(dimethylamino)-N-[(1S)-2-hydroxy-1-{3-[4-(trifluoromethyl)phenyl]-1,2,4-oxadiazol-5-yl}ethyl]benzamide, 4-fluoro-N-[(1S)-2-hydroxy-1-[3-(1H-indol-3-yl)-1,2,4-oxadiazol-5-yl]ethyl]benzamide, 4-fluoro-N-[(1R)-2-hydroxy-1-{3-[4-(trifluoromethyl)phenyl]-1,2,4-oxadiazol-5-yl}ethyl]benzamide, N-[(1R)-2-hydroxy-1-{(3-[4-(trifluoromethyl)phenyl]-1,2,4-oxadiazol-5-yl}ethyl]benzamide, 4-chloro-N-[(1R)-2-hydroxy-1-{3-[4-(trifluoromethyl)phenyl]-1,2,4-oxadiazol-5-yl}ethyl]benzamide, N-[(1S)-1-{3-[3,5-bis(trifluoromethyl)phenyl]-1,2,4-oxadiazol-5-yl}-2-hydroxyethyl]-4-fluorobenzamide, 4-fluoro-N-[(1S)-2-hydroxy-1-{3-[4-(2,2,2-trifluoroethoxy)phenyl]-1,2,4-oxadiazol-5-yl}ethyl]benzamide, 4-fluoro-N-[(1S)-1-{3-[3-fluoro-4-(trifluoromethyl)phenyl]-1,2,4-oxadiazol-5-yl}-2-hydroxyethyl]benzamide, N-[(1S)-1-[3-(3,5-difluorophenyl)-1,2,4-oxadiazol-5-yl]-2-hydroxyethyl]-4-fluorobenzamide, N-[(1S)-1-[3-(2-chloro-4-fluorophenyl)-1,2,4-oxadiazol-5-yl]-2-hydroxyethyl]-4-fluorobenzamide, N-[(1S)-2-hydroxy-1-{3-[3-(trifluoromethyl)phenyl]-1,2,4-oxadiazol-5-yl}ethyl]-4-(morpholin-4-yl)benzamide, N-[(1S)-2-hydroxy-1-{3-[3-(trifluoromethyl)phenyl]-1,2,4-oxadiazol-5-yl}ethyl]-4-(pyrrolidin-1-yl)benzamide, 3-chloro-5-fluoro-N-[(1S)-2-hydroxy-1-{3-[3-(trifluoromethyl)phenyl]-1,2,4-oxadiazol-5-yl}ethyl]benzamide, 4-fluoro-N-[(1S)-2-hydroxy-1-{3-[4-(trimethylsilyl)phenyl]-1,2,4-oxadiazol-5-yl}ethyl]benzamide, N-[(1S)-1-[3-(5-chloro-1H-indol-3-yl)-1,2,4-oxadiazol-5-yl]-2-hydroxyethyl]-4-fluorobenzamide, 4-fluoro-N-[(1S)-1-[3-(5-fluoro-1H-indol-3-yl)-1,2,4-oxadiazol-5-yl]-2-hydroxyethyl] benzamide, 4-chloro-2-fluoro-N-[(1S)-2-hydroxy-1-{3-[4-(trifluoromethyl)phenyl]-1,2,4-oxadiazol-5-yl}ethyl] benzamide, 3-chloro-4-fluoro-N-[(1S)-2-hydroxy-1-{3-[4-(trifluoromethyl)phenyl]-1,2,4-oxadiazol-5-yl}ethyl] benzamide, 3-chloro-4-fluoro-N-[(1S)-2-hydroxy-1-{3-[3-(trifluoromethyl)phenyl]-1,2,4-oxadiazol-5-yl}ethyl] benzamide, 4-fluoro-N-[(1S)-2-hydroxy-1-[3-(1-methyl-1H-indol-3-yl)-1,2,4-oxadiazol-5-yl]ethyl]benzamide, N-[(1S)-1-[3-(5-bromo-1H-indol-3-yl)-1,2,4-oxadiazol-5-yl]-2-hydroxyethyl]-4-fluorobenzamide, 4-fluoro-N-[(1S)-2-hydroxy-1-[3-(1H-indol-6-yl)-1,2,4-oxadiazol-5-yl]ethyl] benzamide, 4-chloro-N-[(1S)-1-[3-(5-chloro-1H-indol-3- yl)-1,2,4-oxadiazol-5-yl]-2-hydroxyethyl]-2-fluorobenzamide, N-[(1S)-1-[3-(5-chloro-1H-indol-3-yl)-1,2,4-oxadiazol-5-yl]-2-hydroxyethyl]-4-(pyrrolidin-1-yl)benzamide, 5-chloro-N-[(1S)-1-[3-(5-chloro-1H-indol-3-yl)-1,2,4-oxadiazol-5-yl]-2-hydroxyethyl]pyridine-2-carboxamide, 4-fluoro-N-[(1S)-2-hydroxy-1-{3-[3-(2,2,2-trifluoroacetyl)-1H-indol-6-yl]-1,2,4-oxadiazol-5-yl}ethyl]benzamide, 4-fluoro-N-[(1S)-1-[3-(6-fluoro-1H-indol-3-yl)-1,2,4-oxadiazol-5-yl]-2-hydroxyethyl]benzamide, 4-fluoro-N-[(1S)-2-hydroxy-1-[3-(5-methoxy-1H-indol-3-yl)-1,2,4-oxadiazol-5-yl]ethyl]benzamide, 4-fluoro-N-[(1S)-2-hydroxy-1-{3-[5-(trifluoromethyl)-1H-indol-3-yl]-1,2,4-oxadiazol-5-yl]ethyl]benzamide, N-[(1S)-1-[3-(6-chloro-1H-indol-3-yl)-1,2,4-oxadiazol-5-yl]-2-hydroxyethyl]-4-fluorobenzamide, 4-fluoro-N-[(1S)-2-hydroxy-1-{3-[1-(2-hydroxyethyl)-1H-indol-3-yl]-1,2,4-oxadiazol-5-yl}ethyl]benzamide, 4-fluoro-N-[(1S)-2-hydroxy-1-[3-(1H-indol-2-yl)-1,2,4-oxadiazol-5-yl]ethyl]benzamide and 4-fluoro-N-[(1S)-1-[3-(5-fluoro-1H-indol-2-yl)-1,2,4-oxadiazol-5-yl]-2-hydroxyethyl]benzamide; or a pharmaceutically acceptable salt thereof or a solvate thereof.

4. The amyloid fibril formation inhibitor according to claim 3, wherein the compound is selected from the group consisting of (S)-4-chloro-N-(2-hydroxy-1-[3-{4-(trifluoromethoxy)phenyl}-1,2,4-oxadiazol-5-yl]ethyl)benzamide, (S)-3-chloro-N-(2-hydroxy-1-[3-{4-(trifluoromethoxy)phenyl}-1,2,4-oxadiazol-5-yl]ethyl)benzamide, (S)-4-fluoro-N-(2-hydroxy-1-[3-{4-(trifluoromethoxy)phenyl}-1,2,4-oxadiazol-5-yl]ethyl)benzamide, 4-chloro-N-[2-hydroxy-1-{3-(4-hydroxyphenyl)-1,2,4-oxadiazol-5-yl}ethyl]benzamide, (R)-4-chloro-N-(2-hydroxy-1-[3-{4-(trifluoromethoxy)phenyl}-1,2,4-oxadiazol-5-yl]ethyl)benzamide, (S)-N-(2-hydroxy-1-[3-{4-(trifluoromethoxy)phenyl}-1,2,4-oxadiazol-5-yl]ethyl)benzamide, (S)-2-fluoro-N-(2-hydroxy-1-[3-{4-(trifluoromethoxy)phenyl}-1,2,4-oxadiazol-5-yl]ethyl)benzamide, (S)-3-fluoro-N-(2-hydroxy-1-[3-{4-(trifluoromethoxy)phenyl}-1,2,4-oxadiazol-5-yl]ethyl)benzamide, (S)-4-chloro-N-(1-(3-(3-fluoro-4-hydroxyphenyl)-1,2,4-oxadiazol-5-yl)-2-hydroxyethyl)benzamide, (S)-4-cyano-N-(1-(3-(3-fluoro-4-hydroxyphenyl)-1,2,4-oxadiazol-5-yl)-2-hydroxyethyl)benzamide, (S)-4-chloro-N-(2-hydroxy-1-(5-(4-(trifluoromethoxy)phenyl)-1,3,4-oxadiazol-2-yl)ethyl)benzamide, (S)-4-chloro-N-(1-(5-(3-cyanophenyl)-1,3,4-oxadiazol-2-yl)-2-hydroxyethyl)benzamide, (R)-4-chloro-N-(2-hydroxy-1-(5-(4-(trifluoromethoxy)phenyl)-1,3,4-oxadiazol-2-yl)ethyl)benzamide, (S)-4-fluoro-N-(2-hydroxy-1-(5-(4-(trifluoromethoxy)phenyl)-1,3,4-oxadiazol-2-yl)ethyl)benzamide, (S)-4-chloro-N-(2-hydroxy-1-(3-(4-methoxyphenyl)-1,2,4-oxadiazol-5-yl ethyl)benzamide, (R)-4-chloro-N-(2-hydroxy-1-(5-(4-(trifluoromethoxy)phenyl)-1,2,4-oxadiazol-3-yl)ethyl)benzamide, (R)-N-(2-hydroxy-1-(5-(4-(trifluoromethoxy)phenyl)-1,2,4-oxadiazol-3-yl)ethyl)benzamide, (S)-4-chloro-N-(2-hydroxy-1-(3-(4-(trifluoromethyl)phenyl)-1,2,4-oxadiazol-5-yl)ethyl)benzamide, (S)-N-(2-hydroxy-1-(3-(4-(trifluoromethyl)phenyl)-1,2,4-oxadiazol-5-yl)ethyl)benzamide, (S)-4-fluoro-N-(2-hydroxy-1-(3-(4-(trifluoromethyl)phenyl)-1,2,4-oxadiazol-5-yl)ethyl)benzamide, N-[(1S)-1-[3-(2-fluoro-4-hydroxyphenyl)-1,2,4-oxadiazol-5-yl]-2-hydroxyethyl]benzamide, N-[(1S)-2-hydroxy-1-[3-(4-methylphenyl)-1,2,4-oxadiazol-5-yl]ethyl]benzamide, N-[(1S)-1-[3-(3-fluoro-4-methoxyphenyl)-1,2,4-oxadiazol-5-yl]-2-hydroxyethyl]benzamide, N-[(1S)-2-hydroxy-1-{3-[4-(propan-2-yl)phenyl]-1,2,4-oxadiazol-5-yl}ethyl]benzamide, N-[(1S)-2-hydroxy-1-[3-(4-hydroxyphenyl)-1,2,4-oxadiazol-5-yl]ethyl]benzamide, 4-{5-[(1S)-1-[(4-fluorophenyl)formamido]-2-hydroxyethyl]-1,2,4-oxadiazol-3-yl}-N-(3-methoxypropyl)benzamide, 4-{5-[(1S)-2-hydroxy-1-(phenylformamido)ethyl]-1,2,4-oxadiazol-3-yl}-N-(3-methoxypropyl)benzamide, N-[(1S)-1-{3-[4-(dimethylamino)phenyl]-1,2,4-oxadiazol-5-yl}-2-hydroxyethyl]benzamide, 4-fluoro-N-[(1R)-2-hydroxy-1-{3-[4-(trifluoromethyl)phenyl]-1,2,4-oxadiazol-5-yl}ethyl]benzamide, N-[(1S)-1-[3-(4-acetylphenyl)-1,2,4-oxadiazol-5-yl]-2-hydroxyethyl]benzamide, N-[(1S)-2-hydroxy-1-{3-[4-(2-hydroxyethoxy)phenyl]-1,2,4-oxadiazol-5-yl}ethyl]benzamide, N-[(1S)-2-hydroxy-1-(3-{4-[2-(morpholin-4-yl)ethoxy]phenyl}-1,2,4-oxadiazol-5-yl)ethyl]benzamide, 4-fluoro-N-[(1S)-1-{3-[4-(fluoromethyl)phenyl]-1,2,4-oxadiazol-5-yl}-2-hydroxyethyl]benzamide, N-[(1S')-1-{3-[4-(fluoromethyl)phenyl]-1,2,4-oxadiazol-5-yl}-2-hydroxyethyl]benzamide, N-[(1S)-1-[3-(4-bromophenyl)-1,2,4-oxadiazol-5-yl]-2-hydroxyethyl]-4-fluorobenzamide, 4-fluoro-N-[(1S)-2-hydroxy-1-{3-[4-(2,2,2-trifluoroacetyl)phenyl]-1,2,4-oxadiazol-5-yl}ethyl]benzamide, N-[(1S)-2-hydroxy-1-{3-[4-(2,2,2-trifluoroacetyl)phenyl]-1,2,4-oxadiazol-5-yl}ethyl]benzamide, N-[(1S)-1-{3-[4-(difluoromethyl)phenyl]-1,2,4-oxadiazol-5-yl}-2-hydroxyethyl]-4-fluorobenzamide, 4-chloro-N-[(1S)-1-{3-[4-(difluoromethyl)phenyl]-1,2,4-oxadiazol-5-yl}-2-hydroxyethyl]benzamide, N-[(1S)-1-{3-[4-(difluoromethyl)phenyl]-1,2,4-oxadiazol-5-yl}-2-hydroxyethyl]benzamide, 4-(2-ethoxyethoxy)-N-[(1S)-2-hydroxy-1-{3-[4-(trifluoromethoxy)phenyl]-1,2,4-oxadiazol-5-yl}ethyl]benzamide, 4-(2-ethoxyethoxy)-N-[(1S)-2-hydroxy-1-{3-[4-(trifluoromethyl)phenyl]-1,2,4-oxadiazol-5-yl}ethyl]benzamide, 4-fluoro-N-[(1S)-1-[3-(4-fluorophenyl)-1,2,4-oxadiazol-5-yl]-2-hydroxyethyl]benzamide, 4-fluoro-N-[(1S)-2-hydroxy-1-[3-(1H-indol-5-yl)-1,2,4-oxadiazol-5-yl]ethyl]benzamide, 4-fluoro-N-[(1S)-2-hydroxy-1-{3-[3-(trifluoromethyl)phenyl]-1,2,4-oxadiazol-5-yl}ethyl]benzamide, N-[(1S)-2-hydroxy-1-{3-[3-(trifluoromethyl)phenyl]-1,2,4-oxadiazol-5-yl}ethyl]benzamide, 4-fluoro-N-[(1S)-2-hydroxy-1-{3-[4-(1H-pyrazol-1-yl)phenyl]-1,2,4-oxadiazol-5-yl}ethyl]benzamide, 4-fluoro-N-[(1S)-2-hydroxy-1-{3-[2-(trifluoromethyl)phenyl]-1,2,4-oxadiazol-5-yl}ethyl]benzamide, N-(2-hydroxy-1-{3-[4-(trifluoromethyl)phenyl]-1,2,4-oxadiazol-5-yl}ethyl)-4-(trifluoromethyl)benzamide, N-[(1S)-2-hydroxy-1-{3-[2-(trifluoromethyl)phenyl]-1,2,4-oxadiazol-5-yl}ethyl]benzamide, 4-fluoro-N-[(1S)-1-{3-[4-(3-fluorooxetan-3-yl)phenyl]-1,2,4-oxadiazol-5-yl}-2-hydroxyethyl]benzamide, 4-fluoro-N-[(1S)-1-[3-(3-fluoro-1H-indol-5-yl)-1,2,4-oxadiazol-5-yl]-2-hydroxyethyl]benzamide, 3-chloro-4-fluoro-N-[(1S)-2-hydroxy-1-{3-[4-(trifluoromethyl)phenyl]-1,2,4-oxadiazol-5-yl}ethyl]benzamide, 3,5-difluoro-N-[(1S)-2-hydroxy-1-{3-[4-(trifluoromethyl)phenyl]-1,2,4-oxadiazol-5-yl}ethyl]benzamide, 2,6-difluoro-N-[(1S)-2-hydroxy-1-{3-[4-(trifluoromethyl)phenyl]-1,2,4-oxadiazol-5-yl}ethyl]benzamide, N-[(1S)-2-hydroxy-1-{3-[4-(trifluoromethyl)phenyl]-1,2,4-oxadiazol-5-yl}ethyl]-4-(trifluoromethoxy)benzamide, N-[(1S)-2-hydroxy-1-{3-[4-(trifluoromethyl)phenyl]-1,2,4-oxadiazol-5-yl}ethyl]-4-(morpholin-4-yl)benzamide, N-[(1S)-2-hydroxy-1-{3-[4-(trifluoromethyl)phenyl]-1,2,4-oxadiazol-5-yl}ethyl]-4-phenoxybenzamide, N-[(1S)-2-hydroxy-1-{(3-[4-(trifluoromethyl)phenyl]-1,2,4-oxadiazol-5-yl}ethyl]-4-(pyrrolidin-1-yl)benzamide, 4-(dimethylamino)-N-[(1S)-2-hydroxy-1-{3-[4-(trifluoromethyl)phenyl]-1,2,4-oxadiazol-5-yl}ethyl]benzamide, 4-fluoro-N-[(1S)-2-hydroxy-1-[3-(1H-indol-3-yl)-1,2,4-oxadiazol-5-yl]ethyl]benzamide, 4-fluoro-N-[(1R)-2-hydroxy-1-{3-[4-(trifluoromethyl)phenyl]-1,2,4-oxadiazol-5- yl}ethyl]benzamide, 4-chloro-N-[(1R)-2-hydroxy-1-{3-[4-(trifluoromethyl)phenyl]-1,2,4-oxadiazol-5-yl}ethyl]benzamide, N-[(1S)-1-{3-[3,5-bis(trifluoromethyl)phenyl]-1,2,4-oxadiazol-5-yl}-2-hydroxyethyl]-4-fluorobenzamide, 4-fluoro-N-[(1S)-1-{3-[3-fluoro-4-(trifluoromethyl)phenyl]-1,2,4-oxadiazol-5-yl}-2-hydroxyethyl]benzamide, N-[(1S)-1-[3-(3,5-difluorophenyl)-1,2,4-oxadiazol-5-yl]-2-hydroxyethyl]-4-fluorobenzamide, N-[(1S)-2-hydroxy-1-{3-[3-(trifluoromethyl)phenyl]-1,2,4-oxadiazol-5-yl}ethyl]-4-(morpholin-4-yl)benzamide, N-[(1S)-2-hydroxy-1-{3-[3-(trifluoromethyl)phenyl]-1,2,4-oxadiazol-5-yl}ethyl]-4-(pyrrolidin-1-yl)benzamide, 3-chloro-5-fluoro-N-[(1S)-2-hydroxy-1-{3-[3-(trifluoromethyl)phenyl]-1,2,4-oxadiazol-5-yl}ethyl]benzamide, 4-fluoro-N-[(1S)-2-hydroxy-1-{3-[4-(trimethylsilyl)phenyl]-1,2,4-oxadiazol-5-yl}ethyl]benzamide, N-[(1S)-1-[3-(5-chloro-1H-indol-3-yl)-1,2,4-oxadiazol-5-yl]-2-hydroxyethyl]-4-fluorobenzamide, 4-fluoro-N-[(1S)-1-[3-(5-fluoro-1H-indol-3-yl)-1,2,4-oxadiazol-5-yl]-2-hydroxyethyl]benzamide, 4-chloro-2-fluoro-N-[(1S)-2-hydroxy-1-{3-[4-(trifluoromethyl)phenyl]-1,2,4-oxadiazol-5-yl}ethyl]benzamide, 3-chloro-4-fluoro-N-[(1S)-2-hydroxy-1-{3-[4-(trifluoromethyl)phenyl]-1,2,4-oxadiazol-5-yl}ethyl]benzamide, 3-chloro-4-fluoro-N-[(1S)-2-hydroxy-1-{3-[3-(trifluoromethyl)phenyl]-1,2,4-oxadiazol-5-yl}ethyl]benzamide, 4-fluoro-N-[(1S)-2-hydroxy-1-r[3-(1-methyl-1H-indol-3-yl)-1,2,4-oxadiazol-5-yl]ethyl]benzamide, N-[(1S)-1-[3-(5-bromo-1H-indol-3-yl)-1,4-oxadiazol-5-yl]-2-hydroxyethyl]-4-fluorobenzamide, 4-fluoro-N-[(1S)-2-hydroxy-1-[3-(1H-indol-6-yl)-1,2,4-oxadiazol-5-yl]ethyl]benzamide, 4-chloro-N-[(1S)-1-[3-(5-chloro-1H-indol-3-yl)-1,2,4-oxadiazol-5-yl]-2-hydroxyethyl]-2-fluorobenzamide, N-[(1S)-1-[3-(5-chloro-1H-indol-3-yl)-1,2,4-oxadiazol-5-yl]-2-hydroxyethyl]-4-(pyrrolidin-1-yl)benzamide, 5-chloro-N-[(1S)-1-[3-(5-chloro-1H-indol-3-yl)-1,2,4-oxadiazol-5-yl]-2-hydroxyethyl]pyridine-2-carboxamide, 4-fluoro-N-[(1S)-2-hydroxy-1-{3-[3-(2,2,2-trifluoroacetyl)-1H-indol-6-yl]-1,2,4-oxadiazol-5-yl}ethyl]benzamide, 4-fluoro-N-[(1S)-1-[3-(6-fluoro-1H-indol-3-yl)-1,2,4-oxadiazol-5-yl]-2-hydroxyethyl]benzamide, 4-fluoro-N-[(1S)-2-hydroxy-1-[3-(5-methoxy-1H-indol-3-yl)-1,2,4-oxadiazol-5-yl]ethyl]benzamide, 4-fluoro-N-[(1S)-2-hydroxy-1-{3-[5-(trifluoromethyl)-1H-indol-3-yl]-1,2,4-oxadiazol-5-yl}ethyl]benzamide, N-[(1S)-1-[3-(6-chloro-1H-indol-3-yl)-1,2,4-oxadiazol-5-yl]-2-hydroxyethyl]-4-fluorobenzamide, 4-fluoro-N-[(1S)-2-hydroxy-1-{3-[1-(2-hydroxyethyl)-1H-indol-3-yl]-1,2,4-oxadiazol-5-yl}ethyl]benzamide, 4-fluoro-N-[(1S)-2-hydroxy-1-[3-(1H-indol-2-yl)-1,2,4-oxadiazol-5-yl]ethyl]benzamide and 4-fluoro-N-[(1S)-1-[3-(5-fluoro-1H-indol-2-yl)-1,2,4-oxadiazol-5-yl]-2-hydroxyethyl]benzamide.

5. The fibril formation inhibitor according to claim 3 wherein the compound is selected from the group consisting of (S)-4-chloro-N-(2-hydroxy-1-[3-{4-(trifluoromethoxy)phenyl}-1,2,4-oxadiazol-5-yl]ethyl)benzamide, (S)-3-chloro-N-(2-hydroxy-1-[3-{4-(trifluoromethoxy)phenyl}-1,2,4-oxadiazol-5-yl]ethyl)benzamide, (S)-4-fluoro-N-(2-hydroxy-1-[3-{4-(trifluoromethoxy)phenyl}-1,2,4-oxadiazol-5-yl]ethyl)benzamide, 4-chloro-N-[2-hydroxy-1-{3-(4-hydroxyphenyl)-1,2,4-oxadiazol-5-yl}ethyl]benzamide, (R)-4-chloro-N-(2-hydroxy-1-[3-{4-(trifluoromethoxy)phenyl}-1,2,4-oxadiazol-5-yl]ethyl)benzamide, (S)-N-(2-hydroxy-1-[3-{4-(trifluoromethoxy)phenyl}-1,2,4-oxadiazol-5-yl]ethyl)benzamide, (S)-2-fluoro-N-(2-hydroxy-1-[3-{4-(trifluoromethoxy)phenyl}-1,2,4-oxadiazol-5-yl]ethyl)benzamide, (S)-3-fluoro-N-(2-hydroxy-1-[3-{4-(trifluoromethoxy)phenyl}-1,2,4-oxadiazol-5-yl]ethyl)benzamide, (S)-4-chloro-N-(2-hydroxy-1-(3-(4-methoxyphenyl)-1,2,4-oxadiazol-5-yl)ethyl)benzamide, (S)-4-chloro-N-(2-hydroxy-1-(3-(4-(trifluoromethyl)phenyl)-1,2,4-oxadiazol-5-yl ethyl)benzamide, (S)-N-(2-hydroxy-1-(3-(4-(trifluoromethyl)phenyl)-1,2,4-oxadiazol-5-yl)ethyl)benzamide, (S)-4-fluoro-N-(2-hydroxy-1-(3-(4-(trifluoromethyl)phenyl)-1,2,4-oxadiazol-5-yl)ethyl)benzamide, N-[(1S)-2-hydroxy-1-[3-(4-methylphenyl)-1,2,4-oxadiazol-5-yl]ethyl]benzamide, N-[(1S)-1-[3-(3-fluoro-4-methoxyphenyl)-1,2,4-oxadiazol-5-yl]-2-hydroxyethyl]benzamide, N-[(1S)-2-hydroxy-1-[3-(4-hydroxyphenyl)-1,2,4-oxadiazol-5-yl]ethyl]benzamide, N-[(1S)-1-{3-[4-(dimethylamino)phenyl]-1,2,4-oxadiazol-5-yl}-2-hydroxyethyl]benzamide, 4-fluoro-N-[(1S)-2-hydroxy-1-{3-[4-(2,2,2-trifluoroacetyl)phenyl]-1,2,4-oxadiazol-5-yl}ethyl]benzamide, N-[(1S)-2-hydroxy-1-{3-[4-(2,2,2-trifluoroacetyl)phenyl]-1,2,4-oxadiazol-5-yl}ethyl]benzamide, 4-chloro-N-[(1S)-1-{3-[4-(difluoromethyl)phenyl]-1,2,4-oxadiazol-5-yl}-2-hydroxyethyl]benzamide, N-[(1S)-1-{3-[4-(difluoromethyl)phenyl]-1,2,4-oxadiazol-5-yl}-2-hydroxyethyl]benzamide, 4-fluoro-N-[(1S)-1-[3-(4-fluorophenyl)-1,2,4-oxadiazol-5-yl]-2-hydroxyethyl]benzamide, 4-fluoro-N-[(1S)-2-hydroxy-1-[3-(1H-indol-5-yl)-1,2,4-oxadiazol-5-yl]ethyl]benzamide, 4-fluoro-N-[(1S)-2-hydroxy-1-{3-[3-(trifluoromethyl)phenyl]-1,2,4-oxadiazol-5-yl}ethyl]benzamide, N-[(1S)-2-hydroxy-1-{3-[3-(trifluoromethyl)phenyl]-1,2,4-oxadiazol-5-yl}ethyl]benzamide, N-(2-hydroxy-1-{3-[4-(trifluoromethyl)phenyl]-1,2,4-oxadiazol-5-yl}ethyl)-4-(trifluoromethyl)benzamide, 3-chloro-4-fluoro-N-[(1S)-2-hydroxy-1-{3-[4-(trifluoromethyl)phenyl]-1,2,4-oxadiazol-5-yl}ethyl]benzamide, 3,5-difluoro-N-[(1S)-2-hydroxy-1-{3-[4-(trifluoromethyl)phenyl]-1,2,4-oxadiazol-5-yl}ethyl]benzamide, N-[(1S)-2-hydroxy-1-{3-[4-(trifluoromethyl)phenyl]-1,2,4-oxadiazol-5-yl}ethyl]-4-(trifluoromethoxy)benzamide, N-[(1S)-2-hydroxy-1-{3-[4-(trifluoromethyl)phenyl]-1,2,4-oxadiazol-5-yl}ethyl]-4-phenoxybenzamide, N-[(1S)-2-hydroxy-1-{3-[4-(trifluoromethyl)phenyl]-1,2,4-oxadiazol-5-yl}ethyl]-4-(pyrrolidin-1-yl)benzamide, 4-(dimethylamino)-N-[(1S)-2-hydroxy-1-{3-[4-(trifluoromethyl)phenyl]-1,2,4-oxadiazol-5-yl}ethyl]benzamide, 4-fluoro-N-[(1S)-2-hydroxy-1-[3-(1H-indol-3-yl)-1,2,4-oxadiazol-5-yl]ethyl]benzamide, 3-chloro-5-fluoro-N-[(1S)-2-hydroxy-1-{3-[3-(trifluoromethyl)phenyl]-1,2,4-oxadiazol-5-yl}ethyl]benzamide, 4-fluoro-N-[(1S)-2-hydroxy-1-{3-[4-(trimethylsilyl)phenyl]-1,2,4-oxadiazol-5-yl}ethyl]benzamide, 4-chloro-2-fluoro-N-[(1S)-2-hydroxy-1-{3-[4-(trifluoromethyl)phenyl]-1,2,4-oxadiazol-5-yl}ethyl]benzamide, 3-chloro-4-fluoro-N-[(1S)-2-hydroxy-1-{3-[4-(trifluoromethyl)phenyl]-1,2,4-oxadiazol-5-yl}ethyl]benzamide, 4-fluoro-N-[(1S)-2-hydroxy-1-[3-(1H-indol-2-yl)-1,2,4-oxadiazol-5-yl]ethyl]benzamide and 4-fluoro-N-[(1S)-1-[3-(5-fluoro-1H-indol-2-yl)-1,2,4-oxadiazol-5-yl]-2-hydroxyethyl]benzamide.

6. A compound selected from the group consisting of (S)-4-chloro-N-(2-hydroxy-1-[3-{4-(trifluoromethoxy)phenyl}-1,2,4-oxadiazol-5-yl]ethyl)benzamide, (S)-3-chloro-N-(2-hydroxy-1-[3-{4-(trifluoromethoxy)phenyl}-1,2,4-oxadiazol-5-yl]ethyl)benzamide, (S)-4-fluoro-N-(2-hydroxy-1-[3-{4-(trifluoromethoxy)phenyl}-1,2,4-oxadiazol-5-yl]ethyl)benzamide, 4-chloro-N-[2-hydroxy-1-{3-(4-hydroxyphenyl)-1,2,4-oxadiazol-5-yl}ethyl]benzamide, (R)-4-chloro-N-(2-hydroxy-1-[3-{4-(trifluoromethoxy)phenyl}-1,2,4-oxadiazol-5-yl]ethyl)benzamide, (S)-N-(2-hydroxy-1-[3-{4-(trifluoromethoxy)phenyl}-1,2,4-oxadiazol-5-yl]ethyl)benzamide, (S)-2-fluoro-N-(2-hydroxy-1-[3-{4-(trifluoromethoxy)phenyl}-1,2,4-oxadiazol-5-yl]ethyl)

benzamide, (S)-3-fluoro-N-(2-hydroxy-1-[3-{4-(trifluoromethoxy)phenyl}-1,2,4-oxadiazol-5-yl]ethyl)benzamide, (S)-3-chloro-4-hydroxy-N-(2-hydroxy-1-[3-{4-(trifluoromethoxy)phenyl}-1,2,4-oxadiazol-5-yl]ethyl)benzamide, (S)-4-chloro-N-(1-(3-(3-fluoro-4-hydroxyphenyl)-1,2,4-oxadiazol-5-yl)-2-hydroxyethyl)benzamide, (S)-4-cyano-N-(1-(3-(3-fluoro-4-hydroxyphenyl)-1,2,4-oxadiazol-5-yl)-2-hydroxyethyl)benzamide, (S)-4-chloro-N-(2-hydroxy-1-(5-(4-(trifluoromethoxy)phenyl)-1,3,4-oxadiazol-2-yl)ethyl)benzamide, (S)-4-chloro-N-(2-hydroxy-1-(5-(4-(methylsulfonamido)phenyl)-1,3,4-oxadiazol-2-yl)ethyl)benzamide, (S)-4-chloro-N-(1-(5-(3-cyanophenyl)-1,3,4-oxadiazol-2-yl)-2-hydroxyethyl)benzamide, (R)-4-chloro-N-(2-hydroxy-1-(5-(4-(trifluoromethoxy)phenyl)-1,3,4-oxadiazol-2-yl ethyl)benzamide, (R)-4-chloro-N-(2-hydroxy-1-(5-(4-(methylsulfonamido)phenyl)-1,3,4-oxadiazol-2-yl)ethyl)benzamide, (R)-4-chloro-N-(1-(5-(3-cyanophenyl)-1,3,4-oxadiazol-2-yl)-2-hydroxyethyl)benzamide, (S)-4-fluoro-N-(2-hydroxy-1-(5-(4-(trifluoromethoxy)phenyl)-1,3,4-oxadiazol-2-yl)ethyl)benzamide, (S)-4-chloro-N-(1-(5-(3-fluoro-4-methoxyphenyl)-1,3,4-oxadiazol-2-yl)-2-hydroxyethyl)benzamide, (S)-4-chloro-N-(1-(5-(3-fluoro-4-hydroxyphenyl)-1,3,4-oxadiazol-2-yl)-2-hydroxyethyl)benzamide, (S)-4-chloro-N-(2-hydroxy-1-(3-(4-methoxyphenyl)-1,2,4-oxadiazol-5-yl)ethyl)benzamide, (R)-4-chloro-N-(2-hydroxy-1-(5-(4-(trifluoromethoxy)phenyl)-1,2,4-oxadiazol-3-yl)ethyl)benzamide, (R)-N-(2-hydroxy-1-(5-(4-(trifluoromethoxy)phenyl)-1,2,4-oxadiazol-3-yl)ethyl)benzamide, (S)-4-chloro-N-(2-hydroxy-1-(3-(4-(trifluoromethyl)phenyl)-1,2,4-oxadiazol-5 yl)ethyl)benzamide, (S)-N-(2-hydroxy-1-(3-(4-(trifluoromethyl)phenyl)-1,2,4-oxadiazol-5-yl)ethyl)benzamide, (S)-4-fluoro-N-(2-hydroxy-1-(3-(4-(trifluoromethyl)phenyl)-1,2,4-oxadiazol-5-yl)ethyl)benzamide, N-[(1S)-1-[3-(2-fluoro-4-hydroxyphenyl)-1,2,4-oxadiazol-5-yl]-2-hydroxyethyl]benzamide, N-[(1S)-2-hydroxy-1-[3-(4-methylphenyl)-1,2,4-oxadiazol-5-yl]ethyl]benzamide, N-[(1S)-1-[3-(3-fluoro-4-methoxyphenyl)-1,2,4-oxadiazol-5-yl]-2-hydroxyethyl]benzamide, N-[(1S)-2-hydroxy-1-{3-[4-(propan-2-yl)phenyl]-1,2,4-oxadiazol-5-yl}ethyl]benzamide, N-[(1S)-2-hydroxy-1-[3-(4-hydroxyphenyl)-1,2,4-oxadiazol-5-yl]ethyl]benzamide, 4-{5-[(1S)-1-[(4-fluorophenyl)formamido]-2-hydroxyethyl]-1,2,4-oxadiazol-3-yl}-N-(3-methoxypropyl)benzamide, 4-{5-[(1S)-2-hydroxy-1-(phenylformamido)ethyl]-1,2,4-oxadiazol-3-yl}-N-(3-methoxypropyl)benzamide, N-[(1S)-1-{3-[4-(dimethylamino)phenyl]-1,2,4-oxadiazol-5-yl}-2-hydroxyethyl]benzamide, 4-fluoro-N-[(1R)-2-hydroxy-1-{3-[4-(trifluoromethyl)phenyl]-1,2,4-oxadiazol-5-yl}ethyl]benzamide, N-[(1S)-1-[3-(4-acetylphenyl)-1,2,4-oxadiazol-5-yl]-2-hydroxyethyl]benzamide, N-[(1S)-2-hydroxy-1-{3-[4-(1-hydroxyethyl)phenyl]-1,2,4-oxadiazol-5-yl}ethyl]benzamide, N-[(1S)-2-hydroxy-1-{3-[4-(2-hydroxypropan-2-yl)phenyl]-1,2,4-oxadiazol-5-yl}ethyl]benzamide, N-[(1S)-2-hydroxy-1-{3-[4-(2-hydroxyethoxy)phenyl]-1,2,4-oxadiazol-5-yl}ethyl]benzamide, N-[(1S) 2=hydroxy-1-(3-{4-[2-(morpholin-4-yl)ethoxy]phenyl}-1,2,4-oxadiazol-5-yl)ethyl]benzamide, 4-{5-[(1S)-2-hydroxy-1-(phenylformamido)ethyl]-1,2,4-oxadiazol-3-yl}phenyl N-ethyl-N-methylcarbamate, 4-fluoro-N-[(1S)-1-{3-[4-(fluoromethyl)phenyl]-1,2,4-oxadiazol-5-yl}-2-hydroxyethyl]benzamide, N-[(1S)-1-{3-[4-(fluoromethyl)phenyl]-1,2,4-oxadiazol-5-yl}-2-hydroxyethyl]benzamide, N-[(1S)-1-[3-(4-bromophenyl)-1,2,4-oxadiazol-5-yl]-2-hydroxyethyl]-4-fluorobenzamide, 4-fluoro-N-[(1S) 2-hydroxy-1-{3-[4-(2,2,2-trifluoroacetyl)phenyl]-1,2,4-oxadiazol-5-yl}ethyl]benzamide, N-[(1S)-2-hydroxy-1-{3-[4-(2,2,2-trifluoroacetyl)phenyl]-1,2,4-oxadiazol-5-yl}ethyl]benzamide, N-[(1S)-1-{3-[4-(difluoromethyl)phenyl]-1,2,4-oxadiazol-5-yl}-2-hydroxyethyl]-4-fluorobenzamide, 4-chloro-N-[(1S)-1-{3-[4-(difluoromethyl)phenyl]-1,2,4-oxadiazol-5-yl}-2-hydroxyethyl]benzamide, N-[(1S)-1-{3-[4-(difluoromethyl)phenyl]-1,2,4-oxadiazol-5-yl}-2-hydroxyethyl]benzamide, 4-(2-ethoxyethoxy)-N-[(1S)-2-hydroxy-1-{3-[4-(trifluoromethoxy)phenyl]-1,2,4-oxadiazol-5-yl}ethyl]benzamide, 4-(2-ethoxyethoxy)-N-[(1S)-2-hydroxy-1-{3-[4-(trifluoromethyl)phenyl]-1,2,4-oxadiazol-5-yl}ethyl]benzamide, 4-[2-(diethylamino)ethoxy]-N-[(1S)-2-hydroxy-1-{3-[4-(trifluoromethoxy)phenyl]-1,2,4-oxadiazol-5-yl}ethyl]benzamide, 4-fluoro-N-[(1S)-1-[3-(4-fluorophenyl)-1,2,4-oxadiazol-5-yl]-2-hydroxyethyl]benzamide, 4-fluoro-N-[(1S)-2-hydroxy-1-[3-(1H-indol-5-yl)-1,2,4-oxadiazol-5-yl] ethyl]benzamide, 4-fluoro-N-[(1S)-2-hydroxy-1-{3-[3-(trifluoromethyl)phenyl]-1,2,4-oxadiazol-5-yl}ethyl]benzamide, N-[(1S)-2-hydroxy-1-{3-[3-(trifluoromethyl)phenyl]-1,2,4-oxadiazol-5-yl}ethyl]benzamide, 4-fluoro-N-[(1S)-2-hydroxy-1-{3-[4-(1H-pyrazol-1-yl)phenyl]-1,2,4-oxadiazol-5-yl}ethyl]benzamide, N-[(1S)-2-hydroxy-1-{3-[4-(1H-pyrazol-1-yl)phenyl]-1,2,4-oxadiazol-5-yl}ethyl]benzamide, 4-fluoro-N-[(1S)-2-hydroxy-1-{3-[2-(trifluoromethyl)phenyl]-1,2,4-oxadiazol-5-yl}ethyl]benzamide, N-[(1S)-2-hydroxy-1-{3-[2-(trifluoromethyl)phenyl]-1,2,4-oxadiazol-5-yl}ethyl]benzamide, N-(2-hydroxy-1-{3-[4-(trifluoromethyl)phenyl]-1,2,4-oxadiazol-5-yl}ethyl)-4-(trifluoromethyl)benzamide, N-[(1S)-2-hydroxy-1-{3-[2-(trifluoromethyl)phenyl]-1,2,4-oxadiazol-5-yl}ethyl]benzamide, 4-fluoro-N-[(1S)-1-{3-[4-(3-fluorooxetan-3-yl)phenyl]-1,2,4-oxadiazol-5-yl}-2-hydroxyethyl]benzamide, 4-fluoro-N-[(1S)-1-[3-(3-fluoro-1H-indol-5-yl)-1,2,4-oxadiazol-5-yl]-2-hydroxyethyl]benzamide, 3-chloro-4-fluoro-N-[(1S)-2-hydroxy-1-{3-[4-(trifluoromethyl)phenyl]-1,2,4-oxadiazol-5-yl}ethyl]benzamide, 3,5-difluoro-N-[(1S)-2-hydroxy-1-{3-[4-(trifluoromethyl)phenyl]-1,2,4-oxadiazol-5-yl}ethyl]benzamide, 2,6-difluoro-N-[(1S)-2-hydroxy-1-{3-[4-(trifluoromethyl)phenyl]-1,2,4-oxadiazol-5-yl}ethyl]benzamide, N-[(1S)-2-hydroxy-1-{3-[4-(trifluoromethyl)phenyl]-1,2,4-oxadiazol-5-yl}ethyl]-4-(trifluoromethoxy)benzamide, N-[(1S)-2-hydroxy-1-{3-[4-(trifluoromethyl)phenyl]-1,2,4-oxadiazol-5-yl}ethyl]-4-(morpholin-4-yl)benzamide, N-[(1S)-2-hydroxy-1-{3-[4-(trifluoromethyl)phenyl]-1,2,4-oxadiazol-5-yl}ethyl]-4-phenoxybenzamide, N-[(1S)-2-hydroxy-1-{3-[4-(trifluoromethyl)phenyl]-1,2,4-oxadiazol-5-yl}ethyl]-4-(pyrrolidin-1-yl)benzamide, 4-(dimethylamino)-N-[(1S)-2-hydroxy-1-{3-[4-(trifluoromethyl)phenyl]-1,2,4-oxadiazol-5-yl}ethyl]benzamide, 4-fluoro-N-[(1S)-2-hydroxy-1-[3-(1H-indol-3-yl)-1,2,4-oxadiazol-5-yl]ethyl]benzamide, 4-fluoro-N-[(1R)-2-hydroxy-1-{3-[4-(trifluoromethyl)phenyl]-1,2,4-oxadiazol-5-yl}ethyl]benzamide, N-[(1R)-2-hydroxy-1-{3-[4-(trifluoromethyl)phenyl]-1,2,4-oxadiazol-5-yl}ethyl]benzamide, 4-chloro-N-[(1R)-2-hydroxy-1-{3-[4-(trifluoromethyl)phenyl]-1,2,4-oxadiazol-5-yl}ethyl]benzamide, N-[(1S)-1-{3-[3,5-bis(trifluoromethyl)phenyl]-1,2,4-oxadiazol-5-yl}-2-hydroxyethyl]-4-fluorobenzamide, 4-fluoro-N-[(1S)-2-hydroxy-1-{3-[4-(2,2,2-trifluoroethoxy)phenyl]-1,2,4-oxadiazol-5-yl}ethyl]benzamide, 4-fluoro-N-[(1S)-1-{3-[3-fluoro-4-(trifluoromethyl)phenyl]-1,2,4-oxadiazol-5-yl}-2-hydroxyethyl]benzamide, N-[(1S)-1-[3-(3,5-difluorophenyl)-1,2,4-oxadiazol-5-yl]-2-hydroxyethyl]-4-fluorobenzamide, N-[(1S)-1-[3-(2-chloro-4-fluorophenyl)-1,2,4-oxadiazol-5-yl]-2-hydroxyethyl]-4-fluorobenzamide, N-[(1S)-2-hydroxy-1-{3-[3-(trifluoromethyl)phenyl]-1,2,4-oxadiazol-5-yl}ethyl]-4-(morpholin-4-yl)benzamide, N-[(1S)-2-hydroxy-1-{3-[3-(trifluoromethyl)phenyl]-1,2,4-oxadiazol-5-yl}ethyl]-4-(pyrrolidin-1-yl)benzamide, 3-chloro-5-fluoro-N-[(1S)-2-hydroxy-1-{3-[3-(trifluoromethyl)phenyl]-1,2,4-oxadiazol-5-yl}ethyl]benzamide, 4-fluoro-N-[(1S)-2-hydroxy-1-{3-[4-(trimethylsilyl)phenyl]-1,2,4-oxadiazol-5-yl}ethyl]benzamide, N-[(1S)-1-[3-(5-chloro-1H-indol-3-yl)-1,2,4-oxadiazol-5-yl]-2-hydroxyethyl]-4-fluorobenzamide, 4-fluoro-N-[(1S)-1-[3-(5-fluoro-1H-indol-3-yl)-1,2,4-oxadiazol-5-yl]-2-hydroxyethyl]benzamide, 2364-chloro-2-fluoro-N-[(1S)-2-hydroxy-1-{3-[4-(trifluoromethyl)phenyl]-1,2,4-oxadiazol-5-yl}ethyl]benzamide, 3-chloro-4-fluoro-N-[(1S)-2-hydroxy-1-{3-[4-(trifluoromethyl)phenyl]-1,2,4-oxadiazol-5-yl}ethyl]benzamide, 3-chloro-4-fluoro-N-[(1S)-2-hydroxy-1-{3-[3-(trifluoromethyl)phenyl]-1,2,4-oxadiazol-5-yl}ethyl]benzamide, 4-fluoro-N-[(1S)-2-hydroxy-1-[3-(1-methyl-1H-indol-3-yl)-1,2,4-oxadiazol-5-yl]ethyl]benzamide, N-[(1S)-1-[3-(5-bromo-1H-indol-3-yl)-1,2,4-oxadiazol-5-yl]-2-hydroxyethyl]-4-fluorobenzamide, 4-fluoro-N-[(1S)-2-hydroxy-1-[3-(1H-indol-6-yl)-1,2,4-oxadiazol-5-yl]ethyl]benzamide, 4-chloro-N-[(1S)-1-[3-(5-chloro-1H-indol-3-yl)-1,2,4-oxadiazol-5-yl]-2-hydroxyethyl]-2-fluorobenzamide, N-[(1S)-1-[3-(5-chloro-1H-indol-3-yl)-1,2,4-oxadiazol-5-yl]-2-hydroxyethyl]-4-(pyrrolidin-1-yl)benzamide, 5-chloro-N-[(1S)-1-[3-(5-chloro-1H-indol-3-yl)-1,2,4-oxadiazol-5-yl]-2-hydroxyethyl]pyridine-2-carboxamide, 4-fluoro-N-[(1S)-2-hydroxy-1-{3-[3-(2,2,2-trifluoroacetyl)-1H-indol-6-yl]-1,2,4-oxadiazol-5-yl}ethyl]benzamide, 4-fluoro-N-[(1S)-1-[3-(6-fluoro-1H-indol-3-yl)-1,2,4-oxadiazol-5-yl]-2-hydroxyethyl]benzamide, 4-fluoro-N-[(1S)-2-hydroxy-1-[3-(5-methoxy-1H-indol-3-yl)-1,2,4-oxadiazol-5-yl]ethyl]benzamide, 4-fluoro-N-[(1S)-2-hydroxy-1-{3-[5-(trifluoromethyl)-1H-indol-3-yl]-1,2,4-oxadiazol-5-yl}ethyl]benzamide, N-[(1S)-1-[3-(6-chloro-1H-indol-3-yl)-1,2,4-oxadiazol-5-yl]-2-hydroxyethyl]-4-fluorobenzamide, 4-fluoro-N-[(1S)-2-hydroxy-1-{3-[1-(2-hydroxyethyl)-1H-indol-3-yl]-1,2,4-oxadiazol-5-yl}ethyl]benzamide, 4-fluoro-N-[(1S)-2-hydroxy-1-[3-(1H-indol-2-yl)-1,2,4-oxadiazol-5-yl]ethyl]benzamide and 4-fluoro-N-[(1S)-1-[3-(5-fluoro-1H-indol-2-yl)-1,2,4-oxadiazol-5-yl]-2-hydroxyethyl]benzamide; or a pharmaceutically acceptable salt thereof or a solvate thereof.

7. A therapeutic agent for a neurodegenerative disease, comprising an amyloid fibril formation inhibitor according to claim 1.

8. The therapeutic agent according to claim 7, wherein the neurodegenerative disease is Alzheimer's disease.

9. A therapeutic agent for a neurodegenerative disease, comprising an amyloid fibril formation inhibitor according to claim 3.

10. The therapeutic agent according to claim 9, wherein the neurodegenerative disease is Alzheimer's disease.

11. The amyloid fibril formation inhibitor according to claim 1, wherein $R_2$ is hydroxymethyl.

12. The amyloid fibril formation inhibitor according to claim 1, wherein
   Ring A1 is a trifluoromethylphenyl, difluoromethylphenyl, trifluoromethoxyphenyl, hydroxyphenyl, methoxyphenyl, or indolyl; and
   Ring A3 is a fluorophenyl, difluorophenyl, chlorophenyl, dichlorophenyl, or chlorofluorophenyl.

13. The amyloid fibril formation inhibitor according to claim 1, wherein $R'_2$ is hydroxymethyl; Ring A1 is 4-trifluoromethoxyphenyl or 4-difluoromethylphenyl; and Ring A3 is 4-chlorophenyl or 3-chlorophenyl.

14. The amyloid fibril formation inhibitor according to claim 1, wherein the compound is (S)-4-chloro-N-(2-hydroxy-1-[3-{4-(trifluoromethoxy)phenyl}-1,2,4-oxadiazol-5-yl]ethyl)benzamide (Compound No. 39), or a pharmaceutically acceptable salt thereof or a solvate thereof.

15. The amyloid fibril formation inhibitor according to claim 1, wherein the compound is (S)-3-chloro-N-(2-hydroxy-1-[3-{4-(trifluoromethoxy)phenyl}-1,2,4-oxadiazol-5-yl]ethyl)benzamide (Compound No. 63), or a pharmaceutically acceptable salt thereof or a solvate thereof.

16. The amyloid fibril formation inhibitor according to claim 1, wherein the compound is 4-chloro-N-[(1S)-1-{3-[4-(difluoromethyl)phenyl]-1,2,4-oxadiazol-5-yl}-2-hydroxyethyl]benzamide (Compound No. 167), or a pharmaceutically acceptable salt thereof or a solvate thereof.

* * * * *

UNITED STATES PATENT AND TRADEMARK OFFICE
CERTIFICATE OF CORRECTION

PATENT NO. : 10,538,516 B2  
APPLICATION NO. : 15/560345  
DATED : January 21, 2020  
INVENTOR(S) : Yanagisawa et al.

Page 1 of 6

It is certified that error appears in the above-identified patent and that said Letters Patent is hereby corrected as shown below:

On the Title Page

Item (54) Title:  
Please insert the word -- NOVEL -- before the word "OXADIAZOLE"

In the Specification

Column 1, Line 1:  
Please insert the word -- NOVEL -- before the word "OXADIAZOLE"

Column 4, Line 18:  
Please correct "Z is —(CH$_2$)—" to read -- Z is —(CH$_2$)$_n$— --

Column 4, Line 18:  
Please correct "—(CH$_2$)—O—" to read -- —(CH$_2$)$_n$—O— --

Column 7, Line 54:  
Please correct "R$_x$b" to read -- R$_{xb}$ --

Column 23, Formula 45:  
Please delete Formula 45 and replace with the following

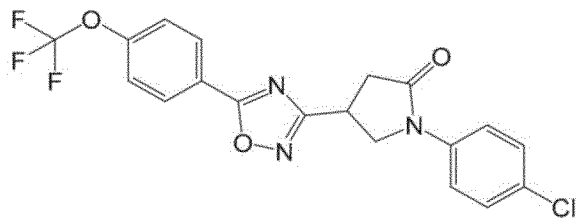

Signed and Sealed this  
Twenty-first Day of July, 2020

Andrei Iancu  
*Director of the United States Patent and Trademark Office*

Column 40, Formula 129:
Please delete Formula 129 and replace with the following 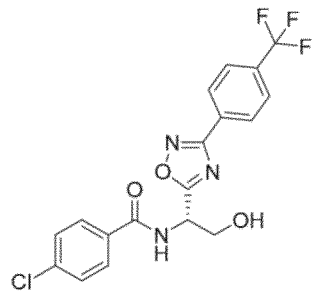
Column 40, Formula 130:
Please delete Formula 130 and replace with the following 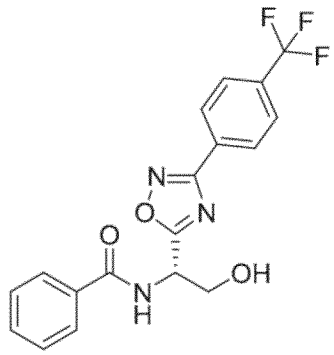
Column 41, Formula 133:
Please delete Formula 133 and replace with the following 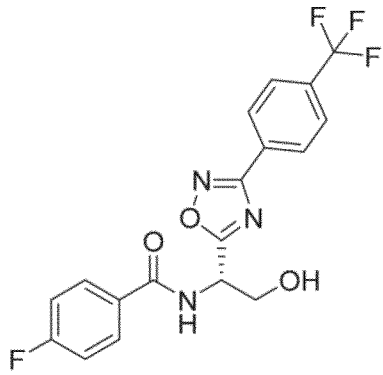
Column 63, Formula 230:
Please delete Formula 230 and replace with the following 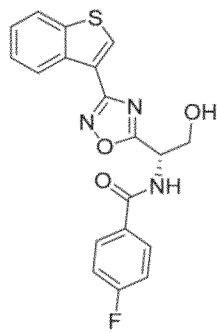

Column 69, Formula 254:
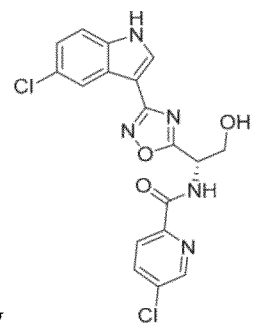
Please delete Formula 254 and replace with the following
Column 88, Line 8:
Please correct "2.2 m" to read -- 2.2 μm --
Column 89-90, Formula 11:
Please delete section 21-1 of Formula 11 " 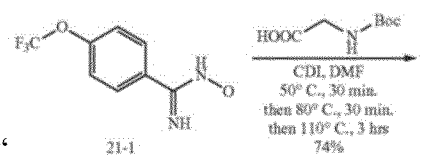 " and replace with the following 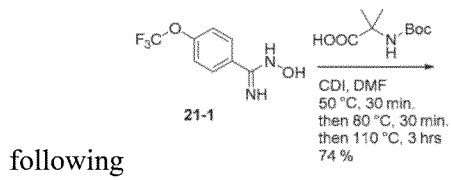
Column 92, Formula 11:
Please delete section 21-3 of Formula 11 " 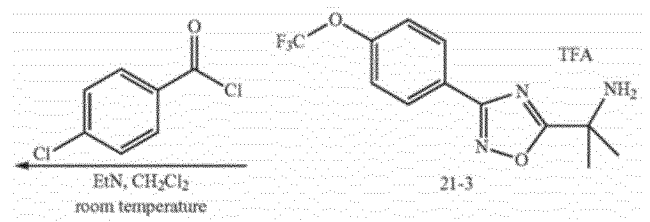 "
and replace with the following 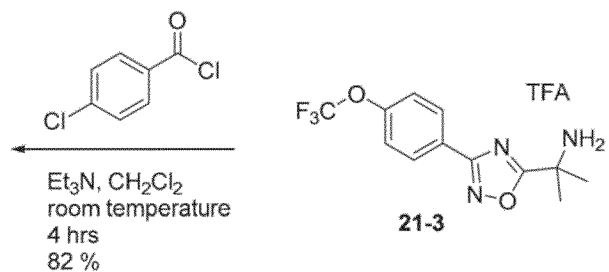

Column 95, Formula 14:
Please delete section 34-4 of Formula 14 " 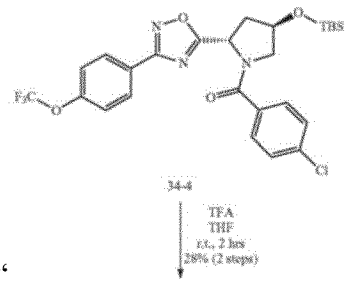 " and replace with the following 
Column 123, Formula 30:
Please delete section 102 of Formula 30 " 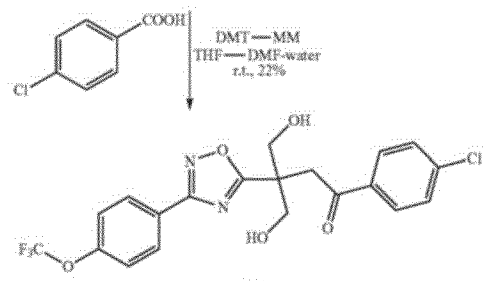 " and replace with the following 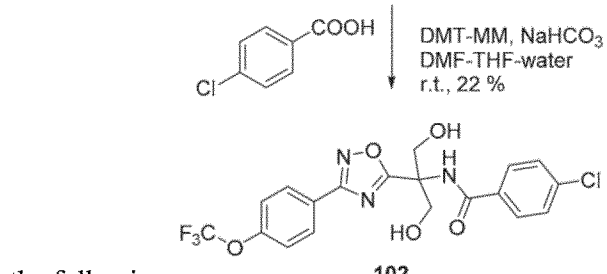

Column 131, Lines 60-65, Formula 35:

Please delete this section of Formula 35 " 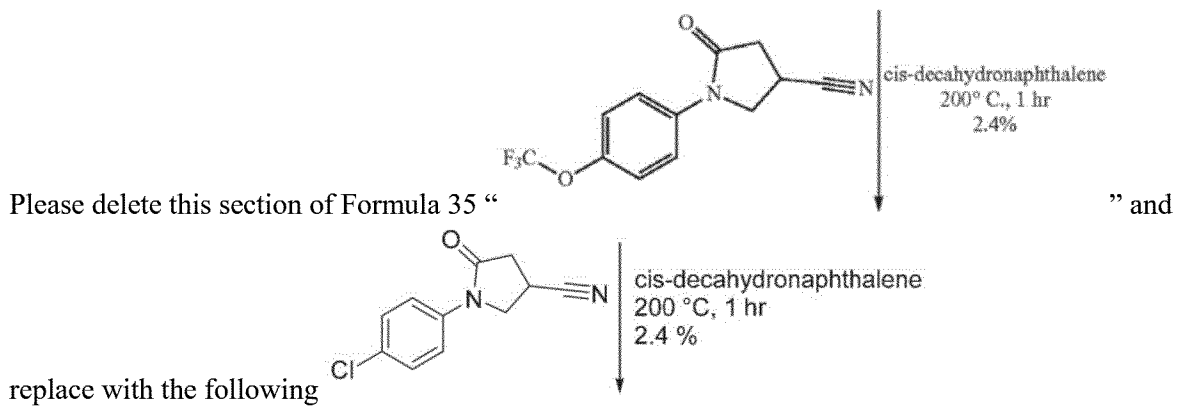 " and replace with the following Column 164, Formula 76, Column 3 of Table 2K:
Please insert -- Not provided --

Column 172, Formula 95, Column 4 of Table 2N:
Please correct "[M +H]– = 449.95" to read -- [M + H]– = 440.95 --

Column 172, Formula 97, Column 3 of Table 2N:
Please insert -- Not provided --

Column 172, Formula 97, Column 5 of Table 2N:
Please insert -- Not provided --

Column 180, Formula 116, Column 3 of Table 2P:
Please insert -- Not provided --

Column 180, Formula 117, Column 3 of Table 2P:
Please insert -- Not provided --

Column 180, Formula 119, Column 3 of Table 2P:
Please insert -- Not provided --

Column 180, Formula 120, Column 3 of Table 2P:
Please insert -- Not provided --

Column 188, Formula 146, Column 5 of Table 2T:
Please insert -- Not provided --

Column 188, Formula 147, Column 5 of Table 2T:
Please insert -- Not provided --

Column 190, Formula 148, Column 5 of Table 2T:
Please insert -- Not provided --

Column 190, Formula 149, Column 5 of Table 2T:
Please insert -- Not provided --

Column 190, Formula 150, Column 5 of Table 2T:
Please insert -- Not provided --

Column 190, Formula 151, Column 5 of Table 2T:
Please insert -- Not provided --

Column 192, Formula 152, Column 5 of Table 2T:
Please insert -- Not provided --

Column 192, Formula 153, Column 5 of Table 2T:
Please insert -- Not provided --

Column 196, Formula 162, Column 4 of Table 2V:
Please correct "[M +H]+ = 360" to read -- [M + H]+ = 342 --

Column 205, Formula 184, Column 1 of Table 2X:

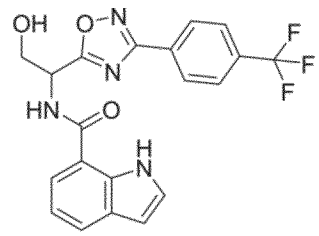

Please delete Formula 184 and replace it with the following

Column 248, Line 50:
Please correct "75 μM" to read -- 750 μM --

In the Claims

Column 258, Line 15, Claim 4:
Please correct "(1S')" to read -- (1S) --

Column 259, Line 26, Claim 4:
Please correct "1-r[3" to read -- 1-[3 --

Column 259, Line 28, Claim 4:
Please correct "-1,4-oxadiazol" to read -- -1,2,4-oxadiazol --

Column 261, Line 58, Claim 6:
Please correct "2=hydroxy" to read -- 2-hydroxy --